US009801576B2

(12) United States Patent
Yang et al.

(10) Patent No.: US 9,801,576 B2
(45) Date of Patent: Oct. 31, 2017

(54) APPLICATION OF ELECTROCHEMICAL IMPEDANCE SPECTROSCOPY IN SENSOR SYSTEMS, DEVICES, AND RELATED METHODS

(71) Applicant: MEDTRONIC MINIMED, INC., Northridge, CA (US)

(72) Inventors: Ning Yang, New York, NY (US); Raghavendhar Gautham, Los Angeles, CA (US); Bradley C. Liang, Bloomfield Hills, MI (US); Rajiv Shah, Rancho Palos Verdes, CA (US)

(73) Assignee: MEDTRONIC MINIMED, INC., Northridge, CA (US)

( * ) Notice: Subject to any disclaimer, the term of this patent is extended or adjusted under 35 U.S.C. 154(b) by 0 days.

(21) Appl. No.: 15/446,886

(22) Filed: Mar. 1, 2017

(65) Prior Publication Data
US 2017/0172474 A1  Jun. 22, 2017

Related U.S. Application Data

(63) Continuation of application No. 15/154,560, filed on May 13, 2016, now Pat. No. 9,625,415, which is a
(Continued)

(51) Int. Cl.
*A61B 5/1495* (2006.01)
*A61B 5/145* (2006.01)
(Continued)

(52) U.S. Cl.
CPC .......... *A61B 5/1495* (2013.01); *A61B 5/0537* (2013.01); *A61B 5/0538* (2013.01);
(Continued)

(58) Field of Classification Search
CPC ................................................... A61B 5/1495
See application file for complete search history.

(56) References Cited

U.S. PATENT DOCUMENTS

| 4,331,528 A | 5/1982 | Beer et al. |
| 4,755,173 A | 7/1988 | Konopka et al. |

(Continued)

FOREIGN PATENT DOCUMENTS

| JP | 2005-044716 | 2/2005 |
| JP | 2007-130482 | 5/2007 |

(Continued)

OTHER PUBLICATIONS

Shervedani et al. (Shervedani et al., Bioelectrochemistry, 69 (2006) pp. 201-208.
(Continued)

*Primary Examiner* — John Breene
*Assistant Examiner* — Jeffrey C Morgan
(74) *Attorney, Agent, or Firm* — Pillsbury Winthrop Shaw Pittman LLP

(57) ABSTRACT

A diagnostic Electrochemical Impedance Spectroscopy (EIS) procedure is applied to measure values of impedance-related parameters for one or more sensing electrodes. The parameters may include real impedance, imaginary impedance, impedance magnitude, and/or phase angle. The measured values of the impedance-related parameters are then used in performing sensor diagnostics, calculating a highly-reliable fused sensor glucose value based on signals from a plurality of redundant sensing electrodes, calibrating sensors, detecting interferents within close proximity of one or more sensing electrodes, and testing surface area characteristics of electroplated electrodes. Advantageously, impedance-related parameters can be defined that are substantially glucose-independent over specific ranges of frequencies. An
(Continued)

Application Specific Integrated Circuit (ASIC) enables implementation of the EIS-based diagnostics, fusion algorithms, and other processes based on measurement of EIS-based parameters.

20 Claims, 72 Drawing Sheets

Related U.S. Application Data continuation of application No. 13/778,416, filed on Feb. 27, 2013, now Pat. No. 9,357,958.

(60) Provisional application No. 61/755,811, filed on Jan. 23, 2013, provisional application No. 61/754,475, filed on Jan. 18, 2013, provisional application No. 61/754,479, filed on Jan. 18, 2013, provisional application No. 61/754,483, filed on Jan. 18, 2013, provisional application No. 61/754,485, filed on Jan. 18, 2013, provisional application No. 61/657,517, filed on Jun. 8, 2012.

(51) Int. Cl.
G01N 27/416 (2006.01)
G01N 27/02 (2006.01)
A61B 5/053 (2006.01)
A61B 5/1486 (2006.01)
A61B 5/00 (2006.01)
G01N 33/66 (2006.01)
G01N 33/49 (2006.01)

(52) U.S. Cl.
CPC ...... *A61B 5/14532* (2013.01); *A61B 5/14865* (2013.01); *A61B 5/6849* (2013.01); *A61B 5/7203* (2013.01); *A61B 5/7221* (2013.01); *A61B 5/7225* (2013.01); *A61B 5/7242* (2013.01); *A61B 5/746* (2013.01); *G01N 27/026* (2013.01); *G01N 27/028* (2013.01); *G01N 27/4163* (2013.01); *G01N 33/49* (2013.01); *G01N 33/66* (2013.01); *A61B 2562/0214* (2013.01); *A61B 2562/04* (2013.01)

(56) References Cited

U.S. PATENT DOCUMENTS

| | | |
|---|---|---|
| 5,391,250 A | 2/1995 | Cheney, II et al. |
| 5,485,408 A | 1/1996 | Blomquist |
| 5,522,803 A | 6/1996 | Teissen-Simony |
| 5,665,065 A | 9/1997 | Colman et al. |
| 5,674,375 A | 10/1997 | Thompson |
| 5,800,420 A | 9/1998 | Gross et al. |
| 5,807,375 A | 9/1998 | Gross et al. |
| 5,925,021 A | 7/1999 | Castellano et al. |
| 5,954,643 A | 9/1999 | Van Antwerp et al. |
| 6,017,328 A | 1/2000 | Fischell et al. |
| 6,186,982 B1 | 2/2001 | Gross et al. |
| 6,246,992 B1 | 6/2001 | Brown |
| 6,248,067 B1 | 6/2001 | Causey, III et al. |
| 6,248,093 B1 | 6/2001 | Moberg |
| 6,355,021 B1 | 3/2002 | Nielsen et al. |
| 6,379,301 B1 | 4/2002 | Worthington et al. |
| 6,392,416 B1 | 5/2002 | Keech |
| 6,485,703 B1 | 11/2002 | Cote et al. |
| 6,517,482 B1 | 2/2003 | Elden et al. |
| 6,544,212 B2 | 4/2003 | Galley et al. |
| 6,558,351 B1 | 5/2003 | Steil et al. |
| 6,591,876 B2 | 7/2003 | Safabash |
| 6,641,533 B2 | 11/2003 | Causey, III et al. |
| 6,736,797 B1 | 5/2004 | Larsen et al. |
| 6,749,587 B2 | 6/2004 | Flaherty |
| 6,766,183 B2 | 7/2004 | Walsh et al. |
| 6,801,420 B2 | 10/2004 | Talbot et al. |
| 6,804,544 B2 | 10/2004 | Van Antwerp et al. |
| 7,003,336 B2 | 2/2006 | Holker et al. |
| 7,029,444 B2 | 4/2006 | Shin et al. |
| 7,066,909 B1 | 6/2006 | Peter et al. |
| 7,137,964 B2 | 11/2006 | Flaherty |
| 7,303,549 B2 | 12/2007 | Flaherty et al. |
| 7,399,277 B2 | 7/2008 | Saidara et al. |
| 7,442,186 B2 | 10/2008 | Blomquist |
| 7,602,310 B2 | 10/2009 | Mann et al. |
| 7,647,237 B2 | 1/2010 | Malave et al. |
| 7,693,561 B2 | 4/2010 | Schrepfer et al. |
| 7,699,807 B2 | 4/2010 | Faust et al. |
| 7,727,148 B2 | 6/2010 | Talbot et al. |
| 7,785,313 B2 | 8/2010 | Mastrototaro |
| 7,806,886 B2 | 10/2010 | Kanderian, Jr. et al. |
| 7,819,843 B2 | 10/2010 | Mann et al. |
| 7,828,764 B2 | 11/2010 | Moberg et al. |
| 7,879,010 B2 | 2/2011 | Hunn et al. |
| 7,890,295 B2 | 2/2011 | Shin et al. |
| 7,892,206 B2 | 2/2011 | Moberg et al. |
| 7,892,748 B2 | 2/2011 | Norrild et al. |
| 7,901,394 B2 | 3/2011 | Ireland et al. |
| 7,942,844 B2 | 5/2011 | Moberg et al. |
| 7,946,985 B2 | 5/2011 | Mastrototaro et al. |
| 7,955,305 B2 | 6/2011 | Moberg et al. |
| 7,963,954 B2 | 6/2011 | Kavazov |
| 7,977,112 B2 | 7/2011 | Burke et al. |
| 7,979,259 B2 | 7/2011 | Brown |
| 7,985,330 B2 | 7/2011 | Wang et al. |
| 8,024,201 B2 | 9/2011 | Brown |
| 8,071,384 B2 | 12/2011 | Burke et al. |
| 8,073,520 B2 | 12/2011 | Kamath et al. |
| 8,100,852 B2 | 1/2012 | Moberg et al. |
| 8,114,268 B2 | 2/2012 | Wang et al. |
| 8,114,269 B2 | 2/2012 | Cooper et al. |
| 8,137,314 B2 | 3/2012 | Mounce et al. |
| 8,181,849 B2 | 5/2012 | Bazargan et al. |
| 8,182,462 B2 | 5/2012 | Istoc et al. |
| 8,192,395 B2 | 6/2012 | Estes et al. |
| 8,195,265 B2 | 6/2012 | Goode, Jr. et al. |
| 8,202,250 B2 | 6/2012 | Stutz, Jr. |
| 8,207,859 B2 | 6/2012 | Enegren et al. |
| 8,226,615 B2 | 7/2012 | Bikovsky |
| 8,257,259 B2 | 9/2012 | Brauker et al. |
| 8,267,921 B2 | 9/2012 | Yodfat et al. |
| 8,271,098 B2 | 9/2012 | Swanson et al. |
| 8,275,437 B2 | 9/2012 | Brauker et al. |
| 8,277,415 B2 | 10/2012 | Mounce et al. |
| 8,292,849 B2 | 10/2012 | Bobroff et al. |
| 8,298,172 B2 | 10/2012 | Nielsen et al. |
| 8,303,572 B2 | 11/2012 | Adair et al. |
| 8,305,580 B2 | 11/2012 | Aasmul |
| 8,308,679 B2 | 11/2012 | Hanson et al. |
| 8,313,433 B2 | 11/2012 | Cohen et al. |
| 8,318,443 B2 | 11/2012 | Norrild et al. |
| 8,323,250 B2 | 12/2012 | Chong et al. |
| 8,343,092 B2 | 1/2013 | Rush et al. |
| 8,352,011 B2 | 1/2013 | Van Antwerp et al. |
| 8,353,829 B2 | 1/2013 | Say et al. |
| 8,682,408 B2 | 3/2014 | Boock et al. |
| 2004/0079652 A1 | 4/2004 | Vreeke et al. |
| 2005/0004439 A1 | 1/2005 | Shin et al. |
| 2005/0027180 A1 | 2/2005 | Goode et al. |
| 2005/0152946 A1 | 7/2005 | Hunter et al. |
| 2006/0019327 A1 | 1/2006 | Brister et al. |
| 2006/0036145 A1 | 2/2006 | Brister et al. |
| 2007/0123819 A1 | 5/2007 | Mernoe et al. |
| 2008/0000779 A1 | 1/2008 | Wang et al. |
| 2008/0033254 A1 | 2/2008 | Kamath et al. |
| 2009/0006021 A1 | 1/2009 | Lensing et al. |
| 2009/0192380 A1 | 7/2009 | Shariati et al. |
| 2010/0081906 A1 | 4/2010 | Hayter et al. |
| 2010/0160861 A1 | 6/2010 | Causey, III et al. |
| 2010/0169035 A1 | 7/2010 | Liang et al. |
| 2011/0040163 A1 | 2/2011 | Telson et al. |
| 2011/0100820 A1 | 5/2011 | Bachmann et al. |
| 2011/0168575 A1 | 7/2011 | Lica et al. |

(56) References Cited

U.S. PATENT DOCUMENTS

| | | |
|---|---|---|
| 2011/0230741 A1 | 9/2011 | Liang et al. |
| 2011/0319734 A1 | 12/2011 | Gottlieb et al. |
| 2012/0037515 A1 | 2/2012 | Solanki |
| 2013/0060105 A1 | 3/2013 | Shah et al. |
| 2013/0328573 A1 | 12/2013 | Yang et al. |
| 2014/0114159 A1 | 4/2014 | Brister et al. |

FOREIGN PATENT DOCUMENTS

| | | |
|---|---|---|
| JP | 2010-510674 | 4/2010 |
| JP | 2010-520462 | 6/2010 |
| JP | 2010-286423 | 12/2010 |
| JP | 2010-540205 | 12/2010 |
| WO | WO 2006/018425 A2 | 2/2006 |
| WO | WO 2007/075410 A2 | 7/2007 |
| WO | WO 2008/061212 A2 | 5/2008 |
| WO | WO 2008/104397 A2 | 9/2008 |
| WO | WO 2009/048921 A1 | 4/2009 |
| WO | WO 2009/107936 A2 | 9/2009 |
| WO | WO 2011/002694 | 1/2011 |
| WO | WO 2011/079938 A2 | 7/2011 |
| WO | WO 2011/084651 A1 | 7/2011 |
| WO | WO 2011/091061 | 7/2011 |

OTHER PUBLICATIONS

Gamry Instruments Technical Note, "Accuracy Contour Plots".
A.W. Tarulli, C.A. Chiffman, R. Arron, A.B. Chin, S.B. Rutkove, ICEPBI 2007, IFMBE Proceedings 17, pp. 647-650, 2007.
PCT International Searching Authority, "Invitation to Pay Additional Fees", International Application No. PCT/US2013/042680, dated Aug. 13, 2013, 9-pgs.
PCT International Searching Authority, "International Search Report", International Application No. PCT/US2013/042680, dated Jan. 2, 2014, 10-pgs.
PCT International Searching Authority, "Written Opinion of the International Searching Authority", International Application No. PCT/US2013/042680, dated Jan. 2, 2014, 19-pgs.
PCT International Searching Authority, "International Search Report", "Written Opinion of the International Searching Authority", International Application No. PCT/US2014/067725, dated May 9, 2015, 12-pgs.
Reza Karimi Shervedani, Seyed Ahmad Mozaffari, "Preparation and electrochemical characterization of a new nanosensor based on self-assembled monolayer of cysteamine functionalized with phosphate groups", Surface and Coatings Technology 198 (2005) pp. 123-128.

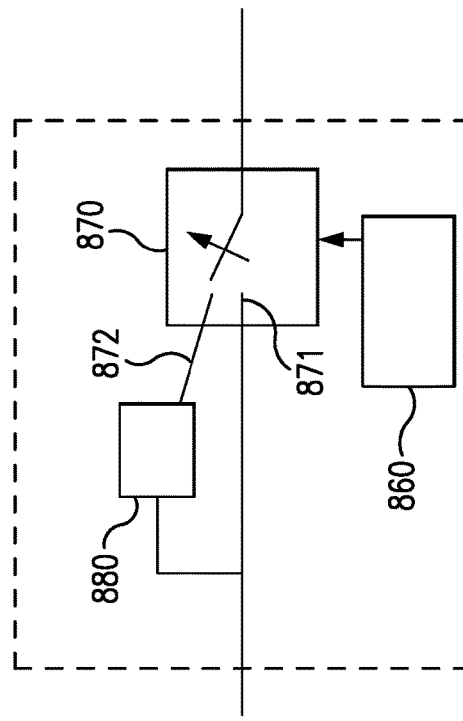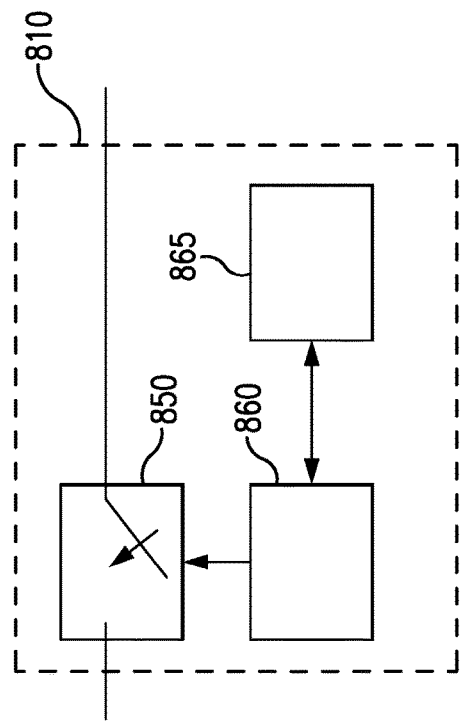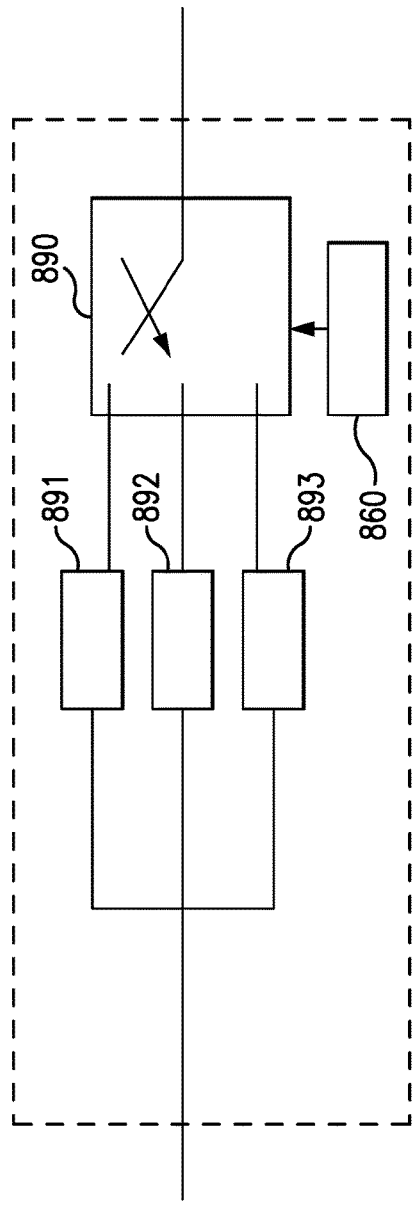

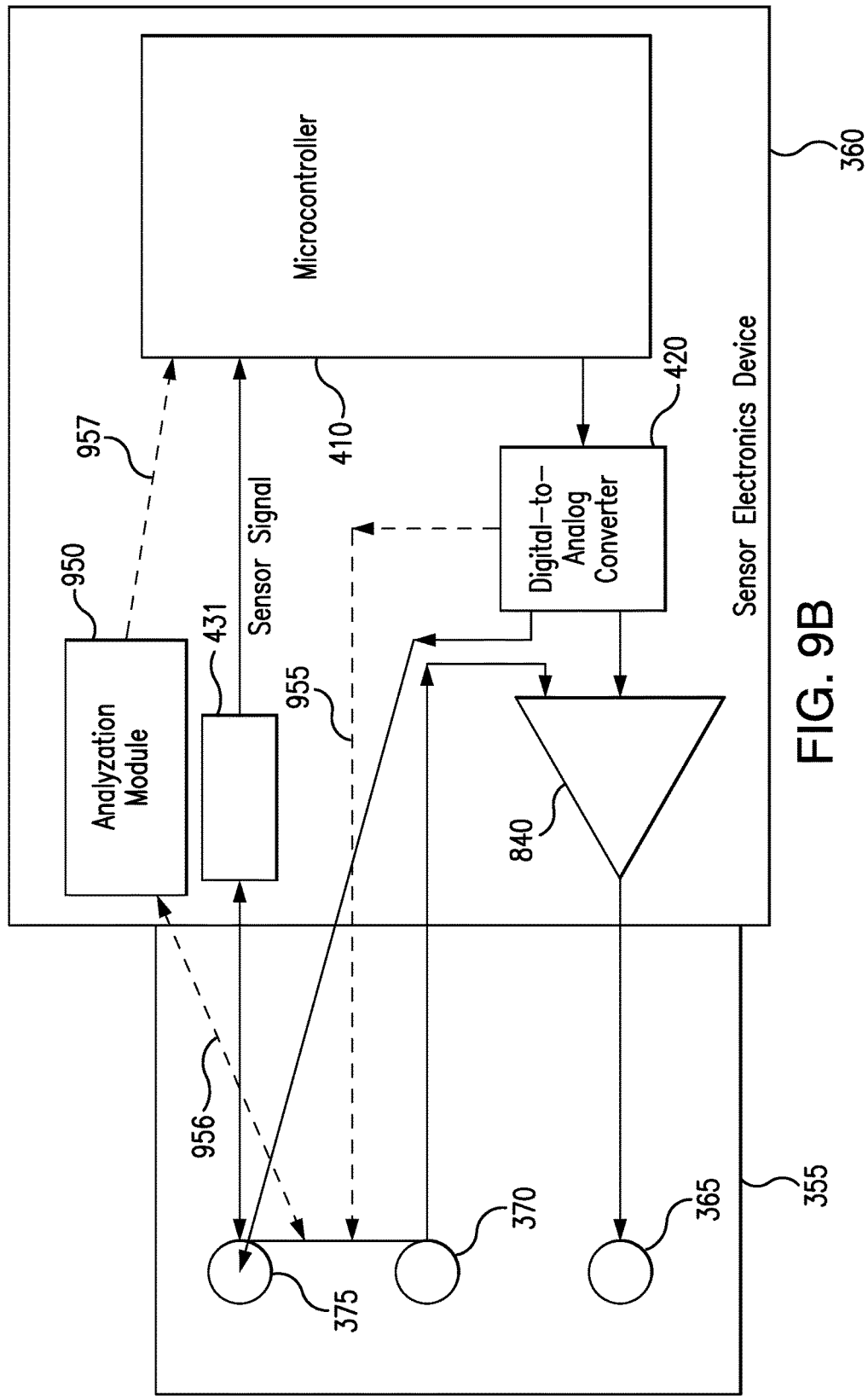

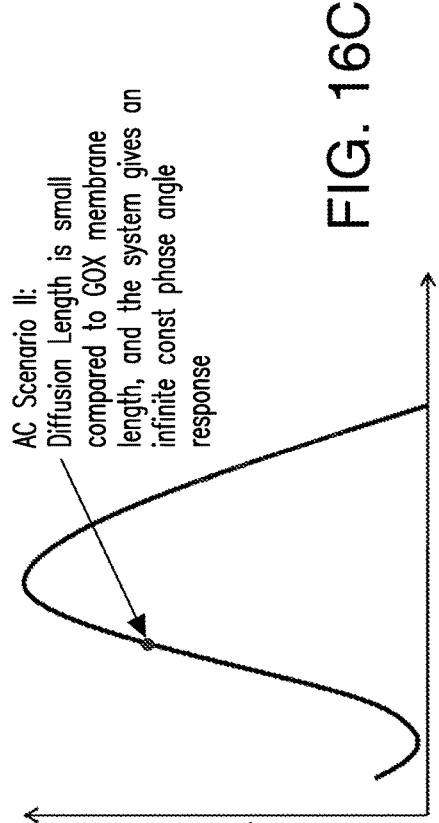
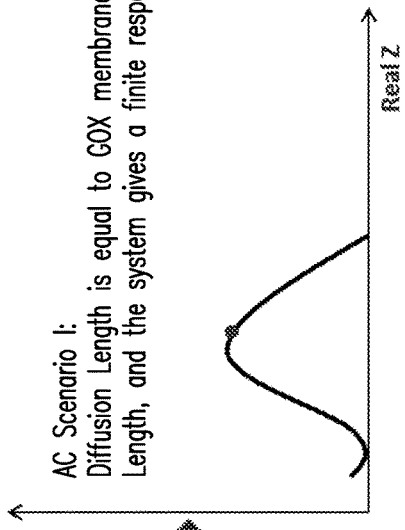
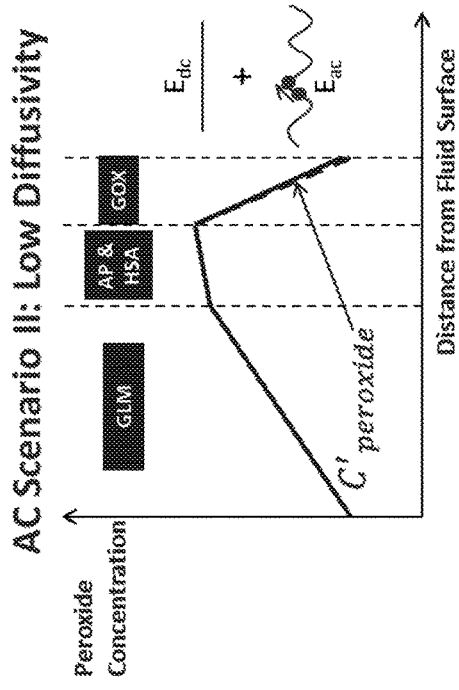
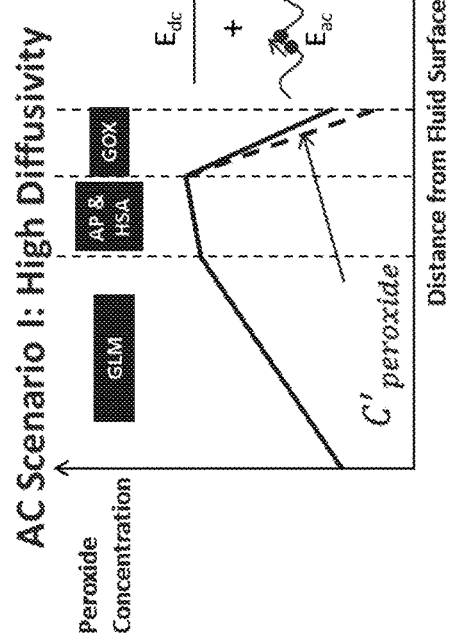
FIG. 16C
FIG. 16D

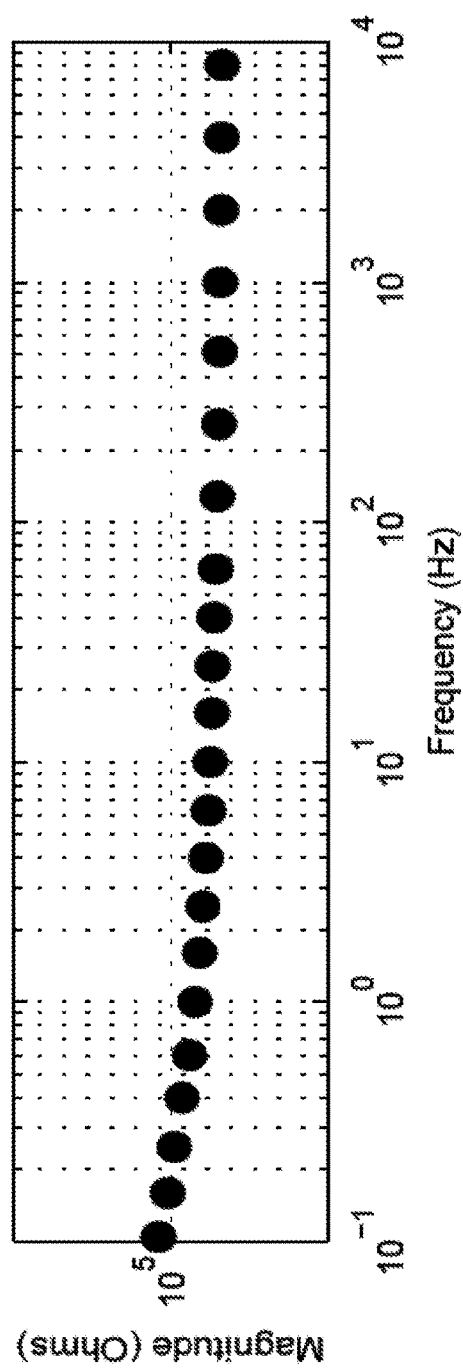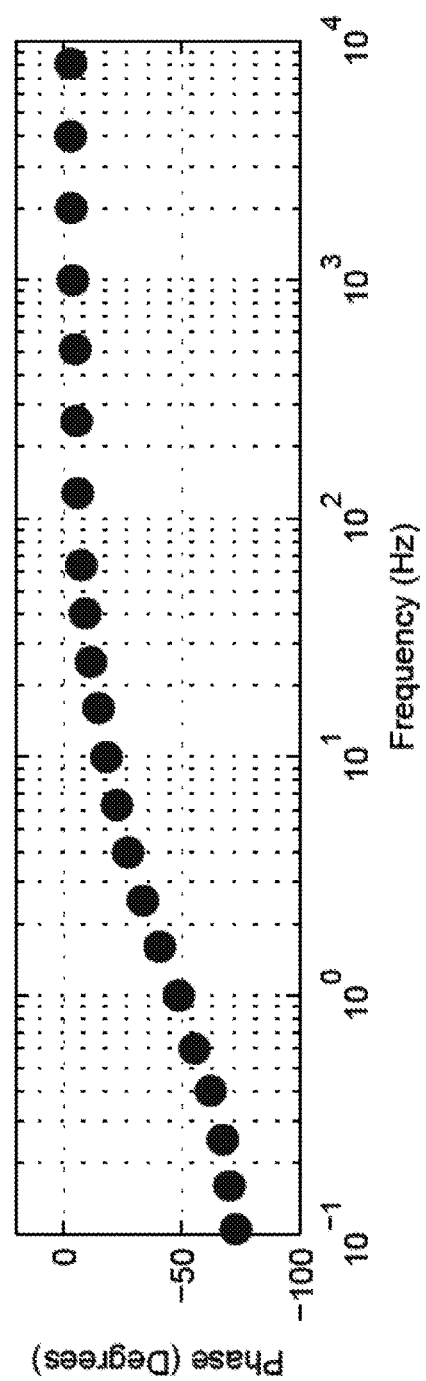
FIG. 16E
FIG. 16F

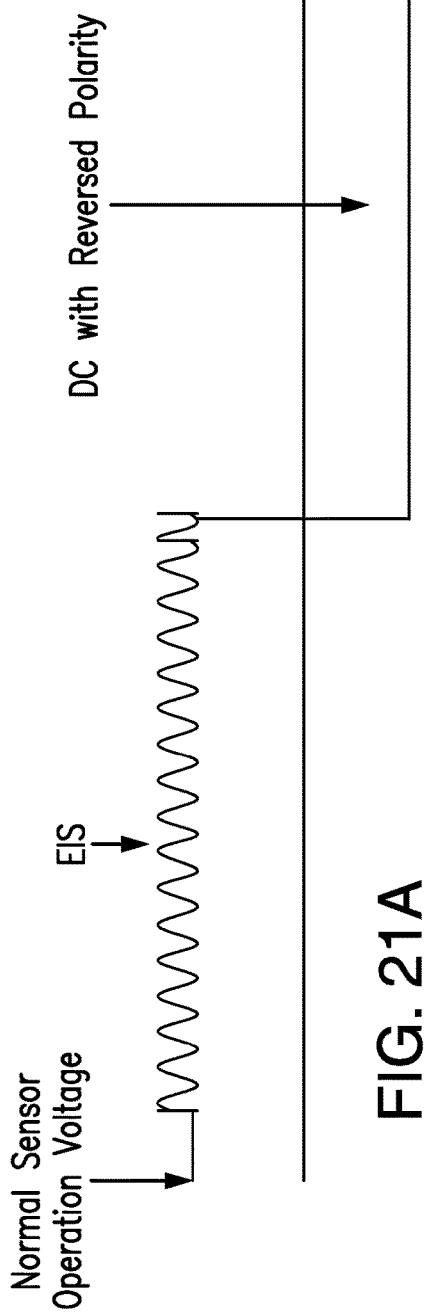
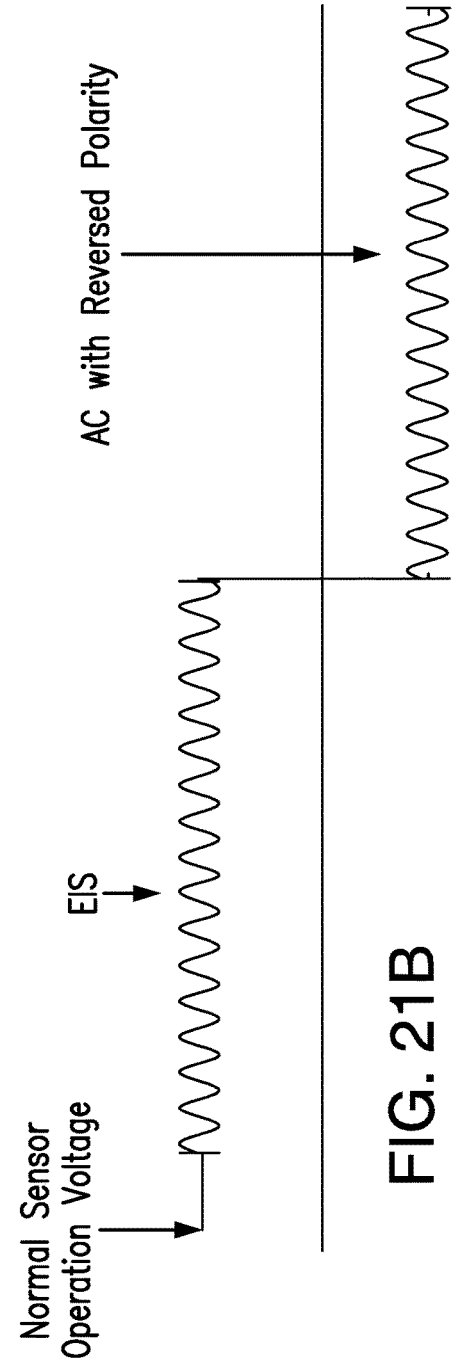
FIG. 21A
FIG. 21B

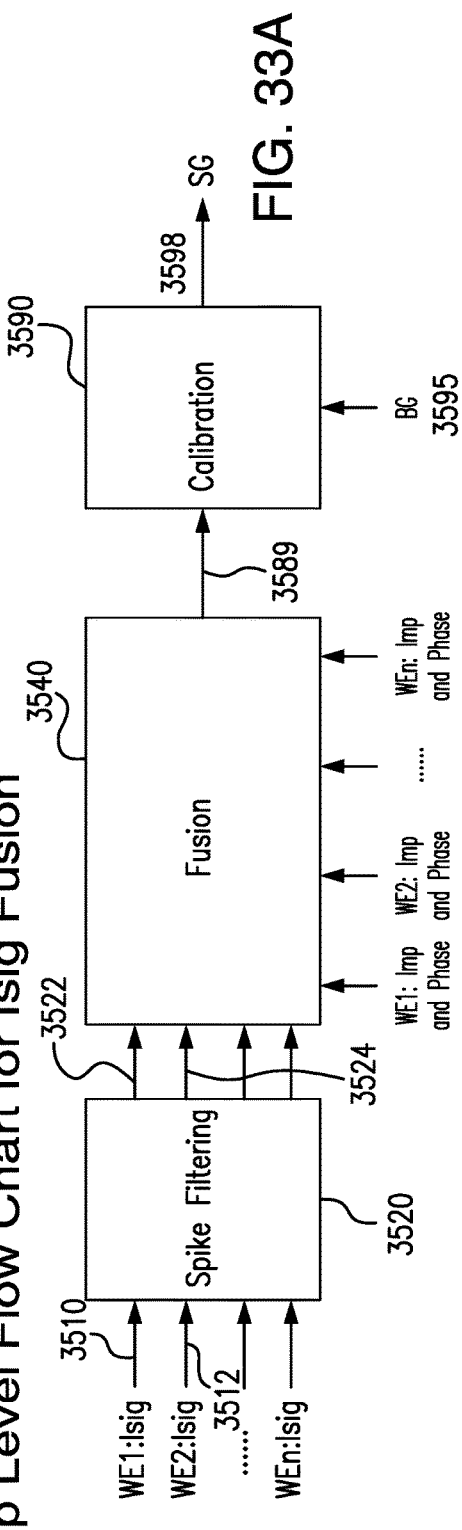
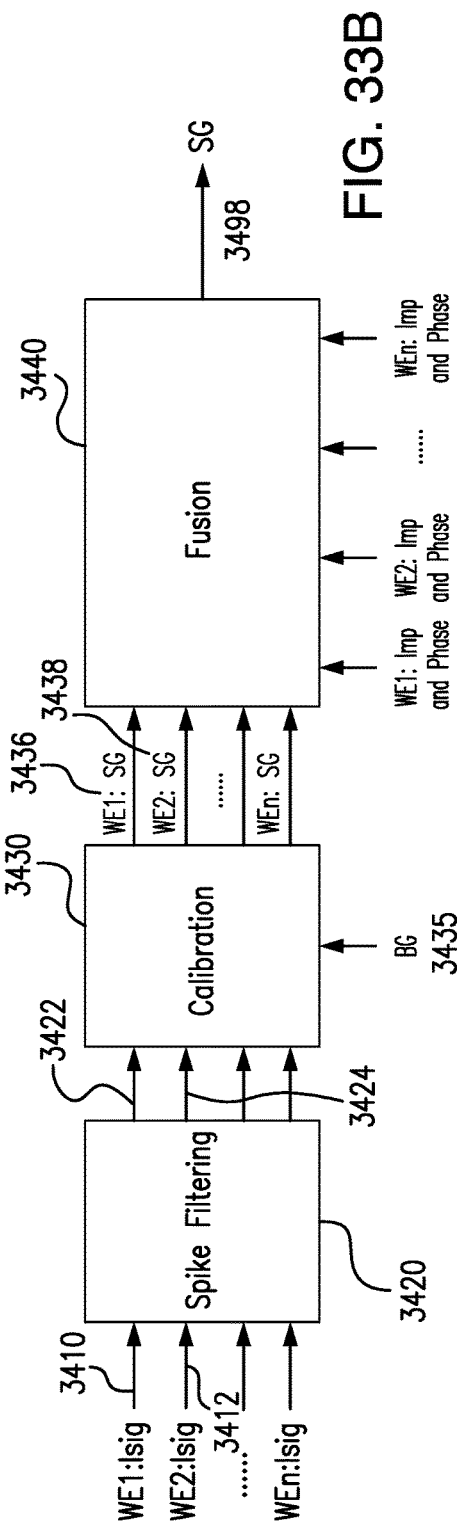

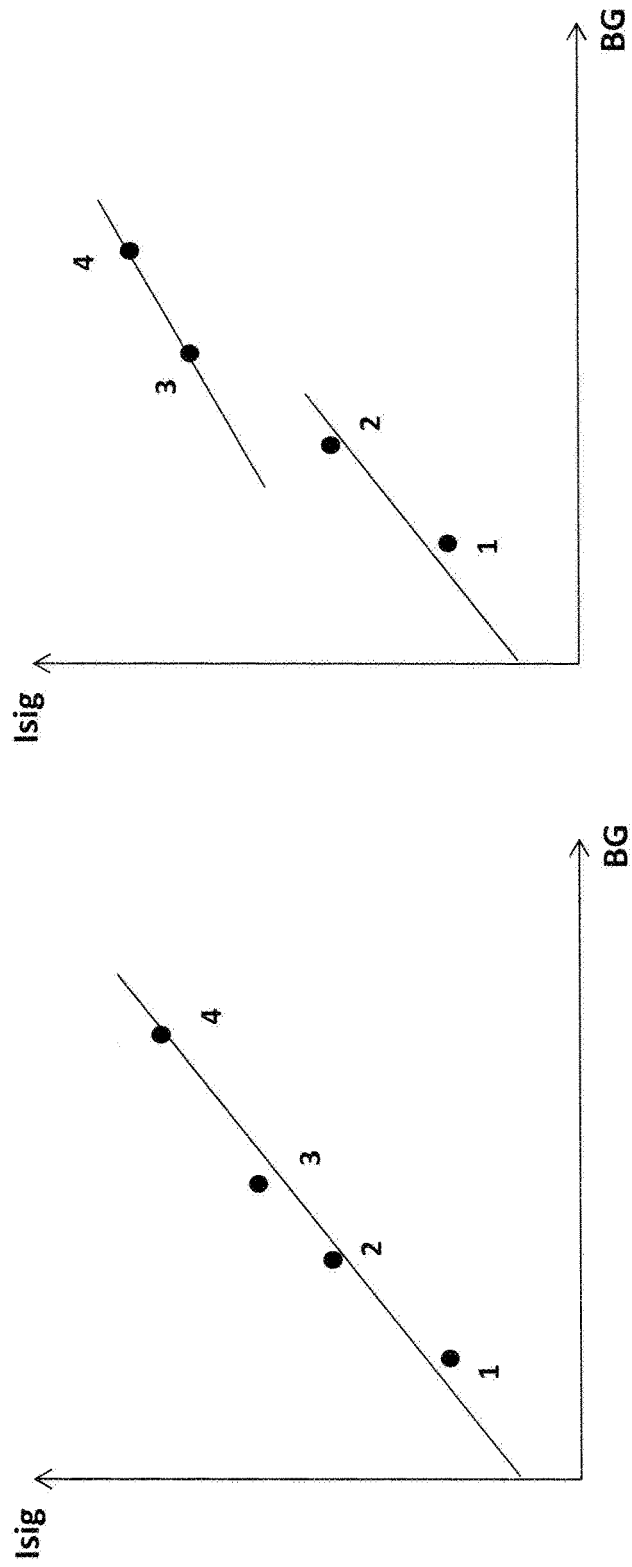

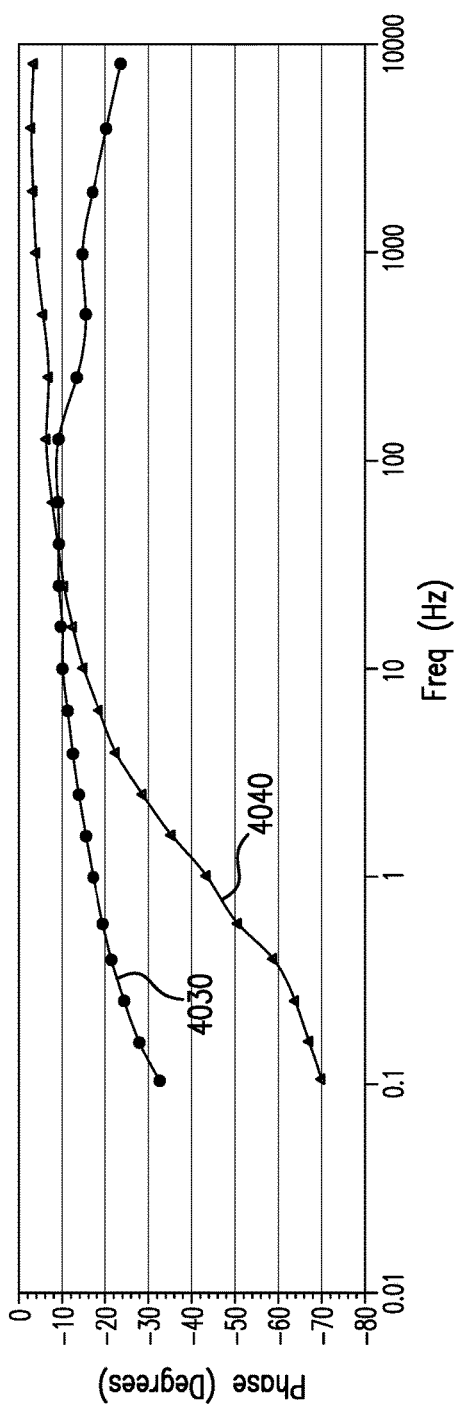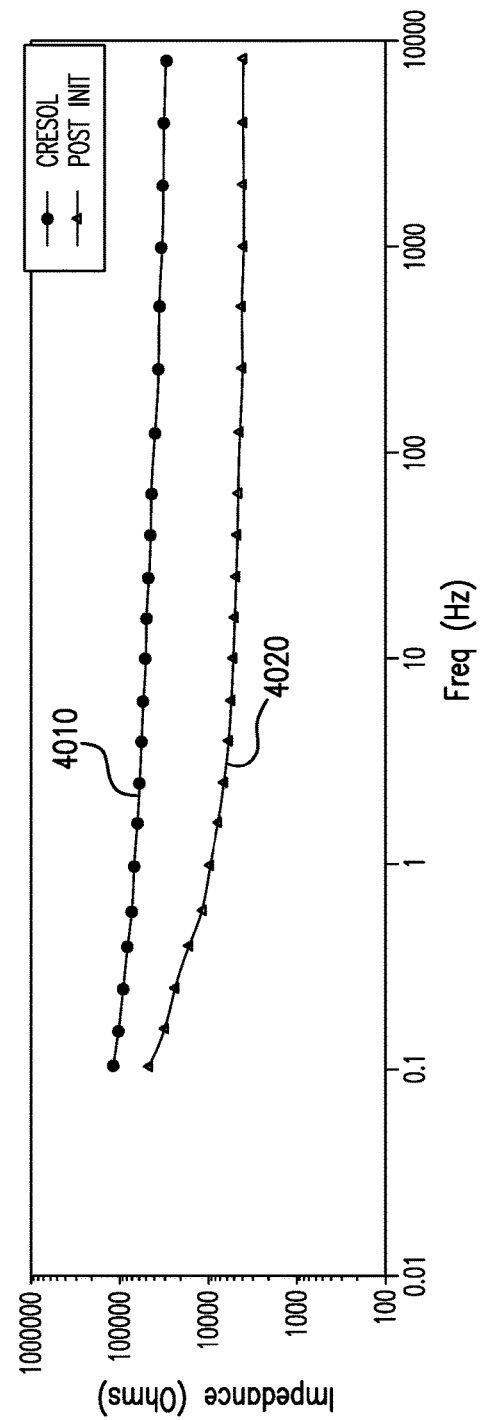
FIG. 40A
FIG. 40B

POTENTIOSTAT CONFIGURATION

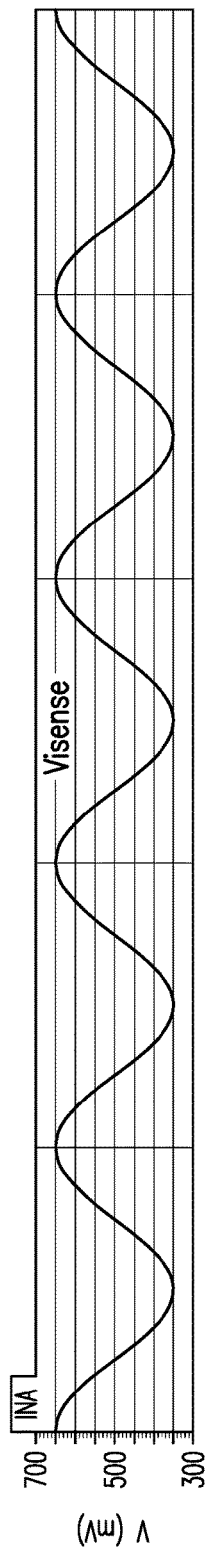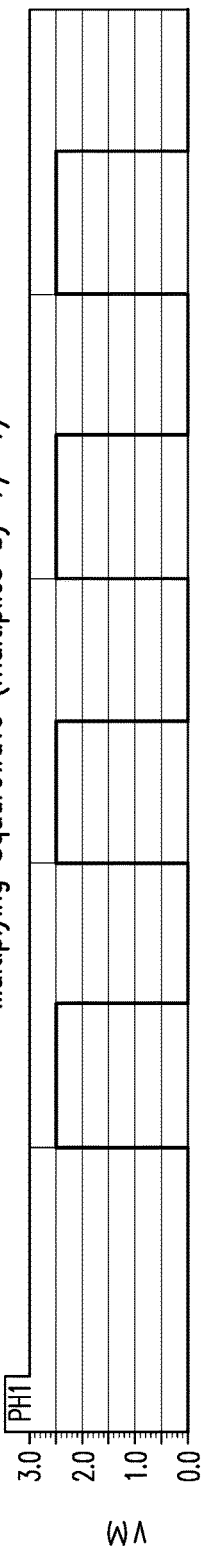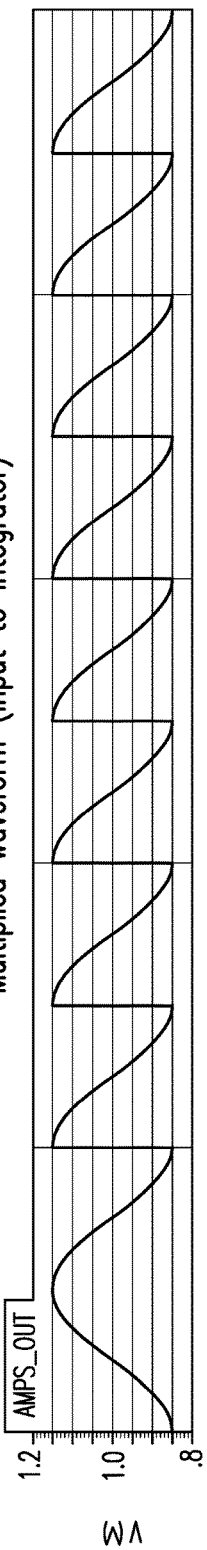
FIG. 47A
FIG. 47B
FIG. 47C

APPLICATION OF ELECTROCHEMICAL IMPEDANCE SPECTROSCOPY IN SENSOR SYSTEMS, DEVICES, AND RELATED METHODS

RELATED APPLICATION DATA

This application is a continuation of U.S. patent application Ser. No. 15/154,560, filed May 13, 2016, now U.S. Pat. No. 9,625,415, which is a continuation of U.S. patent application Ser. No. 13/778,416, filed Feb. 27, 2013, now U.S. Pat. No. 9,357,958, which claims the benefit of U.S. Provisional Application Ser. No. 61/755,811, filed Jan. 23, 2013, and of U.S. Provisional Application Ser. No. 61/754,475, filed Jan. 18, 2013, and of U.S. Provisional Application Ser. No. 61/754,479, filed Jan. 18, 2013, and of U.S. Provisional Application Ser. No. 61/754,483, filed Jan. 18, 2013, and of U.S. Provisional Application Ser. No. 61/754,485, filed Jan. 18, 2013, and of U.S. Provisional Application Ser. No. 61/657,517, filed Jun. 8, 2012, all of which are incorporated herein by reference in their entirety.

FIELD OF THE INVENTION

Embodiments of this invention are related generally to methods and systems of using Electrochemical Impedance Spectroscopy (EIS) in conjunction with continuous glucose monitors and, more particularly, to the use of EIS in sensor diagnostics and fault detection, sensor calibration, sensor-signal optimization via one or more fusion algorithms, contaminant/interferent detection, and electrode-surface characterization, as well as to Application Specific Integrated Circuits (ASICs) for implementing such use of EIS for both single-electrode and multi-electrode (redundant) sensors.

BACKGROUND OF THE INVENTION

Subjects and medical personnel wish to monitor readings of physiological conditions within the subject's body. Illustratively, subjects wish to monitor blood glucose levels in a subject's body on a continuing basis. Presently, a patient can measure his/her blood glucose (BG) using a BG measurement device (i.e. glucose meter), such as a test strip meter, a continuous glucose measurement system (or a continuous glucose monitor), or a hospital hemacue. BG measurement devices use various methods to measure the BG level of a patient, such as a sample of the patient's blood, a sensor in contact with a bodily fluid, an optical sensor, an enzymatic sensor, or a fluorescent sensor. When the BG measurement device has generated a BG measurement, the measurement is displayed on the BG measurement device.

Current continuous glucose measurement systems include subcutaneous (or short-term) sensors and implantable (or long-term) sensors. For each of the short-term sensors and the long-term sensors, a patient has to wait a certain amount of time in order for the continuous glucose sensor to stabilize and to provide accurate readings. In many continuous glucose sensors, the subject must wait three hours for the continuous glucose sensor to stabilize before any glucose measurements are utilized. This is an inconvenience for the patient and in some cases may cause the patient not to utilize a continuous glucose measurement system.

Further, when a glucose sensor is first inserted into a patient's skin or subcutaneous layer, the glucose sensor does not operate in a stable state. The electrical readings from the sensor, which represent the glucose level of the patient, vary over a wide range of readings. In the past, sensor stabilization used to take several hours. A technique for sensor stabilization is detailed in U.S. Pat. No. 6,809,653, ("the '653 patent"), application Ser. No. 09/465,715, filed Dec. 19, 1999, issued Oct. 26, 2004, to Mann et al., assigned to Medtronic Minimed, Inc., which is incorporated herein by reference. In the '653 patent, the initialization process for sensor stabilization may be reduced to approximately one hour. A high voltage (e.g., 1.0-1.2 volts) may be applied for 1 to 2 minutes to allow the sensor to stabilize and then a low voltage (e.g., between 0.5-0.6 volts) may be applied for the remainder of the initialization process (e.g., 58 minutes or so). Thus, even with this procedure, sensor stabilization still requires a large amount of time.

It is also desirable to allow electrodes of the sensor to be sufficiently "wetted" or hydrated before utilization of the electrodes of the sensor. If the electrodes of the sensor are not sufficiently hydrated, the result may be inaccurate readings of the patient's physiological condition. A user of current blood glucose sensors is instructed to not power up the sensors immediately. If they are utilized too early, current blood glucose sensors do not operate in an optimal or efficient fashion. No automatic procedure or measuring technique is utilized to determine when to power on the sensor. This manual process is inconvenient and places too much responsibility on the patient, who may forget to apply or turn on the power source.

Besides the stabilization and wetting problems during the initial stages of sensor life, there can be additional issues during the sensor's life. For instance, all sensors are pre-set with a specified operating life. For example, in current short-term sensors on the market today, the sensors are typically good for 3 to 5 days. Although sensors may continue to function and deliver a signal after the pre-set operating life of the sensor, the sensor readings eventually become less consistent and thus less reliable after the pre-set operating life of the sensor has passed. The exact sensor life of each individual sensor varies from sensor to sensor, but all sensors have been approved for at least the pre-set operating life of the sensor. Therefore, manufacturers have required the users of the sensors to replace the sensors after the pre-set operating life has passed. Although the continuous glucose measurement system can monitor the length of time since the sensor was inserted and indicate the end of the operating life of a sensor to warn the user to replace the sensor, it does not have enough safeguards to prevent the sensor from being used beyond the operating life. Even though the characteristic monitors can simply stop functioning once the operating life of the sensor is reached, a patient may bypass these safeguards by simply disconnecting and re-connecting the same sensor. Thus, there is a loophole in the system where a user can keep the sensors active longer than recommended and thus compromise the accuracy of the blood glucose values returned by the glucose monitor.

Moreover, the sensor often absorbs polluting species, such as peptides and small protein molecules during the life of the sensor. Such polluting species can reduce the electrode surface area or diffusion pathway of analytes and/or reaction byproducts, thus reducing the sensor accuracy. Determining when such pollutants are affecting the sensor signal and how to remedy such conditions is quite significant in sensor operation.

The current state of the art in continuous glucose monitoring (CGM) is largely adjunctive, meaning that the readings provided by a CGM device (including, e.g., an implantable or subcutaneous sensor) cannot be used without a reference value in order to make a clinical decision. The reference value, in turn, must be obtained from a finger stick using, e.g., a BG meter. The reference value is needed because there is a limited amount of information that is available from the sensor/sensing component. Specifically, the only pieces of information that are currently provided by the sensing component for processing are the raw sensor value (i.e., the sensor current or Isig) and the counter voltage. Therefore, during analysis, if it appears that the raw sensor signal is abnormal (e.g., if the signal is decreasing), the only way one can distinguish between a sensor failure and a physiological change within the user/patient (i.e., glucose level changing in the body) is by acquiring a reference glucose value via a finger stick. As is known, the reference finger stick is also used for calibrating the sensor.

The art has searched for ways to eliminate or, at the very least, minimize, the number of finger sticks that are necessary for calibration and for assessing sensor health. However, given the number and level of complexity of the multitude of sensor failure modes, no satisfactory solution has been found. At most, diagnostics have been developed that are based on either direct assessment of the Isig, or on comparison of two Isigs. In either case, because the Isig tracks the level of glucose in the body, by definition, it is not analyte independent. As such, by itself, the Isig is not a reliable source of information for sensor diagnostics, nor is it a reliable predictor for continued sensor performance.

Another limitation that has existed in the art thus far has been the lack of sensor electronics that can not only run the sensor, but also perform real-time sensor and electrode diagnostics, and do so for redundant electrodes, all while managing the sensor's power supply. To be sure, the concept of electrode redundancy has been around for quite some time. However, up until now, there has been little to no success in using electrode redundancy not only for obtaining more than one reading at a time, but also for assessing the relative health of the redundant electrodes, the overall reliability of the sensor, and the frequency of the need, if at all, for calibration reference values.

In addition, even when redundant sensing electrodes have been used, the number has typically been limited to two. Again, this has been due partially to the absence of advanced electronics that run, assess, and manage a multiplicity of independent working electrodes (e.g., up to 5 or more) in real time. Another reason, however, has been the limited view that redundant electrodes are used in order to obtain "independent" sensor signals and, for that purpose, two redundant electrodes are sufficient. As noted, while this is one function of utilizing redundant electrodes, it is not the only one.

There have also been attempts in the art to detect the presence of interferents in the sensor's environment, and to assess the effect(s) of such interferents on the glucose sensor. However, heretofore, no glucose-independent means for performing such detection and assessment have been found.

SUMMARY

According to an embodiment of the invention, a method of performing real-time sensor diagnostics on a subcutaneous or implanted sensor having at least one working electrode, comprises performing a first electrochemical impedance spectroscopy (EIS) procedure to generate a first set of impedance-related data for the at least one working electrode; after a predetermined time interval, performing a second EIS procedure to generate a second set of impedance-related data for the at least one electrode; and, based solely on the first and second sets of impedance-related data, determining whether the sensor is functioning normally.

In accordance with another embodiment of the invention, a method of calculating a single, fused sensor glucose value is disclosed. The fused sensor glucose value is calculated based on glucose measurement signals from a plurality of redundant sensing electrodes by performing respective electrochemical impedance spectroscopy (EIS) procedures for each of the plurality of redundant sensing electrodes to obtain values of at least one impedance-based parameter for each the sensing electrode; measuring the electrode current (Isig) for each of the plurality of redundant sensing electrodes; independently calibrating each of the measured Isigs to obtain respective calibrated sensor glucose values; performing a bound check and a noise check on the measured Isig and the values of the at least one impedance-based parameter and assigning a bound-check reliability index and a noise-check reliability index to each of the sensing electrodes; performing signal-dip analysis based on one or more of the at least one impedance-based parameter and assigning a dip reliability index to each of the sensing electrodes; performing sensitivity-loss analysis based on one or more of the at least one impedance-based parameter and assigning a sensitivity-loss index to each of the sensing electrodes; for each of the plurality of electrodes, calculating a total reliability index based on the electrode's bound-check reliability index, noise-check reliability index, dip reliability index, and sensitivity-loss reliability index; for each of the plurality of electrodes, calculating a weight based on the electrode's total reliability index; and calculating the fused sensor glucose value based on the respective weights and calibrated sensor glucose values of each of the plurality of redundant sensing electrodes.

In yet another embodiment of the invention, a method is disclosed for detecting an interferent in close proximity to an electrode of a glucose sensor that is implanted or subcutaneously disposed in the body of a patient. An EIS procedure is periodically performed to obtain values of impedance magnitude for the electrode, and values of measured current (Isig) for the electrode are obtained. The Isig and the values of impedance magnitude for the electrode are monitored over time. When a sudden spike in the monitored Isig is detected, a determination is made as to whether, at about the time of Isig spike, there is also a large increase in the monitored values of the impedance magnitude, and if there is, then it is determined that an interferent exists in close proximity to the electrode.

In accordance with another embodiment of the invention, a method is disclosed for testing the surface area characteristics of an electroplated electrode, wherein an EIS procedure is performed to obtain a value of an impedance-related parameter for the electrode. The obtained value is correlated to the electrode's electrochemical surface area and, based on the correlation, lower and upper threshold values for the value of the impedance-related parameter are set. Lastly, a determination is made as to whether the electrode is acceptable based on whether the value of the impedance-related parameter falls within the lower and upper threshold values.

According to another embodiment of the invention, a method is disclosed for calibrating a sensor during a period of sensor transition by defining an electrochemical impedance spectroscopy (EIS)-based sensor status vector (V) for each one of a plurality of sensor current (Isig)-blood glucose (BG) pairs; monitoring the status vectors for the plurality of Isig-BG pairs over time; detecting when there is a difference between a first status vector for a first Isig-BG pair and a subsequent status vector for a subsequent Isig-BG pair, wherein a first offset value is assigned to the first Isig-BG pair; and, if the magnitude of the difference is larger than a predetermined threshold, assigning a dynamic offset value for the subsequent Isig-BG pair that is different from the first offset value so as to maintain a substantially linear relationship between the subsequent Isig and BG.

In accordance with another embodiment of the invention, a method of calibrating a sensor comprises performing an electrochemical impedance spectroscopy (EIS) procedure for a working electrode of a sensor to obtain values of at least one impedance-based parameter for the working electrode; performing a bound check on the values of the at least one impedance-based parameter to determine whether the at least one impedance-based parameter is in-bounds and, based on the bound check, calculating a reliability-index value for the working electrode; and, based on the value of the reliability index, determining whether calibration should be performed now, or whether it should be delayed until a later time.

In accordance with a further embodiment of the invention, a method is disclosed for real-time detection of low start-up for a working electrode of a sensor by inserting the sensor into subcutaneous tissue; performing a first electrochemical impedance spectroscopy (EIS) procedure to generate a first set of impedance-related data for the working electrode; and, based on the first set of impedance-related data, determining whether the working electrode is experiencing low start-up.

According to another embodiment of the invention, a method for real-time detection of a signal dip for a working electrode of a sensor comprises periodically performing an electrochemical impedance spectroscopy (EIS) procedure to obtain values of real impedance for the electrode; monitoring the values of real impedance over time; and, based on the values of real impedance, determining whether a dip exists in the signal generated by the working electrode.

In yet a further embodiment of the invention, a method is disclosed for real-time detection of sensitivity loss for a working electrode of a sensor by periodically performing an electrochemical impedance spectroscopy (EIS) procedure to generate multiple sets of impedance-related data for the working electrode; calculating values of one or more impedance-related parameters based on the multiple sets of impedance-related data; monitoring the values over time; and, based on the values, determining whether the working electrode is experiencing sensitivity loss.

In accordance with yet another embodiment of the invention, a sensor system includes a subcutaneous or implanted sensor having a plurality of independent working electrodes, a counter electrode, and a reference electrode, and sensor electronics operably coupled to the sensor. The sensor electronics, in turn, include electronic circuitry configured to selectively perform an electrochemical impedance spectroscopy (EIS) procedure for one or more of the plurality of independent working electrodes to generate impedance-related data for the one or more working electrodes; a programmable sequencer configured to provide a start stimulus and a stop stimulus for performing the EIS procedure; and a microcontroller interface configured to operably couple the sensor electronics to a microcontroller.

BRIEF DESCRIPTION OF THE DRAWINGS

A detailed description of embodiments of the invention will be made with reference to the accompanying drawings, wherein like numerals designate corresponding parts in the figures.

FIG. 8B illustrates a voltage generation device to implement this embodiment of the invention;

FIG. 8C illustrates a voltage generation device to generate two voltage values according to an embodiment of the invention;

FIG. 8D illustrates a voltage generation device having three voltage generation systems, according to embodiments of the invention;

FIG. 9B illustrates a sensor electronics device including an analyzation module according to an embodiment of the invention;

FIGS. 16C and 16D show, respectively, infinite and finite glucose sensor response to a sinusoidal working potential;

FIG. 16E shows a Bode plot for magnitude in accordance with embodiments of the invention;

FIG. 16F shows a Bode plot for phase in accordance with embodiments of the invention;

FIGS. 21A and 21B illustrate examples of a sensor remedial action in accordance with embodiments of the invention;

FIG. 33A shows a top-level flowchart involving a current (Isig)-based fusion algorithm in accordance with embodiments of the invention;

FIG. 33B shows a top-level flowchart involving a sensor glucose (SG)-based fusion algorithm in accordance with embodiments of the invention;

FIG. 36 is an illustration of calibration for a sensor in steady state, in accordance with embodiments of the invention;

FIG. 37 is an illustration of calibration for a sensor in transition, in accordance with embodiments of the invention;

FIGS. 40A and 40B show Bode plots for phase and impedance, respectively, for the simulation shown in FIG. 39;

FIGS. 47A-47F show a simulation of the signals of the EIS circuitry shown in FIG. 45 for a current of 0-degree phase with a 90-degree phase multiply.

DETAILED DESCRIPTION

In the following description, reference is made to the accompanying drawings which form a part hereof and which illustrate several embodiments of the present inventions. It is understood that other embodiments may be utilized and structural and operational changes may be made without departing from the scope of the present inventions.

The inventions herein are described below with reference to flowchart illustrations of methods, systems, devices, apparatus, and programming and computer program products. It will be understood that each block of the flowchart illustrations, and combinations of blocks in the flowchart illustrations, can be implemented by programing instructions, including computer program instructions (as can any menu screens described in the figures). These computer program instructions may be loaded onto a computer or other programmable data processing apparatus (such as a controller, microcontroller, or processor in a sensor electronics device) to produce a machine, such that the instructions which execute on the computer or other programmable data processing apparatus create instructions for implementing the functions specified in the flowchart block or blocks. These computer program instructions may also be stored in a computer-readable memory that can direct a computer or other programmable data processing apparatus to function in a particular manner, such that the instructions stored in the computer-readable memory produce an article of manufacture including instructions which implement the function specified in the flowchart block or blocks. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions specified in the flowchart block or blocks, and/or menus presented herein. Programming instructions may also be stored in and/or implemented via electronic circuitry, including integrated circuits (ICs) and Application Specific Integrated Circuits (ASICs) used in conjunction with sensor devices, apparatuses, and systems.

Figure 1:
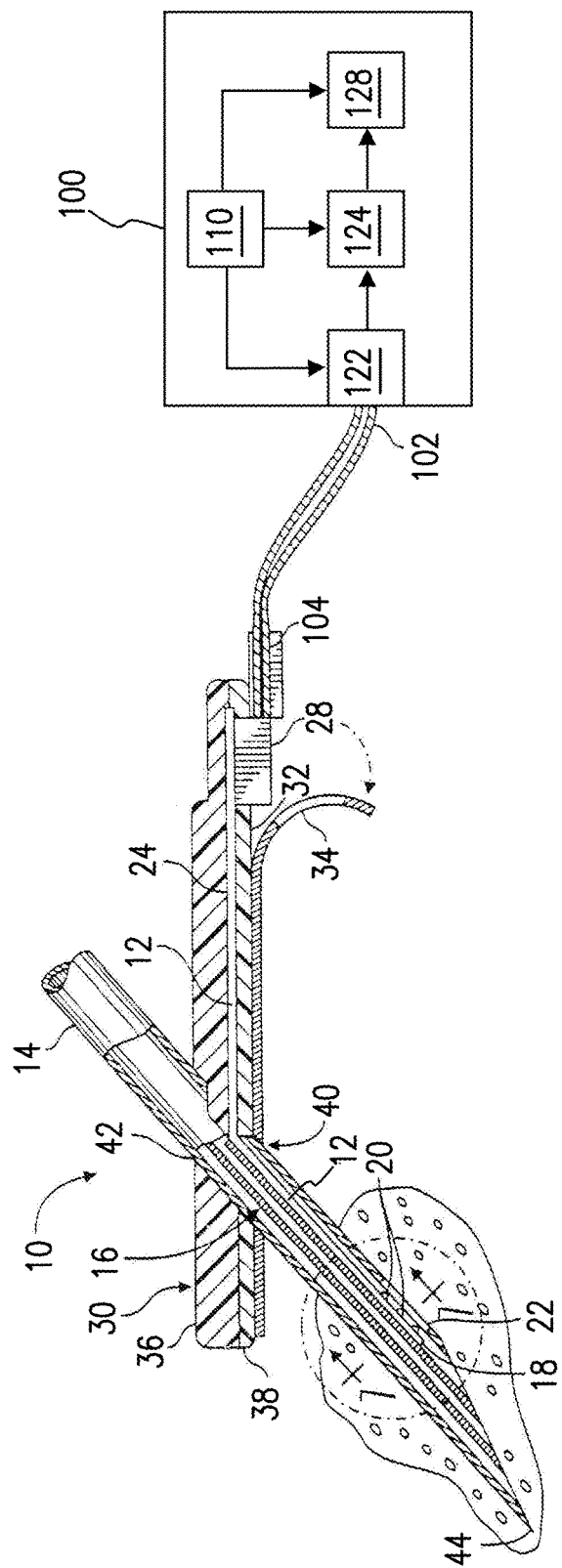
FIG. 1 is a perspective view of a subcutaneous sensor insertion set and block diagram of a sensor electronics device according to an embodiment of the invention.

FIG. 1 is a perspective view of a subcutaneous sensor insertion set and a block diagram of a sensor electronics device according to an embodiment of the invention. As illustrated in FIG. 1, a subcutaneous sensor set 10 is provided for subcutaneous placement of an active portion of a flexible sensor 12 (see, e.g., FIG. 2), or the like, at a selected site in the body of a user. The subcutaneous or percutaneous portion of the sensor set 10 includes a hollow, slotted insertion needle 14, and a cannula 16. The needle 14 is used to facilitate quick and easy subcutaneous placement of the cannula 16 at the subcutaneous insertion site. Inside the cannula 16 is a sensing portion 18 of the sensor 12 to expose one or more sensor electrodes 20 to the user's bodily fluids through a window 22 formed in the cannula 16. In an embodiment of the invention, the one or more sensor electrodes 20 may include a counter electrode, a reference electrode, and one or more working electrodes. After insertion, the insertion needle 14 is withdrawn to leave the cannula 16 with the sensing portion 18 and the sensor electrodes 20 in place at the selected insertion site.

In particular embodiments, the subcutaneous sensor set 10 facilitates accurate placement of a flexible thin film electrochemical sensor 12 of the type used for monitoring specific blood parameters representative of a user's condition. The sensor 12 monitors glucose levels in the body, and may be used in conjunction with automated or semi-automated medication infusion pumps of the external or implantable type as described, e.g., in U.S. Pat. Nos. 4,562,751; 4,678,408; 4,685,903 or 4,573,994, to control delivery of insulin to a diabetic patient.

Particular embodiments of the flexible electrochemical sensor 12 are constructed in accordance with thin film mask techniques to include elongated thin film conductors embedded or encased between layers of a selected insulative material such as polyimide film or sheet, and membranes. The sensor electrodes 20 at a tip end of the sensing portion 18 are exposed through one of the insulative layers for direct contact with patient blood or other body fluids, when the sensing portion 18 (or active portion) of the sensor 12 is subcutaneously placed at an insertion site. The sensing portion 18 is joined to a connection portion 24 that terminates in conductive contact pads, or the like, which are also exposed through one of the insulative layers. In alternative embodiments, other types of implantable sensors, such as chemical based, optical based, or the like, may be used.

As is known in the art, the connection portion 24 and the contact pads are generally adapted for a direct wired electrical connection to a suitable monitor or sensor electronics device 100 for monitoring a user's condition in response to signals derived from the sensor electrodes 20. Further description of flexible thin film sensors of this general type are be found in U.S. Pat. No. 5,391,250, entitled METHOD OF FABRICATING THIN FILM SENSORS, which is herein incorporated by reference. The connection portion 24 may be conveniently connected electrically to the monitor or sensor electronics device 100 or by a connector block 28 (or the like) as shown and described in U.S. Pat. No. 5,482,473, entitled FLEX CIRCUIT CONNECTOR, which is also herein incorporated by reference. Thus, in accordance with embodiments of the present invention, subcutaneous sensor sets 10 may be configured or formed to work with either a wired or a wireless characteristic monitor system.

The sensor electrodes 20 may be used in a variety of sensing applications and may be configured in a variety of ways. For example, the sensor electrodes 20 may be used in physiological parameter sensing applications in which some type of biomolecule is used as a catalytic agent. For example, the sensor electrodes 20 may be used in a glucose and oxygen sensor having a glucose oxidase (GOx) enzyme catalyzing a reaction with the sensor electrodes 20. The sensor electrodes 20, along with a biomolecule or some other catalytic agent, may be placed in a human body in a vascular or non-vascular environment. For example, the sensor electrodes 20 and biomolecule may be placed in a vein and be subjected to a blood stream, or may be placed in a subcutaneous or peritoneal region of the human body.

The monitor 100 may also be referred to as a sensor electronics device 100. The monitor 100 may include a power source 110, a sensor interface 122, processing electronics 124, and data formatting electronics 128. The monitor 100 may be coupled to the sensor set 10 by a cable 102 through a connector that is electrically coupled to the connector block 28 of the connection portion 24. In an alternative embodiment, the cable may be omitted. In this embodiment of the invention, the monitor 100 may include an appropriate connector for direct connection to the connection portion 104 of the sensor set 10. The sensor set 10 may be modified to have the connector portion 104 positioned at a different location, e.g., on top of the sensor set to facilitate placement of the monitor 100 over the sensor set.

In embodiments of the invention, the sensor interface 122, the processing electronics 124, and the data formatting electronics 128 are formed as separate semiconductor chips, however, alternative embodiments may combine the various semiconductor chips into a single or multiple customized semiconductor chips. The sensor interface 122 connects with the cable 102 that is connected with the sensor set 10.

The power source 110 may be a battery. The battery can include three series silver oxide 357 battery cells. In alternative embodiments, different battery chemistries may be utilized, such as lithium based chemistries, alkaline batteries, nickel metalhydride, or the like, and a different number of batteries may be used. The monitor 100 provides power to the sensor set via the power source 110, through the cable 102 and cable connector 104. In an embodiment of the invention, the power is a voltage provided to the sensor set 10. In an embodiment of the invention, the power is a current provided to the sensor set 10. In an embodiment of the invention, the power is a voltage provided at a specific voltage to the sensor set 10.

Figure 2A:
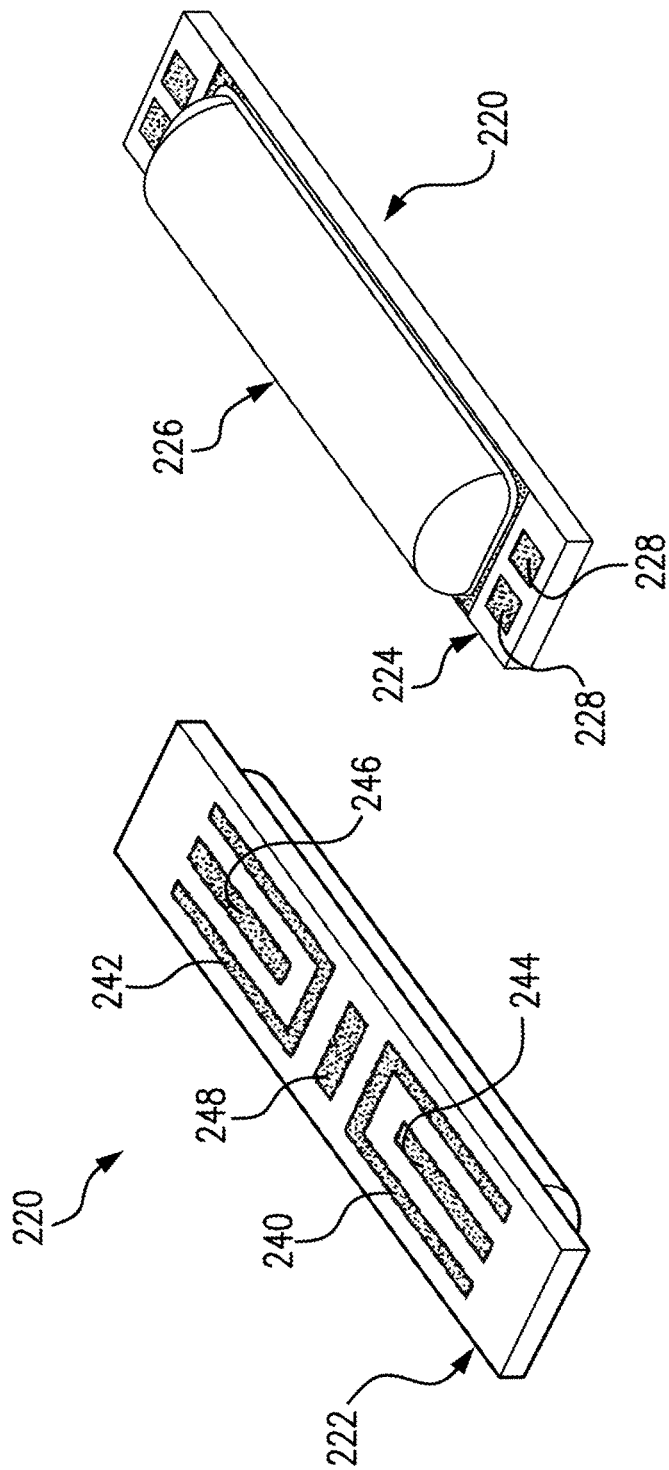
FIG. 2A illustrates a substrate having two sides, a first side which contains an electrode configuration and a second side which contains electronic circuitry.
Figure 2B:
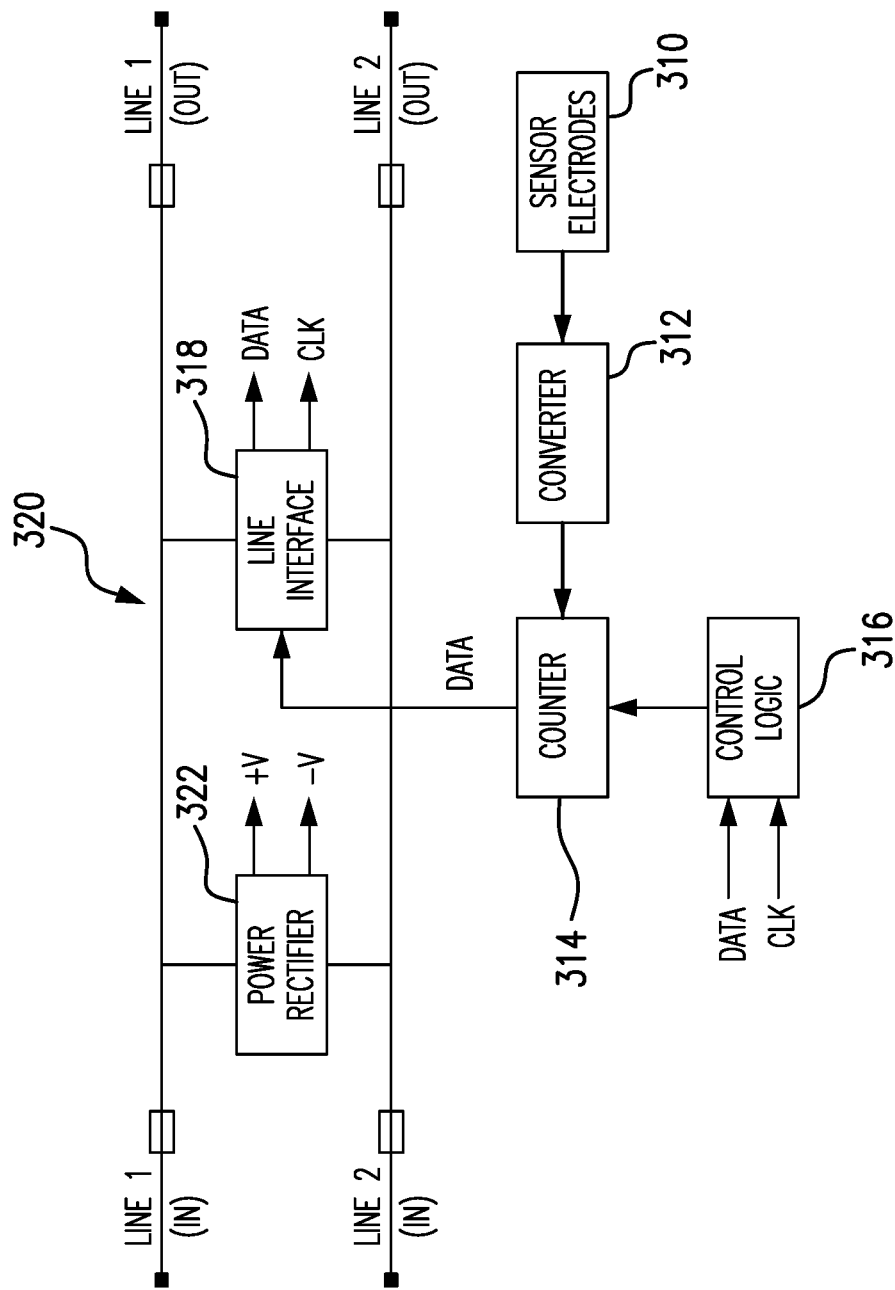
FIG. 2B illustrates a general block diagram of an electronic circuit for sensing an output of a sensor.

FIGS. 2A and 2B illustrate an implantable sensor and electronics for driving the implantable sensor according to an embodiment of the present invention. FIG. 2A shows a substrate 220 having two sides, a first side 222 of which contains an electrode configuration and a second side 224 of which contains electronic circuitry. As may be seen in FIG. 2A, a first side 222 of the substrate comprises two counter electrode-working electrode pairs 240, 242, 244, 246 on opposite sides of a reference electrode 248. A second side 224 of the substrate comprises electronic circuitry. As shown, the electronic circuitry may be enclosed in a hermetically sealed casing 226, providing a protective housing for the electronic circuitry. This allows the sensor substrate 220 to be inserted into a vascular environment or other environment which may subject the electronic circuitry to fluids. By sealing the electronic circuitry in a hermetically sealed casing 226, the electronic circuitry may operate without risk of short circuiting by the surrounding fluids. Also shown in FIG. 2A are pads 228 to which the input and output lines of the electronic circuitry may be connected. The electronic circuitry itself may be fabricated in a variety of ways. According to an embodiment of the present invention, the electronic circuitry may be fabricated as an integrated circuit using techniques common in the industry.

FIG. 2B illustrates a general block diagram of an electronic circuit for sensing an output of a sensor according to an embodiment of the present invention. At least one pair of sensor electrodes 310 may interface to a data converter 312, the output of which may interface to a counter 314. The counter 314 may be controlled by control logic 316. The output of the counter 314 may connect to a line interface 318. The line interface 318 may be connected to input and output lines 320 and may also connect to the control logic 316. The input and output lines 320 may also be connected to a power rectifier 322.

The sensor electrodes 310 may be used in a variety of sensing applications and may be configured in a variety of ways. For example, the sensor electrodes 310 may be used in physiological parameter sensing applications in which some type of biomolecule is used as a catalytic agent. For example, the sensor electrodes 310 may be used in a glucose and oxygen sensor having a glucose oxidase (GOx) enzyme catalyzing a reaction with the sensor electrodes 310. The sensor electrodes 310, along with a biomolecule or some other catalytic agent, may be placed in a human body in a vascular or non-vascular environment. For example, the sensor electrodes 310 and biomolecule may be placed in a vein and be subjected to a blood stream.

Figure 3:
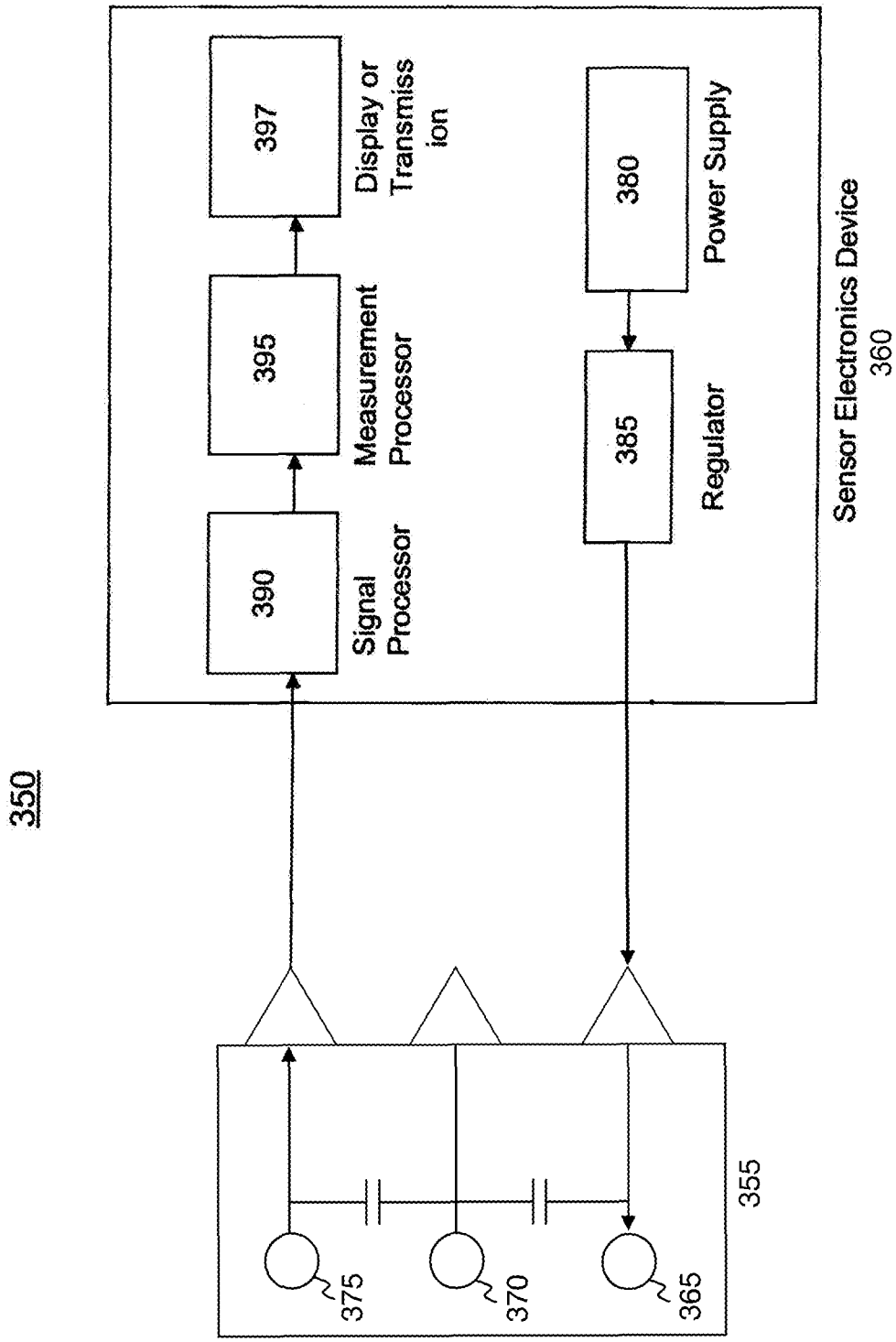
FIG. 3 illustrates a block diagram of a sensor electronics device and a sensor including a plurality of electrodes according to an embodiment of the invention.

FIG. 3 illustrates a block diagram of a sensor electronics device and a sensor including a plurality of electrodes according to an embodiment of the invention. The sensor set or system 350 includes a sensor 355 and a sensor electronics device 360. The sensor 355 includes a counter electrode 365, a reference electrode 370, and a working electrode 375. The sensor electronics device 360 includes a power supply 380, a regulator 385, a signal processor 390, a measurement processor 395, and a display/transmission module 397. The power supply 380 provides power (in the form of either a voltage, a current, or a voltage including a current) to the regulator 385. The regulator 385 transmits a regulated voltage to the sensor 355. In an embodiment of the invention, the regulator 385 transmits a voltage to the counter electrode 365 of the sensor 355.

The sensor 355 creates a sensor signal indicative of a concentration of a physiological characteristic being measured. For example, the sensor signal may be indicative of a blood glucose reading. In an embodiment of the invention utilizing subcutaneous sensors, the sensor signal may represent a level of hydrogen peroxide in a subject. In an embodiment of the invention where blood or cranial sensors are utilized, the amount of oxygen is being measured by the sensor and is represented by the sensor signal. In an embodiment of the invention utilizing implantable or long-term sensors, the sensor signal may represent a level of oxygen in the subject. The sensor signal is measured at the working electrode 375. In an embodiment of the invention, the sensor signal may be a current measured at the working electrode. In an embodiment of the invention, the sensor signal may be a voltage measured at the working electrode.

The signal processor 390 receives the sensor signal (e.g., a measured current or voltage) after the sensor signal is measured at the sensor 355 (e.g., the working electrode). The signal processor 390 processes the sensor signal and generates a processed sensor signal. The measurement processor 395 receives the processed sensor signal and calibrates the processed sensor signal utilizing reference values. In an embodiment of the invention, the reference values are stored in a reference memory and provided to the measurement processor 395. The measurement processor 395 generates sensor measurements. The sensor measurements may be stored in a measurement memory (not shown). The sensor measurements may be sent to a display/transmission device to be either displayed on a display in a housing with the sensor electronics or transmitted to an external device.

The sensor electronics device 360 may be a monitor which includes a display to display physiological characteristics readings. The sensor electronics device 360 may also be installed in a desktop computer, a pager, a television including communications capabilities, a laptop computer, a server, a network computer, a personal digital assistant (PDA), a portable telephone including computer functions, an infusion pump including a display, a glucose sensor including a display, and/or a combination infusion pump/ glucose sensor. The sensor electronics device 360 may be housed in a blackberry, a network device, a home network device, or an appliance connected to a home network.

Figure 4:
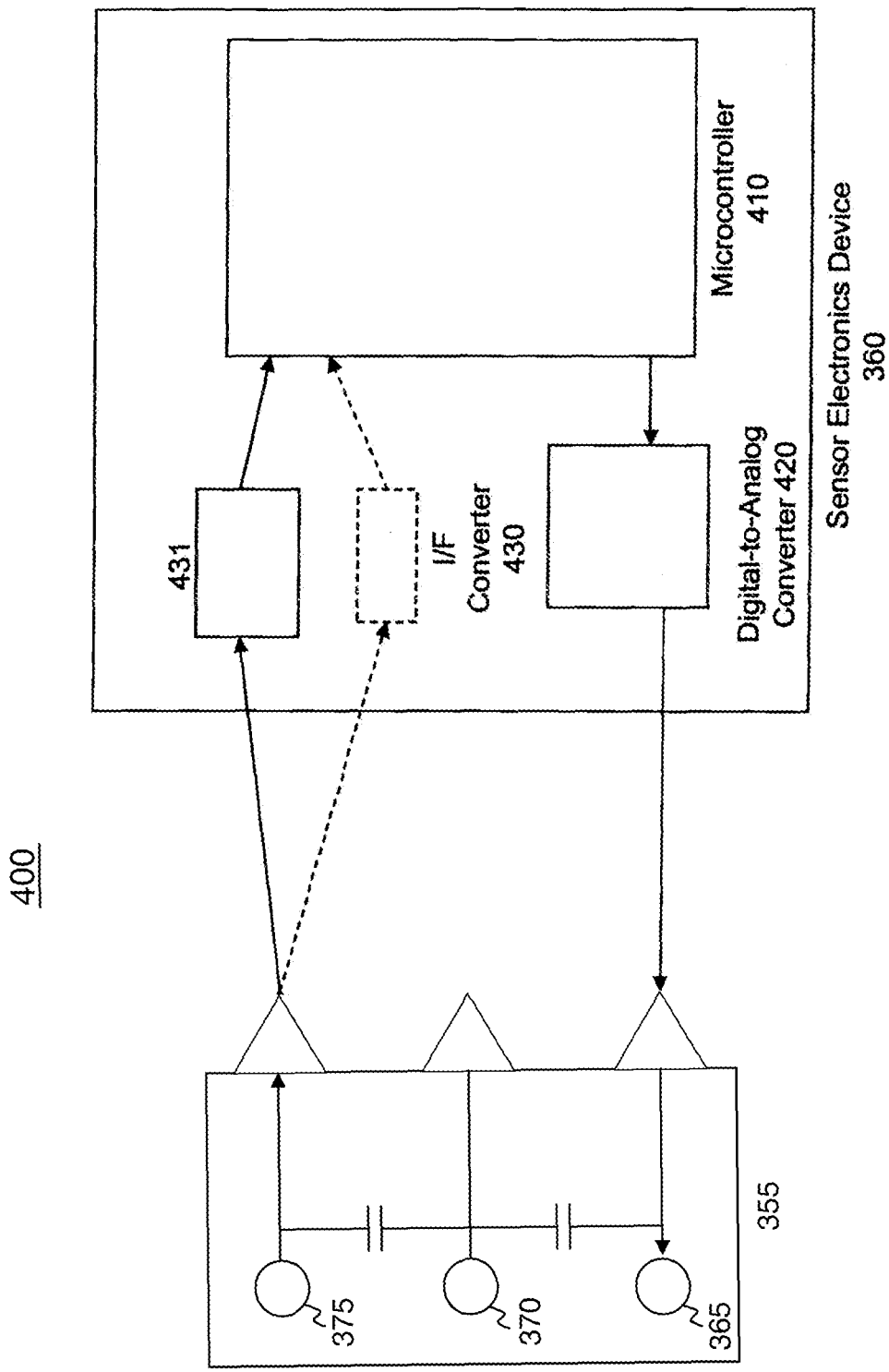
FIG. 4 illustrates an alternative embodiment of the invention including a sensor and a sensor electronics device according to an embodiment of the invention.

FIG. 4 illustrates an alternative embodiment of the invention including a sensor and a sensor electronics device according to an embodiment of the present invention. The sensor set or sensor system 400 includes a sensor electronics device 360 and a sensor 355. The sensor includes a counter electrode 365, a reference electrode 370, and a working electrode 375. The sensor electronics device 360 includes a microcontroller 410 and a digital-to-analog converter (DAC) 420. The sensor electronics device 360 may also include a current-to-frequency converter (I/F converter) 430.

The microcontroller 410 includes software program code, which when executed, or programmable logic which, causes the microcontroller 410 to transmit a signal to the DAC 420, where the signal is representative of a voltage level or value that is to be applied to the sensor 355. The DAC 420 receives the signal and generates the voltage value at the level instructed by the microcontroller 410. In embodiments of the invention, the microcontroller 410 may change the representation of the voltage level in the signal frequently or infrequently. Illustratively, the signal from the microcontroller 410 may instruct the DAC 420 to apply a first voltage value for one second and a second voltage value for two seconds.

The sensor 355 may receive the voltage level or value. In an embodiment of the invention, the counter electrode 365 may receive the output of an operational amplifier which has as inputs the reference voltage and the voltage value from the DAC 420. The application of the voltage level causes the sensor 355 to create a sensor signal indicative of a concentration of a physiological characteristic being measured. In an embodiment of the invention, the microcontroller 410 may measure the sensor signal (e.g., a current value) from the working electrode. Illustratively, a sensor signal measurement circuit 431 may measure the sensor signal. In an embodiment of the invention, the sensor signal measurement circuit 431 may include a resistor and the current may be passed through the resistor to measure the value of the sensor signal. In an embodiment of the invention, the sensor signal may be a current level signal and the sensor signal measurement circuit 431 may be a current-to-frequency (I/F) converter 430. The current-to-frequency converter 430 may measure the sensor signal in terms of a current reading, convert it to a frequency-based sensor signal, and transmit the frequency-based sensor signal to the microcontroller 410. In embodiments of the invention, the microcontroller 410 may be able to receive frequency-based sensor signals easier than non-frequency-based sensor signals. The microcontroller 410 receives the sensor signal, whether frequency-based or non frequency-based, and determines a value for the physiological characteristic of a subject, such as a blood glucose level. The microcontroller 410 may include program code, which when executed or run, is able to receive the sensor signal and convert the sensor signal to a physiological characteristic value. In an embodiment of the invention, the microcontroller 410 may convert the sensor signal to a blood glucose level. In an embodiment of the invention, the microcontroller 410 may utilize measurements stored within an internal memory in order to determine the blood glucose level of the subject. In an embodiment of the invention, the microcontroller 410 may utilize measurements stored within a memory external to the microcontroller 410 to assist in determining the blood glucose level of the subject.

After the physiological characteristic value is determined by the microcontroller 410, the microcontroller 410 may store measurements of the physiological characteristic values for a number of time periods. For example, a blood glucose value may be sent to the microcontroller 410 from the sensor every second or five seconds, and the microcontroller may save sensor measurements for five minutes or ten minutes of BG readings. The microcontroller 410 may transfer the measurements of the physiological characteristic values to a display on the sensor electronics device 360. For example, the sensor electronics device 360 may be a monitor which includes a display that provides a blood glucose reading for a subject. In an embodiment of the invention, the microcontroller 410 may transfer the measurements of the physiological characteristic values to an output interface of the microcontroller 410. The output interface of the microcontroller 410 may transfer the measurements of the physiological characteristic values, e.g., blood glucose values, to an external device, e.g., an infusion pump, a combined infusion pump/glucose meter, a computer, a personal digital assistant, a pager, a network appliance, a server, a cellular phone, or any computing device.

Figure 5:
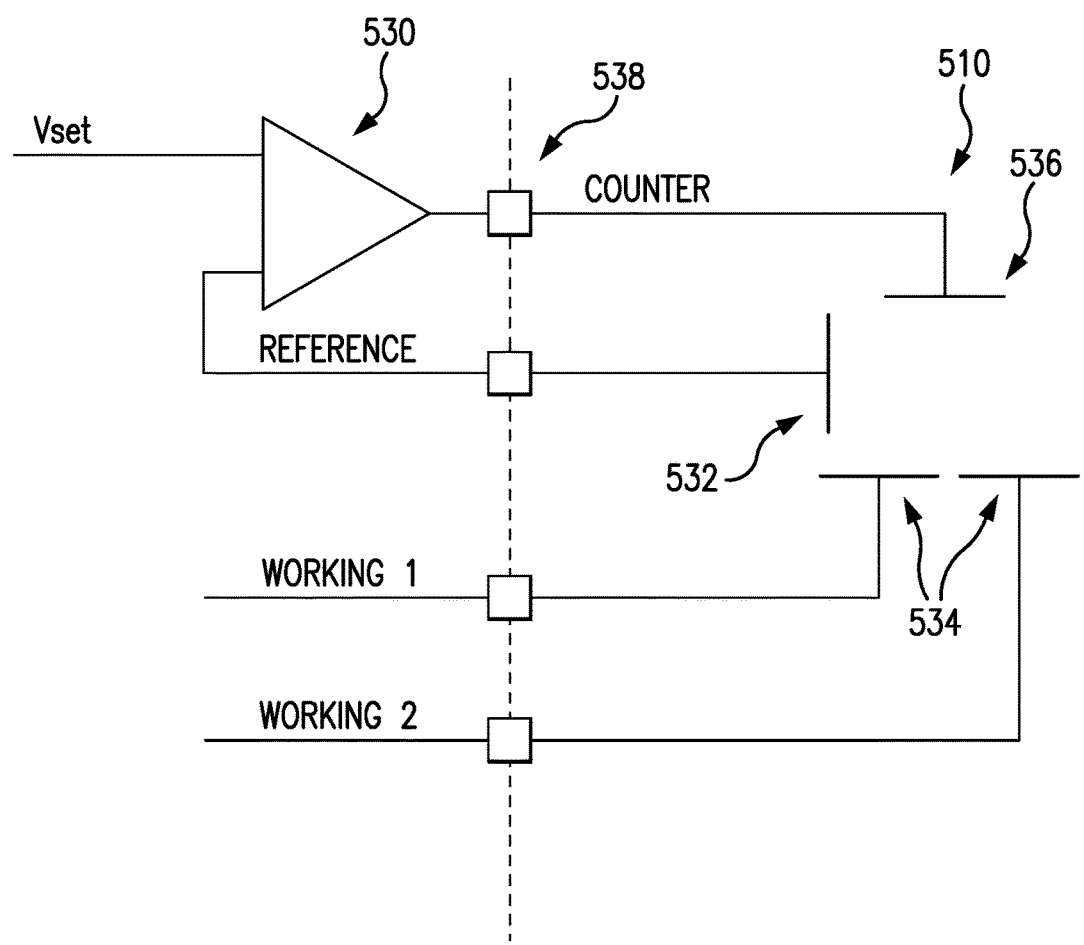
FIG. 5 illustrates an electronic block diagram of the sensor electrodes and a voltage being applied to the sensor electrodes according to an embodiment of the invention.

FIG. 5 illustrates an electronic block diagram of the sensor electrodes and a voltage being applied to the sensor electrodes according to an embodiment of the present invention. In the embodiment of the invention illustrated in FIG. 5, an op amp 530 or other servo controlled device may connect to sensor electrodes 510 through a circuit/electrode interface 538. The op amp 530, utilizing feedback through the sensor electrodes, attempts to maintain a prescribed voltage (what the DAC may desire the applied voltage to be) between a reference electrode 532 and a working electrode 534 by adjusting the voltage at a counter electrode 536. Current may then flow from a counter electrode 536 to a working electrode 534. Such current may be measured to ascertain the electrochemical reaction between the sensor electrodes 510 and the biomolecule of a sensor that has been placed in the vicinity of the sensor electrodes 510 and used as a catalyzing agent. The circuitry disclosed in FIG. 5 may be utilized in a long-term or implantable sensor or may be utilized in a short-term or subcutaneous sensor.

In a long-term sensor embodiment, where a glucose oxidase (GOx) enzyme is used as a catalytic agent in a sensor, current may flow from the counter electrode 536 to a working electrode 534 only if there is oxygen in the vicinity of the enzyme and the sensor electrodes 510. Illustratively, if the voltage set at the reference electrode 532 is maintained at about 0.5 volts, the amount of current flowing from the counter electrode 536 to a working electrode 534 has a fairly linear relationship with unity slope to the amount of oxygen present in the area surrounding the enzyme and the electrodes. Thus, increased accuracy in determining an amount of oxygen in the blood may be achieved by maintaining the reference electrode 532 at about 0.5 volts and utilizing this region of the current-voltage curve for varying levels of blood oxygen. Different embodiments of the present invention may utilize different sensors having biomolecules other than a glucose oxidase enzyme and may, therefore, have voltages other than 0.5 volts set at the reference electrode.

As discussed above, during initial implantation or insertion of the sensor 510, the sensor 510 may provide inaccurate readings due to the adjusting of the subject to the sensor and also electrochemical byproducts caused by the catalyst utilized in the sensor. A stabilization period is needed for many sensors in order for the sensor 510 to provide accurate readings of the physiological parameter of the subject. During the stabilization period, the sensor 510 does not provide accurate blood glucose measurements. Users and manufacturers of the sensors may desire to improve the stabilization timeframe for the sensor so that the sensors can be utilized quickly after insertion into the subject's body or a subcutaneous layer of the subject.

Figure 6A:
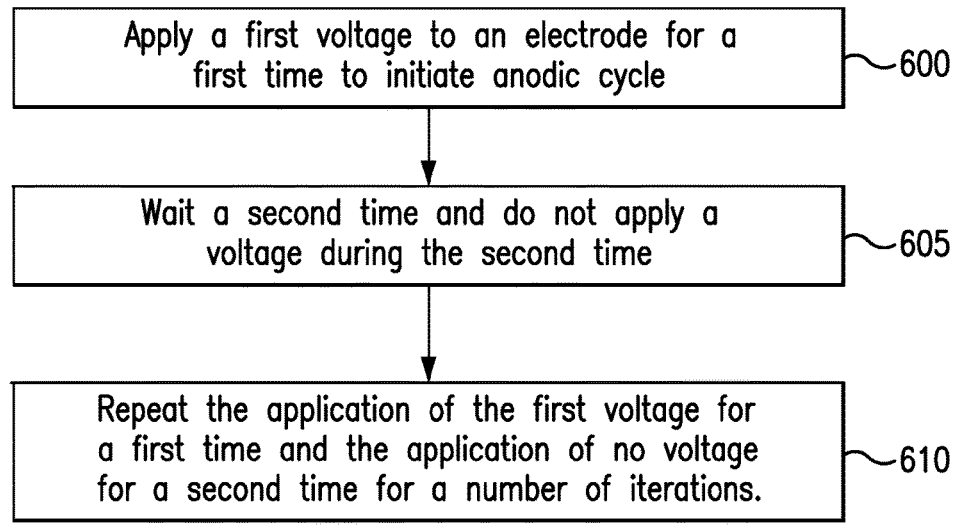
FIG. 6A illustrates a method of applying pulses during a stabilization timeframe in order to reduce the stabilization timeframe according to an embodiment of the invention.

In previous sensor electrode systems, the stabilization period or timeframe was one hour to three hours. In order to decrease the stabilization period or timeframe and increase the timeliness of accuracy of the sensor, a sensor (or electrodes of a sensor) may be subjected to a number of pulses rather than the application of one pulse followed by the application of another voltage. FIG. 6A illustrates a method of applying pulses during a stabilization timeframe in order to reduce the stabilization timeframe according to an embodiment of the present invention. In this embodiment of the invention, a voltage application device applies 600 a first voltage to an electrode for a first time or time period. In an embodiment of the invention, the first voltage may be a DC constant voltage. This results in an anodic current being generated. In an alternative embodiment of the invention, a digital-to-analog converter or another voltage source may supply the voltage to the electrode for a first time period. The anodic current means that electrons are being driven towards the electrode to which the voltage is applied. In an embodiment of the invention, an application device may apply a current instead of a voltage. In an embodiment of the invention where a voltage is applied to a sensor, after the application of the first voltage to the electrode, the voltage regulator may wait (i.e., not apply a voltage) for a second time, timeframe, or time period 605. In other words, the voltage application device waits until a second time period elapses. The non-application of voltage results in a cathodic current, which results in the gaining of electrons by the electrode to which the voltage is not applied. The application of the first voltage to the electrode for a first time period followed by the non-application of voltage for a second time period is repeated 610 for a number of iterations. This may be referred to as an anodic and cathodic cycle. In an embodiment of the invention, the number of total iterations of the stabilization method is three, i.e., three applications of the voltage for the first time period, each followed by no application of the voltage for the second time period. In an embodiment of the invention, the first voltage may be 1.07 volts. In an embodiment of the invention, the first voltage may be 0.535 volts. In an embodiment of the invention, the first voltage may be approximately 0.7 volts.

The repeated application of the voltage and the non-application of the voltage results in the sensor (and thus the electrodes) being subjected to an anodic-cathodic cycle. The anodic-cathodic cycle results in the reduction of electrochemical byproducts which are generated by a patient's body reacting to the insertion of the sensor or the implanting of the sensor. In an embodiment of the invention, the electrochemical byproducts cause generation of a background current, which results in inaccurate measurements of the physiological parameter of the subject. In an embodiment of the invention, the electrochemical byproduct may be eliminated. Under other operating conditions, the electrochemical byproducts may be reduced or significantly reduced. A successful stabilization method results in the anodic-cathodic cycle reaching equilibrium, electrochemical byproducts being significantly reduced, and background current being minimized.

In an embodiment of the invention, the first voltage being applied to the electrode of the sensor may be a positive voltage. In an embodiment of the invention, the first voltage being applied may be a negative voltage. In an embodiment of the invention, the first voltage may be applied to a working electrode. In an embodiment of the invention, the first voltage may be applied to the counter electrode or the reference electrode.

In embodiments of the invention, the duration of the voltage pulse and the non-application of voltage may be equal, e.g., such as three minutes each. In embodiments of the invention, the duration of the voltage application or voltage pulse may be different values, e.g., the first time and the second time may be different. In an embodiment of the invention, the first time period may be five minutes and the waiting period may be two minutes. In an embodiment of the invention, the first time period may be two minutes and the waiting period (or second timeframe) may be five minutes. In other words, the duration for the application of the first voltage may be two minutes and there may be no voltage applied for five minutes. This timeframe is only meant to be illustrative and should not be limiting. For example, a first timeframe may be two, three, five or ten minutes and the second timeframe may be five minutes, ten minutes, twenty minutes, or the like. The timeframes (e.g., the first time and the second time) may depend on unique characteristics of different electrodes, the sensors, and/or the patient's physiological characteristics.

In embodiments of the invention, more or less than three pulses may be utilized to stabilize the glucose sensor. In other words, the number of iterations may be greater than 3 or less than three. For example, four voltage pulses (e.g., a high voltage followed by no voltage) may be applied to one of the electrodes or six voltage pulses may be applied to one of the electrodes.

Illustratively, three consecutive pulses of 1.07 volts (followed by respective waiting periods) may be sufficient for a sensor implanted subcutaneously. In an embodiment of the invention, three consecutive voltage pulses of 0.7 volts may be utilized. The three consecutive pulses may have a higher or lower voltage value, either negative or positive, for a sensor implanted in blood or cranial fluid, e.g., the long-term or permanent sensors. In addition, more than three pulses (e.g., five, eight, twelve) may be utilized to create the anodic-cathodic cycling between anodic and cathodic currents in any of the subcutaneous, blood, or cranial fluid sensors.

Figure 6B:
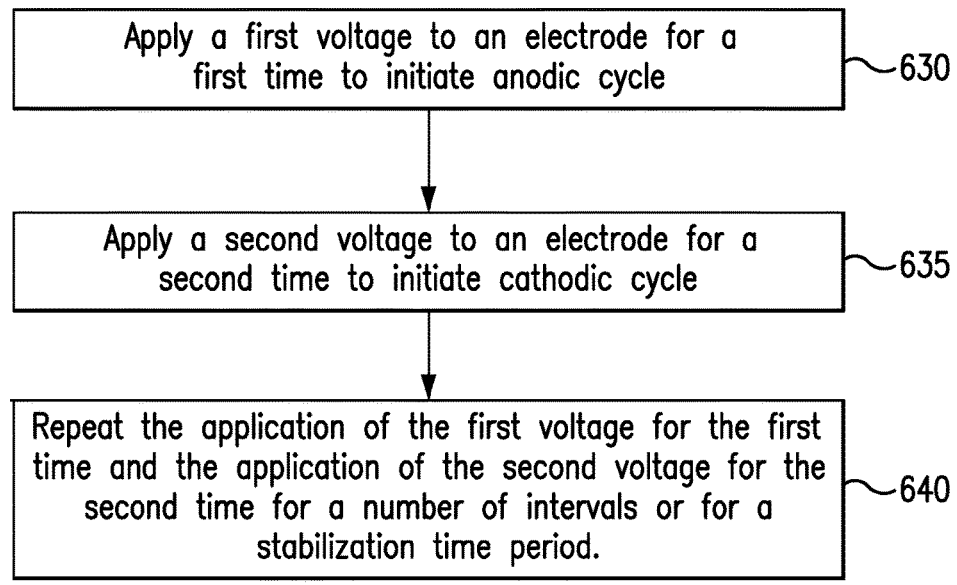
FIG. 6B illustrates a method of stabilizing sensors according to an embodiment of the invention.

FIG. 6B illustrates a method of stabilizing sensors according to an embodiment of the present invention. In the embodiment of the invention illustrated in FIG. 6B, a voltage application device may apply 630 a first voltage to the sensor for a first time to initiate an anodic cycle at an electrode of the sensor. The voltage application device may be a DC power supply, a digital-to-analog converter, or a voltage regulator. After the first time period has elapsed, a second voltage is applied 635 to the sensor for a second time to initiate a cathodic cycle at an electrode of the sensor. Illustratively, rather than no voltage being applied, as is illustrated in the method of FIG. 6A, a different voltage (from the first voltage) is applied to the sensor during the second timeframe. In an embodiment of the invention, the application of the first voltage for the first time and the application of the second voltage for the second time is repeated 640 for a number of iterations. In an embodiment of the invention, the application of the first voltage for the first time and the application of the second voltage for the second time may each be applied for a stabilization timeframe, e.g., 10 minutes, 15 minutes, or 20 minutes rather than for a number of iterations. This stabilization timeframe is the entire timeframe for the stabilization sequence, e.g., until the sensor (and electrodes) are stabilized. The benefit of this stabilization methodology is a faster run-in of the sensors, less background current (in other words a suppression of some the background current), and a better glucose response.

In an embodiment of the invention, the first voltage may be 0.535 volts applied for five minutes, the second voltage may be 1.070 volts applied for two minutes, the first voltage of 0.535 volts may be applied for five minutes, the second voltage of 1.070 volts may be applied for two minutes, the first voltage of 0.535 volts may be applied for five minutes, and the second voltage of 1.070 volts may be applied for two minutes. In other words, in this embodiment, there are three iterations of the voltage pulsing scheme. The pulsing methodology may be changed in that the second timeframe, e.g., the timeframe of the application of the second voltage may be lengthened from two minutes to five minutes, ten minutes, fifteen minutes, or twenty minutes. In addition, after the three iterations are applied in this embodiment of the invention, a nominal working voltage of 0.535 volts may be applied.

The 1.070 and 0.535 volts are illustrative values. Other voltage values may be selected based on a variety of factors. These factors may include the type of enzyme utilized in the sensor, the membranes utilized in the sensor, the operating period of the sensor, the length of the pulse, and/or the magnitude of the pulse. Under certain operating conditions, the first voltage may be in a range of 1.00 to 1.09 volts and the second voltage may be in a range of 0.510 to 0.565 volts. In other operating embodiments, the ranges that bracket the first voltage and the second voltage may have a higher range, e.g., 0.3 volts, 0.6 volts, 0.9 volts, depending on the voltage sensitivity of the electrode in the sensor. Under other operating conditions, the voltage may be in a range of 0.8 volts to 1.34 volts and the other voltage may be in a range of 0.335 to 0.735. Under other operating conditions, the range of the higher voltage may be smaller than the range of the lower voltage. Illustratively, the higher voltage may be in a range of 0.9 to 1.09 volts and the lower voltage may be in a range of 0.235 to 0.835 volts.

In an embodiment of the invention, the first voltage and the second voltage may be positive voltages, or alternatively in other embodiments of the invention, negative voltages. In an embodiment of the invention, the first voltage may be positive and the second voltage may be negative, or alternatively, the first voltage may be negative and the second voltage may be positive. The first voltage may be different voltage levels for each of the iterations. In an embodiment of the invention, the first voltage may be a D.C. constant voltage. In other embodiments of the invention, the first voltage may be a ramp voltage, a sinusoid-shaped voltage, a stepped voltage, or other commonly utilized voltage waveforms. In an embodiment of the invention, the second voltage may be a D.C. constant voltage, a ramp voltage, a sinusoid-shaped voltage, a stepped voltage, or other commonly utilized voltage waveforms. In an embodiment of the invention, the first voltage or the second voltage may be an AC signal riding on a DC waveform. In an embodiment of the invention, the first voltage may be one type of voltage, e.g., a ramp voltage, and the second voltage may be a second type of voltage, e.g., a sinusoid-shaped voltage. In an embodiment of the invention, the first voltage (or the second voltage) may have different waveform shapes for each of the iterations. For example, if there are three cycles in a stabilization method, in a first cycle, the first voltage may be a ramp voltage, in the second cycle, the first voltage may be a constant voltage, and in the third cycle, the first voltage may be a sinusoidal voltage.

In an embodiment of the invention, a duration of the first timeframe and a duration of the second timeframe may have the same value, or alternatively, the duration of the first timeframe and the second timeframe may have different values. For example, the duration of the first timeframe may be two minutes and the duration of the second timeframe may be five minutes and the number of iterations may be three. As discussed above, the stabilization method may include a number of iterations. In embodiments of the invention, during different iterations of the stabilization method, the duration of each of the first timeframes may change and the duration of each of the second timeframes may change. Illustratively, during the first iteration of the anodic-cathodic cycling, the first timeframe may be 2 minutes and the second timeframe may be 5 minutes. During the second iteration, the first timeframe may be 1 minute and the second timeframe may be 3 minutes. During the third iteration, the first timeframe may be 3 minutes and the second timeframe may be 10 minutes.

In an embodiment of the invention, a first voltage of 0.535 volts is applied to an electrode in a sensor for two minutes to initiate an anodic cycle, then a second voltage of 1.07 volts is applied to the electrode for five minutes to initiate a cathodic cycle. The first voltage of 0.535 volts is then applied again for two minutes to initiate the anodic cycle and a second voltage of 1.07 volts is applied to the sensor for five minutes. In a third iteration, 0.535 volts is applied for two minutes to initiate the anodic cycle and then 1.07 volts is applied for five minutes. The voltage applied to the sensor is then 0.535 during the actual working timeframe of the sensor, e.g., when the sensor provides readings of a physiological characteristic of a subject.

Shorter duration voltage pulses may be utilized in the embodiment of FIGS. 6A and 6B. The shorter duration voltage pulses may be utilized to apply the first voltage, the second voltage, or both. In an embodiment of the present invention, the magnitude of the shorter duration voltage pulse for the first voltage is −1.07 volts and the magnitude of the shorter duration voltage pulse for the second voltage is approximately half of the high magnitude, e.g., −0.535 volts. Alternatively, the magnitude of the shorter duration pulse for the first voltage may be 0.535 volts and the magnitude of the shorter duration pulse for the second voltage is 1.07 volts.

In embodiments of the invention utilizing short duration pulses, the voltage may not be applied continuously for the entire first time period. Instead, the voltage application device may transmit a number of short duration pulses during the first time period. In other words, a number of mini-width or short duration voltage pulses may be applied to the electrodes of the sensor over the first time period. Each mini-width or short duration pulse may have a width of a number of milliseconds. Illustratively, this pulse width may be 30 milliseconds, 50 milliseconds, 70 milliseconds or 200 milliseconds. These values are meant to be illustrative and not limiting. In an embodiment of the invention, such as the embodiment illustrated in FIG. 6A, these short duration pulses are applied to the sensor (electrode) for the first time period and then no voltage is applied for the second time period.

In an embodiment of the invention, each short duration pulse may have the same time duration within the first time period. For example, each short duration voltage pulse may have a time width of 50 milliseconds and each pulse delay between the pulses may be 950 milliseconds. In this example, if two minutes is the measured time for the first timeframe, then 120 short duration voltage pulses may be applied to the sensor. In an embodiment of the invention, each of the short duration voltage pulses may have different time durations. In an embodiment of the invention, each of the short duration voltage pulses may have the same amplitude values. In an embodiment of the invention, each of the short duration voltage pulses may have different amplitude values. By utilizing short duration voltage pulses rather than a continuous application of voltage to the sensor, the same anodic and cathodic cycling may occur and the sensor (e.g., electrodes) is subjected to less total energy or charge over time. The use of short duration voltage pulses utilizes less power as compared to the application of continuous voltage to the electrodes because there is less energy applied to the sensors (and thus the electrodes).

Figure 6C:
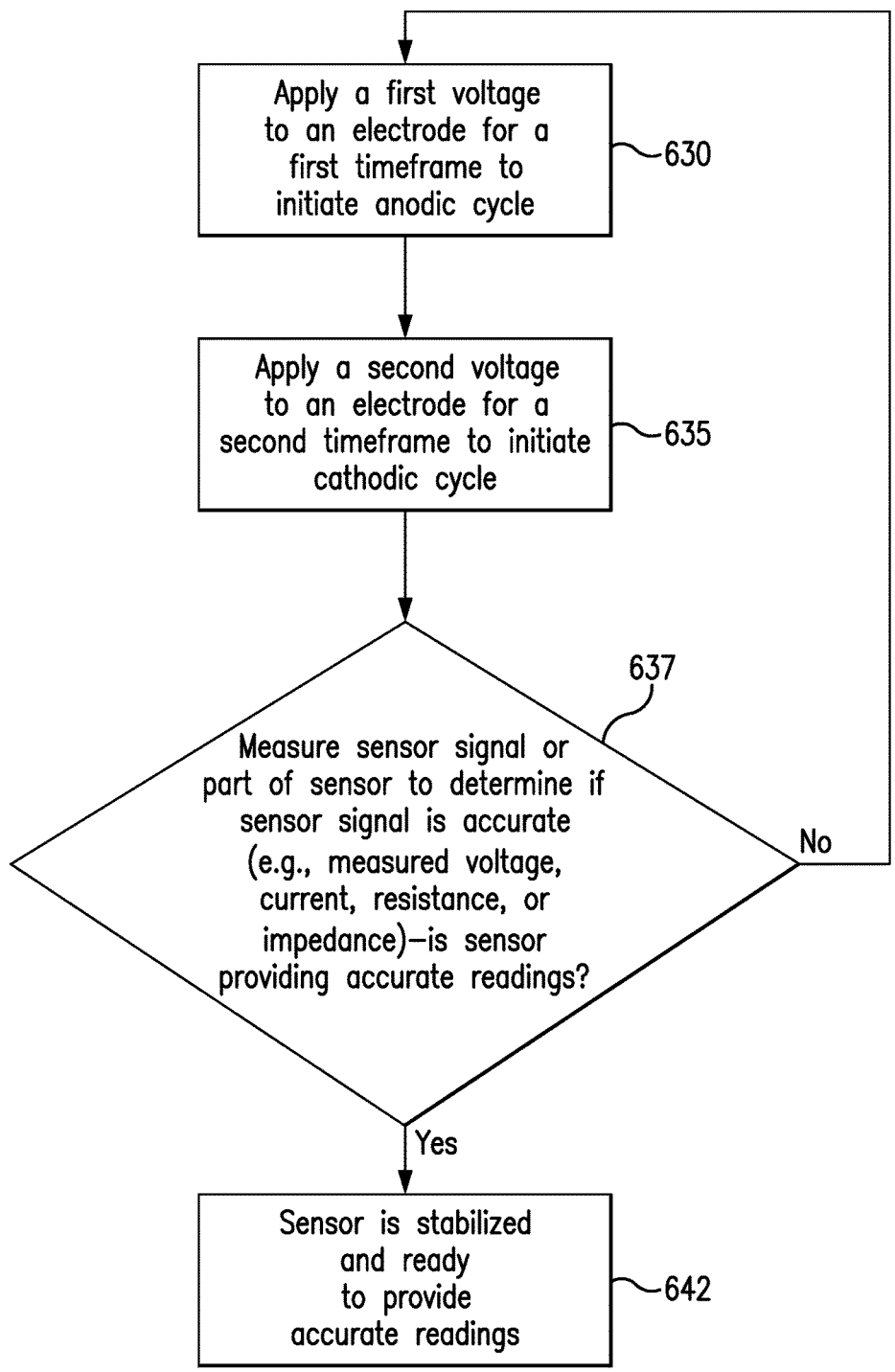
FIG. 6C illustrates utilization of feedback in stabilizing the sensors according to an embodiment of the invention.

FIG. 6C illustrates utilization of feedback in stabilizing the sensor according to an embodiment of the present invention. The sensor system may include a feedback mechanism to determine if additional pulses are needed to stabilize a sensor. In an embodiment of the invention, a sensor signal generated by an electrode (e.g., a working electrode) may be analyzed to determine if the sensor signal is stabilized. A first voltage is applied 630 to an electrode for a first timeframe to initiate an anodic cycle. A second voltage is applied 635 to an electrode for a second timeframe to initiate a cathodic cycle. In an embodiment of the invention, an analyzation module may analyze a sensor signal (e.g., the current emitted by the sensor signal, a resistance at a specific point in the sensor, an impedance at a specific node in the sensor) and determine if a threshold measurement has been reached 637 (e.g., determining if the sensor is providing accurate readings by comparing against the threshold measurement). If the sensor readings are determined to be accurate, which represents that the electrode (and thus the sensor) is stabilized 642, no additional application of the first voltage and/or the second voltage may be generated. If stability was not achieved, in an embodiment of the invention, then an additional anodic/cathodic cycle is initiated by the application 630 of a first voltage to an electrode for a first time period and then the application 635 of the second voltage to the electrode for a second time period.

In embodiments of the invention, the analyzation module may be employed after an anodic/cathodic cycle of three applications of the first voltage and the second voltage to an electrode of the sensor. In an embodiment of the invention, an analyzation module may be employed after one application of the first voltage and the second voltage, as is illustrated in FIG. 6C.

In an embodiment of the invention, the analyzation module may be utilized to measure a voltage emitted after a current has been introduced across an electrode or across two electrodes. The analyzation module may monitor a voltage level at the electrode or at the receiving level. In an embodiment of the invention, if the voltage level is above a certain threshold, this may mean that the sensor is stabilized. In an embodiment of the invention, if the voltage level falls below a threshold level, this may indicate that the sensor is stabilized and ready to provide readings. In an embodiment of the invention, a current may be introduced to an electrode or across a couple of electrodes. The analyzation module may monitor a current level emitted from the electrode. In this embodiment of the invention, the analyzation module may be able to monitor the current if the current is different by an order of magnitude from the sensor signal current. If the current is above or below a current threshold, this may signify that the sensor is stabilized.

In an embodiment of the invention, the analyzation module may measure an impedance between two electrodes of the sensor. The analyzation module may compare the impedance against a threshold or target impedance value and if the measured impedance is lower than the target or threshold impedance, the sensor (and hence the sensor signal) may be stabilized. In an embodiment of the invention, the analyzation module may measure a resistance between two electrodes of the sensor. In this embodiment of the invention, if the analyzation module compares the resistance against a threshold or target resistance value and the measured resistance value is less than the threshold or target resistance value, then the analyzation module may determine that the sensor is stabilized and that the sensor signal may be utilized.

Figure 7:
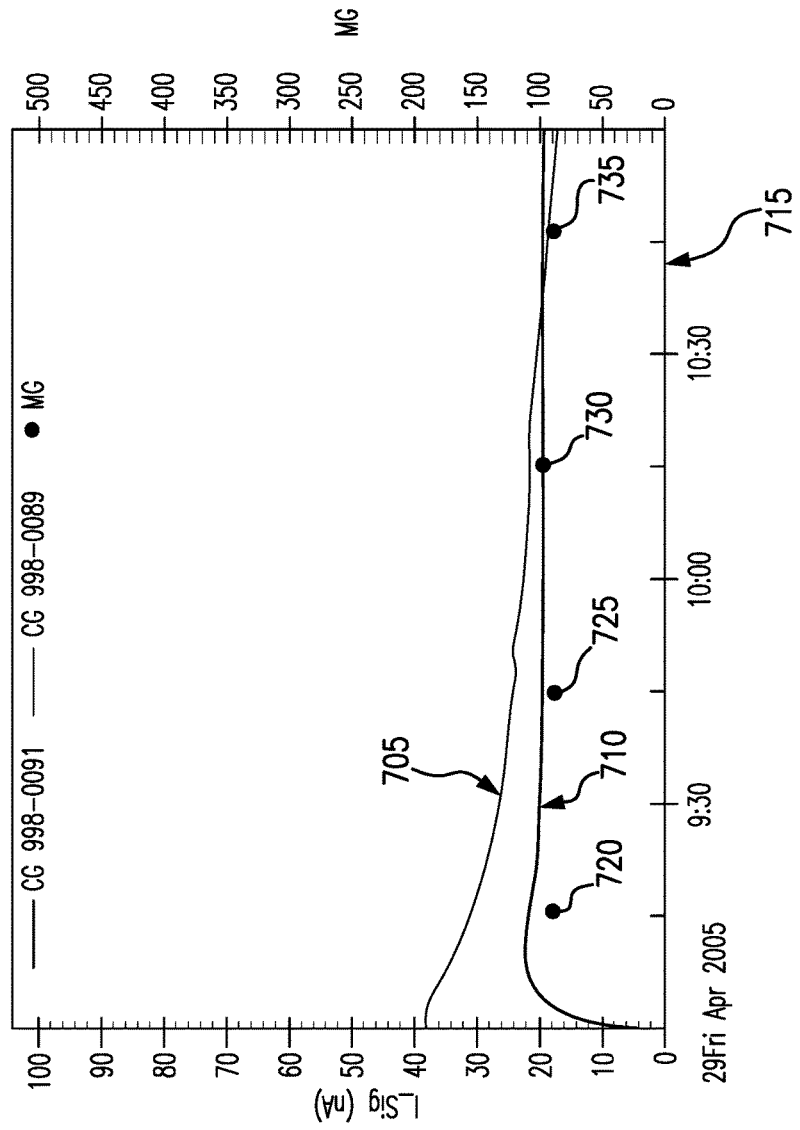
FIG. 7 illustrates an effect of stabilizing a sensor according to an embodiment of the invention.

FIG. 7 illustrates an effect of stabilizing a sensor according to an embodiment of the invention. Line 705 represents blood glucose sensor readings for a glucose sensor where a previous single pulse stabilization method was utilized. Line 710 represents blood glucose readings for a glucose sensor where three voltage pulses are applied (e.g., 3 voltage pulses having a duration of 2 minutes each followed by 5 minutes of no voltage being applied). The x-axis 715 represents an amount of time. The dots 720, 725, 730, and 735 represent measured glucose readings, taken utilizing a finger stick and then input into a glucose meter. As illustrated by the graph, the previous single pulse stabilization method took approximately 1 hour and 30 minutes in order to stabilize to the desired glucose reading, e.g., 100 units. In contrast, the three pulse stabilization method took only approximately 15 minutes to stabilize the glucose sensor and results in a drastically improved stabilization timeframe.

Figure 8A:
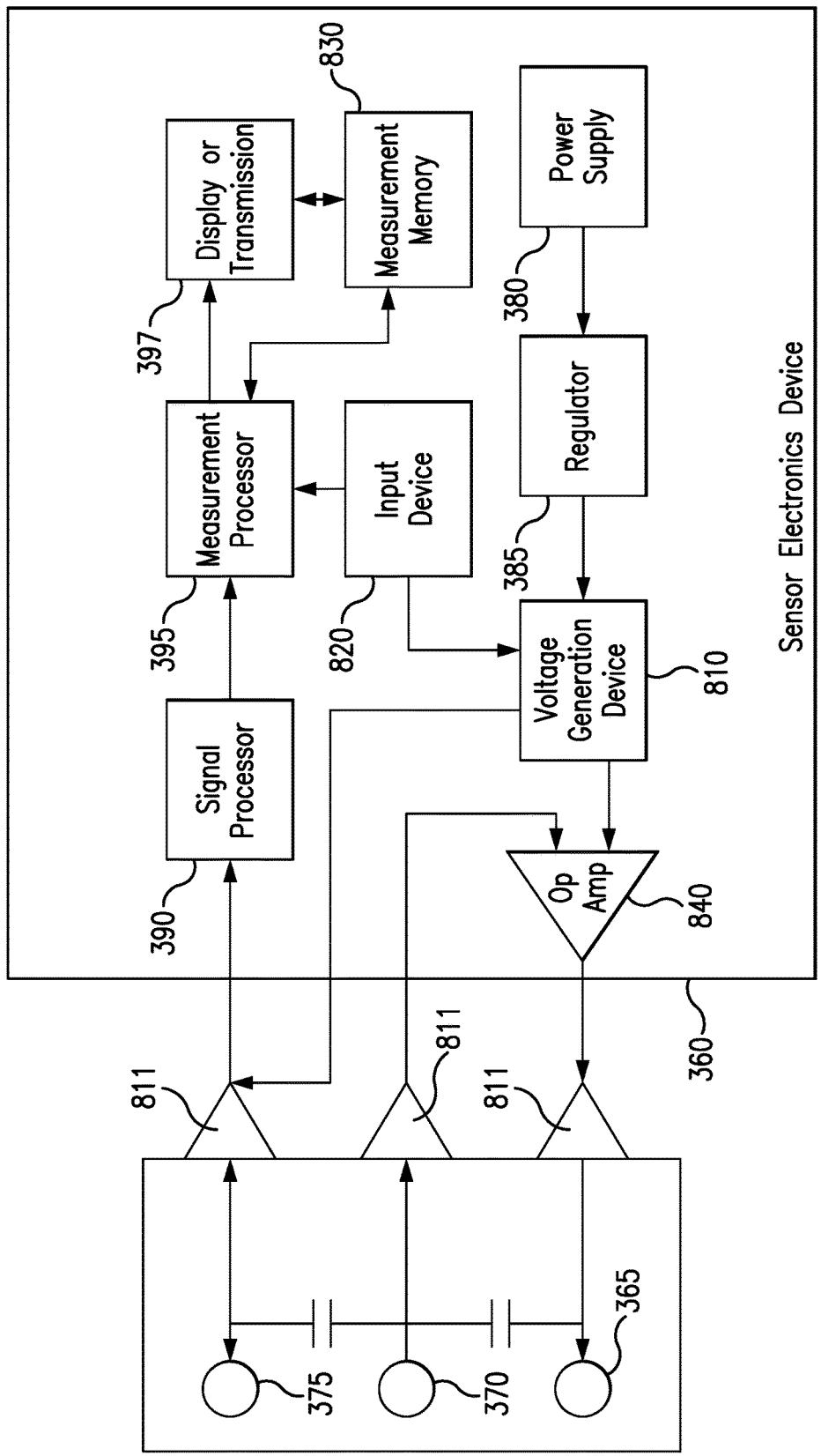
FIG. 8A illustrates a block diagram of a sensor electronics device and a sensor including a voltage generation device according to an embodiment of the invention.

FIG. 8A illustrates a block diagram of a sensor electronics device and a sensor including a voltage generation device according to an embodiment of the invention. The voltage generation or application device 810 includes electronics, logic, or circuits which generate voltage pulses. The sensor electronics device 360 may also include an input device 820 to receive reference values and other useful data. In an embodiment of the invention, the sensor electronics device may include a measurement memory 830 to store sensor measurements. In this embodiment of the invention, the power supply 380 may supply power to the sensor electronics device. The power supply 380 may supply power to a regulator 385, which supplies a regulated voltage to the voltage generation or application device 810. The connection terminals 811 represent that in the illustrated embodiment of the invention, the connection terminal couples or connects the sensor 355 to the sensor electronics device 360.

In an embodiment of the invention illustrated in FIG. 8A, the voltage generation or application device 810 supplies a voltage, e.g., the first voltage or the second voltage, to an input terminal of an operational amplifier 840. The voltage generation or application device 810 may also supply the voltage to a working electrode 375 of the sensor 355. Another input terminal of the operational amplifier 840 is coupled to the reference electrode 370 of the sensor. The application of the voltage from the voltage generation or application device 810 to the operational amplifier 840 drives a voltage measured at the counter electrode 365 to be close to or equal to the voltage applied at the working electrode 375. In an embodiment of the invention, the voltage generation or application device 810 could be utilized to apply the desired voltage between the counter electrode and the working electrode. This may occur by the application of the fixed voltage to the counter electrode directly.

In an embodiment of the invention as illustrated in FIGS. 6A and 6B, the voltage generation device 810 generates a first voltage that is to be applied to the sensor during a first timeframe. The voltage generation device 810 transmits this first voltage to an op amp 840 which drives the voltage at a counter electrode 365 of the sensor 355 to the first voltage. In an embodiment of the invention, the voltage generation device 810 also could transmit the first voltage directly to the counter electrode 365 of the sensor 355. In the embodiment of the invention illustrated in FIG. 6A, the voltage generation device 810 then does not transmit the first voltage to the sensor 355 for a second timeframe. In other words, the voltage generation device 810 is turned off or switched off. The voltage generation device 810 may be programmed to continue cycling between applying the first voltage and not applying a voltage for either a number of iterations or for a stabilization timeframe, e.g., for twenty minutes. FIG. 8B illustrates a voltage generation device to implement this embodiment of the invention. The voltage regulator 385 transfers the regulated voltage to the voltage generation device 810. A control circuit 860 controls the closing and opening of a switch 850. If the switch 850 is closed, the voltage is applied. If the switch 850 is opened, the voltage is not applied. The timer 865 provides a signal to the control circuit 860 to instruct the control circuit 860 to turn on and off the switch 850. The control circuit 860 includes logic which can instruct the circuit to open and close the switch 850 a number of times (to match the necessary iterations). In an embodiment of the invention, the timer 865 may also transmit a stabilization signal to identify that the stabilization sequence is completed, i.e., that a stabilization timeframe has elapsed.

In an embodiment of the invention, the voltage generation device generates a first voltage for a first timeframe and generates a second voltage for a second timeframe. FIG. 8C illustrates a voltage generation device to generate two voltage values to implement this embodiment of the invention. In this embodiment of the invention, a two position switch 870 is utilized. Illustratively, if the first switch position 871 is turned on or closed by the timer 865 instructing the control circuit 860, then the voltage generation device 810 generates a first voltage for the first timeframe. After the first voltage has been applied for the first timeframe, the timer sends a signal to the control circuit 860 indicating the first timeframe has elapsed and the control circuit 860 directs the switch 870 to move to the second position 872. When the switch 870 is at the second position 872, the regulated voltage is directed to a voltage step-down or buck converter 880 to reduce the regulated voltage to a lesser value. The lesser value is then delivered to the op amp 840 for the second timeframe. After the timer 865 has sent a signal to the control circuit 860 that the second timeframe has elapsed, the control circuit 860 moves the switch 870 back to the first position. This continues until the desired number of iterations has been completed or the stabilization timeframe has elapsed. In an embodiment of the invention, after the sensor stabilization timeframe has elapsed, the sensor transmits a sensor signal 350 to the signal processor 390.

FIG. 8D illustrates a voltage application device 810 utilized to perform more complex applications of voltage to the sensor. The voltage application device 810 may include a control device 860, a switch 890, a sinusoid voltage generation device 891, a ramp voltage generation device 892, and a constant voltage generation device 893. In other embodiments of the invention, the voltage application may generate an AC wave on top of a DC signal or other various voltage pulse waveforms. In the embodiment of the invention illustrated in FIG. 8D, the control device 860 may cause the switch to move to one of the three voltage generation systems 891 (sinusoid), 892 (ramp), 893 (constant DC). This results in each of the voltage generation systems generating the identified voltage waveform. Under certain operating conditions, e.g., where a sinusoidal pulse is to be applied for three pulses, the control device 860 may cause the switch 890 to connect the voltage from the voltage regulator 385 to the sinusoid voltage generator 891 in order for the voltage application device 810 to generate a sinusoidal voltage. Under other operating conditions, e.g., when a ramp voltage is applied to the sensor as the first voltage for a first pulse of three pulses, a sinusoid voltage is applied to the sensor as the first voltage for a second pulse of the three pulses, and a constant DC voltage is applied to the sensor as the first voltage for a third pulse of the three pulses, the control device 860 may cause the switch 890, during the first timeframes in the anodic/cathodic cycles, to move between connecting the voltage from the voltage generation or application device 810 to the ramp voltage generation system 892, then to the sinusoidal voltage generation system 891, and then to the constant DC voltage generation system 893. In this embodiment of the invention, the control device 860 may also be directing or controlling the switch to connect certain ones of the voltage generation subsystems to the voltage from the regulator 385 during the second timeframe, e.g., during application of the second voltage.

Figure 9A:
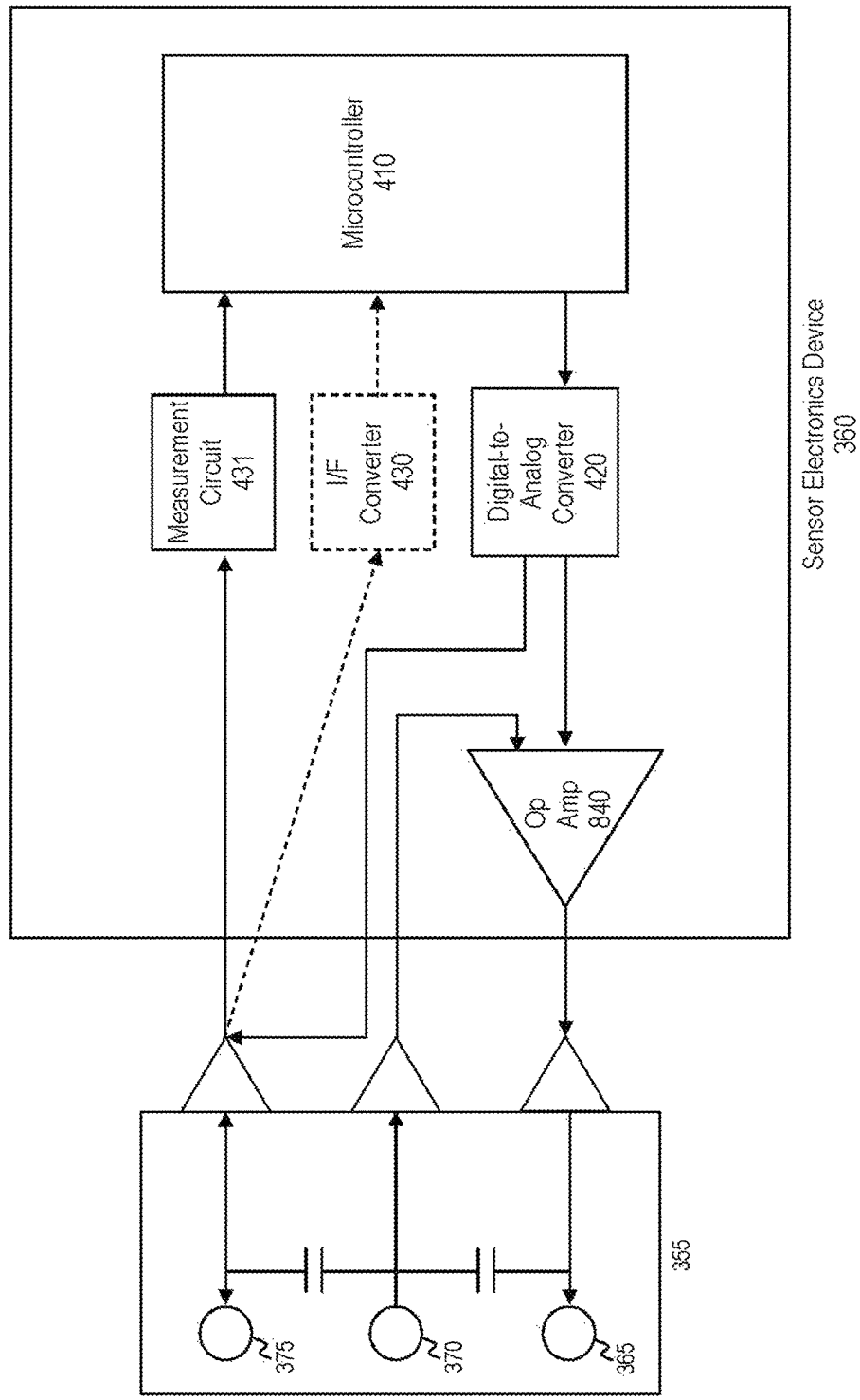
FIG. 9A illustrates a sensor electronics device including a microcontroller for generating voltage pulses according to an embodiment of the invention.

FIG. 9A illustrates a sensor electronics device including a microcontroller for generating voltage pulses according to an embodiment of the present invention. The advanced sensor electronics device may include a microcontroller 410 (see FIG. 4), a digital-to-analog converter (DAC) 420, an op amp 840, and a sensor signal measurement circuit 431. In an embodiment of the invention, the sensor signal measurement circuit may be a current-to-frequency (I/F) converter 430. In the embodiment of the invention illustrated in FIG. 9A, software or programmable logic in the microcontroller 410 provides instructions to transmit signals to the DAC 420, which in turn instructs the DAC 420 to output a specific voltage to the operational amplifier 840. The microcontroller 410 may also be instructed to output a specific voltage to the working electrode 375, as is illustrated by line 911 in FIG. 9A. As discussed above, the application of the specific voltage to operational amplifier 840 and the working electrode 375 may drive the voltage measured at the counter electrode to the specific voltage magnitude. In other words, the microcontroller 410 outputs a signal which is indicative of a voltage or a voltage waveform that is to be applied to the sensor 355 (e.g., the operational amplifier 840 coupled to the sensor 355). In an alternative embodiment of the invention, a fixed voltage may be set by applying a voltage directly from the DAC 420 between the reference electrode and the working electrode 375. A similar result may also be obtained by applying voltages to each of the electrodes with the difference equal to the fixed voltage applied between the reference and working electrode. In addition, the fixed voltage may be set by applying a voltage between the reference and the counter electrode. Under certain operating conditions, the microcontroller 410 may generate a pulse of a specific magnitude which the DAC 420 understands represents that a voltage of a specific magnitude is to be applied to the sensor. After a first timeframe, the microcontroller 410 (via the program or programmable logic) outputs a second signal which either instructs the DAC 420 to output no voltage (for a sensor electronics device 360 operating according to the method described in FIG. 6A) or to output a second voltage (for a sensor electronics device 360 operating according to the method described in FIG. 6B). The microcontroller 410, after the second timeframe has elapsed, then repeats the cycle of sending the signal indicative of a first voltage to be applied (for the first timeframe) and then sending the signal to instruct no voltage is to be applied or that a second voltage is to be applied (for the second timeframe).

Under other operating conditions, the microcontroller 410 may generate a signal to the DAC 420 which instructs the DAC to output a ramp voltage. Under other operating conditions, the microcontroller 410 may generate a signal to the DAC 420 which instructs the DAC 420 to output a voltage simulating a sinusoidal voltage. These signals could be incorporated into any of the pulsing methodologies discussed above in the preceding paragraph or earlier in the application. In an embodiment of the invention, the microcontroller 410 may generate a sequence of instructions and/or pulses, which the DAC 420 receives and understands to mean that a certain sequence of pulses is to be applied. For example, the microcontroller 410 may transmit a sequence of instructions (via signals and/or pulses) that instruct the DAC 420 to generate a constant voltage for a first iteration of a first timeframe, a ramp voltage for a first iteration of a second timeframe, a sinusoidal voltage for a second iteration of a first timeframe, and a squarewave having two values for a second iteration of the second timeframe.

The microcontroller 410 may include programmable logic or a program to continue this cycling for a stabilization timeframe or for a number of iterations. Illustratively, the microcontroller 410 may include counting logic to identify when the first timeframe or the second timeframe has elapsed. Additionally, the microcontroller 410 may include counting logic to identify that a stabilization timeframe has elapsed. After any of the preceding timeframes have elapsed, the counting logic may instruct the microcontroller to either send a new signal or to stop transmission of a signal to the DAC 420.

The use of the microcontroller 410 allows a variety of voltage magnitudes to be applied in a number of sequences for a number of time durations. In an embodiment of the invention, the microcontroller 410 may include control logic or a program to instruct the digital-to-analog converter 420 to transmit a voltage pulse having a magnitude of approximately 1.0 volt for a first time period of 1 minute, to then transmit a voltage pulse having a magnitude of approximately 0.5 volts for a second time period of 4 minutes, and to repeat this cycle for four iterations. In an embodiment of the invention, the microcontroller 420 may be programmed to transmit a signal to cause the DAC 420 to apply the same magnitude voltage pulse for each first voltage in each of the iterations. In an embodiment of the invention, the microcontroller 410 may be programmed to transmit a signal to cause the DAC to apply a different magnitude voltage pulse for each first voltage in each of the iterations. In this embodiment of the invention, the microcontroller 410 may also be programmed to transmit a signal to cause the DAC 420 to apply a different magnitude voltage pulse for each second voltage in each of the iterations. Illustratively, the microcontroller 410 may be programmed to transmit a signal to cause the DAC 420 to apply a first voltage pulse of approximately 1.0 volt in the first iteration, to apply a second voltage pulse of approximately 0.5 volts in the first iteration, to apply a first voltage of 0.7 volts and a second voltage of 0.4 volts in the second iteration, and to apply a first voltage of 1.2 volts and a second voltage of 0.8 volts in the third iteration.

The microcontroller 410 may also be programmed to instruct the DAC 420 to provide a number of short duration voltage pulses for a first timeframe. In this embodiment of the invention, rather than one voltage being applied for the entire first timeframe (e.g., two minutes), a number of shorter duration pulses may be applied to the sensor. In this embodiment, the microcontroller 410 may also be programmed to instruct the DAC 420 to provide a number of short duration voltage pulses for the second timeframe to the sensor. Illustratively, the microcontroller 410 may send a signal to cause the DAC to apply a number of short duration voltage pulses where the short duration is 50 milliseconds or 100 milliseconds. In between these short duration pulses the DAC may apply no voltage or the DAC may apply a minimal voltage. The microcontroller may cause the DAC 420 to apply the short duration voltage pulses for the first timeframe, e.g., two minutes. The microcontroller 410 may then send a signal to cause the DAC to either not apply any voltage or to apply the short duration voltage pulses at a magnitude of a second voltage for a second timeframe to the sensor, e.g., the second voltage may be 0.75 volts and the second timeframe may be 5 minutes. In an embodiment of the invention, the microcontroller 410 may send a signal to the DAC 420 to cause the DAC 420 to apply a different magnitude voltage for each of the short duration pulses in the first timeframe and/or in the second timeframe. In an embodiment of the invention, the microcontroller 410 may send a signal to the DAC 420 to cause the DAC 420 to apply a pattern of voltage magnitudes to the short durations voltage pulses for the first timeframe or the second timeframe. For example, the microcontroller may transmit a signal or pulses instructing the DAC 420 to apply thirty 20-millisecond pulses to the sensor during the first timeframe. Each of the thirty 20-millisecond pulses may have the same magnitude or may have a different magnitude. In this embodiment of the invention, the microcontroller 410 may instruct the DAC 420 to apply short duration pulses during the second timeframe or may instruct the DAC 420 to apply another voltage waveform during the second timeframe.

Although the disclosures in FIGS. 6-8 disclose the application of a voltage, a current may also be applied to the sensor to initiate the stabilization process. Illustratively, in the embodiment of the invention illustrated in FIG. 6B, a first current may be applied during a first timeframe to initiate an anodic or cathodic response and a second current may be applied during a second timeframe to initiate the opposite anodic or cathodic response. The application of the first current and the second current may continue for a number of iterations or may continue for a stabilization timeframe. In an embodiment of the invention, a first current may be applied during a first timeframe and a first voltage may be applied during a second timeframe. In other words, one of the anodic or cathodic cycles may be triggered by a current being applied to the sensor and the other of the anodic or cathodic cycles may be triggered by a voltage being applied to the sensor. As described above, a current applied may be a constant current, a ramp current, a stepped pulse current, or a sinusoidal current. Under certain operating conditions, the current may be applied as a sequence of short duration pulses during the first timeframe.

FIG. 9B illustrates a sensor and sensor electronics utilizing an analyzation module for feedback in a stabilization period according to an embodiment of the present invention. FIG. 9B introduces an analyzation module 950 to the sensor electronics device 360. The analyzation module 950 utilizes feedback from the sensor to determine whether or not the sensor is stabilized. In an embodiment of the invention, the microcontroller 410 may include instructions or commands to control the DAC 420 so that the DAC 420 applies a voltage or current to a part of the sensor 355. FIG. 9B illustrates that a voltage or current could be applied between a reference electrode 370 and a working electrode 375. However, the voltage or current can be applied in between electrodes or directly to one of the electrodes and the invention should not be limited by the embodiment illustrated in FIG. 9B. The application of the voltage or current is illustrated by dotted line 955. The analyzation module 950 may measure a voltage, a current, a resistance, or an impedance in the sensor 355. FIG. 9B illustrates that the measurement occurs at the working electrode 375, but this should not limit the invention because other embodiments of the invention may measure a voltage, a current, a resistance, or an impedance in between electrodes of the sensor or directly at either the reference electrode 370 or the counter electrode 365. The analyzation module 950 may receive the measured voltage, current, resistance, or impedance and may compare the measurement to a stored value (e.g., a threshold value). Dotted line 956 represents the analyzation module 950 reading or taking a measurement of the voltage, current, resistance, or impedance. Under certain operating conditions, if the measured voltage, current, resistance, or impedance is above the threshold, the sensor is stabilized and the sensor signal is providing accurate readings of a physiological condition of a patient. Under other operating conditions, if the measured voltage, current, resistance, or impedance is below the threshold, the sensor is stabilized. Under other operating conditions, the analyzation module 950 may verify that the measured voltage, current, resistance, or impedance is stable for a specific timeframe, e.g., one minute or two minutes. This may represent that the sensor 355 is stabilized and that the sensor signal is transmitting accurate measurements of a subject's physiological parameter, e.g., blood glucose level. After the analyzation module 950 has determined that the sensor is stabilized and the sensor signal is providing accurate measurements, the analyzation module 950 may transmit a signal (e.g., a sensor stabilization signal) to the microcontroller 410 indicating that the sensor is stabilized and that the microcontroller 410 can start using or receiving the sensor signal from the sensor 355. This is represented by dotted line 957.

Figure 10:
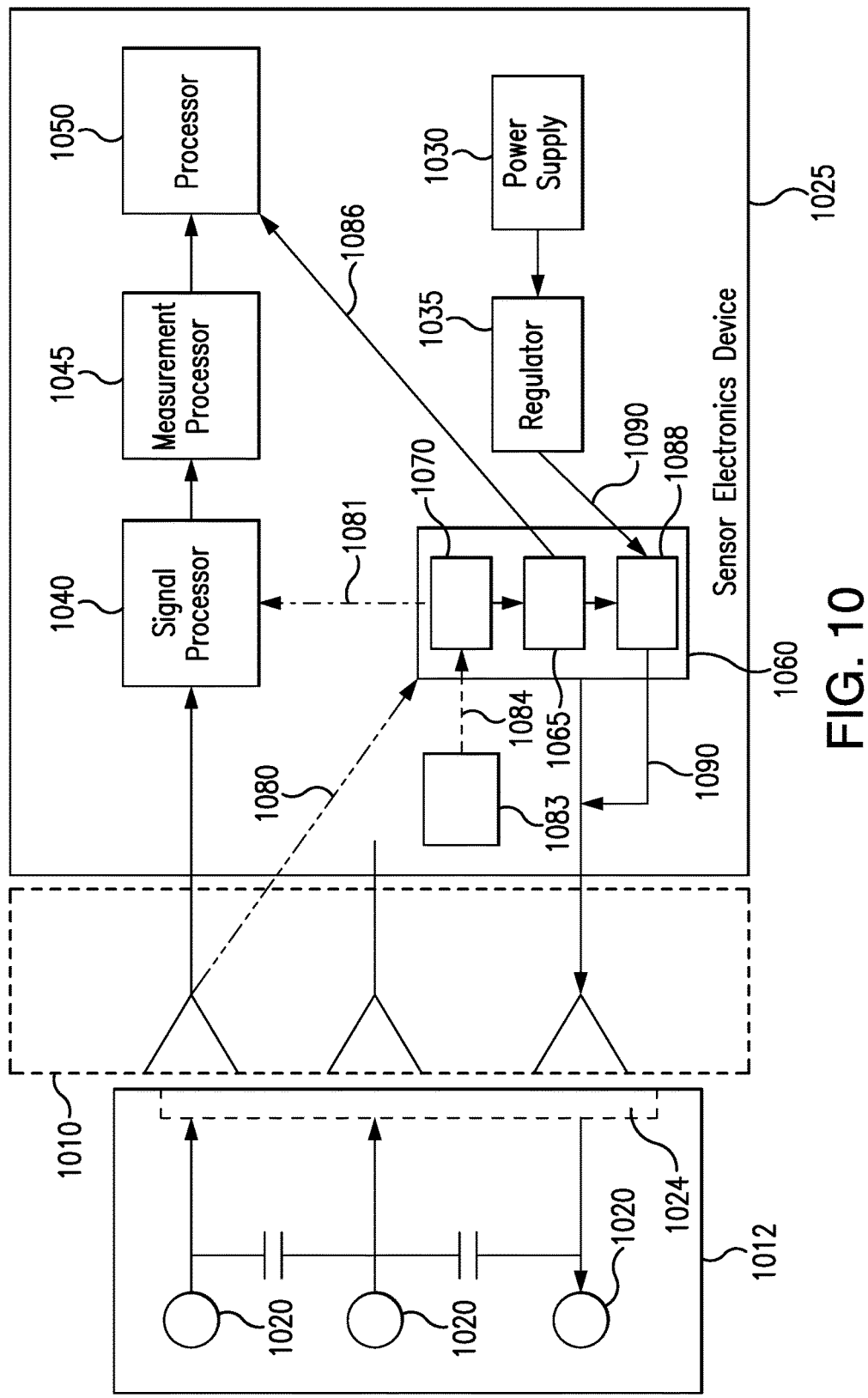
FIG. 10 illustrates a block diagram of a sensor system including hydration electronics according to an embodiment of the invention.

FIG. 10 illustrates a block diagram of a sensor system including hydration electronics according to an embodiment of the present invention. The sensor system includes a connector 1010, a sensor 1012, and a monitor or sensor electronics device 1025. The sensor 1012 includes electrodes 1020 and a connection portion 1024. In an embodiment of the invention, the sensor 1012 may be connected to the sensor electronics device 1025 via a connector 1010 and a cable. In other embodiments of the invention, the sensor 1012 may be directly connected to the sensor electronics device 1025. In other embodiments of the invention, the sensor 1012 may be incorporated into the same physical device as the sensor electronics device 1025. The monitor or sensor electronics device 1025 may include a power supply 1030, a regulator 1035, a signal processor 1040, a measurement processor 1045, and a processor 1050. The monitor or sensor electronics device 1025 may also include a hydration detection circuit 1060. The hydration detection circuit 1060 interfaces with the sensor 1012 to determine if the electrodes 1020 of the sensor 1012 are sufficiently hydrated. If the electrodes 1020 are not sufficiently hydrated, the electrodes 1020 do not provide accurate glucose readings, so it is important to know when the electrodes 1020 are sufficiently hydrated. Once the electrodes 1020 are sufficiently hydrated, accurate glucose readings may be obtained.

In an embodiment of the invention illustrated in FIG. 10, the hydration detection circuit 1060 may include a delay or timer module 1065 and a connection detection module 1070. In an embodiment of the invention utilizing the short term sensor or the subcutaneous sensor, after the sensor 1012 has been inserted into the subcutaneous tissue, the sensor electronics device or monitor 1025 is connected to the sensor 1012. The connection detection module 1070 identifies that the sensors electronics device 1025 has been connected to the sensor 1012 and sends a signal to the timer module 1065. This is illustrated in FIG. 10 by the arrow 1084 which represents a detector 1083 detecting a connection and sending a signal to the connection detection module 1070 indicating the sensor 1012 has been connected to the sensor electronics device 1025. In an embodiment of the invention where implantable or long-term sensors are utilized, a connection detection module 1070 identifies that the implantable sensor has been inserted into the body. The timer module 1065 receives the connection signal and waits a set or established hydration time. Illustratively, the hydration time may be two minutes, five minutes, ten minutes, or 20 minutes. These examples are meant to be illustrative and not to be limiting. The timeframe does not have to be a set number of minutes and can include any number of seconds. In an embodiment of the invention, after the timer module 1065 has waited for the set hydration time, the timer module 1065 may notify the processor 1050 that the sensor 1012 is hydrated by sending a hydration signal, which is illustrated by line 1086.

In this embodiment of the invention, the processor 1050 may receive the hydration signal and only start utilizing the sensor signal (e.g., sensor measurements) after the hydration signal has been received. In another embodiment of the invention, the hydration detection circuit 1060 may be coupled between the sensor (the sensor electrodes 1020) and the signal processor 1040. In this embodiment of the invention, the hydration detection circuit 1060 may prevent the sensor signal from being sent to signal processor 1040 until the timer module 1065 has notified the hydration detection circuit 1060 that the set hydration time has elapsed. This is illustrated by the dotted lines labeled with reference numerals 1080 and 1081. Illustratively, the timer module 1065 may transmit a connection signal to a switch (or transistor) to turn on the switch and let the sensor signal proceed to the signal processor 1040. In an alternative embodiment of the invention, the timer module 1065 may transmit a connection signal to turn on a switch 1088 (or close the switch 1088) in the hydration detection circuit 1060 to allow a voltage from the regulator 1035 to be applied to the sensor 1012 after the hydration time has elapsed. In other words, in this embodiment of the invention, the voltage from the regulator 1035 is not applied to the sensor 1012 until after the hydration time has elapsed.

Figure 11:
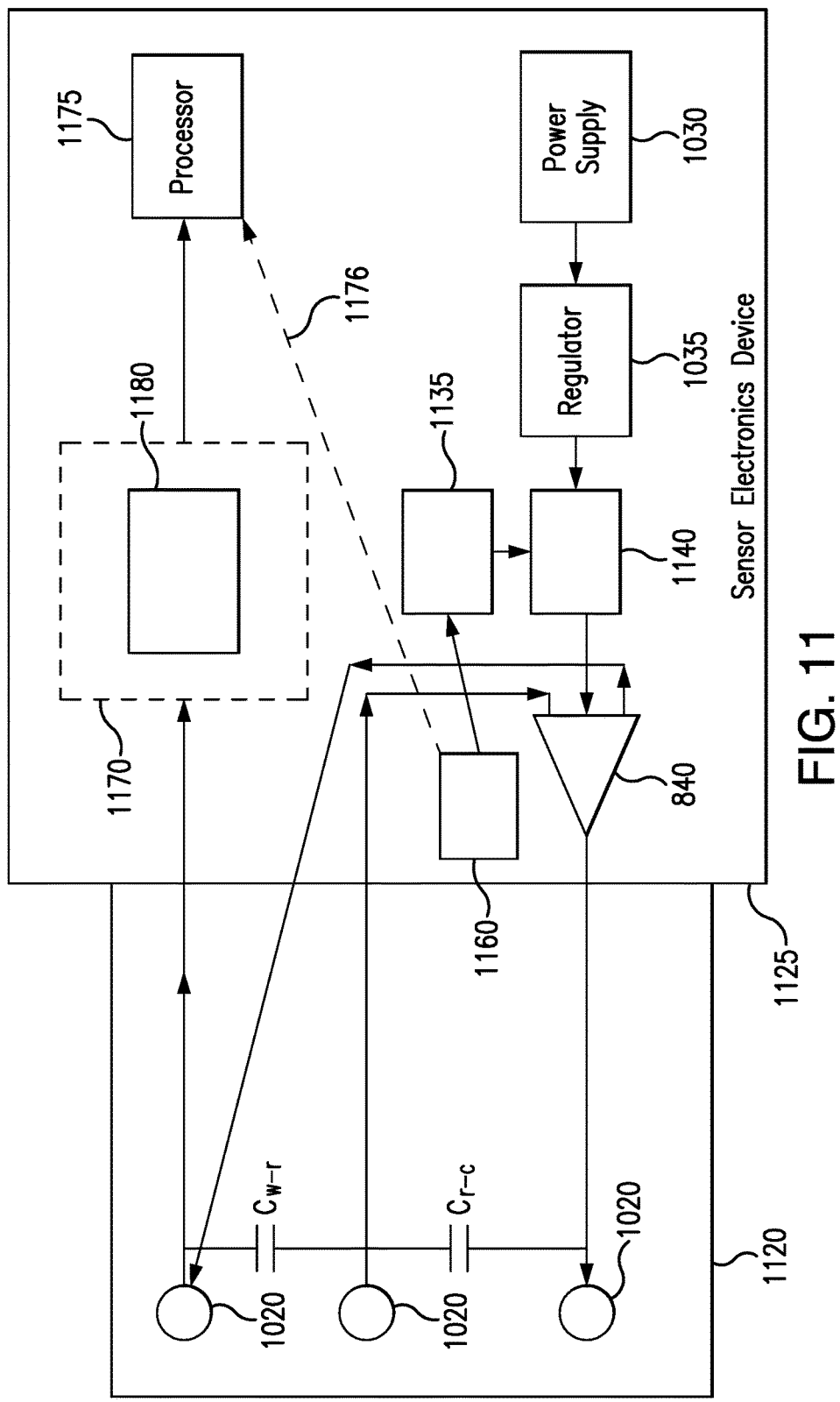
FIG. 11 illustrates an embodiment of the invention including a mechanical switch to assist in determining a hydration time.

FIG. 11 illustrates an embodiment of the invention including a mechanical switch to assist in determining a hydration time. In an embodiment of the invention, a single housing may include a sensor assembly 1120 and a sensor electronics device 1125. In an embodiment of the invention, the sensor assembly 1120 may be in one housing and the sensor electronics device 1125 may be in a separate housing, but the sensor assembly 1120 and the sensor electronics device 1125 may be connected together. In this embodiment of the invention, a connection detection mechanism 1160 may be a mechanical switch. The mechanical switch may detect that the sensor 1120 is physically connected to the sensor electronics device 1125. In an embodiment of the invention, a timer circuit 1135 may also be activated when the mechanical switch 1160 detects that the sensor 1120 is connected to the sensor electronics device 1125. In other words, the mechanical switch may close and a signal may be transferred to a timer circuit 1135. Once a hydration time has elapsed, the timer circuit 1135 transmits a signal to the switch 1140 to allow the regulator 1035 to apply a voltage to the sensor 1120. In other words, no voltage is applied until the hydration time has elapsed. In an embodiment of the invention, current may replace voltage as what is being applied to the sensor once the hydration time elapses. In an alternative embodiment of the invention, when the mechanical switch 1160 identifies that a sensor 1120 has been physically connected to the sensor electronics device 1125, power may initially be applied to the sensor 1120. Power being sent to the sensor 1120 results in a sensor signal being output from the working electrode in the sensor 1120. The sensor signal may be measured and sent to a processor 1175. The processor 1175 may include a counter input. Under certain operating conditions, after a set hydration time has elapsed from when the sensor signal was input into the processor 1175, the processor 1175 may start processing the sensor signal as an accurate measurement of the glucose in a subject's body. In other words, the processor 1170 has received the sensor signal from the potentiostat circuit 1170 for a certain amount of time, but will not process the signal until receiving an instruction from the counter input of the processor identifying that a hydration time has elapsed. In an embodiment of the invention, the potentiostat circuit 1170 may include a current-to-frequency converter 1180. In this embodiment of the invention, the current-to-frequency converter 1180 may receive the sensor signal as a current value and may convert the current value into a frequency value, which is easier for the processor 1175 to handle.

In an embodiment of the invention, the mechanical switch 1160 may also notify the processor 1175 when the sensor 1120 has been disconnected from the sensor electronics device 1125. This is represented by dotted line 1176 in FIG. 11. This may result in the processor 1170 powering down or reducing power to a number of components, chips, and/or circuits of the sensor electronics device 1125. If the sensor 1120 is not connected, the battery or power source may be drained if the components or circuits of the sensor electronics device 1125 are in a power on state. Accordingly, if the mechanical switch 1160 detects that the sensor 1120 has been disconnected from the sensor electronics device 1125, the mechanical switch may indicate this to the processor 1175, and the processor 1175 may power down or reduce power to one or more of the electronic circuits, chips, or components of the sensor electronics device 1125.

Figure 12:
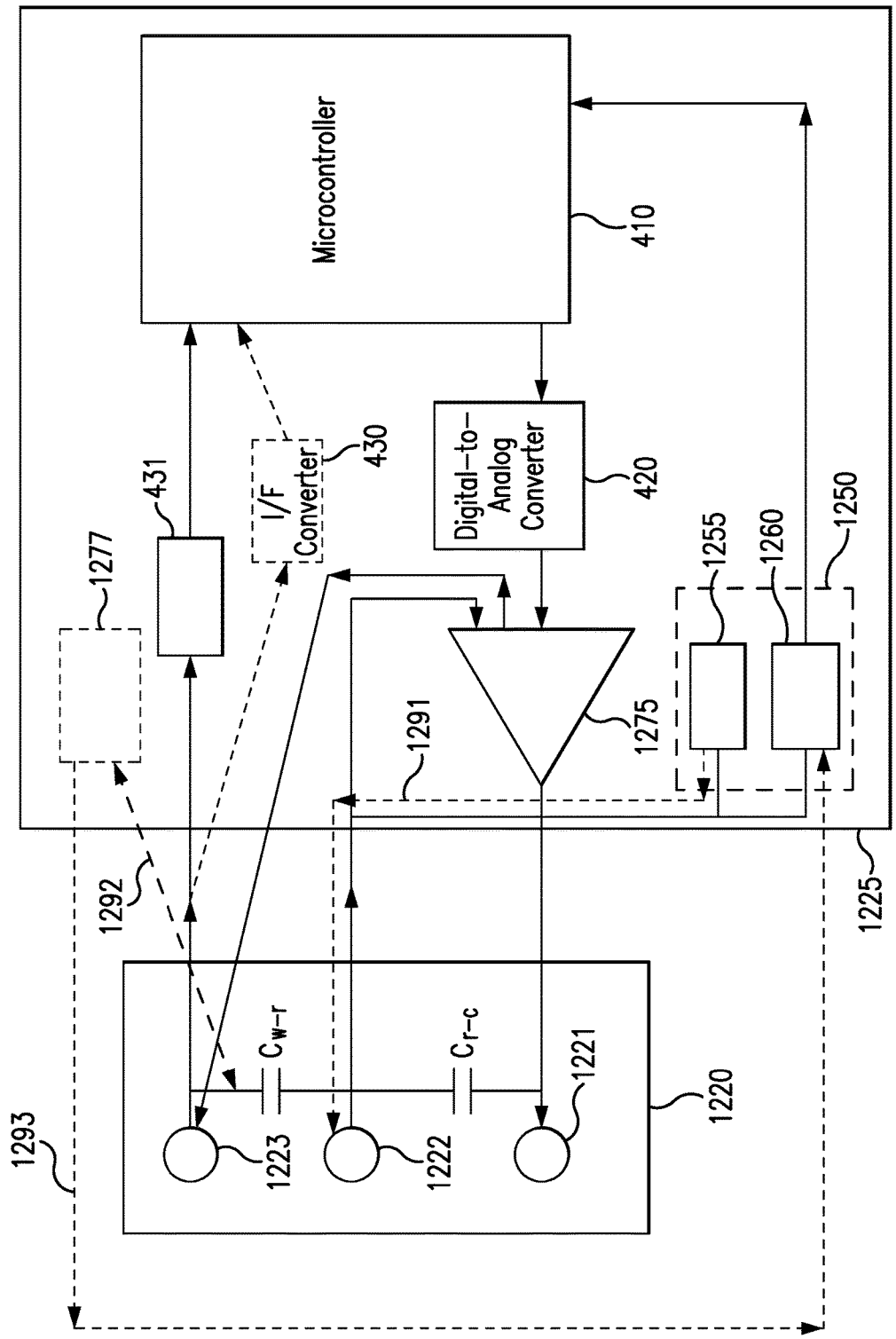
FIG. 12 illustrates a method of detection of hydration according to an embodiment of the invention.

FIG. 12 illustrates an electrical method of detection of hydration according to an embodiment of the invention. In an embodiment of the invention, an electrical detecting mechanism for detecting connection of a sensor may be utilized. In this embodiment of the invention, the hydration detection electronics 1250 may include an AC source 1255 and a detection circuit 1260. The hydration detection electronics 1250 may be located in the sensor electronics device 1225. The sensor 1220 may include a counter electrode 1221, a reference electrode 1222, and a working electrode 1223. As illustrated in FIG. 12, the AC source 1255 is coupled to a voltage setting device 1275, the reference electrode 1222, and the detection circuit 1260. In this embodiment of the invention, an AC signal from the AC source is applied to the reference electrode connection, as illustrated by dotted line 1291 in FIG. 12. In an embodiment of the invention, the AC signal is coupled to the sensor 1220 through an impedance and the coupled signal is attenuated significantly if the sensor 1220 is connected to the sensor electronics device 1225. Thus, a low level AC signal is present at an input to the detection circuit 1260. This may also be referred to as a highly attenuated signal or a signal with a high level of attenuation. Under certain operating conditions, the voltage level of the AC signal may be Vapplied*(Ccoupling)/(Ccoupling+Csensor). If the detection circuit 1260 detects that a high level AC signal (lowly attenuated signal) is present at an input terminal of the detection circuit 1260, no interrupt is sent to the microcontroller 410 because the sensor 1220 has not been sufficiently hydrated or activated. For example, the input of the detection circuit 1260 may be a comparator. If the sensor 1220 is sufficiently hydrated (or wetted), an effective capacitance forms between the counter electrode and the reference electrode (e.g., capacitance $C_{r-c}$ in FIG. 12), and an effective capacitance forms between the reference electrode and the working electrode (e.g., capacitance $C_{w-r}$ in FIG. 12). In other words, an effective capacitance relates to capacitance being formed between two nodes and does not represent that an actual capacitor is placed in a circuit between the two electrodes. In an embodiment of the invention, the AC signal from the AC source 1255 is sufficiently attenuated by capacitances $C_{r-c}$ and $C_{w-r}$ and the detection circuit 1260 detects the presence of a low level or highly attenuated AC signal from the AC source 1255 at the input terminal of the detection circuit 1260. This embodiment of the invention is significant because the utilization of the existing connections between the sensor 1120 and the sensor electronics device 1125 reduces the number of connections to the sensor. In other words, the mechanical switch, disclosed in FIG. 11, requires a switch and associated connections between the sensor 1120 and the sensor electronics device 1125. It is advantageous to eliminate the mechanical switch because the sensor 1120 is continuously shrinking in size and the elimination of components helps achieve this size reduction. In alternative embodiments of the invention, the AC signal may be applied to different electrodes (e.g., the counter electrode or the working electrode) and the invention may operate in a similar fashion.

As noted above, after the detection circuit 1260 has detected that a low level AC signal is present at the input terminal of the detection circuit 1260, the detection circuit 1260 may later detect that a high level AC signal, with low attenuation, is present at the input terminal. This represents that the sensor 1220 has been disconnected from the sensor electronics device 1225 or that the sensor is not operating properly. If the sensor has been disconnected from the sensor electronics device 1225, the AC source may be coupled with little or low attenuation to the input of the detection circuit 1260. As noted above, the detection circuit 1260 may generate an interrupt to the microcontroller. This interrupt may be received by the microcontroller and the microcontroller may reduce or eliminate power to one or a number of components or circuits in the sensor electronics device 1225. This may be referred to as the second interrupt. Again, this helps reduce power consumption of the sensor electronics device 1225, specifically when the sensor 1220 is not connected to the sensor electronics device 1225.

In an alternative embodiment of the invention illustrated in FIG. 12, the AC signal may be applied to the reference electrode 1222, as is illustrated by reference numeral 1291, and an impedance measuring device 1277 may measure the impedance of an area in the sensor 1220. Illustratively, the area may be an area between the reference electrode and the working electrode, as illustrated by dotted line 1292 in FIG. 12. Under certain operating conditions, the impedance measuring device 1277 may transmit a signal to the detection circuit 1260 if a measured impedance has decreased to below an impedance threshold or other set criteria. This represents that the sensor is sufficiently hydrated. Under other operating conditions, the impedance measuring device 1277 may transmit a signal to the detection circuit 1260 once the impedance is above an impedance threshold. The detection circuit 1260 then transmits the interrupt to the microcontroller 410. In another embodiment of the invention, the impedance measuring device 1277 may transmit an interrupt or signal directly to the microcontroller.

In an alternative embodiment of the invention, the AC source 1255 may be replaced by a DC source. If a DC source is utilized, then a resistance measuring element may be utilized in place of an impedance measuring element 1277. In an embodiment of the invention utilizing the resistance measuring element, once the resistance drops below a resistance threshold or a set criteria, the resistance measuring element may transmit a signal to the detection circuit 1260 (represented by dotted line 1293) or directly to the microcontroller indicating that the sensor is sufficiently hydrated and that power may be applied to the sensor.

In the embodiment of the invention illustrated in FIG. 12, if the detection circuit 1260 detects a low level or highly attenuated AC signal from the AC source, an interrupt is generated to the microcontroller 410. This interrupt indicates that sensor is sufficiently hydrated. In this embodiment of the invention, in response to the interrupt, the microcontroller 410 generates a signal that is transferred to a digital-to-analog converter 420 to instruct or cause the digital-to-analog converter 420 to apply a voltage or current to the sensor 1220. Any of the different sequence of pulses or short duration pulses described above in FIGS. 6A, 6B, or 6C or the associated text describing the application of pulses, may be applied to the sensor 1220. Illustratively, the voltage from the DAC 420 may be applied to an op-amp 1275, the output of which is applied to the counter electrode 1221 of the sensor 1220. This results in a sensor signal being generated by the sensor, e.g., the working electrode 1223 of the sensor. Because the sensor is sufficiently hydrated, as identified by the interrupt, the sensor signal created at the working electrode 1223 is accurately measuring glucose. The sensor signal is measured by a sensor signal measuring device 431 and the sensor signal measuring device 431 transmits the sensor signal to the microcontroller 410 where a parameter of a subject's physiological condition is measured. The generation of the interrupt represents that a sensor is sufficiently hydrated and that the sensor 1220 is now supplying accurate glucose measurements. In this embodiment of the invention, the hydration period may depend on the type and/or the manufacturer of the sensor and on the sensor's reaction to insertion or implantation in the subject. Illustratively, one sensor 1220 may have a hydration time of five minutes and one sensor 1220 may have a hydration time of one minute, two minutes, three minutes, six minutes, or 20 minutes. Again, any amount of time may be an acceptable amount of hydration time for the sensor, but smaller amounts of time are preferable.

If the sensor 1220 has been connected, but is not sufficiently hydrated or wetted, the effective capacitances $C_{r-c}$ and $C_{w-r}$ may not attenuate the AC signal from the AC source 1255. The electrodes in the sensor 1120 are dry before insertion and because the electrodes are dry, a good electrical path (or conductive path) does not exist between the two electrodes. Accordingly, a high level AC signal or lowly attenuated AC signal may still be detected by the detection circuit 1260 and no interrupt may be generated. Once the sensor has been inserted, the electrodes become immersed in the conductive body fluid. This results in a leakage path with lower DC resistance. Also, boundary layer capacitors form at the metal/fluid interface. In other words, a rather large capacitance forms between the metal/fluid interface and this large capacitance looks like two capacitors in series between the electrodes of the sensor. This may be referred to as an effective capacitance. In practice, a conductivity of an electrolyte above the electrode is being measured. In some embodiments of the invention, the glucose limiting membrane (GLM) also illustrates impedance blocking electrical efficiency. An unhydrated GLM results in high impedance, whereas a high moisture GLM results in low impedance. Low impedance is desired for accurate sensor measurements.

Figure 13A:
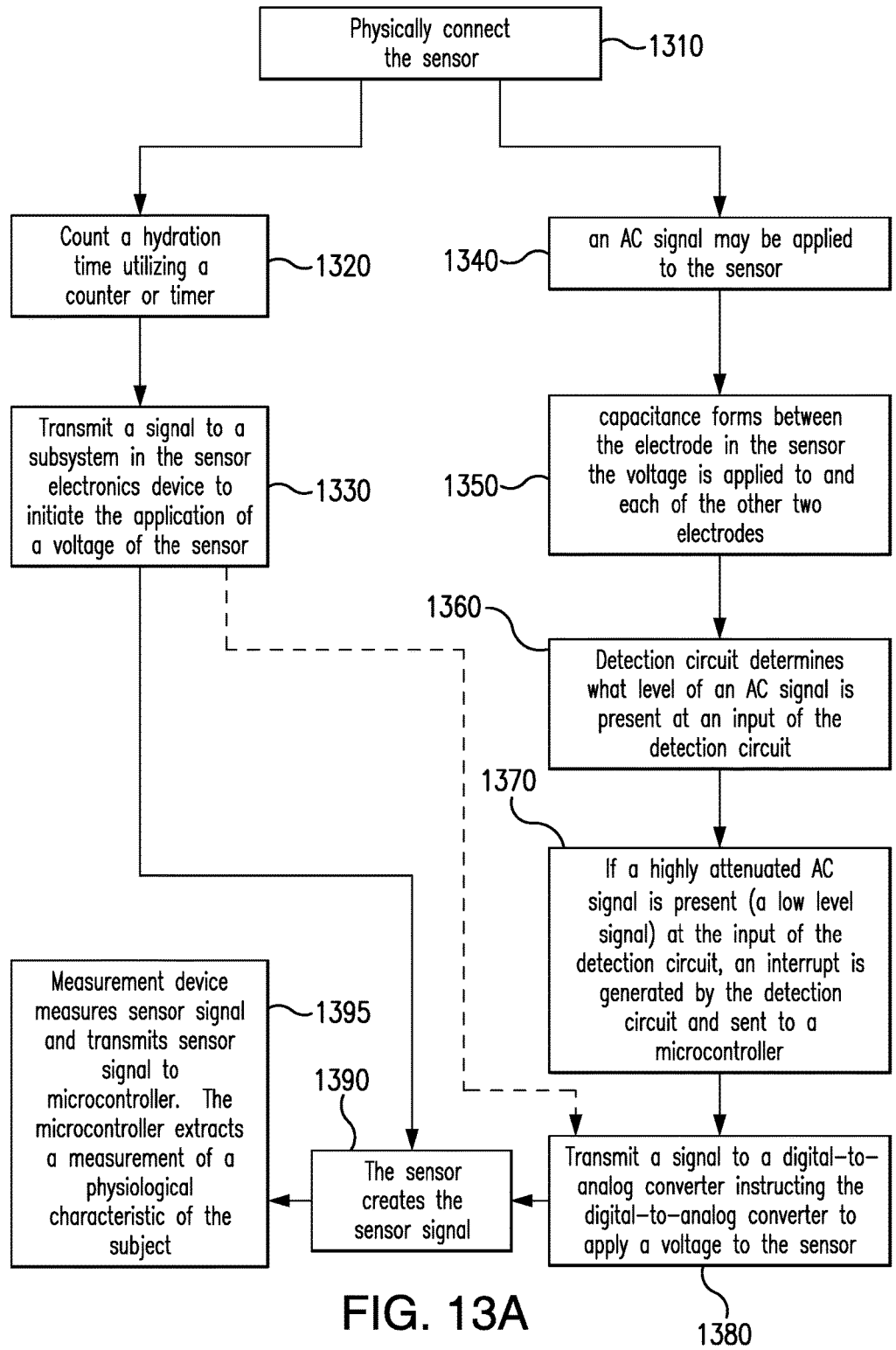
FIG. 13A illustrates a method of hydrating a sensor according to an embodiment of the present invention.

FIG. 13A illustrates a method of hydrating a sensor according to an embodiment of the present invention. In an embodiment of the invention, the sensor may be physically connected 1310 to the sensor electronics device. After the connection, in one embodiment of the invention, a timer or counter may be initiated to count 1320 a hydration time. After the hydration time has elapsed, a signal may be transmitted 1330 to a subsystem in the sensor electronics device to initiate the application of a voltage to the sensor. As discussed above, in an embodiment of the invention, a microcontroller may receive the signal and instruct the DAC to apply a voltage to the sensor or in another embodiment of the invention, a switch may receive a signal which allows a regulator to apply a voltage to the sensor. The hydration time may be five minutes, two minutes, ten minutes and may vary depending on the subject and also on the type of sensor.

In an alternative embodiment of the invention, after the connection of the sensor to the sensor electronics device, an AC signal (e.g., a low voltage AC signal) may be applied 1340 to the sensor, e.g., the reference electrode of the sensor. The AC signal may be applied because the connection of the sensor to the sensor electronics device allows the AC signal to be applied to the sensor. After application of the AC signal, an effective capacitance forms 1350 between the electrode in the sensor that the voltage is applied to and the other two electrodes. A detection circuit determines 1360 what level of the AC signal is present at the input of the detection circuit. If a low level AC signal (or highly attenuated AC signal) is present at the input of the detection circuit, due to the effective capacitance forming a good electrical conduit between the electrodes and the resulting attenuation of the AC signal, an interrupt is generated 1370 by the detection circuit and sent to a microcontroller.

The microcontroller receives the interrupt generated by the detection circuit and transmits 1380 a signal to a digital-to-analog converter instructing or causing the digital-to-analog converter to apply a voltage to an electrode of the sensor, e.g., the counter electrode. The application of the voltage to the electrode of the sensor results in the sensor creating or generating a sensor signal 1390. A sensor signal measurement device 431 measures the generated sensor signal and transmits the sensor signal to the microcontroller. The microcontroller receives 1395 the sensor signal from the sensor signal measurement device, which is coupled to the working electrode, and processes the sensor signal to extract a measurement of a physiological characteristic of the subject or patient.

Figure 13B:
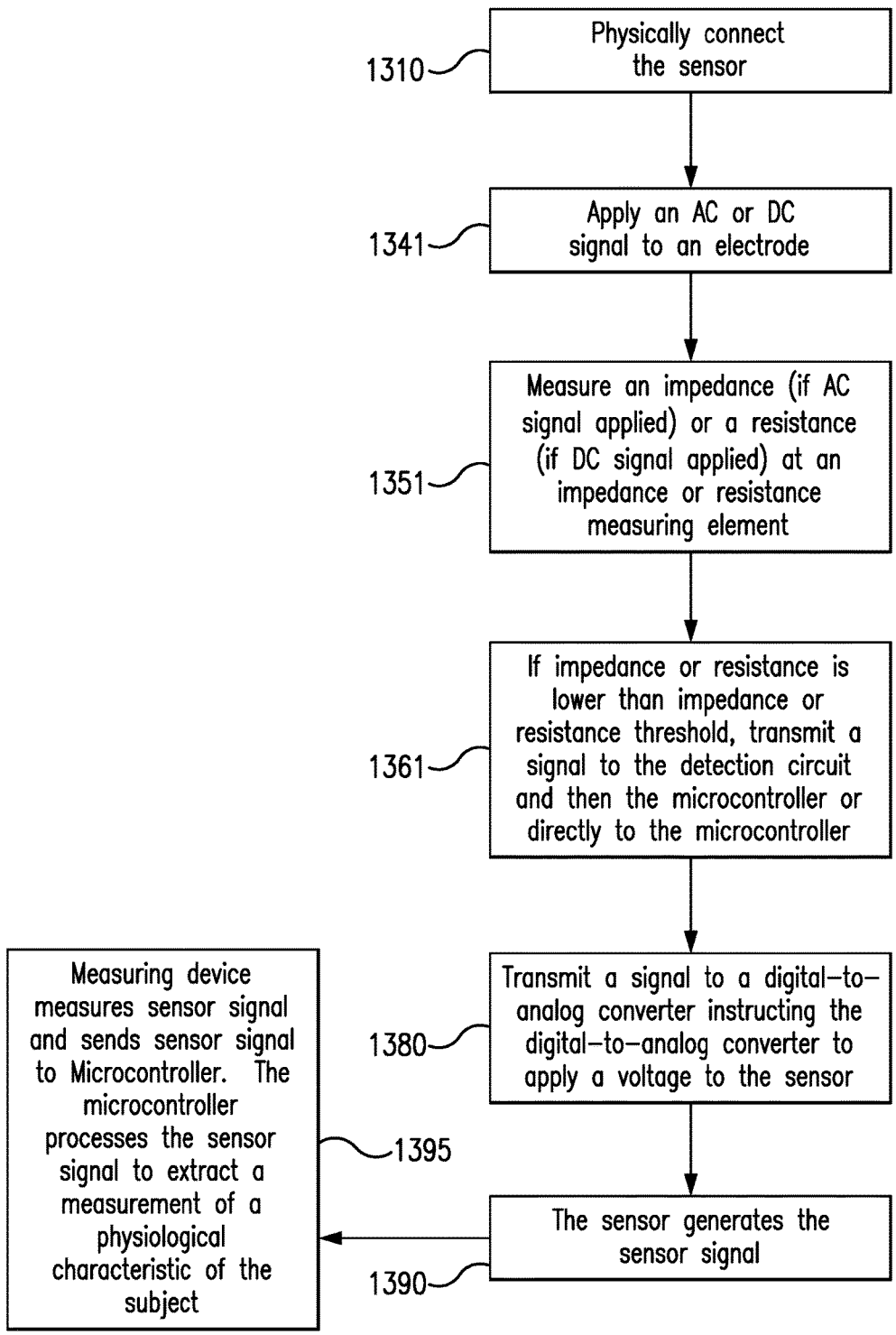
FIG. 13B illustrates an additional method for verifying hydration of a sensor according to an embodiment of the invention.

FIG. 13B illustrates an additional method for verifying hydration of a sensor according to an embodiment of the present invention. In the embodiment of the invention illustrated in FIG. 13B, the sensor is physically connected 1310 to the sensor electronics device. In an embodiment of the invention, an AC signal is applied 1341 to an electrode, e.g., a reference electrode, in the sensor. Alternatively, in an embodiment of the invention, a DC signal is applied 1341 to an electrode in the sensor. If an AC signal is applied, an impedance measuring element measures 1351 an impedance at a point within the sensor. Alternatively, if a DC signal is applied, a resistance measuring element measures 1351 a resistance at a point within the sensor. If the resistance or impedance is lower than a resistance threshold or an impedance threshold, respectively, (or other set criteria), then the impedance (or resistance) measuring element transmits 1361

(or allows a signal to be transmitted) to the detection circuit, and the detection circuit transmits an interrupt to the microcontroller identifying that the sensor is hydrated. The reference numbers 1380, 1390, and 1395 are the same in FIGS. 13A and 13B because they represent the same action.

The microcontroller receives the interrupt and transmits 1380 a signal to a digital-to-analog converter to apply a voltage to the sensor. In an alternative embodiment of the invention, the digital-to-analog converter can apply a current to the sensor, as discussed above. The sensor, e.g., the working electrode, creates 1390 a sensor signal, which represents a physiological parameter of a patient. The microcontroller receives 1395 the sensor signal from a sensor signal measuring device, which measures the sensor signal at an electrode in the sensor, e.g., the working electrode. The microcontroller processes the sensor signal to extract a measurement of the physiological characteristic of the subject or patient, e.g., the blood glucose level of the patient.

Figure 14A:
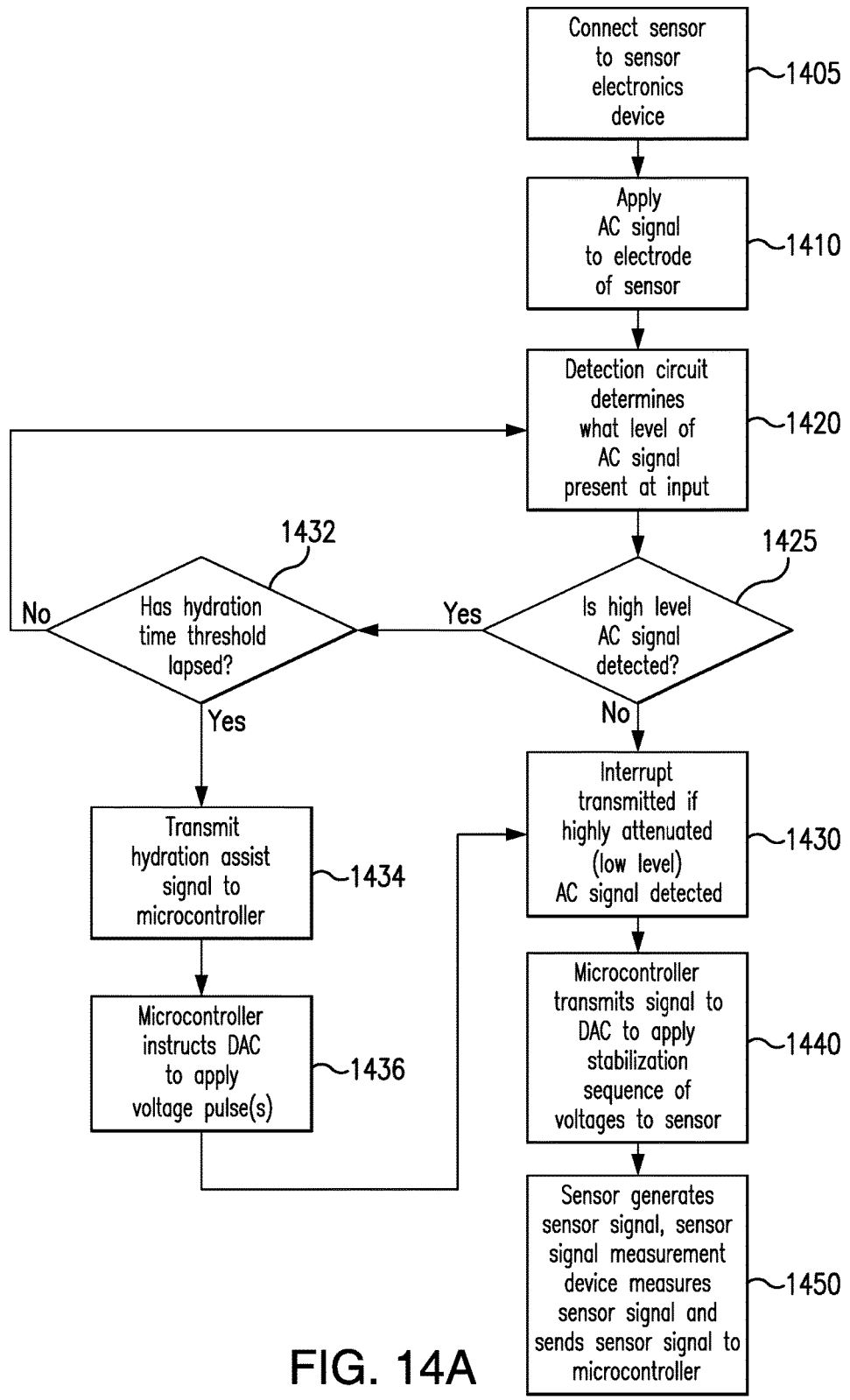
FIGS. 14A, 14B, and 14C illustrate methods of combining hydrating of a sensor with stabilizing a sensor according to an embodiment of the invention.
Figure 14B:
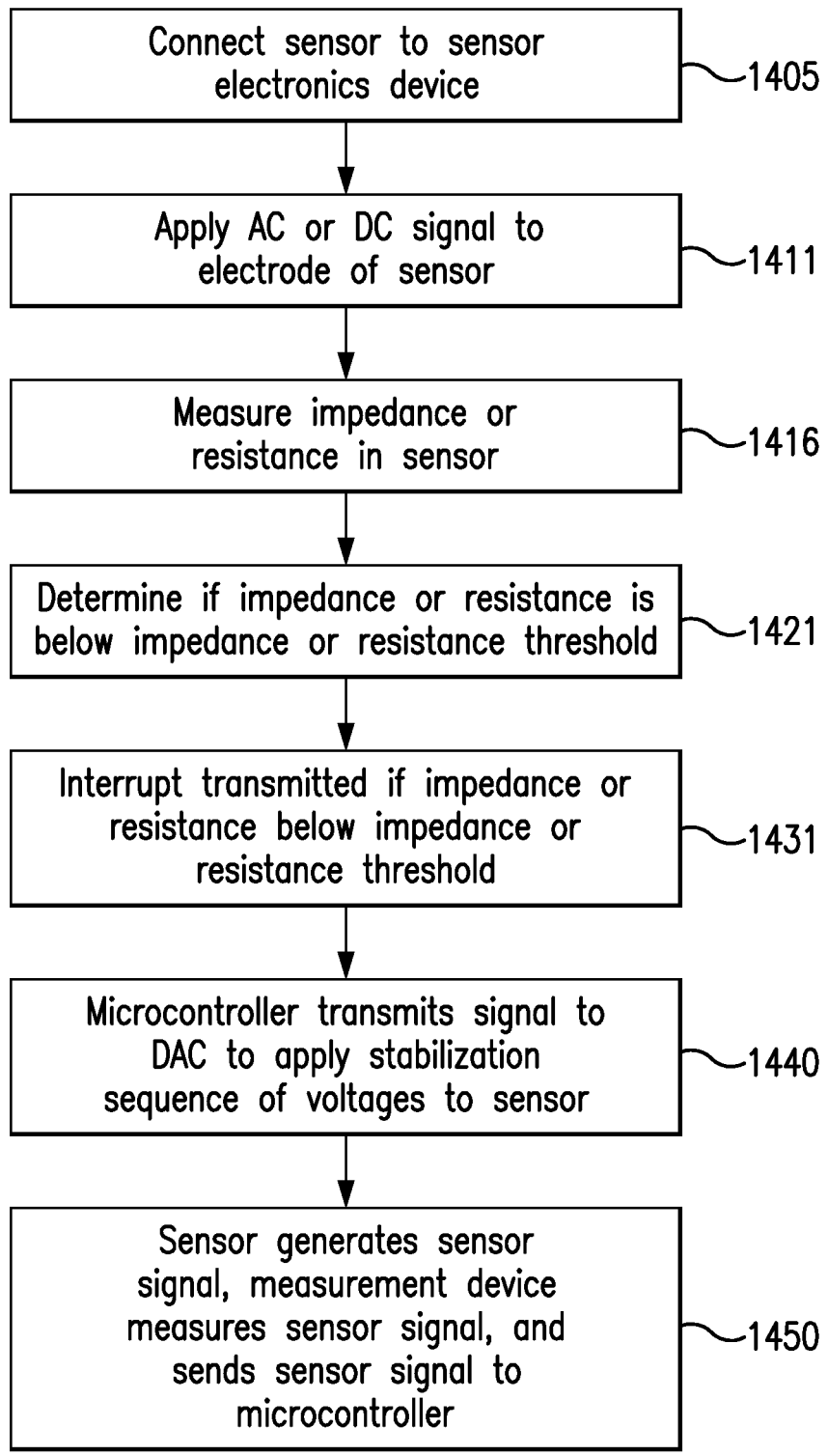

FIGS. 14A and 14B illustrate methods of combining hydrating of a sensor with stabilizing of a sensor according to an embodiment of the present invention. In an embodiment of the invention illustrated in FIG. 14A, the sensor is connected 1405 to the sensor electronics device. The AC signal is applied 1410 to an electrode of the sensor. The detection circuit determines 1420 what level of the AC signal is present at an input of the detection circuit. If the detection circuit determines that a low level of the AC signal is present at the input (representing a high level of attenuation to the AC signal), an interrupt is sent 1430 to microcontroller. Once the interrupt is sent to the microcontroller, the microcontroller knows to begin or initiate 1440 a stabilization sequence, i.e., the application of a number of voltage pulses to an electrode of the sensors, as described above. For example, the microcontroller may cause a digital-to-analog converter to apply three voltage pulses (having a magnitude of +0.535 volts) to the sensor with each of the three voltage pulses followed by a period of three voltage pulses (having a magnitude of 1.07 volts to be applied). This may be referred to transmitting a stabilization sequence of voltages. The microcontroller may cause this by the execution of a software program in a read-only memory (ROM) or a random access memory. After the stabilization sequence has finished executing, the sensor may generate 1450 a sensor signal, which is measured and transmitted to a microcontroller.

In an embodiment of the invention, the detection circuit may determine 1432 that a high level AC signal has continued to be present at the input of the detection circuit (e.g., an input of a comparator), even after a hydration time threshold has elapsed. For example, the hydration time threshold may be 10 minutes. After 10 minutes has elapsed, the detection circuit may still be detecting that a high level AC signal is present. At this point in time, the detection circuit may transmit 1434 a hydration assist signal to the microcontroller. If the microcontroller receives the hydration assist signal, the microcontroller may transmit 1436 a signal to cause a DAC to apply a voltage pulse or a series of voltage pulses to assist the sensor in hydration. In an embodiment of the invention, the microcontroller may transmit a signal to cause the DAC to apply a portion of the stabilization sequence or other voltage pulses to assist in hydrating the sensor. In this embodiment of the invention, the application of voltage pulses may result in the low level AC signal (or highly attenuated signal) being detected 1438 at the detection circuit. At this point, the detection circuit may transmit an interrupt, as is disclosed in step 1430, and the microcontroller may initiate a stabilization sequence.

FIG. 14B illustrates a second embodiment of a combination of a hydration method and a stabilization method where feedback is utilized in the stabilization process. A sensor is connected 1405 to a sensor electronics device. An AC signal (or a DC signal) is applied 1411 to the sensor. In an embodiment of the invention, the AC signal (or the DC signal) is applied to an electrode of the sensor, e.g. the reference electrode. An impedance measuring device (or resistance measuring device) measures 1416 the impedance (or resistance) within a specified area of the sensor. In an embodiment of the invention, the impedance (or resistance) may be measured between the reference electrode and the working electrode. The measured impedance (or resistance) may be compared 1421 to an impedance or resistance value to see if the impedance (or resistance) is low enough in the sensor, which indicates the sensor is hydrated. If the impedance (or resistance) is below the impedance (or resistance) value or other set criteria, (which may be a threshold value), an interrupt is transmitted 1431 to the microcontroller. After receiving the interrupt, the microcontroller transmits 1440 a signal to the DAC instructing the DAC to apply a stabilization sequence of voltages (or currents) to the sensor. After the stabilization sequence has been applied to the sensor, a sensor signal is created in the sensor (e.g., at the working electrode), is measured by a sensor signal measuring device, is transmitted by the sensor signal measuring device, and is received 1450 by the microcontroller. Because the sensor is hydrated and the stabilization sequence of voltages has been applied to the sensor, the sensor signal is accurately measuring a physiological parameter (i.e., blood glucose).

Figure 14C:
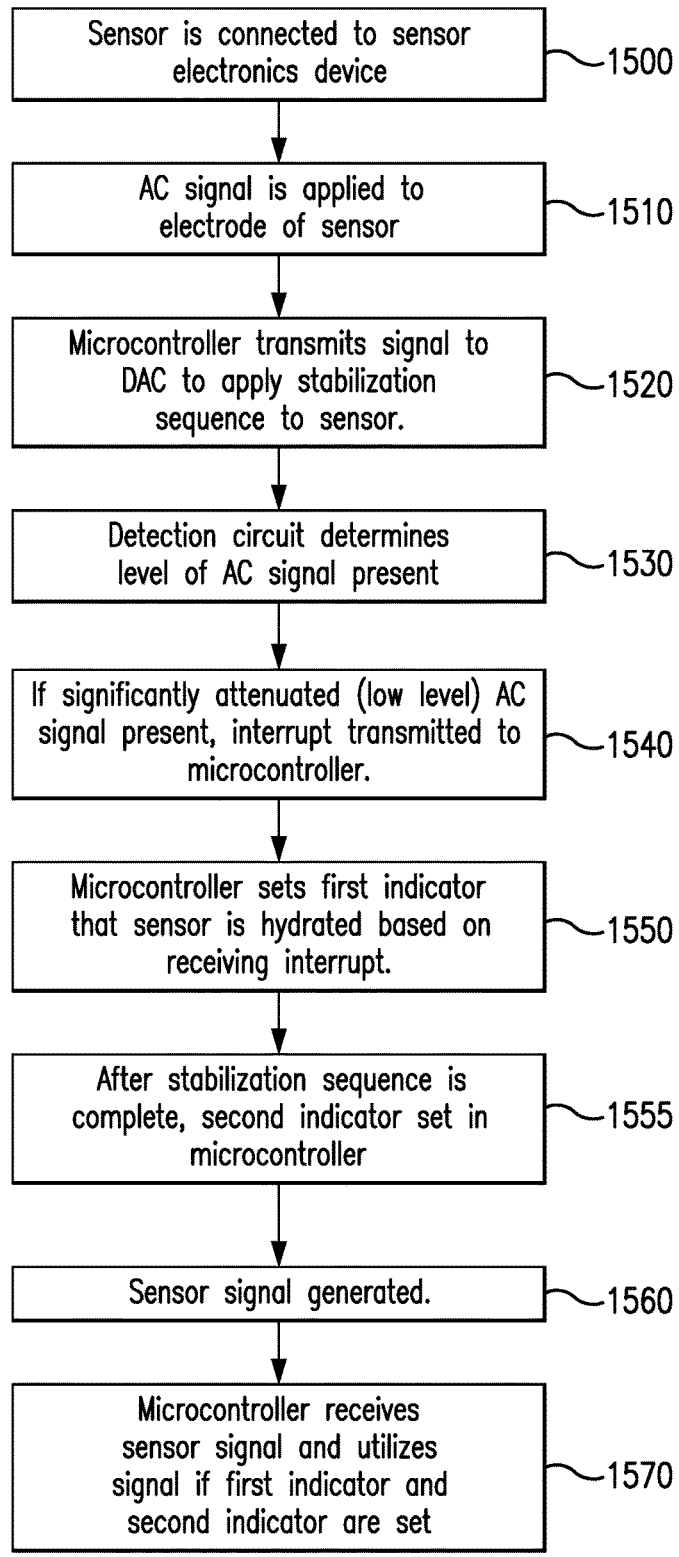

FIG. 14C illustrates a third embodiment of the invention where a stabilization method and hydration method are combined. In this embodiment of the invention, the sensor is connected 1500 to the sensor electronics device. After the sensor is physically connected to the sensor electronics device, an AC signal (or DC signal) is applied 1510 to an electrode (e.g., reference electrode) of the sensor. At the same time, or around the same time, the microcontroller transmits a signal to cause the DAC to apply 1520 a stabilization voltage sequence to the sensor. In an alternative embodiment of the invention, a stabilization current sequence may be applied to the sensor instead of a stabilization voltage sequence. The detection circuit determines 1530 what level of an AC signal (or DC signal) is present at an input terminal of the detection circuit. If there is a low level AC signal (or DC signal), representing a highly attenuated AC signal (or DC signal), present at the input terminal of the detection circuit, an interrupt is transmitted 1540 to the microcontroller. Because the microcontroller has already initiated the stabilization sequence, the microcontroller receives the interrupt and sets 1550 a first indicator that the sensor is sufficiently hydrated. After the stabilization sequence is complete, the microcontroller sets 1555 a second indicator indicating the completion of the stabilization sequence. The application of the stabilization sequence voltages results in the sensor, e.g., the working electrode, creating 1560 a sensor signal, which is measured by a sensor signal measuring circuit, and sent to the microcontroller. If the second indicator that the stabilization sequence is complete is set and the first indicator that the hydration is complete is set, the microcontroller is able to utilize 1570 the sensor signal. If one or both of the indicators are not set, the microcontroller may not utilize the sensor signal because the sensor signal may not represent accurate measurements of the physiological measurements of the subject.

The above-described hydration and stabilization processes may be used, in general, as part of a larger continuous glucose monitoring (CGM) methodology. The current state of the art in continuous glucose monitoring is largely adjunctive, meaning that the readings provided by a CGM device (including, e.g., an implantable or subcutaneous sensor) cannot be used without a reference value in order to make a clinical decision. The reference value, in turn, must be obtained from a finger stick using, e.g., a BG meter. The reference value is needed because there is a limited amount of information that is available from the sensor/sensing component. Specifically, the only pieces of information that are currently provided by the sensing component for processing are the raw sensor value (i.e., the sensor current or Isig) and the counter voltage, which is the voltage between the counter electrode and the reference electrode (see, e.g., FIG. 5). Therefore, during analysis, if it appears that the raw sensor signal is abnormal (e.g., if the signal is decreasing), the only way one can distinguish between a sensor failure and a physiological change within the user/patient (i.e., glucose level changing in the body) is by acquiring a reference glucose value via a finger stick. As is known, the reference finger stick is also used for calibrating the sensor.

Embodiments of the inventions described herein are directed to advancements and improvements in continuous glucose monitoring resulting in a more autonomous system, as well as related devices and methodologies, wherein the requirement of reference finger sticks may be minimized, or eliminated, and whereby clinical decisions may be made based on information derived from the sensor signal alone, with a high level of reliability. From a sensor-design standpoint, in accordance with embodiments of the present inventions, such autonomy may be achieved through electrode redundancy, sensor diagnostics, and Isig and/or sensor glucose (SG) fusion.

As will be explored further hereinbelow, redundancy may be achieved through the use of multiple working electrodes (e.g., in addition to a counter electrode and a reference electrode) to produce multiple signals indicative of the patient's blood glucose (BG) level. The multiple signals, in turn, may be used to assess the relative health of the (working) electrodes, the overall reliability of the sensor, and the frequency of the need, if at all, for calibration reference values.

Sensor diagnostics includes the use of additional (diagnostic) information which can provide a real-time insight into the health of the sensor. In this regard, it has been discovered that Electrochemical Impedance Spectroscopy (EIS) provides such additional information in the form of sensor impedance and impedance-related parameters at different frequencies. Moreover, advantageously, it has been further discovered that, for certain ranges of frequencies, impedance and/or impedance-related data are substantially glucose independent. Such glucose independence enables the use of a variety of EIS-based markers or indicators for not only producing a robust, highly-reliable sensor glucose value (through fusion methodologies), but also assessing the condition, health, age, and efficiency of individual electrode (s) and of the overall sensor substantially independently of the glucose-dependent Isig.

For example, analysis of the glucose-independent impedance data provides information on the efficiency of the sensor with respect to how quickly it hydrates and is ready for data acquisition using, e.g., values for 1 kHz real-impedance, 1 kHz imaginary impedance, and Nyquist Slope (to be described in more detail hereinbelow). Moreover, glucose-independent impedance data provides information on potential occlusion(s) that may exist on the sensor membrane surface, which occlusion(s) may temporarily block passage of glucose into the sensor and thus cause the signal to dip (using, e.g., values for 1 kHz real impedance). In addition, glucose-independent impedance data provides information on loss of sensor sensitivity during extended wear—potentially due to local oxygen deficit at the insertion site—using, e.g., values for phase angle and/or imaginary impedance at 1 kHz and higher frequencies.

Within the context of electrode redundancy and EIS, a fusion algorithm may be used to take the diagnostic information provided by EIS for each redundant electrode and assess the reliability of each electrode independently. Weights, which are a measure of reliability, may then be added for each independent signal, and a single fused signal may be calculated that can be used to generate sensor glucose values as seen by the patient/subject.

As can be seen from the above, the combined use of redundancy, sensor diagnostics using EIS, and EIS-based fusion algorithms allows for an overall CGM system that is more reliable than what is currently available. Redundancy is advantageous in at least two respects. First, redundancy removes the risk of a single point of failure by providing multiple signals. Second, providing multiple (working) electrodes where a single electrode may be sufficient allows the output of the redundant electrode to be used as a check against the primary electrode, thereby reducing, and perhaps eliminating, the need for frequent calibrations. In addition, EIS diagnostics scrutinize the health of each electrode autonomously without the need for a reference glucose value (finger stick), thereby reducing the number of reference values required. However, the use of EIS technology and EIS diagnostic methods is not limited to redundant systems, i.e., those having more than one working electrode. Rather, as will be discussed below in connection with embodiments of the present invention, EIS may be advantageously used in connection with single- and/or multiple-electrode sensors.

Figure 15A:
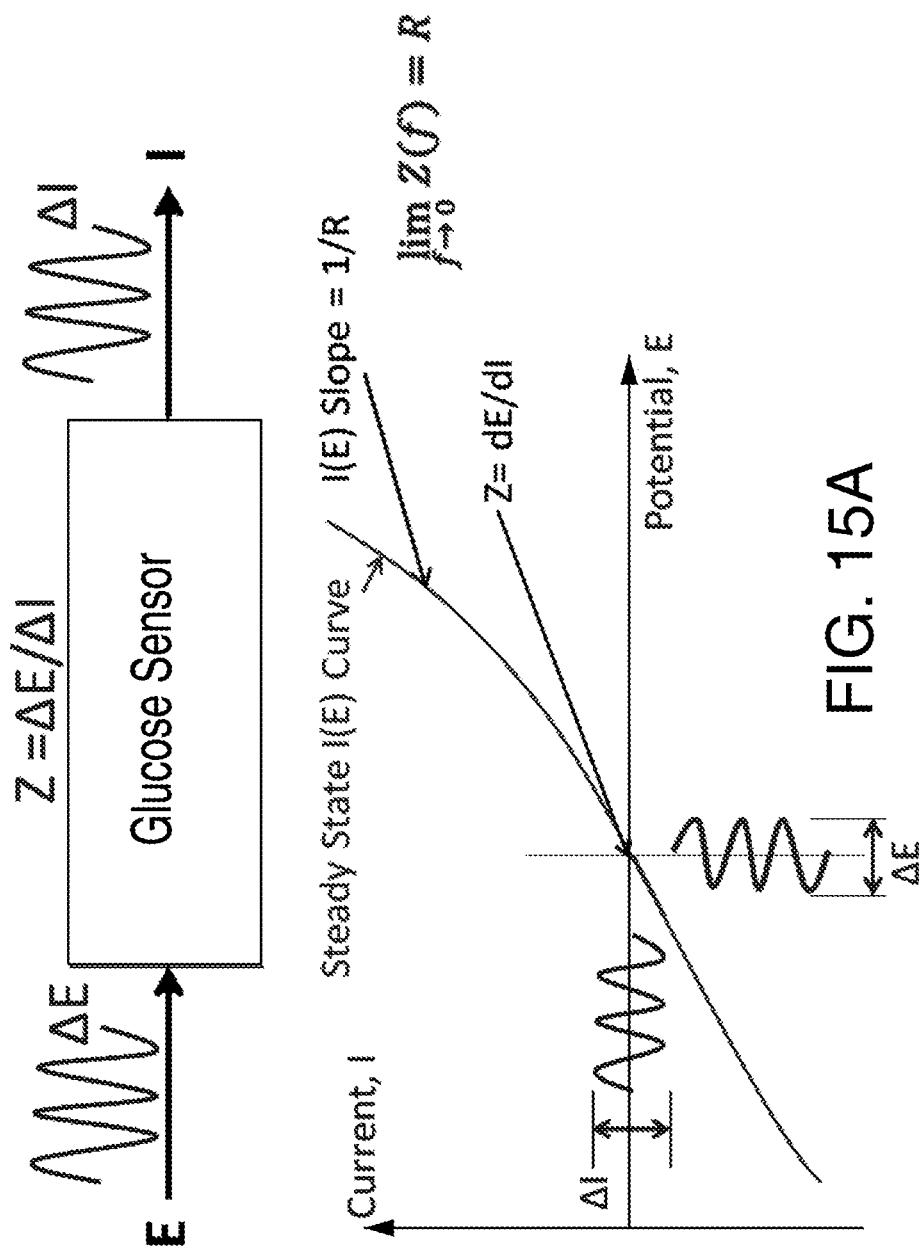
FIG. 15A illustrates EIS-based analysis of system response to the application of a periodic AC signal in accordance with embodiments of the invention.

EIS, or AC impedance methods, study the system response to the application of a periodic small amplitude AC signal. This is shown illustratively in FIG. 15A, where E is the applied potential, I is the current, and impedance (Z) is defined as $\Delta E/\Delta I$. However, although impedance, per se, may be mathematically simply defined as $\Delta E/\Delta I$, heretofore, there has been no commercialization success in application of EIS technology to continuous glucose monitoring. This has been due, in part, to the fact that glucose sensors are very complicated systems and, so far, no mathematical models have been developed which can completely explain the complexity of the EIS output for a glucose sensor.

Figure 15B:
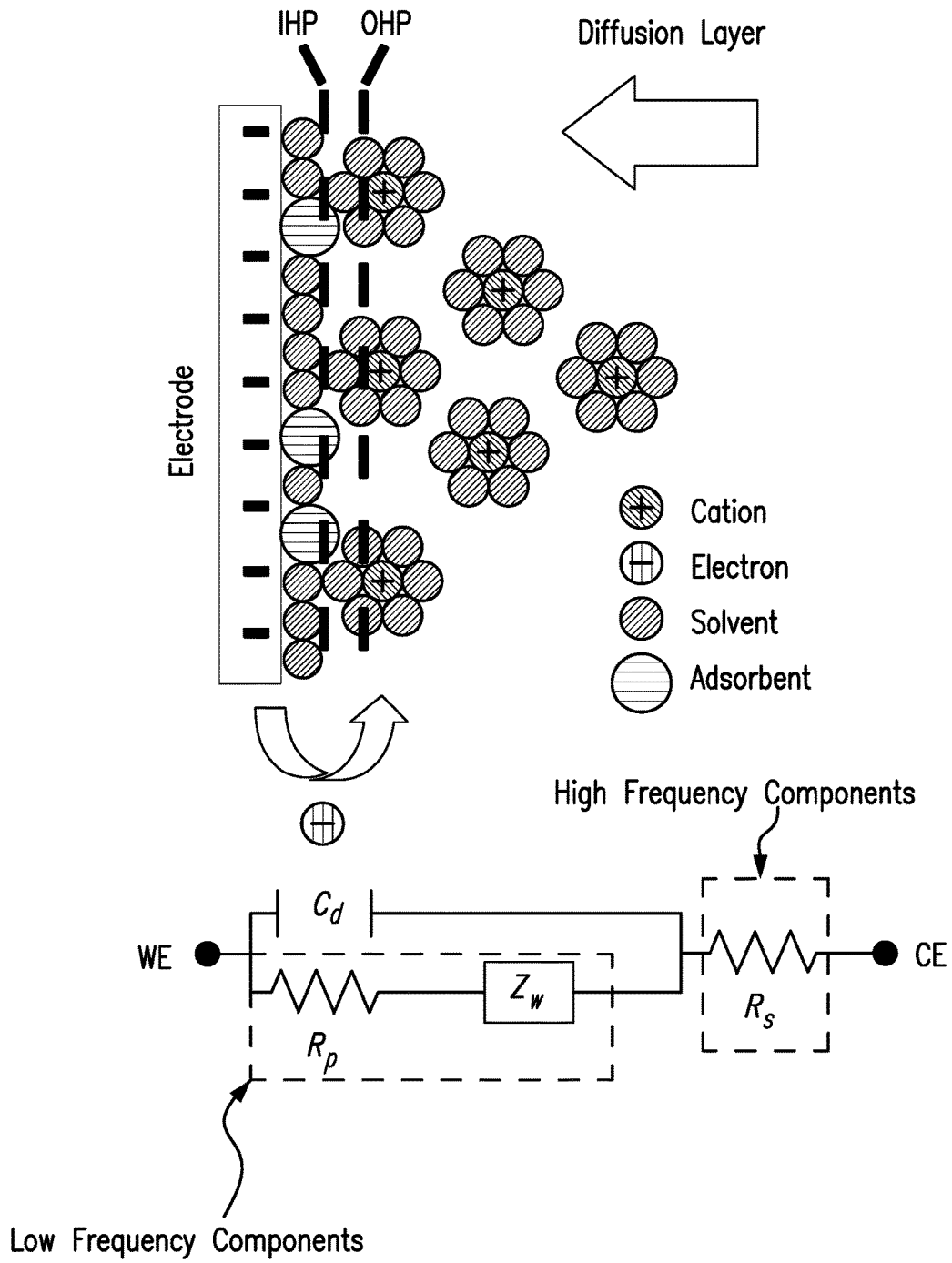
FIG. 15B illustrates a known circuit model for electrochemical impedance spectroscopy.

One simplified electrical circuit model that has been used to describe electrochemical impedance spectroscopy is shown in FIG. 15B. In this illustration, IHP stands for Inner Helmholtz Plane, OHP stands for Outer Helmholtz Plane, CE is the counter electrode, WE is the working electrode, $C_d$ is double layer capacitance, $R_p$ is polarization resistance, $Z_w$ is Warburg impedance, and $R_s$ is solution resistance. Each of the latter four components—double layer capacitance ($C_d$), Warburg impedance ($Z_w$), polarization resistance ($R_p$), and solution resistance ($R_s$)—may play a significant role in sensor performance, and can be measured separately by applying low- or high-frequency alternating working potential. For example, Warburg impedance is closely related to diffusional impedance of electrochemical systems—which is primarily a low-frequency impedance—and, as such, exists in all diffusion-limited electrochemical sensors. Thus, by correlating one or more of these components with one or more components and/or layers of a glucose sensor, one may use EIS technology as a sensor-diagnostics tool.

As is known, impedance may be defined in terms of its magnitude and phase, where the magnitude (|Z|) is the ratio of the voltage difference amplitude to the current amplitude, and the phase (θ) is the phase shift by which the current is ahead of the voltage. When a circuit is driven solely with direct current (DC), the impedance is the same as the resistant, i.e., resistance is a special case of impedance with zero phase angle. However, as a complex quantity, impedance may also be represented by its real and imaginary parts. In this regard, the real and imaginary impedance can be derived from the impedance magnitude and phase using the following equations:

Real Impedance(ω)=Magnitude(ω)×cos(Phase(ω)/180×π)

Imaginary Impedance(ω)=Magnitude(ω)×sin(Phase(ω)/180×π)

where ω represents the input frequency at which the magnitude (in ohms) and the phase (in degrees) are measured. The relationship between impedance, on the one hand, and current and voltage on the other—including how the former may be calculated based on measurement of the latter—will be explored more fully below in connection with the sensor electronics, including the Application Specific Integrated Circuit (ASIC), that has been developed for use in embodiments of the invention.

Continuing with the circuit model shown in FIG. 15B, total system impedance may be simplified as:

$$Z_t(\omega) = Z_w(\omega) + R_s + \frac{R_p}{1+\omega^2 R_p^2 C_d^2} - j\frac{\omega R_p^2 C_d}{1+\omega^2 R_p^2 C_d^2}$$

where $Z_w(\omega)$ is the Warburg impedance, ω is the angular velocity, j is the imaginary unit (used instead of the traditional "i" so as not to be confused with electric current), and $C_d$, $R_p$, and $R_s$ are the double layer capacitance, the polarization resistance, and the solution resistance, respectively (as defined previously). Warburg impedance can be calculated as $$Z_w(\omega) = Z_0 \frac{\tanh((js)^m)}{(js)^m}$$

$$s = \frac{L^2}{\omega/D} = \left(\frac{\text{Membrane Thickness}}{\text{Frequency Dependent Diffusion Length}}\right)^2$$

$$Z_0 = \frac{RTL}{n^2 F^2 DC}$$

where D is diffusivity, L is the sensor membrane thickness, C is Peroxide concentration, and m: ½ corresponds to a 45° Nyquist slope.

Figure 16A:
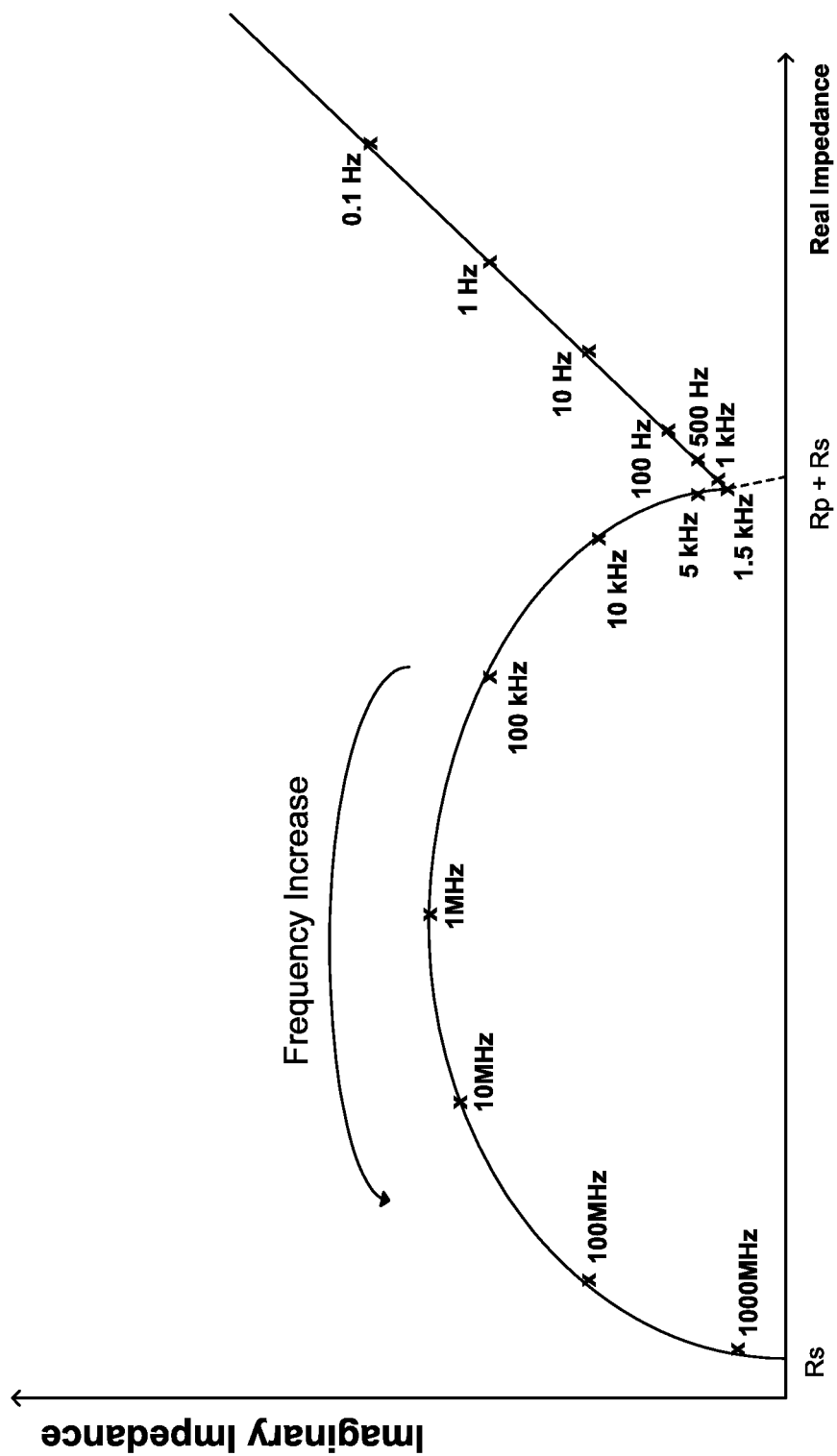
FIG. 16A illustrates an example of a Nyquist plot where, for a selected frequency spectrum from 0.1 Hz to 1000 Mhz, AC voltages plus a DC voltage (DC bias) are applied to the working electrode in accordance with embodiments of the invention.

A Nyquist plot is a graphical representation, wherein the real part of impedance (Real Z) is plotted against its imaginary part (Img Z) across a spectrum of frequencies. FIG. 16A shows a generalized example of a Nyquist Plot, where the X value is the real part of the impedance and the Y value is the imaginary part of the impedance. The phase angle is the angle between the impedance point (X, Y)—which defines a vector having magnitude |Z|—and the X axis.

The Nyquist plot of FIG. 16A is generated by applying AC voltages plus a DC voltage (DC bias) between the working electrode and the counter electrode at selected frequencies from 0.1 Hz to 1000 MHz (i.e., a frequency sweep). Starting from the right, the frequency increases from 0.1 Hz. With each frequency, the real and imaginary impedance can be calculated and plotted. As shown, a typical Nyquist plot of an electrochemical system may look like a semicircle joined with a straight line at an inflection point, wherein the semicircle and the line indicate the plotted impedance. In certain embodiments, the impedance at the inflection point is of particular interest since it is easiest to identify in the Nyquist plot and may define an intercept. Typically, the inflection point is close to the X axis, and the X value of the inflection point approximates the sum of the polarization resistance and solution resistance ($R_p$+$R_s$).

Figure 16B:
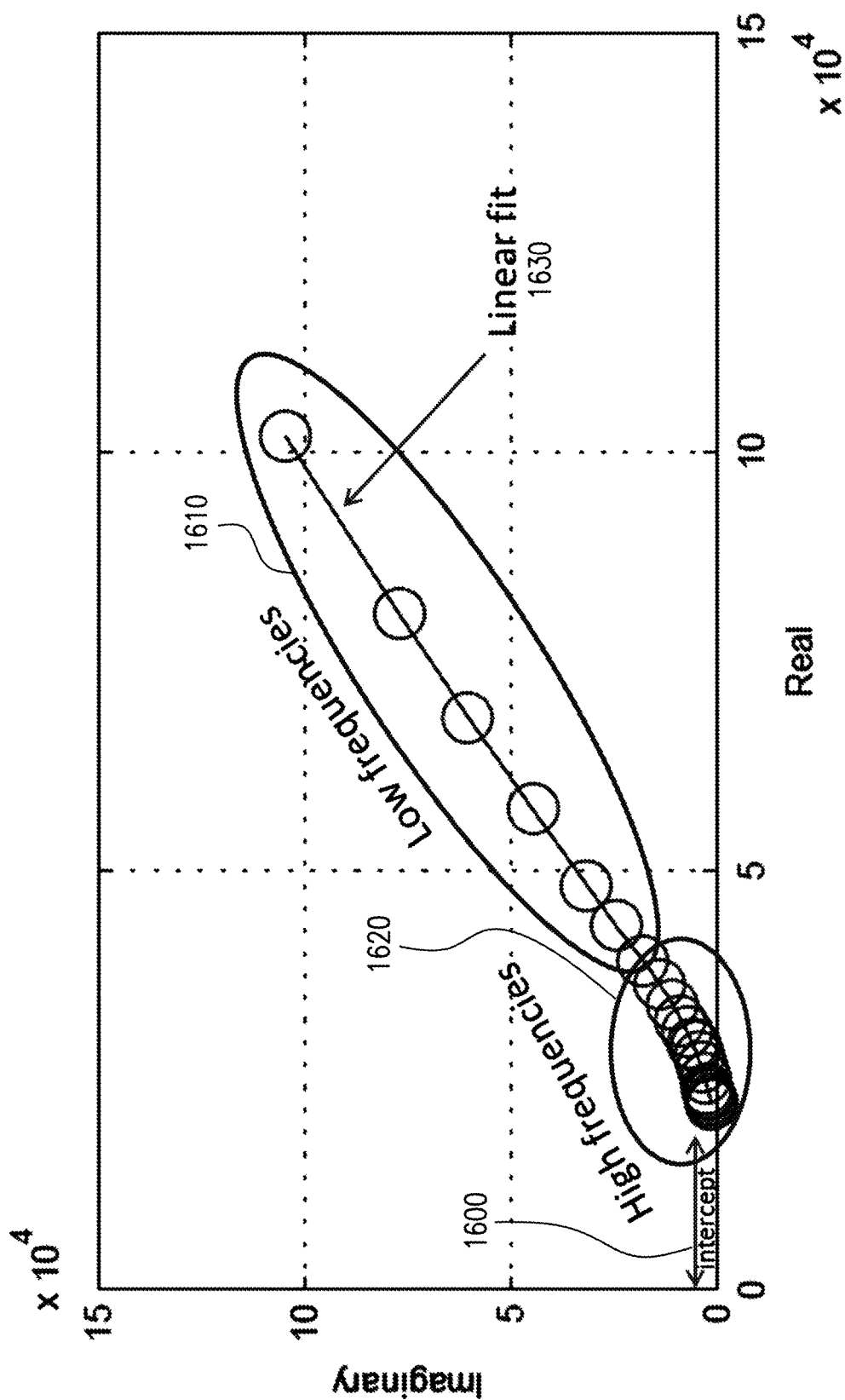
FIG. 16B shows another example of a Nyquist plot with a linear fit for the relatively-lower frequencies and the intercept approximating the value of real impedance at the relatively-higher frequencies.

With reference to FIG. 16B, a Nyquist plot may typically be described in terms of a lower-frequency region 1610 and a higher-frequency region 1620, where the labels "higher frequency" and "lower frequency" are used in a relative sense, and are not meant to be limiting. Thus, for example, the lower-frequency region 1610 may illustratively include data points obtained for a frequency range between about 0.1 Hz and about 100 Hz (or higher), and the higher-frequency region 1620 may illustratively include data points obtained for a frequency range between about 1 kHz (or lower) and about 8 kHz (and higher). In the lower-frequency region 1610, the Nyquist slope represents the gradient of the linear fit 1630 of the lower-frequency data points in the Nyquist plot. As shown, in the higher-frequencies region 1620, the value of imaginary impedance is minimal, and may become negligible. As such, the intercept 1600 is essentially the value of the real impedance at the higher frequencies (e.g., approximately in the 1 kHz to 8 kHz range in this case). In FIG. 16B, the intercept 1600 is at about 25 kOhms.

FIGS. 16C and 16D demonstrate how a glucose sensor responds to a sinusoidal (i.e., alternating) working potential. In these figures, GLM is the sensor's glucose limiting membrane, AP is the adhesion promoter, HSA is human serum albumin, GOX is glucose oxidase enzyme (layer), $E_{dc}$ is DC potential, $E_{ac}$ is AC potential, and $C'_{peroxide}$ is peroxide concentration during AC application. As shown in FIG. 16C, if the sensor diffusion length, which is a function of AC potential frequency, molecular diffusivity, and membrane thickness, is small compared to the membrane (GOX) length, the system gives a relatively linear response with a constant phase angle (i.e., infinite). In contrast, if the diffusion length is equal to the membrane (GOX) length, the system response will become finite, resulting in a semicircle Nyquist plot, as shown in FIG. 16D. The latter usually holds true for low-frequency EIS, where the non-Faradaic process is negligible.

In performing an EIS analysis, an AC voltage of various frequencies and a DC bias may be applied between, e.g., the working and reference electrodes. In this regard, EIS is an improvement over previous methodologies that may have limited the application to a simple DC current or an AC voltage of single frequency. Although, generally, EIS may be performed at frequencies in the μHz to MHz range, in embodiments of the present invention, a narrower range of frequencies (e.g., between about 0.1 Hz and about 8 kHz) may be sufficient. Thus, in embodiments of the invention, AC potentials may be applied that fall within a frequency range of between about 0.1 Hz and about 8 kHz, with a programmable amplitude of up to at least 100 mV, and preferably at about 50 mV.

Within the above-mentioned frequency range, the relatively-higher frequencies—i.e., those that fall generally between about 1 kHz and about 8 kHz—are used to scrutinize the capacitive nature of the sensor. Depending on the thickness and permeability of membranes, a typical range of impedance at the relatively-higher frequencies may be, e.g., between about 500 Ohms and 25 kOhms, and a typical range for the phase may be, e.g., between 0 degrees and −40 degrees. The relatively-lower frequencies—i.e., those that fall generally between about 0.1 Hz and about 100 Hz—on the other hand, are used to scrutinize the resistive nature of the sensor. Here, depending on electrode design and the extent of metallization, a typical functioning range for output real impedance may be, e.g., between about 50 kOhms and 300 kOhms, and a typical range for the phase may be between about −50 degrees to about −90 degrees. The above illustrative ranges are shown, e.g., in the Bode plots of FIGS. 16E and 16F.

As noted previously, the phrases "higher frequencies" and "lower frequencies" are meant to be used relative to one another, rather than in an absolute sense, and they, as well as the typical impedance and phase ranges mentioned above, are meant to be illustrative, and not limiting. Nevertheless, the underlying principle remains the same: the capacitive and resistive behavior of a sensor can be scrutinized by analyzing the impedance data across a frequency spectrum, wherein, typically, the lower frequencies provide information about the more resistive components (e.g., the electrode, etc.), while the higher frequencies provide information about the capacitive components (e.g., membranes). However, the actual frequency range in each case is dependent on the overall design, including, e.g., the type(s) of electrode(s), the surface area of the electrode(s), membrane thickness, the permeability of the membrane, and the like. See also FIG. 15B regarding general correspondence between high-frequency circuit components and the sensor membrane, as well as between low-frequency circuit components and the Faradaic process, including, e.g., the electrode(s).

Figure 17:
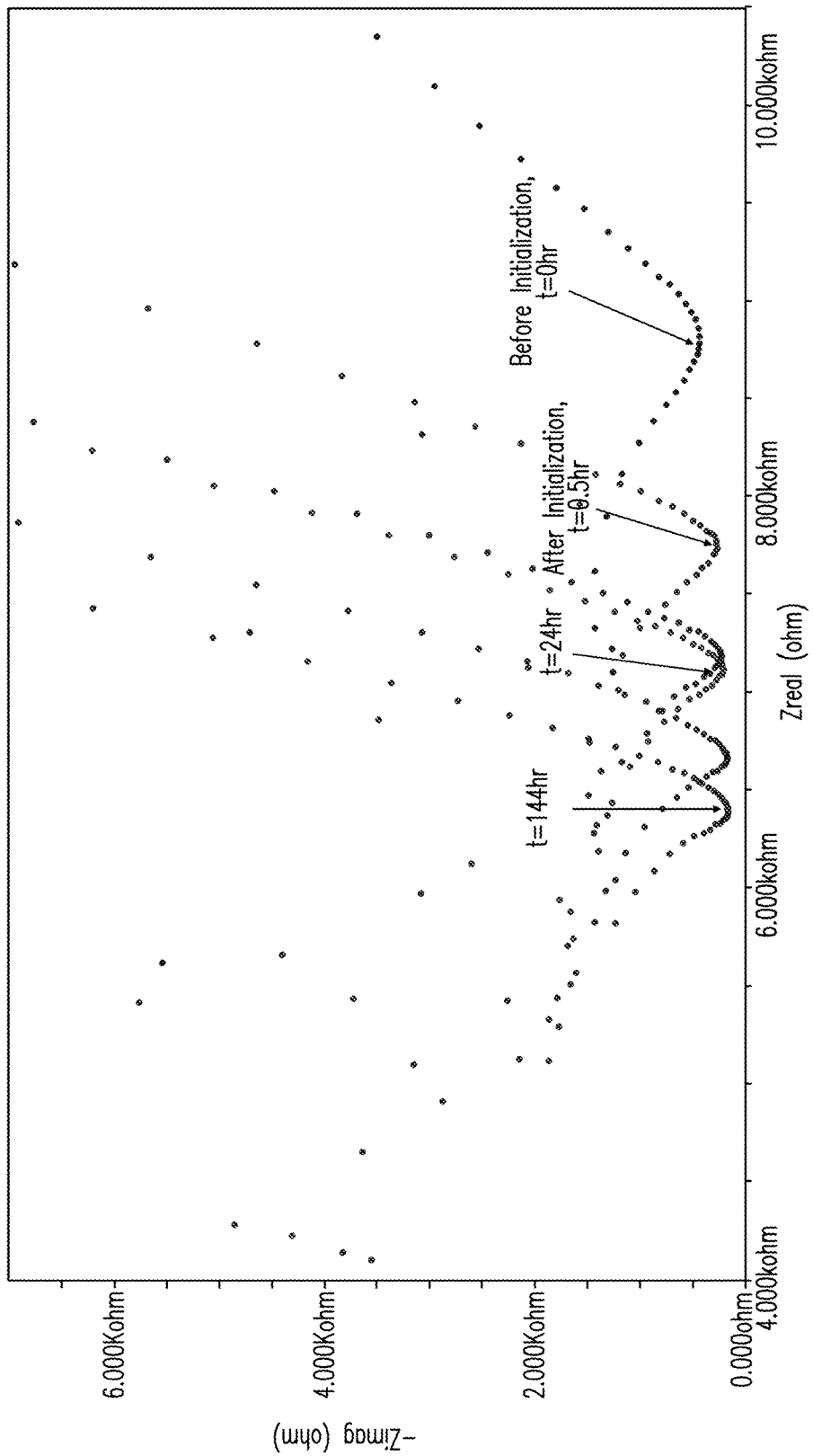
FIG. 17 illustrates the changing Nyquist plot of sensor impedance as the sensor ages in accordance with embodiments of the invention.

EIS may be used in sensor systems where the sensor includes a single working electrode, as well those in which the sensor includes multiple (redundant) working electrodes. In one embodiment, EIS provides valuable information regarding the age (or aging) of the sensor. Specifically, at different frequencies, the magnitude and the phase angle of the impedance vary. As seen in FIG. 17, the sensor impedance—in particular, the sum of Rp and Rs—reflects the sensor age as well as the sensor's operating conditions. Thus, a new sensor normally has higher impedance than a used sensor as seen from the different plots in FIG. 17. In this way, by considering the X-value of the sum of Rp and Rs, a threshold can be used to determine when the sensor's age has exceeded the specified operating life of the sensor. It is noted that, although for the illustrative examples shown in FIGS. 17-21 and discussed below, the value of real impedance at the inflection point (i.e., Rp+Rs) is used to determine the aging, status, stabilization, and hydration of the sensor, alternative embodiments may use other EIS-based parameters, such as, e.g., imaginary impedance, phase angle, Nyquist slope, etc. in addition to, or in place of, real impedance.

FIG. 17 illustrates an example of a Nyquist plot over the life time of a sensor. The points indicated by arrows are the respective inflection points for each of the sweeps across the frequency spectrum. For example, before initialization (at time t=0), Rs+Rp is higher than 8.5 kOhms, and after initialization (at time t=0.5 hr), the value of Rs+Rp dropped to below 8 kOhms. Over the next six days, Rs+Rp continues to decrease, such that, at the end of the specified sensor life, Rs+Rp dropped to below 6.5 kOhms. Based on such examples, a threshold value can be set to specify when the Rs+Rp value would indicate the end of the specified operating life of the sensor. Therefore, the EIS technique allows closure of the loophole of allowing a sensor to be re-used beyond the specified operating time. In other words, if the patient attempts to re-use a sensor after the sensor has reached its specified operating time by disconnecting and then re-connecting the sensor again, the EIS will measure abnormally-low impedance, thereby enabling the system to reject the sensor and prompt the patient for a new sensor.

Additionally, EIS may enable detection of sensor failure by detecting when the sensor's impedance drops below a low impedance threshold level indicating that the sensor may be too worn to operate normally. The system may then terminate the sensor before the specified operating life. As will be explored in more detail below, sensor impedance can also be used to detect other sensor failure (modes). For example, when a sensor goes into a low-current state (i.e., sensor failure) due to any variety of reasons, the sensor impedance may also increase beyond a certain high impedance threshold. If the impedance becomes abnormally high during sensor operation, due, e.g., to protein or polypeptide fouling, macrophage attachment or any other factor, the system may also terminate the sensor before the specified sensor operating life.

Figure 18:
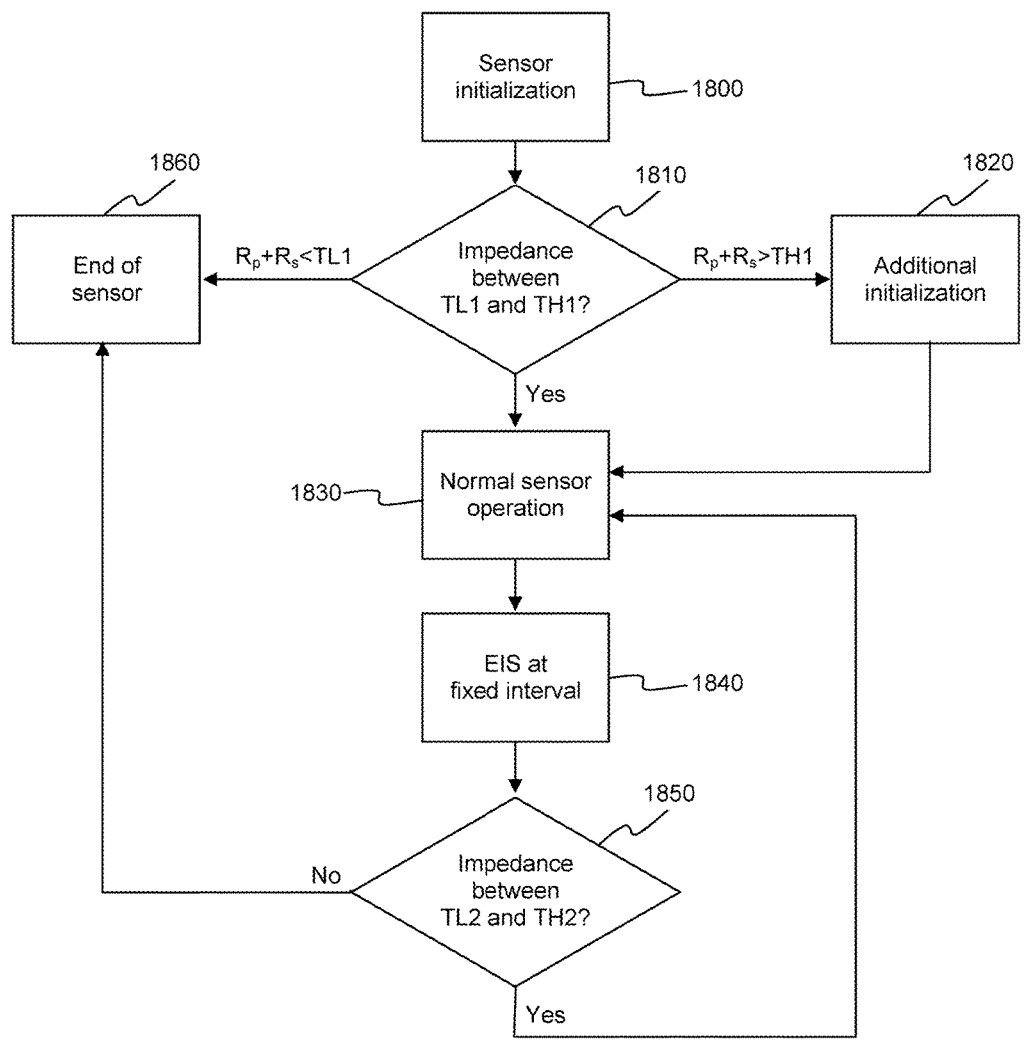
FIG. 18 illustrates methods of applying EIS technique in stabilizing and detecting the age of the sensor in accordance with embodiments of the invention.

FIG. 18 illustrates how the EIS technique can be applied during sensor stabilization and in detecting the age of the sensor in accordance with embodiments of the present invention. The logic of FIG. 18 begins at 1800 after the hydration procedure and sensor initialization procedure described previously has been completed. In other words, the sensor has been deemed to be sufficiently hydrated, and the first initialization procedure has been applied to initialize the sensor. The initialization procedure may preferably be in the form of voltage pulses as described previously in the detailed description. However, in alternative embodiments, different waveforms can be used for the initialization procedure. For example, a sine wave can be used, instead of the pulses, to accelerate the wetting or conditioning of the sensor. In addition, it may be necessary for some portion of the waveform to be greater than the normal operating voltage of the sensor, i.e., 0.535 volt.

At block 1810, an EIS procedure is applied and the impedance is compared to both a first high and a first low threshold. An example of a first high and first low threshold value would be 7 kOhms and 8.5 kOhms, respectively, although the values can be set higher or lower as needed. If the impedance, for example, Rp+Rs, is higher than the first high threshold, the sensor undergoes an additional initialization procedure (e.g., the application of one or more additional pulses) at block 1820. Ideally, the number of total initialization procedures applied to initialize the sensor would be optimized to limit the impact on both the battery life of the sensor and the overall amount of time needed to stabilize a sensor. Thus, by applying EIS, fewer initializations can be initially performed, and the number of initializations can be incrementally added to give just the right amount of initializations to ready the sensor for use. Similarly, in an alternative embodiment, EIS can be applied to the hydration procedure to minimize the number of initializations needed to aid the hydration process as described in FIGS. 13-14.

On the other hand, if the impedance, for example, Rp+Rs, is below the first low threshold, the sensor will be determined to be faulty and would be terminated immediately at block 1860. A message will be given to the user to replace the sensor and to begin the hydration process again. If the impedance is within the high and low thresholds, the sensor will begin to operate normally at block 1830. The logic than proceeds to block 1840 where an additional EIS is performed to check the age of the sensor. The first time the logic reaches block 1840, the microcontroller will perform an EIS to gauge the age of the sensor to close the loophole of the user being able to plug in and plug out the same sensor. In future iterations of the EIS procedure as the logic returns to block 1840, the microprocessor will perform an EIS at fixed intervals during the specified life of the sensor. In one preferred embodiment, the fixed interval is set for every 2 hours, however, longer or shorter periods of time can easily be used.

At block 1850, the impedance is compared to a second set of high and low thresholds. An example of such second high and low threshold values may be 5.5 kOhms and 8.5 kOhms, respectively, although the values can be set higher or lower as needed. As long as the impedance values stay within a second high and low threshold, the logic proceeds to block 1830, where the sensor operates normally until the specified sensor life, for example, 5 days, is reached. Of course, as described with respect to block 1840, EIS will be performed at the regularly scheduled intervals throughout the specified sensor life. However, if, after the EIS is performed, the impedance is determined to have dropped below a second lower threshold or risen above a second higher threshold at block 1850, the sensor is terminated at block 1860. In further alternative embodiments, a secondary check can be implemented of a faulty sensor reading. For example, if the EIS indicates that the impedance is out of the range of the second high and low thresholds, the logic can perform a second EIS to confirm that the second set of thresholds is indeed not met (and confirm that the first EIS was correctly performed) before determining the end of sensor at block 1860.

Figure 19:
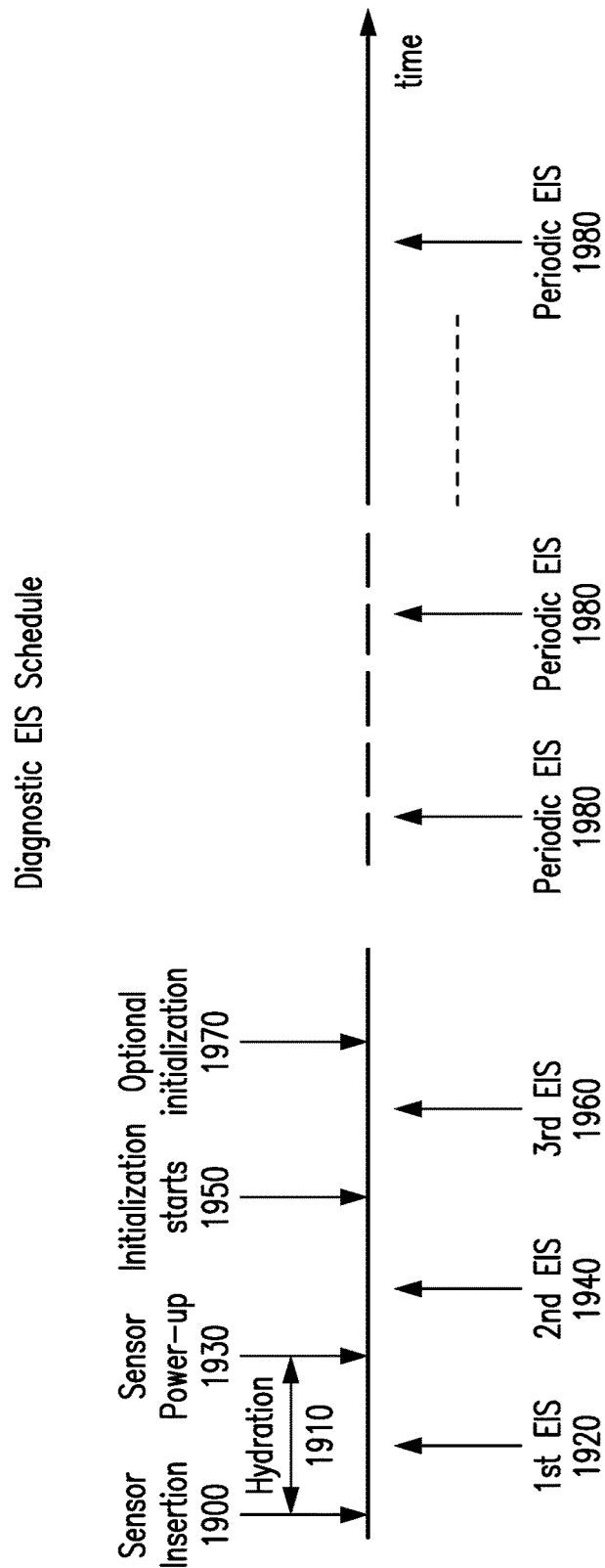
FIG. 19 illustrates a schedule for performing the EIS procedure in accordance with embodiments of the invention.

FIG. 19 builds upon the above description and details a possible schedule for performing diagnostic EIS procedures in accordance with preferred embodiments of the present invention. Each diagnostic EIS procedure is optional and it is possible to not schedule any diagnostic EIS procedure or to have any combination of one or more diagnostic EIS procedures, as deemed needed. The schedule of FIG. 19 begins at sensor insertion at point 1900. Following sensor insertion, the sensor undergoes a hydration period 1910. This hydration period is important because a sensor that is not sufficiently hydrated may give the user inaccurate readings, as described previously. The first optional diagnostic EIS procedure at point 1920 is scheduled during this hydration period 1910 to ensure that the sensor is sufficiently hydrated. The first diagnostic EIS procedure 1920 measures the sensor impedance value to determine if the sensor has been sufficiently hydrated. If the first diagnostic EIS procedure 1920 determines impedance is within a set high and low threshold, indicating sufficient hydration, the sensor controller will allow the sensor power-up at point 1930. Conversely, if the first diagnostic EIS procedure 1920 determines impedance is outside a set high and low threshold, indicating insufficient hydration, the sensor hydration period 1910 may be prolonged. After prolonged hydration, once a certain capacitance has been reached between the sensor's electrodes, meaning the sensor is sufficiently hydrated, power-up at point 1930 can occur.

A second optional diagnostic EIS procedure 1940 is scheduled after sensor power-up at point 1930, but before sensor initialization starts at point 1950. Scheduled here, the second diagnostic EIS procedure 1940 can detect if a sensor is being re-used prior to the start of initialization at 1950. The test to determine if the sensor is being reused was detailed in the description of FIG. 18. However, unlike the previous description with respect to FIG. 18, where the aging test is performed after initialization is completed, the aging test is shown in FIG. 19 as being performed before initialization. It is important to appreciate that the timeline of EIS procedures described in FIG. 19 can be rearranged without affecting the overall teaching of the application, and that the order of some of the steps can be interchanged. As explained previously, the second diagnostic EIS procedure 1940 detects a re-used sensor by determining the sensor's impedance value and then comparing it to a set high and low threshold. If impedance falls outside of the set threshold, indicating the sensor is being re-used, the sensor may then be rejected and the user prompted to replace it with a new sensor. This prevents the complications that may arise out of re-use of an old sensor. Conversely, if impedance falls within a set threshold, sensor initialization 1950 can start with the confidence that a new sensor is being used.

A third optional diagnostic EIS procedure 1960 is scheduled after initialization starts at point 1950. The third diagnostic EIS procedure 1960 tests the sensor's impedance value to determine if the sensor is fully initialized. The third diagnostic EIS procedure 1960 should be performed at the minimum amount of time needed for any sensor to be fully initialized. When performed at this time, sensor life is maximized by limiting the time a fully initialized sensor goes unused, and over-initialization is averted by confirming full initialization of the sensor before too much initialization occurs. Preventing over-initialization is important because over-initialization results in a suppressed current which can cause inaccurate readings. However, under-initialization is also a problem, so if the third diagnostic EIS procedure 1960 indicates the sensor is under-initialized, an optional initialization at point 1970 may be performed in order to fully initialize the sensor. Under-initialization is disadvantageous because an excessive current results that does not relate to the actual glucose concentration. Because of the danger of under- and over-initialization, the third diagnostic EIS procedure plays an important role in ensuring the sensor functions properly when used.

In addition, optional periodic diagnostic EIS procedures 1980 can be scheduled for the time after the sensor is fully initialized. The EIS procedures 1980 can be scheduled at any set interval. As will be discussed in more detail below, EIS procedures 1980 may also be triggered by other sensor signals, such as an abnormal current or an abnormal counter electrode voltage. Additionally, as few or as many EIS procedures 1980 can be scheduled as desired. In preferred embodiments, the EIS procedure used during the hydration process, sensor life check, initialization process, or the periodic diagnostic tests is the same procedure. In alternative embodiments, the EIS procedure can be shortened or lengthened (i.e., fewer or more ranges of frequencies checked) for the various EIS procedures depending on the need to focus on specific impedance ranges. The periodic diagnostic EIS procedures 1980 monitor impedance values to ensure that the sensor is continuing to operate at an optimal level.

The sensor may not be operating at an optimal level if the sensor current has dropped due to polluting species, sensor age, or a combination of polluting species and sensor age. A sensor that has aged beyond a certain length is no longer useful, but a sensor that has been hampered by polluting species can possibly be repaired. Polluting species can reduce the surface area of the electrode or the diffusion pathways of analytes and reaction byproducts, thereby causing the sensor current to drop. These polluting species are charged and gradually gather on the electrode or membrane surface under a certain voltage. Previously, polluting species would destroy the usefulness of a sensor. Now, if periodic diagnostic EIS procedures 1980 detect impedance values which indicate the presence of polluting species, remedial action can be taken. When remedial action is to be taken is described with respect to FIG. 20. Periodic diagnostic EIS procedures 1980 therefore become extremely useful because they can trigger sensor remedial action which can possibly restore the sensor current to a normal level and prolong the life of the sensor. Two possible embodiments of sensor remedial actions are described below in the descriptions of FIGS. 21A and 21B.

Additionally, any scheduled diagnostic EIS procedure 1980 may be suspended or rescheduled when certain events are determined imminent. Such events may include any circumstance requiring the patient to check the sensor reading, including for example when a patient measures his or her BG level using a test strip meter in order to calibrate the sensor, when a patient is alerted to a calibration error and the need to measure his or her BG level using a test strip meter a second time, or when a hyperglycemic or hypoglycemic alert has been issued but not acknowledged.

Figure 20:
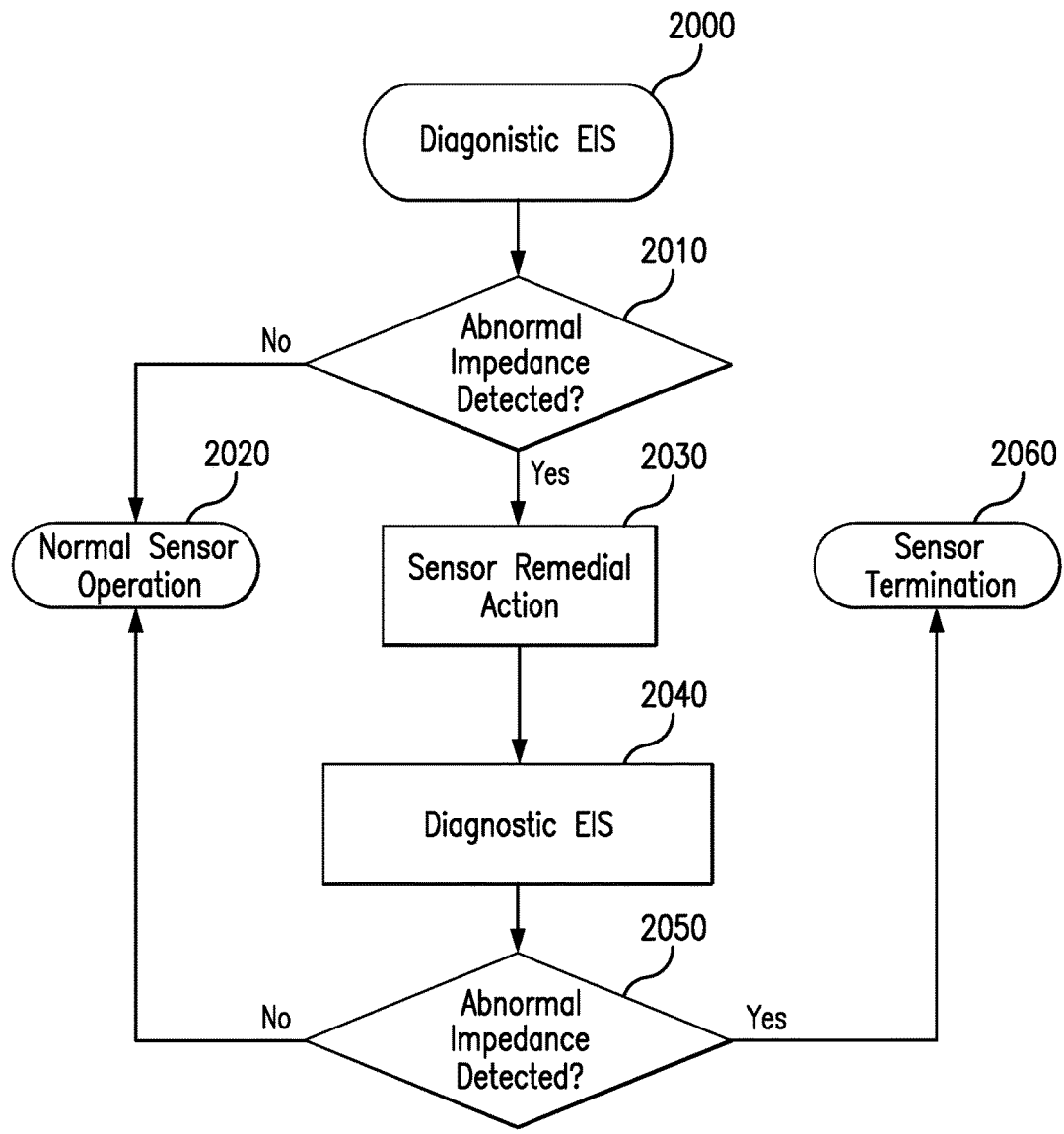
FIG. 20 illustrates a method of detecting and repairing a sensor using EIS procedures in conjunction with remedial action in accordance with embodiments of the invention.

FIG. 20 illustrates a method of combining diagnostic EIS procedures with sensor remedial action in accordance with embodiments of the present invention. The block 2000 diagnostic procedure may be any of the periodic diagnostic EIS procedures 1980 as detailed in FIG. 19. The logic of this method begins when a diagnostic EIS procedure is performed at block 2000 in order to detect the sensor's impedance value. As noted, in specific embodiments, the EIS procedure applies a combination of a DC bias and an AC voltage of varying frequencies wherein the impedance detected by performing the EIS procedure is mapped on a Nyquist plot, and an inflection point in the Nyquist plot approximates a sum of polarization resistance and solution resistance (i.e., the real impedance value). After the block 2000 diagnostic EIS procedure detects the sensor's impedance value, the logic moves to block 2010.

At block 2010, the impedance value is compared to a set high and low threshold to determine if it is normal. If impedance is within the set boundaries of the high and low thresholds at block 2010, normal sensor operation is resumed at block 2020 and the logic of FIG. 20 will end until a time when another diagnostic EIS procedure is scheduled. Conversely, if impedance is determined to be abnormal (i.e., outside the set boundaries of the high and low thresholds) at block 2010, remedial action at block 2030 is triggered. An example of a high and low threshold value that would be acceptable during a sensor life would be 5.5 kOhms and 8.5 kOhms, respectively, although the values can be set higher or lower as needed.

The block 2030 remedial action is performed to remove any of the polluting species, which may have caused the abnormal impedance value. In preferred embodiments, the remedial action is performed by applying a reverse current, or a reverse voltage between the working electrode and the reference electrode. The specifics of the remedial action will be described in more detail with respect to FIG. 21. After the remedial action is performed at block 2030, impedance value is again tested by a diagnostic EIS procedure at block 2040. The success of the remedial action is then determined at block 2050 when the impedance value from the block 2040 diagnostic EIS procedure is compared to the set high or low threshold. As in block 2010, if impedance is within the set thresholds, it is deemed normal, and if impedance is outside the set thresholds, it is deemed abnormal.

If the sensor's impedance value is determined to have been restored to normal at block 2050, normal sensor operation at block 2020 will occur. If impedance is still not normal, indicating that either sensor age is the cause of the abnormal impedance or the remedial action was unsuccessful in removing the polluting species, the sensor is then terminated at block 2060. In alternative embodiments, instead of immediately terminating the sensor, the sensor may generate a sensor message initially requesting the user to wait and then perform further remedial action after a set period of time has elapsed. This alternative step may be coupled with a separate logic to determine if the impedance values are getting closer to being within the boundary of the high and low threshold after the initial remedial action is performed. For example, if no change is found in the sensor impedance values, the sensor may then decide to terminate. However, if the sensor impedance values are getting closer to the preset boundary, yet still outside the boundary after the initial remedial action, an additional remedial action could be performed. In yet another alternative embodiment, the sensor may generate a message requesting the user to calibrate the sensor by taking a finger stick meter measurement to further confirm whether the sensor is truly failing. All of the above embodiments work to prevent a user from using a faulty sensor that produces inaccurate readings.

FIG. 21A illustrates one embodiment of the sensor remedial action previously mentioned. In this embodiment, blockage created by polluting species is removed by reversing the voltage being applied to the sensor between the working electrode and the reference electrode. The reversed DC voltage lifts the charged, polluting species from the electrode or membrane surface, clearing diffusion pathways. With cleared pathways, the sensor's current returns to a normal level and the sensor can give accurate readings. Thus, the remedial action saves the user the time and money associated with replacing an otherwise effective sensor.

FIG. 21B illustrates an alternative embodiment of the sensor remedial action previously mentioned. In this embodiment, the reversed DC voltage applied between the working electrode and the reference electrode is coupled with an AC voltage. By adding the AC voltage, certain tightly absorbed species or species on the superficial layer can be removed since the AC voltage can extend its force further from the electrode and penetrate all layers of the sensor. The AC voltage can come in any number of different waveforms. Some examples of waveforms that could be used include square waves, triangular waves, sine waves, or pulses. As with the previous embodiment, once polluting species are cleared, the sensor can return to normal operation, and both sensor life and accuracy are improved.

While the above examples illustrate the use, primarily, of real impedance data in sensor diagnostics, embodiments of the invention are also directed to the use of other EIS-based, and substantially analyte-independent, parameters (in addition to real impedance) in sensor diagnostic procedures. For example, as mentioned previously, analysis of (substantially) glucose-independent impedance data, such as, e.g., values for 1 kHz real-impedance and 1 kHz imaginary impedance, as well as Nyquist slope, provide information on the efficiency of the sensor with respect to how quickly it hydrates and is ready for data acquisition. Moreover, (substantially) glucose-independent impedance data, such as, e.g., values for 1 kHz real impedance, provides information on potential occlusion(s) that may exist on the sensor membrane surface, which occlusion(s) may temporarily block passage of glucose into the sensor and thus cause the signal to dip.

In addition, (substantially) glucose-independent impedance data, such as, e.g., values for higher-frequency phase angle and/or imaginary impedance at 1 kHz and higher frequencies, provides information on loss of sensor sensitivity during extended wear, which sensitivity loss may potentially be due to local oxygen deficit at the insertion site. In this regard, the underlying mechanism for oxygen deficiency-led sensitivity loss may be described as follows: when local oxygen is deficient, sensor output (i.e., Isig and SG) will be dependent on oxygen rather than glucose and, as such, the sensor will lose sensitivity to glucose. Other markers, including 0.1 Hz real impedance, the counter electrode voltage (Vcntr), and EIS-induced spikes in the Isig may also be used for the detection of oxygen deficiency-led sensitivity loss. Moreover, in a redundant sensor system, the relative differences in 1 kHz real impedance, 1 kHz imaginary impedance, and 0.1 Hz real impedance between two or more working electrodes may be used for the detection of sensitivity loss due to biofouling.

In accordance with embodiments of the invention, EIS-based sensor diagnostics entails consideration and analysis of EIS data relating to one or more of at least three primary factors, i.e., potential sensor failure modes: (1) signal start-up; (2) signal dip; and (3) sensitivity loss. Significantly, the discovery herein that a majority of the impedance-related parameters that are used in such diagnostic analyses and procedures can be studied at a frequency, or within a range of frequencies, where the parameter is substantially analyte-independent allows for implementation of sensor-diagnostic procedures independently of the level of the analyte in a patient's body. Thus, while EIS-based sensor diagnostics may be triggered by, e.g., large fluctuations in Isig, which is analyte-dependent, the impedance-related parameters that are used in such sensor diagnostic procedures are themselves substantially independent of the level of the analyte. As will be explored in more detail below, it has also been found that, in a majority of situations where glucose may be seen to have an effect on the magnitude (or other characteristic) of an EIS-based parameter, such effect is usually small enough—e.g., at least an order of magnitude difference between the EIS-based measurement and the glucose effect thereon—such that it can be filtered out of the measurement, e.g., via software in the IC.

By definition, "start-up" refers to the integrity of the sensor signal during the first few hours (e.g., t=0-6 hours) after insertion. For example, in current devices, the signal during the first 2 hours after insertion is deemed to be unreliable and, as such, the sensor glucose values are blinded to the patient/user. In situations where the sensor takes an extended amount of time to hydrate, the sensor signal is low for several hours after insertion. With the use of EIS, additional impedance information is available (by running an EIS procedure) right after the sensor has been inserted. In this regard, the total impedance equation may be used to explain the principle behind low-startup detection using 1 kHz real impedance. At relatively higher frequencies—in this case, 1 kHz and above—imaginary impedance is very small (as confirmed with in-vivo data), such that total impedance reduces to:

$$Z_t(\omega) = R_s + \frac{R_p}{1 + \omega^2 R_p^2 C_d^2}$$

As sensor wetting is gradually completed, the double layer capacitance ($C_d$) increases. As a result, the total impedance will decrease because, as indicated in the equation above, total impedance is inversely proportional to $C_d$. This is illustrated in the form of the intercept 1600 on the real impedance axis shown, e.g., in FIG. 16B. Importantly, the 1 kHz imaginary impedance can also be used for the same purpose, as it also includes, and is inversely proportional to, a capacitance component.

Figure 22:
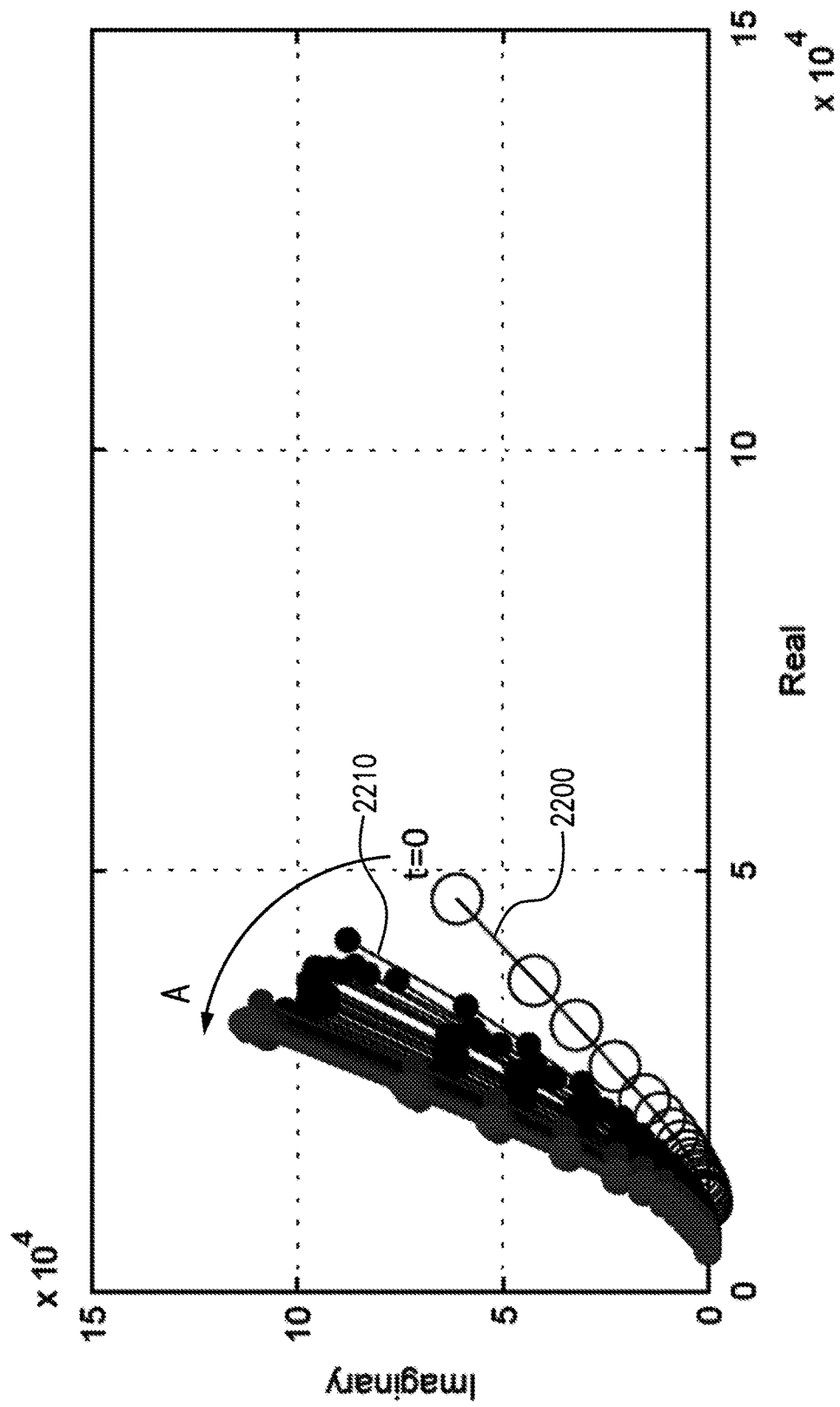
FIG. 22 shows a Nyquist plot for a normally-functioning sensor where the Nyquist slope gradually increases, and the intercept gradually decreases, as the sensor wear-time progresses.

Another marker for low startup detection is Nyquist slope, which relies solely on the relatively lower-frequency impedance which, in turn, corresponds to the Warburg impedance component of total impedance (see, e.g., FIG. 15B). FIG. 22 shows a Nyquist plot for a normally-functioning sensor, where Arrow A is indicative of the progression of time, i.e., sensor wear time, starting from t=0. Thus, EIS at the relatively-lower frequencies is performed right after sensor insertion (time t=0), which generates real and imaginary impedance data that is plotted with a first linear fit 2200 having a first (Nyquist) slope. At a time interval after t=0, a second (lower) frequency sweep is run that produces a second linear fit 2210 having a second (Nyquist) slope larger than the first Nyquist slope, and so on. As the sensor becomes more hydrated, the Nyquist slope increases, and the intercept decrease, as reflected by the lines 2200, 2210, etc. becoming steeper and moving closer to the Y-axis. In connection with low startup detection, clinical data indicates that there is typically a dramatic increase of Nyquist slope after sensor insertion and initialization, which is then stabilized to a certain level. One explanation for this is that, as the sensor is gradually wetted, the species diffusivity as well as concentration undergo dramatic change, which is reflected in Warburg impedance.

Figure 23A:
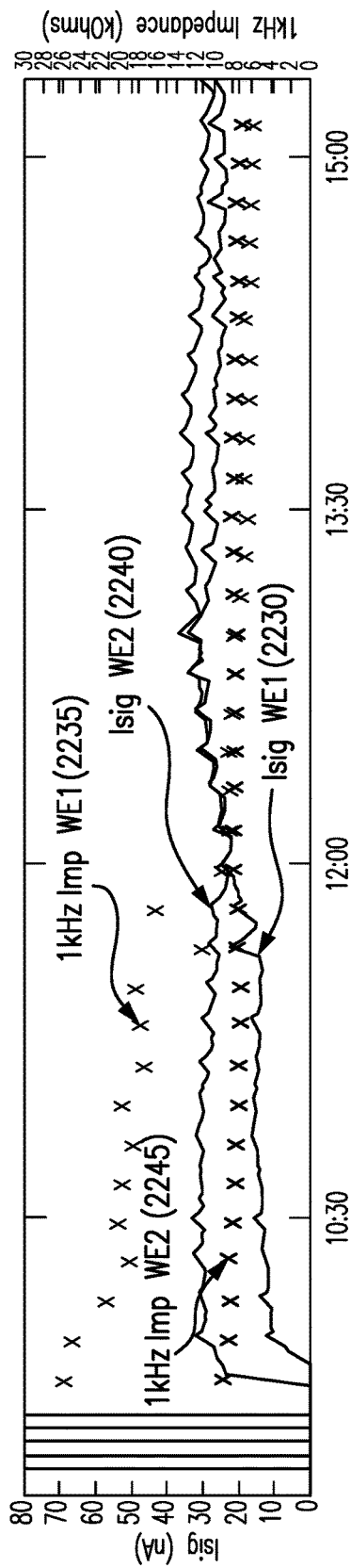
FIG. 23A shows raw current signal (Isig) from two redundant working electrodes, and the electrodes' respective real impedances at 1 kHz, in accordance with embodiments of the invention.
Figure 23B:
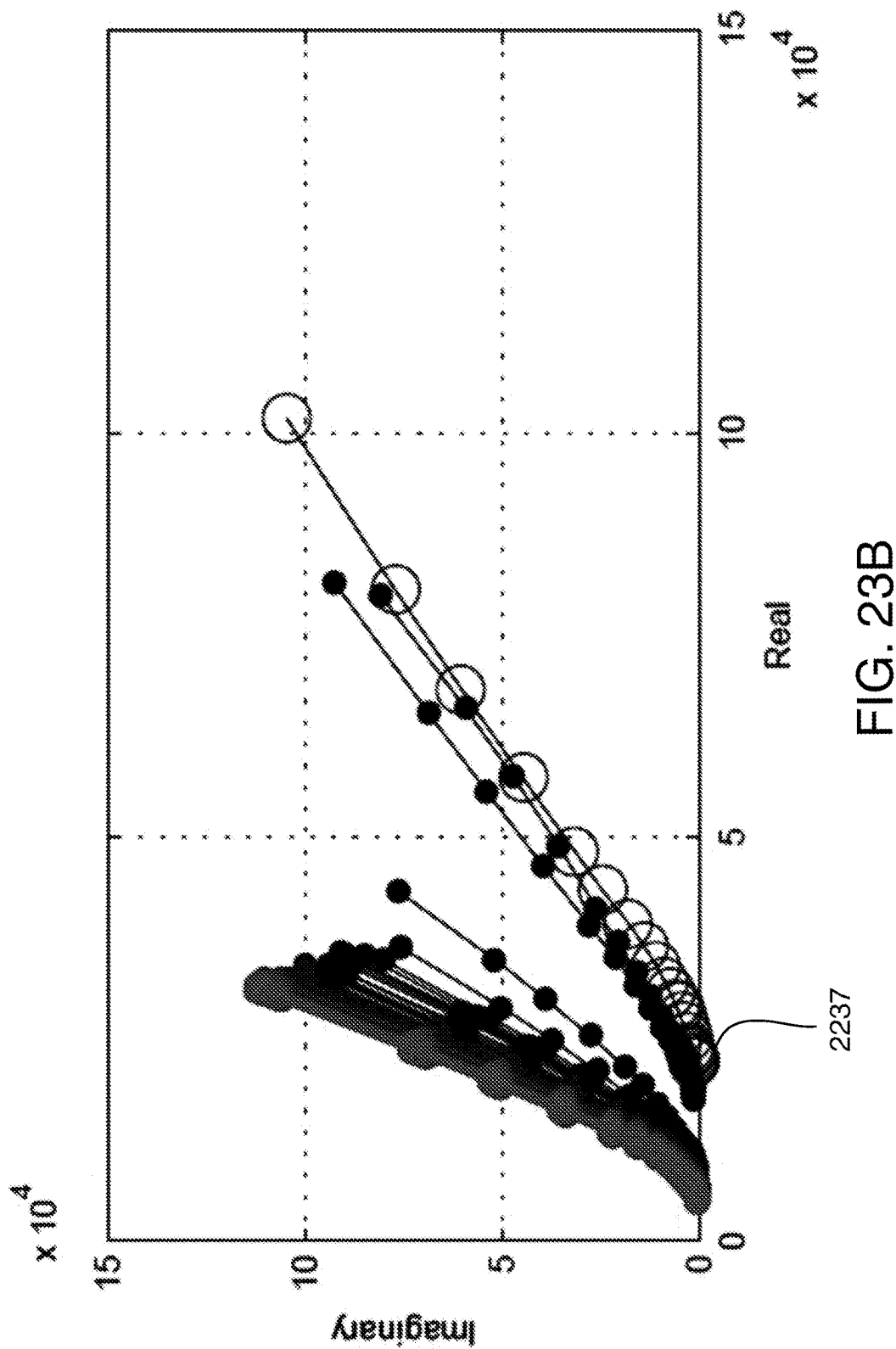
FIG. 23B shows the Nyquist plot for the first working electrode (WE1) of FIG. 23A.
Figure 23C:
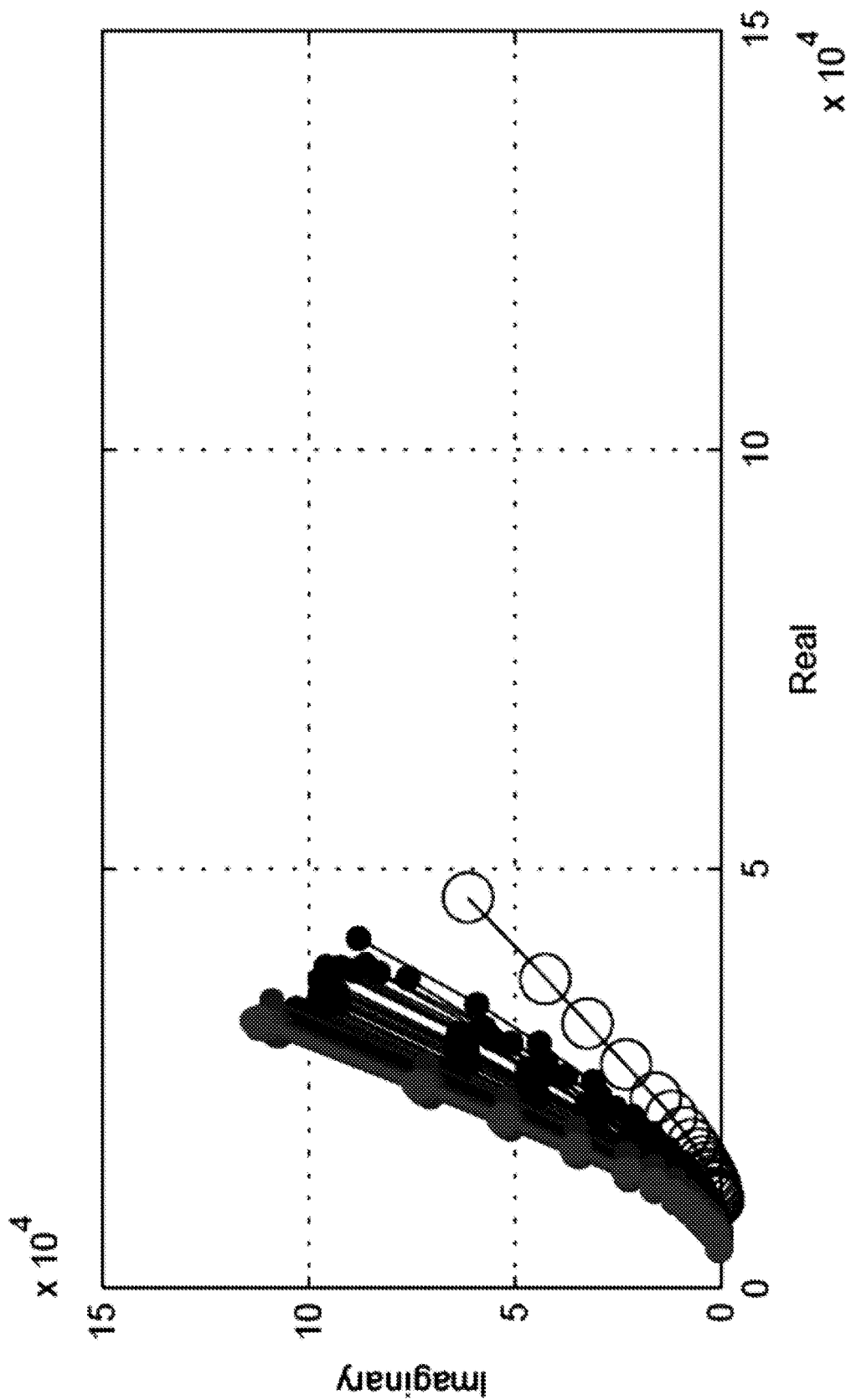
FIG. 23C shows the Nyquist plot for the second working electrode (WE2) of FIG. 23A.

In FIG. 23A, the Isig 2230 for a first working electrode WE1 starts off lower than expected (at about 10 nA), and takes some time to catch up with the Isig 2240 for a second working electrode WE2. Thus, in this particular example, WE1 is designated as having a low start-up. The EIS data reflects this low start-up in two ways. First, as shown in FIG. 23A, the real impedance at 1 kHz (2235) of WE1 is much higher than the 1 kHz real impedance 2245 of WE2. Second, when compared to the Nyquist slope for WE2 (FIG. 23C), the Nyquist slope for WE1 (FIG. 23B) starts out lower, has a larger intercept 2237, and takes more time to stabilize. As will be discussed later, these two signatures—the 1 kHz real impedance and the Nyquist slope—can be used as diagnostic inputs in a fusion algorithm to decide which of the two electrodes can carry a higher weight when the fused signal is calculated. In addition, one or both of these markers may be used in a diagnostic procedure to determine whether the sensor, as a whole, is acceptable, or whether it should be terminated and replaced.

By definition, signal (or Isig) dips refer to instances of low sensor signal, which are mostly temporary in nature, e.g., on the order of a few hours. Such low signals may be caused, for example, by some form of biological occlusion on the sensor surface, or by pressure applied at the insertion site (e.g., while sleeping on the side). During this period, the sensor data is deemed to be unreliable; however, the signal does recover eventually. In the EIS data, this type of signal dip—as opposed to one that is caused by a glycemic change in the patient's body—is reflected in the 1 kHz real impedance data, as shown in FIG. 24.

Figure 24:
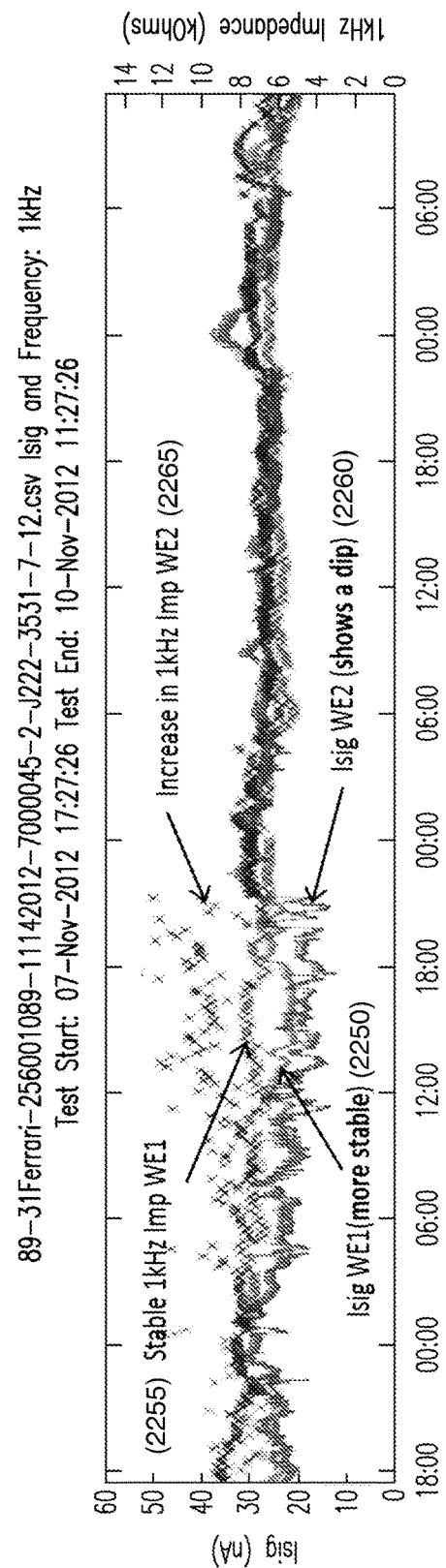
FIG. 24 illustrates examples of signal dip for two redundant working electrodes, and the electrodes' respective real impedances at 1 kHz, in accordance with embodiments of the invention.

Specifically, in FIG. 24, both the Isig 2250 for the first working electrode WE1 and the Isig 2260 for the second working electrode WE2 start out at about 25 nA at the far left end (i.e., at 6 pm). As time progresses, both Isigs fluctuate, which is reflective of glucose fluctuations in the vicinity of the sensor. For about the first 12 hours or so (i.e., until about 6 am), both Isigs are fairly stable, as are their respective 1 kHz real impedances 2255, 2265. However, between about 12 and 18 hours—i.e., between 6 am and noon—the Isig 2260 for WE2 starts to dip, and continues a downward trend for the next several hours, until about 9 pm. During this period, the Isig 2250 for WE1 also exhibits some dipping, but Isig 2250 is much more stable, and dips quite a bit less, than Isig 2260 for WE2. The behavior of the Isigs for WE1 and WE2 is also reflected in their respective 1 kHz real impedance data. Thus, as shown in FIG. 24, during the time period noted above, while the 1 kHz real impedance for WE1 (2255) remains fairly stable, there is a marked increase in the 1 kHz real impedance for WE2 (2265).

By definition, sensitivity loss refers to instances where the sensor signal (Isig) becomes low and non-responsive for an extended period of time, and is usually unrecoverable. Sensitivity loss may occur for a variety of reasons. For example, electrode poisoning drastically reduces the active surface area of the working electrode, thereby severely limiting current amplitude. Sensitivity loss may also occur due to hypoxia, or oxygen deficit, at the insertion site. In addition, sensitivity loss my occur due to certain forms of extreme surface occlusion (i.e., a more permanent form of the signal dip caused by biological or other factors) that limit the passage of both glucose and oxygen through the sensor membrane, thereby lowering the number/frequency of the chemical reactions that generate current in the electrode and, ultimately, the sensor signal (Isig). It is noted that the various causes of sensitivity loss mentioned above apply to both short-term (7-10 day wear) and long term (6 month wear) sensors.

Figure 25A:
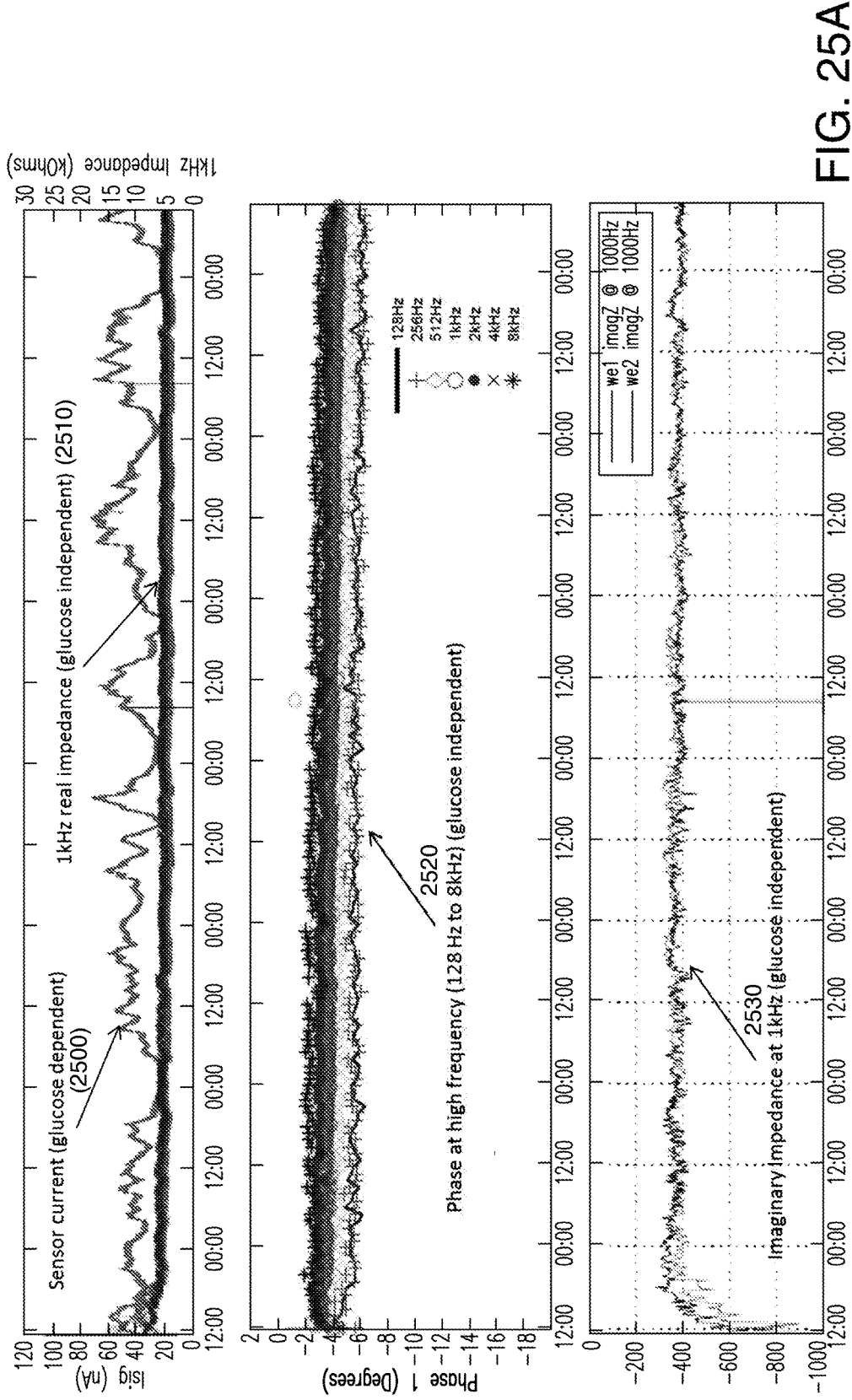
FIG. 25A illustrates substantial glucose independence of real impedance, imaginary impedance, and phase at relatively-higher frequencies for a normally-functioning glucose sensor in accordance with embodiments of the invention.

In the EIS data, sensitivity loss is often preceded by an increase in the absolute value of phase (|phase|) and of the imaginary impedance (|imaginary impedance|) at the relatively higher frequency ranges (e.g., 128 Hz and above, and 1 kHz and above, respectively). FIG. 25A shows an example of a normally-functioning glucose sensor where the sensor current 2500 is responsive to glucose—i.e., Isig 2500 tracks glucose fluctuations—but all relevant impedance outputs, such as, e.g., 1 kHz real impedance 2510, 1 kHz imaginary impedance 2530, and phase for frequencies at or above about 128 Hz (2520), remain steady, as they are substantially glucose-independent.

Specifically, the top graph in FIG. 25A shows that, after the first few hours, the 1 kHz real impedance 2510 holds fairly steady at about 5 kOhms (and the 1 kHz imaginary impedance 2530 holds fairly steady at about −400 Ohms). In other words, at 1 kHz, the real impedance data 2510 and the imaginary impedance data 2530 are substantially glucose-independent, such that they can be used as signatures for, or independent indicators of, the health, condition, and ultimately, reliability of the specific sensor under analysis. However, as mentioned previously, different impedance-related parameters may exhibit glucose-independence at different frequency ranges, and the range, in each case, may depend on the overall sensor design, e.g., electrode type, surface area of electrode, thickness of membrane, permeability of membrane, etc.

Figure 25B:
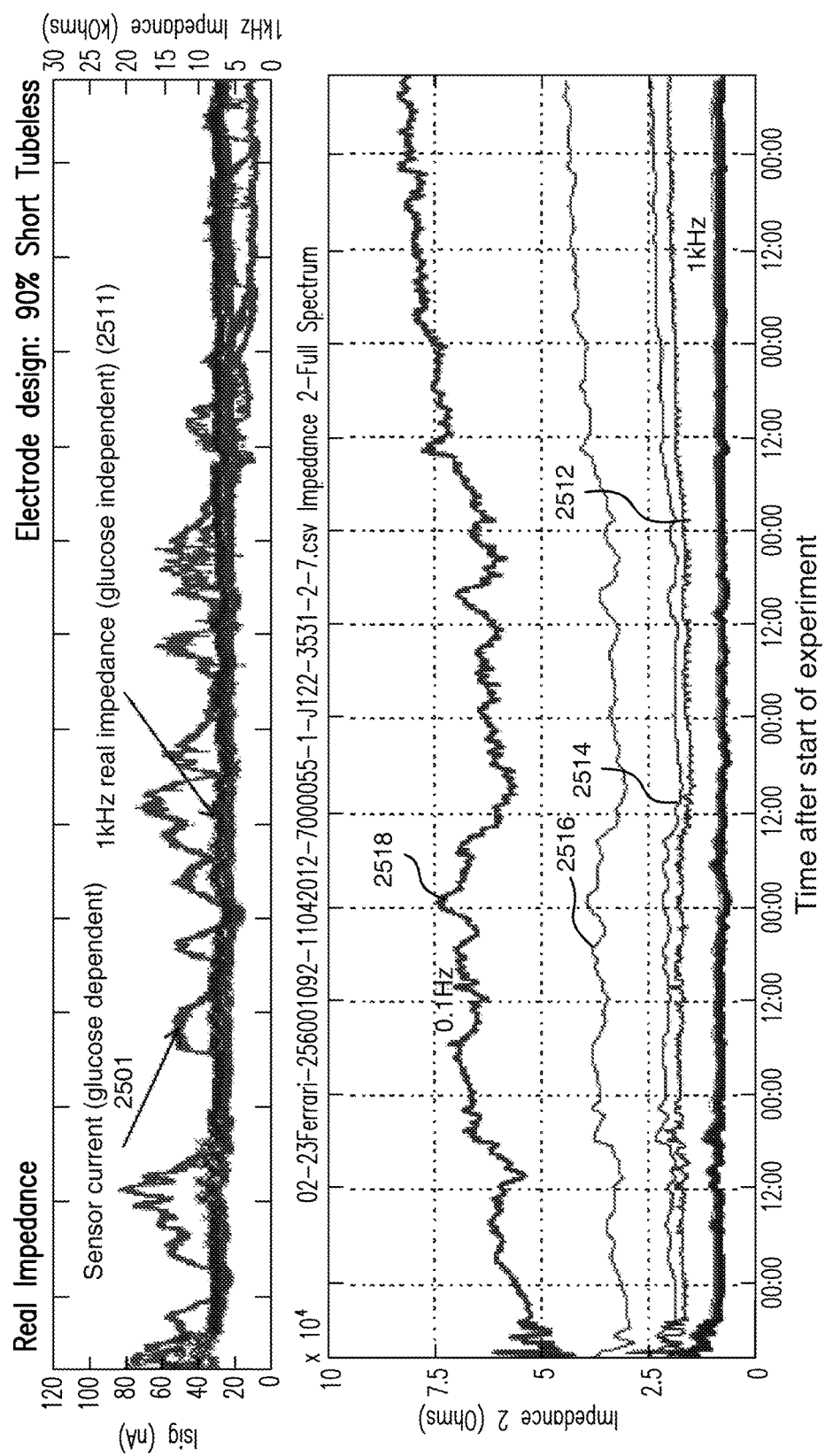
FIG. 25B shows illustrative examples of varying levels of glucose dependence of real impedance at the relatively-lower frequencies in accordance with embodiments of the invention.

Thus, in the example FIG. 25B—for a 90% short tubeless electrode design—the top graph again shows that sensor current 2501 is responsive to glucose, and that, after the first few hours, the 1 kHz real impedance 2511 holds fairly steady at about 7.5 kOhms. The bottom graph in FIG. 25B shows real impedance data for frequencies between 0.1 Hz (2518) and 1 kHz (2511). As can be seen, the real impedance data at 0.1 Hz (2518) is quite glucose-dependent. However, as indicated by reference numerals 2516, 2514, and 2512, real impedance becomes more and more glucose-independent as the frequency increases from 0.1 Hz to 1 kHz, i.e., for impedance data measured at frequencies closer to 1 kHz.

Figure 25C:
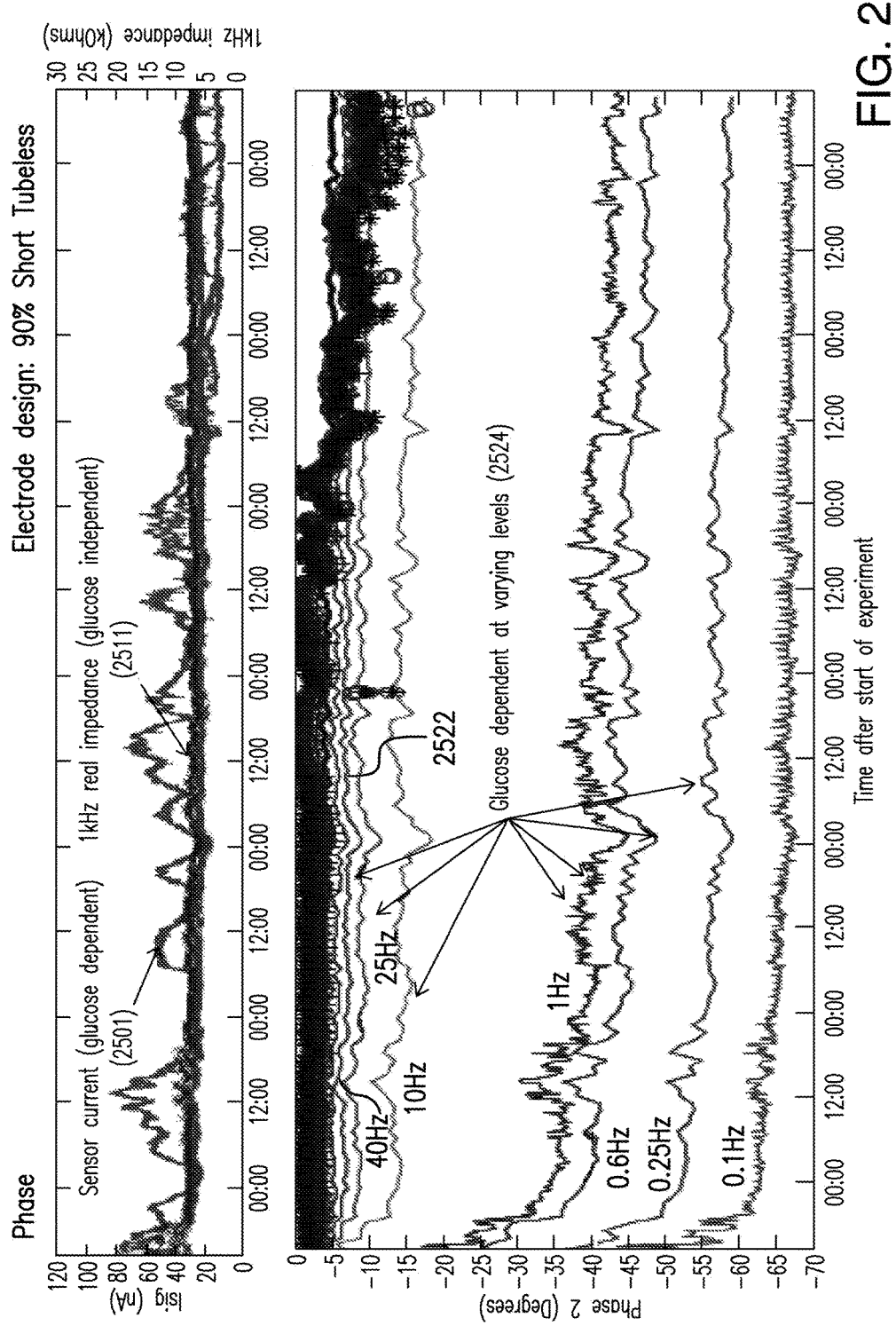
FIG. 25C shows illustrative examples of varying levels of glucose dependence of phase at the relatively-lower frequencies in accordance with embodiments of the invention.

Returning to FIG. 25A, the middle graph shows that the phase 2520 at the relatively-higher frequencies is substantially glucose-independent. It is noted, however, that "relatively-higher frequencies" in connection with this parameter (phase) for the sensor under analysis means frequencies of 128 Hz and above. In this regard, the graph shows that the phase for all frequencies between 128 Hz and 8 kHz is stable throughout the period shown. On the other hand, as can be seen in the bottom graph of FIG. 25C, while the phase 2522 at 128 Hz (and above) is stable, the phase 2524 fluctuates—i.e., it becomes more and more glucose-dependent, and to varying degrees—at frequencies that are increasingly smaller than 128 Hz. It is noted that the electrode design for the example of FIG. 25C is the same as that used in FIG. 25B, and that the top graph in the former is identical to the top graph in the latter.

Figure 26:
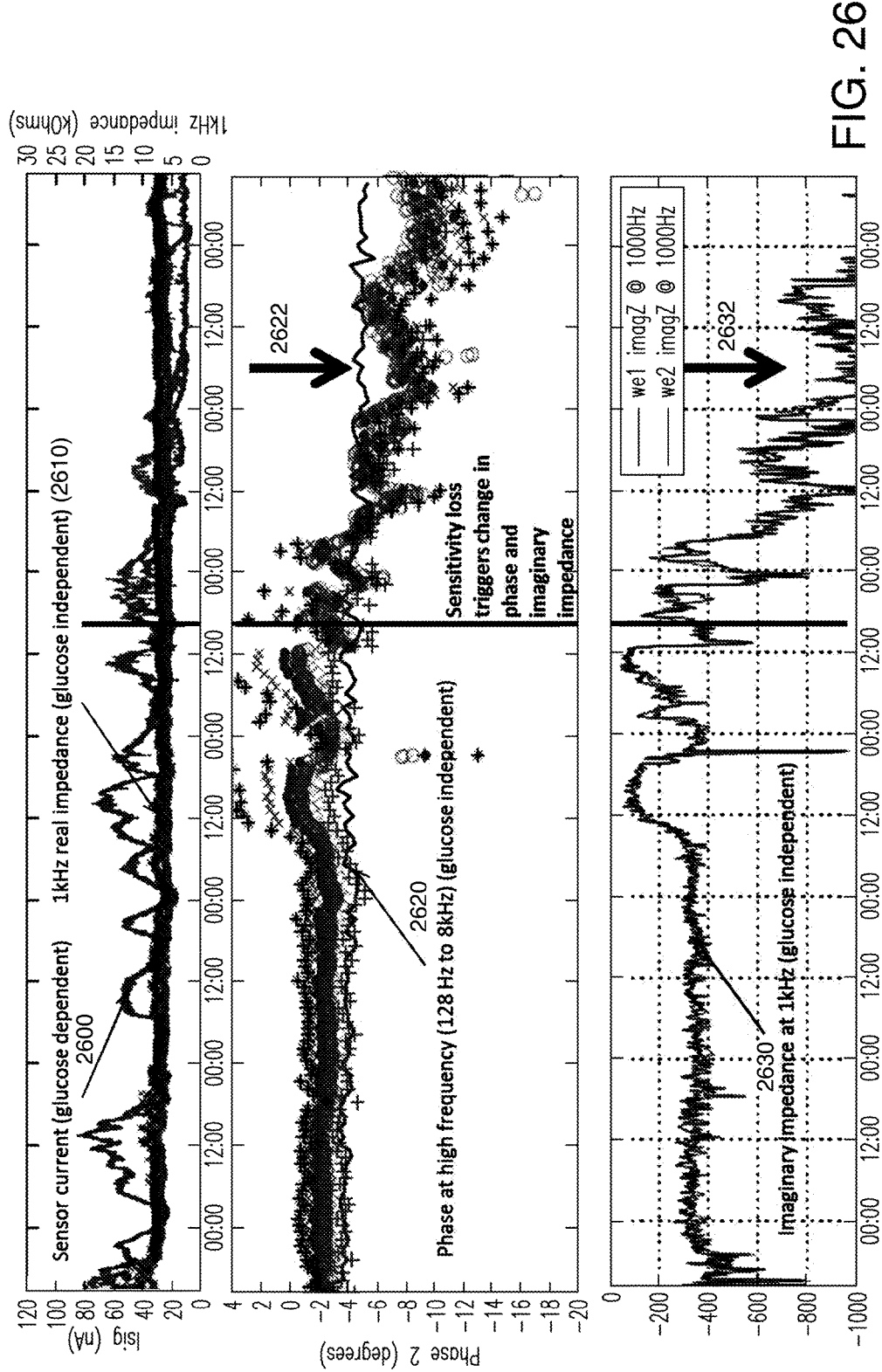
FIG. 26 shows the trending for 1 kHz real impedance, 1 kHz imaginary impedance, and relatively-higher frequency phase as a glucose sensor loses sensitivity as a result of oxygen deficiency at the sensor insertion site, according to embodiments of the invention.

FIG. 26 shows an example of sensitivity loss due to oxygen deficiency at the insertion site. In this case, the insertion site becomes oxygen deprived just after day 4 (designated by dark vertical line in FIG. 26), causing the sensor current 2600 to become low and non-responsive. The 1 kHz real impedance 2610 remains stable, indicating no physical occlusion on the sensor. However, as shown by the respective downward arrows, changes in the relatively higher-frequency phase 2622 and 1 kHz imaginary impedance 2632 coincide with loss in sensitivity, indicating that this type of loss is due to an oxygen deficit at the insertion site. Specifically, FIG. 26 shows that the phase at higher frequencies (2620) and the 1 kHz imaginary impedance (2630) become more negative prior to the sensor losing sensitivity—indicated by the dark vertical line—and continue their downward trend as the sensor sensitivity loss continues. Thus, as noted above, this sensitivity loss is preceded, or predicted, by an increase in the absolute value of phase (|phase|) and of the imaginary impedance (|imaginary impedance|) at the relatively higher frequency ranges (e.g., 128 Hz and above, and 1 kHz and above, respectively).

Figure 27:
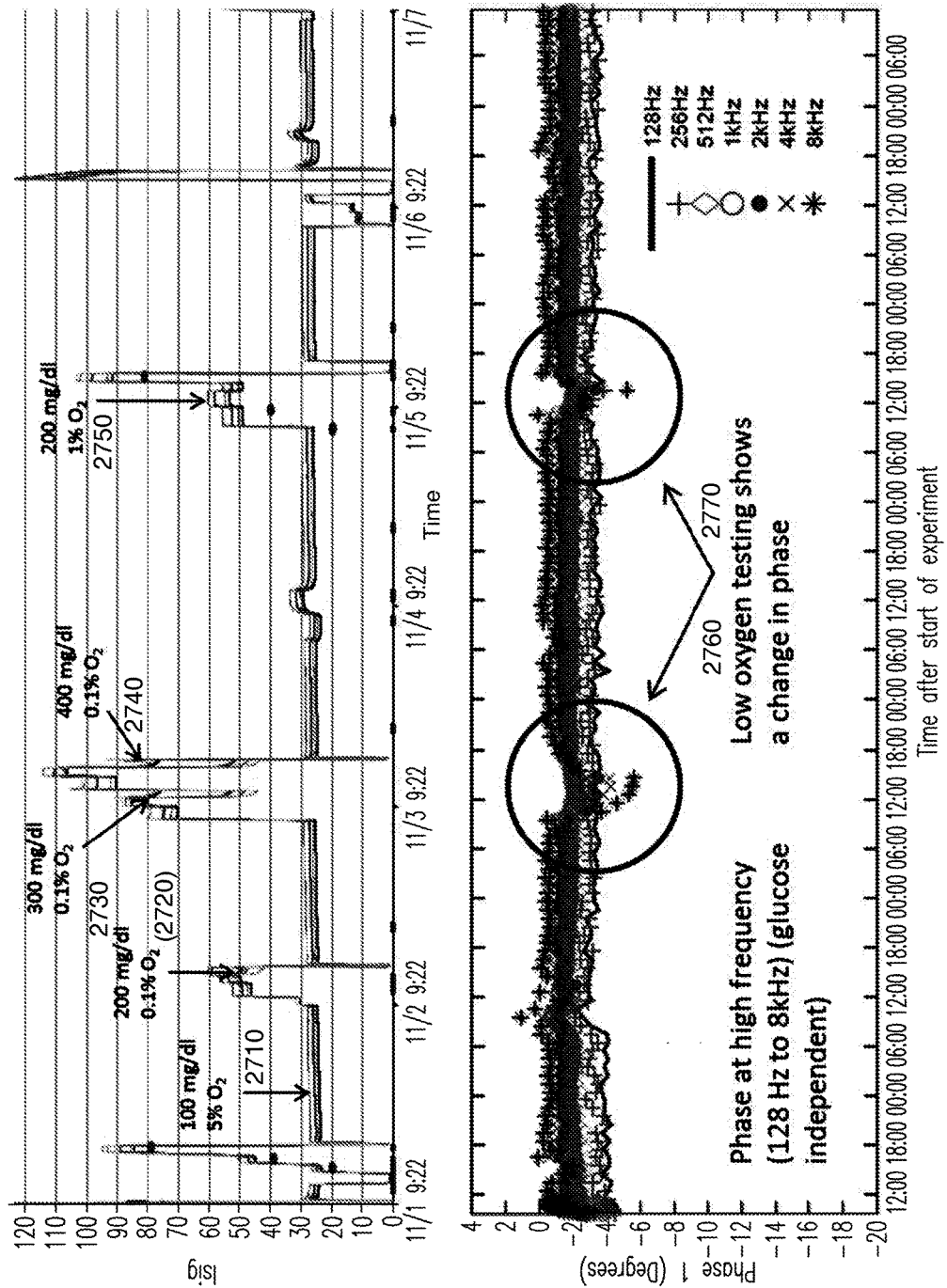
FIG. 27 shows Isig and phase for an in-vitro simulation of oxygen deficit at different glucose concentrations in accordance with embodiments of the invention.

The above-described signatures may be verified by in-vitro testing, an example of which is shown in FIG. 27. FIG. 27 shows the results of in-vitro testing of a sensor, where oxygen deficit at different glucose concentrations is simulated. In the top graph, the Isig fluctuates with the glucose concentration as the latter is increased from 100 mg/dl (2710) to 200 mg/dl (2720), 300 mg/dl (2730), and 400 mg/dl (2740), and then decreased back down to 200 and/dl (2750). In the bottom graph, the phase at the relatively-higher frequencies is generally stable, indicating that it is glucose-independent. However, at very low oxygen concentrations, such as, e.g., at 0.1% $O_2$, the relatively high-frequency phase fluctuates, as indicated by the encircled areas and arrows 2760, 2770. It is noted that the magnitude and/or direction (i.e., positive or negative) of fluctuation depend on various factors. For example, the higher the ratio of glucose concentration to oxygen concentration, the higher the magnitude of the fluctuation in phase. In addition, the specific sensor design, as well as the age of the sensor (i.e., as measured by time after implant), affect such fluctuations. Thus, e.g., the older a sensor is, the more susceptible it is to perturbations.

Figure 28A:
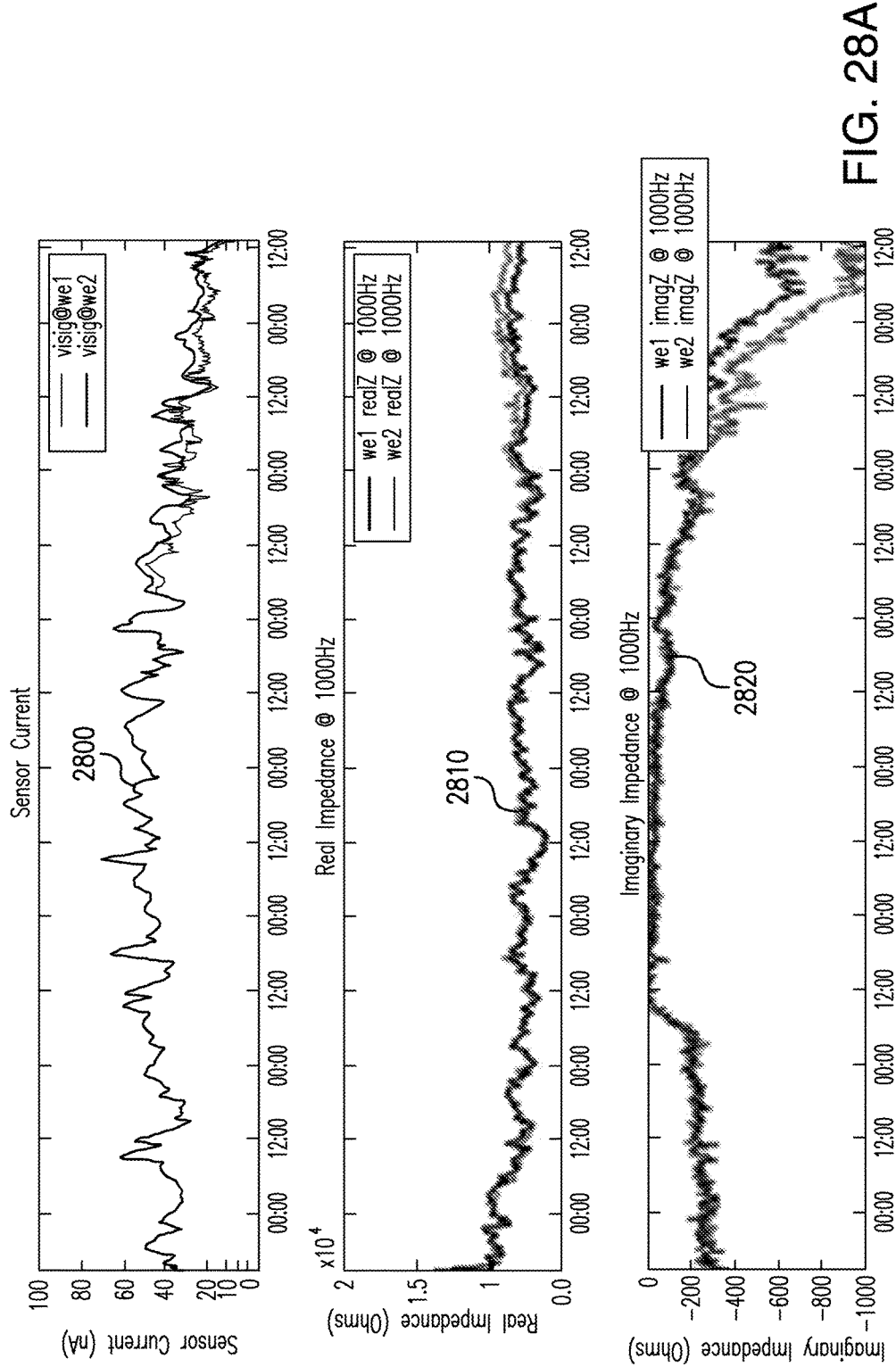
FIGS. 28A-28C show an example of oxygen deficiency-led sensitivity loss with redundant working electrodes WE1 and WE2, as well as the electrodes' EIS-based parameters, in accordance with embodiments of the invention.
Figure 28B:
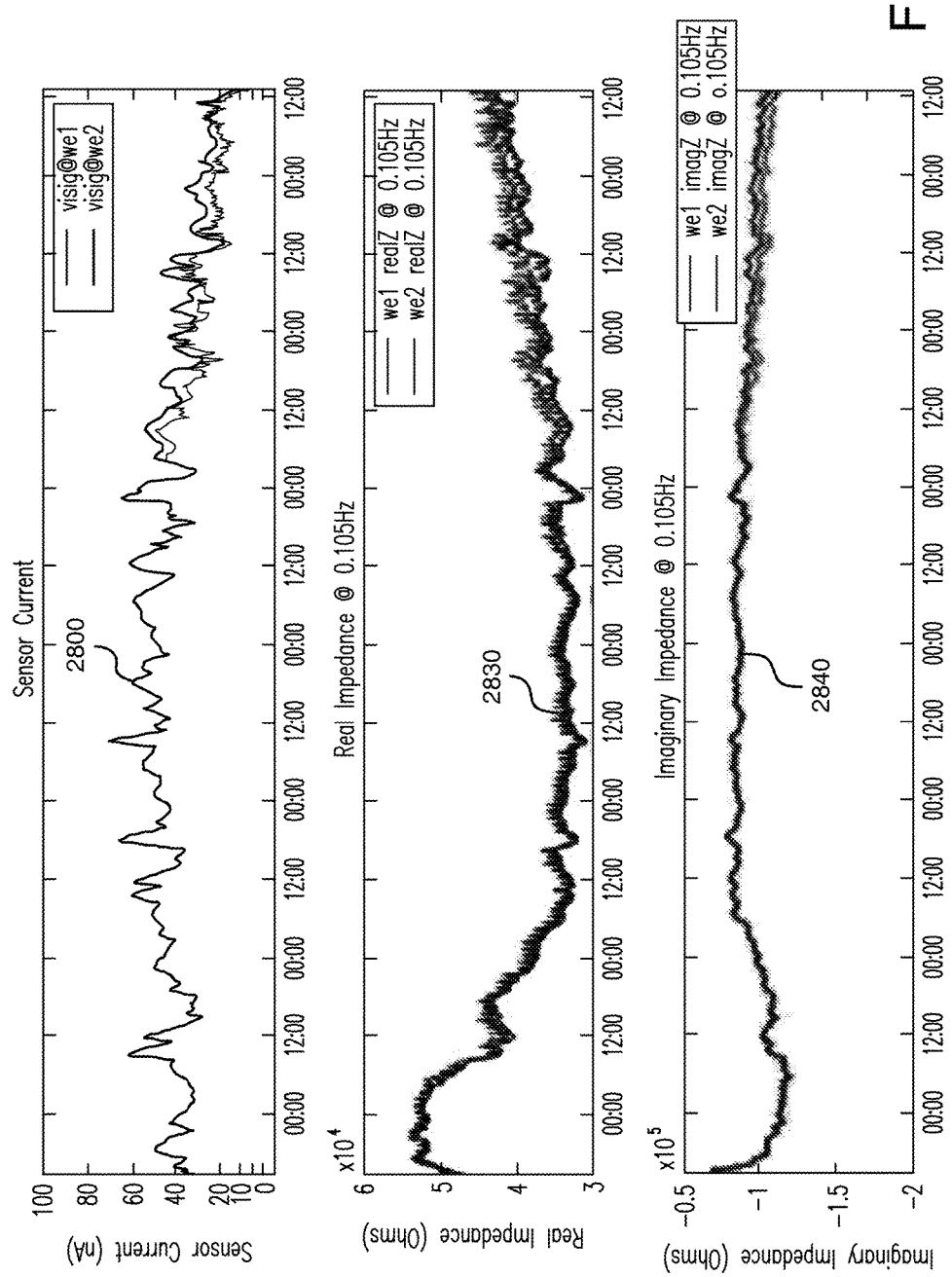
Figure 28C:
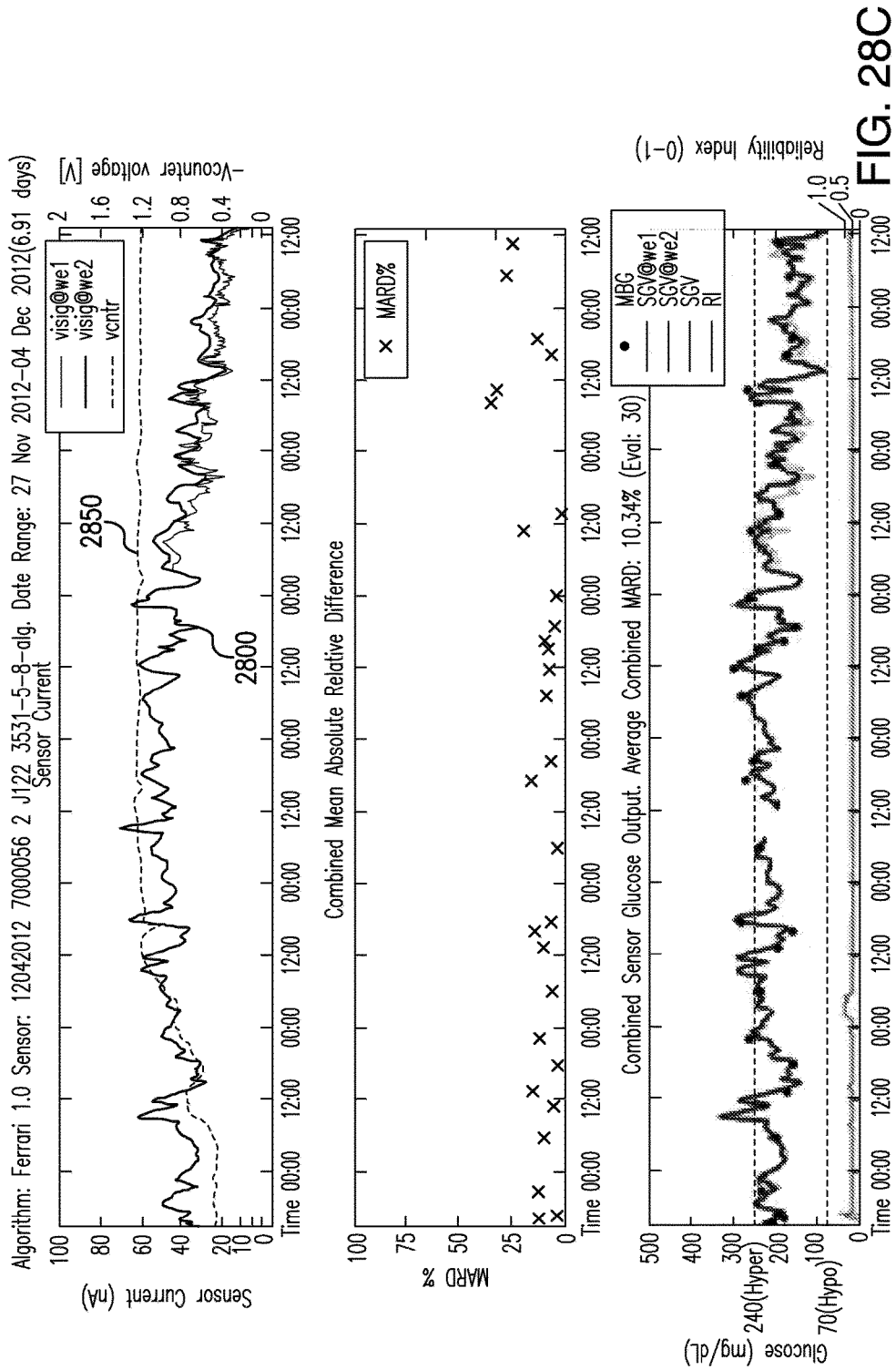

FIGS. 28A-28D show another example of oxygen deficiency-led sensitivity loss with redundant working electrodes WE1 and WE2. As shown in FIG. 28A, the 1 kHz real impedance 2810 is steady, even as sensor current 2800 fluctuates and eventually becomes non-responsive. Also, as before, the change in 1 kHz imaginary impedance 2820 coincides with the sensor's loss of sensitivity. In addition, however, FIG. 28B shows real impedance data and imaginary impedance data (2830 and 2840, respectively) at 0.105 Hz. The latter, which may be more commonly referred to as "0.1 kHz data", indicates that, whereas imaginary impedance at 0.1 kHz appears to be fairly steady, 0.1 kHz real impedance 2830 increases considerably as the sensor loses sensitivity. Moreover, as shown in FIG. 28C, with loss of sensitivity due to oxygen deficiency, $V_{cntr}$ 2850 rails to 1.2 Volts.

In short, the diagrams illustrate the discovery that oxygen deficiency-led sensitivity loss is coupled with lower 1 kHz imaginary impedance (i.e., the latter becomes more negative), higher 0.105 Hz real impedance (i.e., the latter becomes more positive), and $V_{cntr}$ rail. Moreover, the oxygen-deficiency process and $V_{cntr}$-rail are often coupled with the increase of the capacitive component in the electrochemical circuit. It is noted that, in some of the diagnostic procedures to be described later, the 0.105 Hz real impedance may not be used, as it appears that this relatively lower-frequency real impedance data may be analyte-dependent.

Figure 28D:
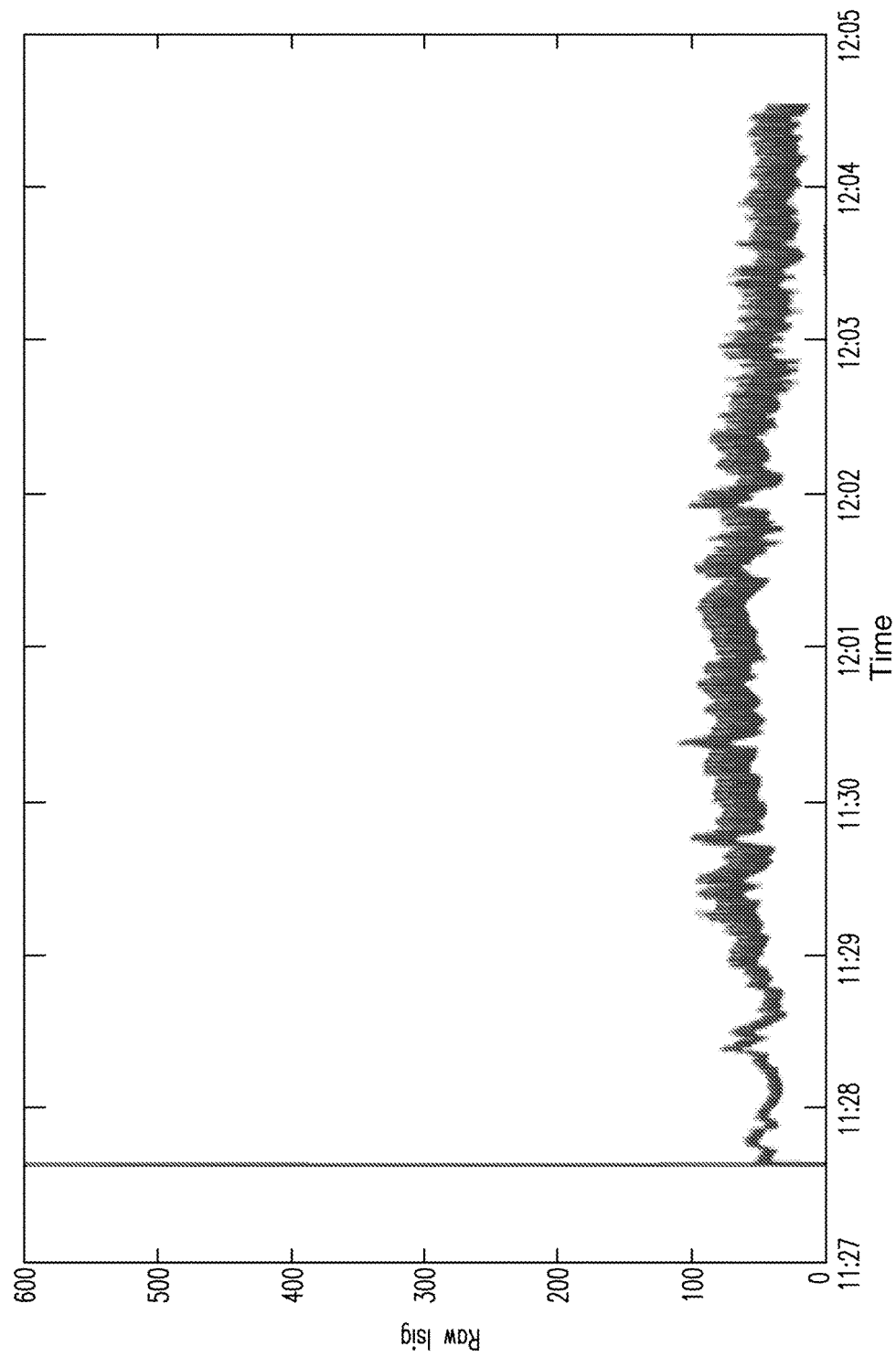
FIG. 28D shows EIS-induced spikes in the raw Isig for the example of FIGS. 28A-28C.

Finally, in connection with the example of FIGS. 28A-28D, it is noted that 1 kHz or higher-frequency impedance measurement typically causes EIS-induced spikes in the Isig. This is shown in FIG. 28D, where the raw Isig for WE2 is plotted against time. The drastic increase of Isig when the spike starts is a non-Faradaic process, due to double-layer capacitance charge. Thus, oxygen deficiency-led sensitivity loss may also be coupled with higher EIS-induced spikes, in addition to lower 1 kHz imaginary impedance, higher 0.105 Hz real impedance, and $V_{cntr}$ rail, as discussed above.

Figure 29:
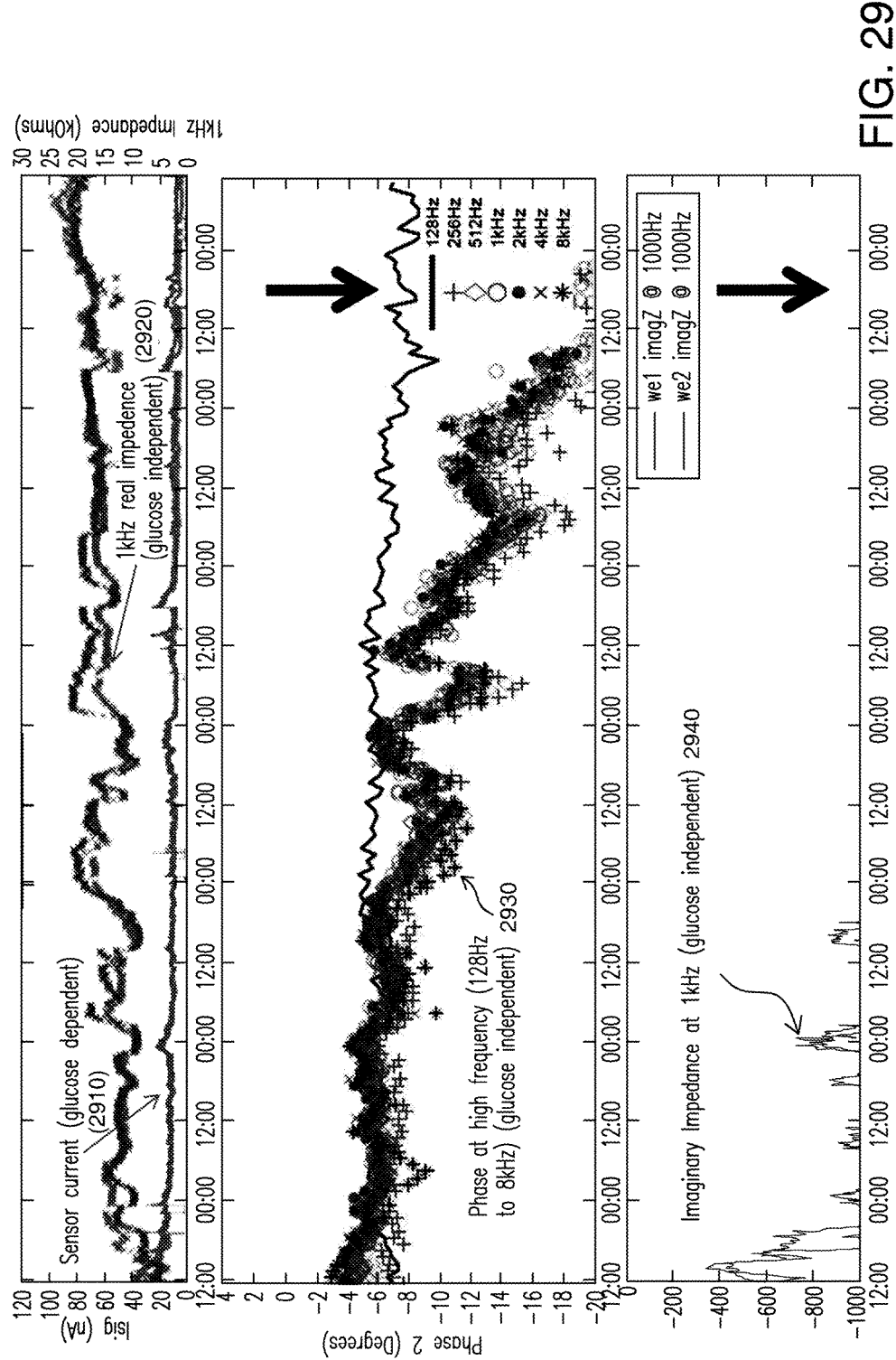
FIG. 29 shows an example of sensitivity loss due to oxygen deficiency that is caused by an occlusion, in accordance with embodiments of the invention.

FIG. 29 illustrates another example of sensitivity loss. This case may be thought of as an extreme version of the Isig dip described above in connection with FIG. 24. Here, the sensor current 2910 is observed to be low from the time of insertion, indicating that there was an issue with an insertion procedure resulting in electrode occlusion. The 1 kHz real-impedance 2920 is significantly higher, while the relatively higher-frequency phase 2930 and the 1 kHz imaginary impedance 2940 are both shifted to much more negative values, as compared to the same parameter values for the normally-functioning sensor shown in FIG. 25A. The shift in the relatively higher-frequency phase 2930 and 1 kHz imaginary impedance 2940 indicates that the sensitivity loss may be due to an oxygen deficit which, in turn, may have been caused by an occlusion on the sensor surface.

Figure 30A:
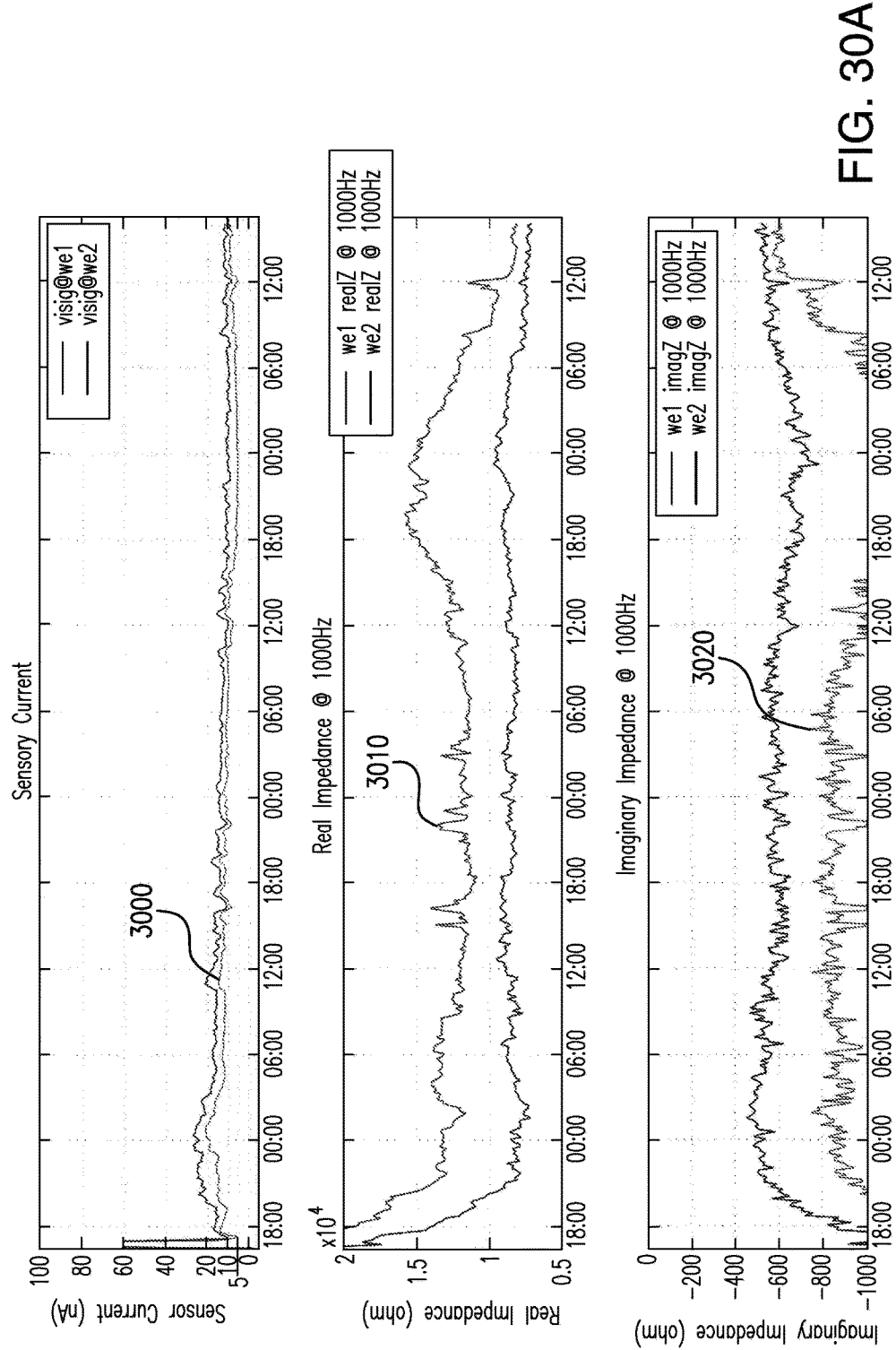
FIGS. 30A-30C show an example of sensitivity loss due to bio-fouling, with redundant working electrodes WE1 and WE2, as well as the electrodes' EIS-based parameters, in accordance with embodiments of the invention.
Figure 30B:
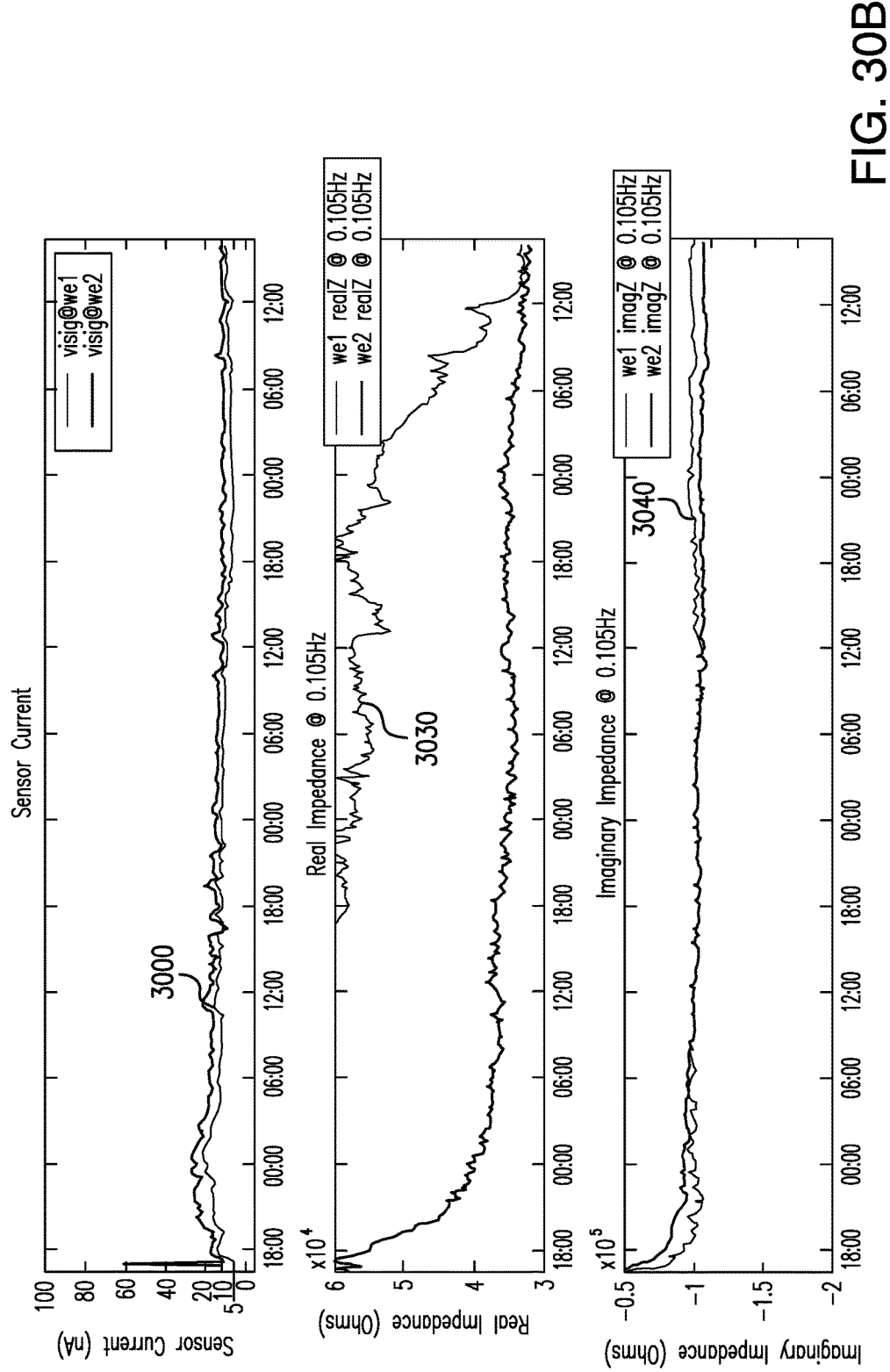
Figure 30C:
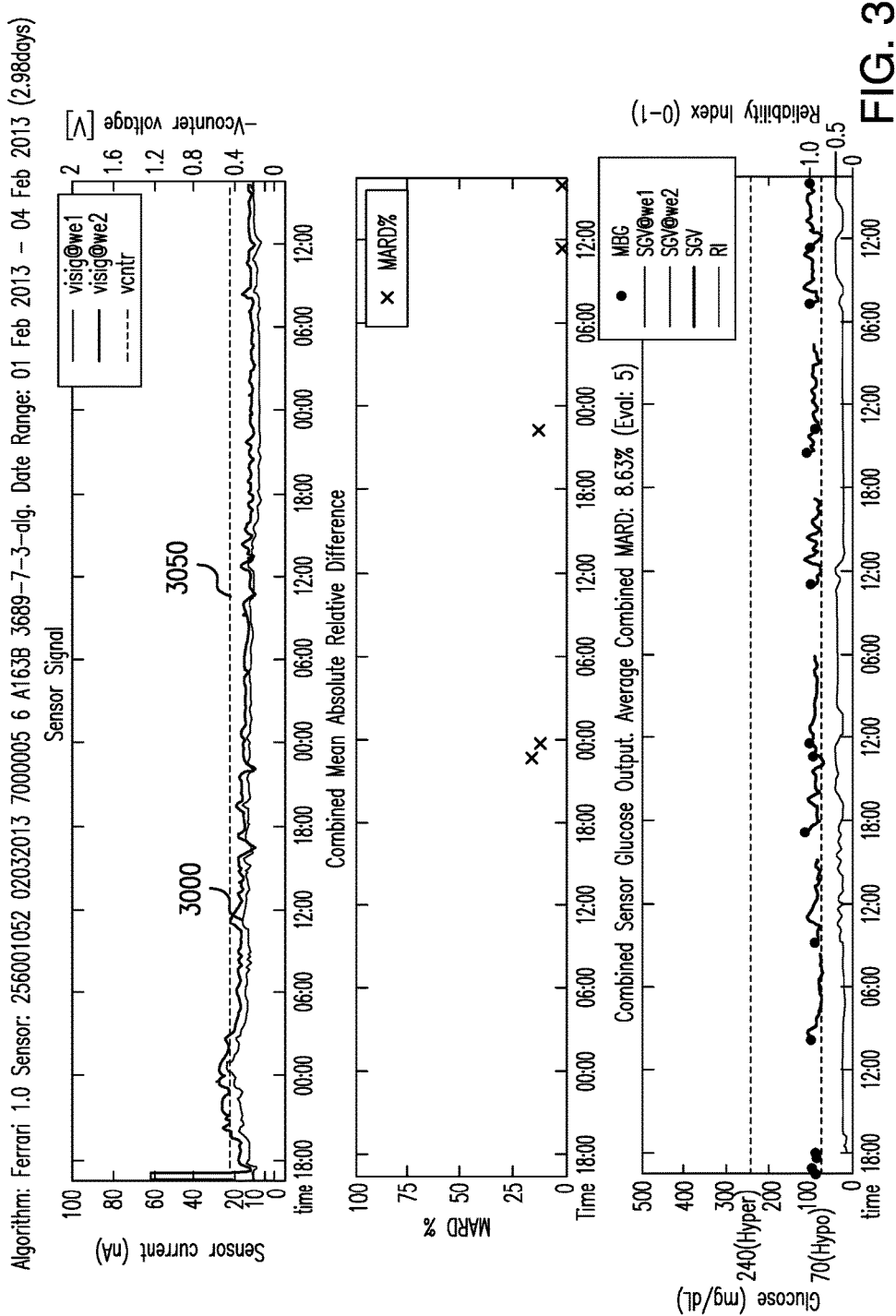
Figure 30D:
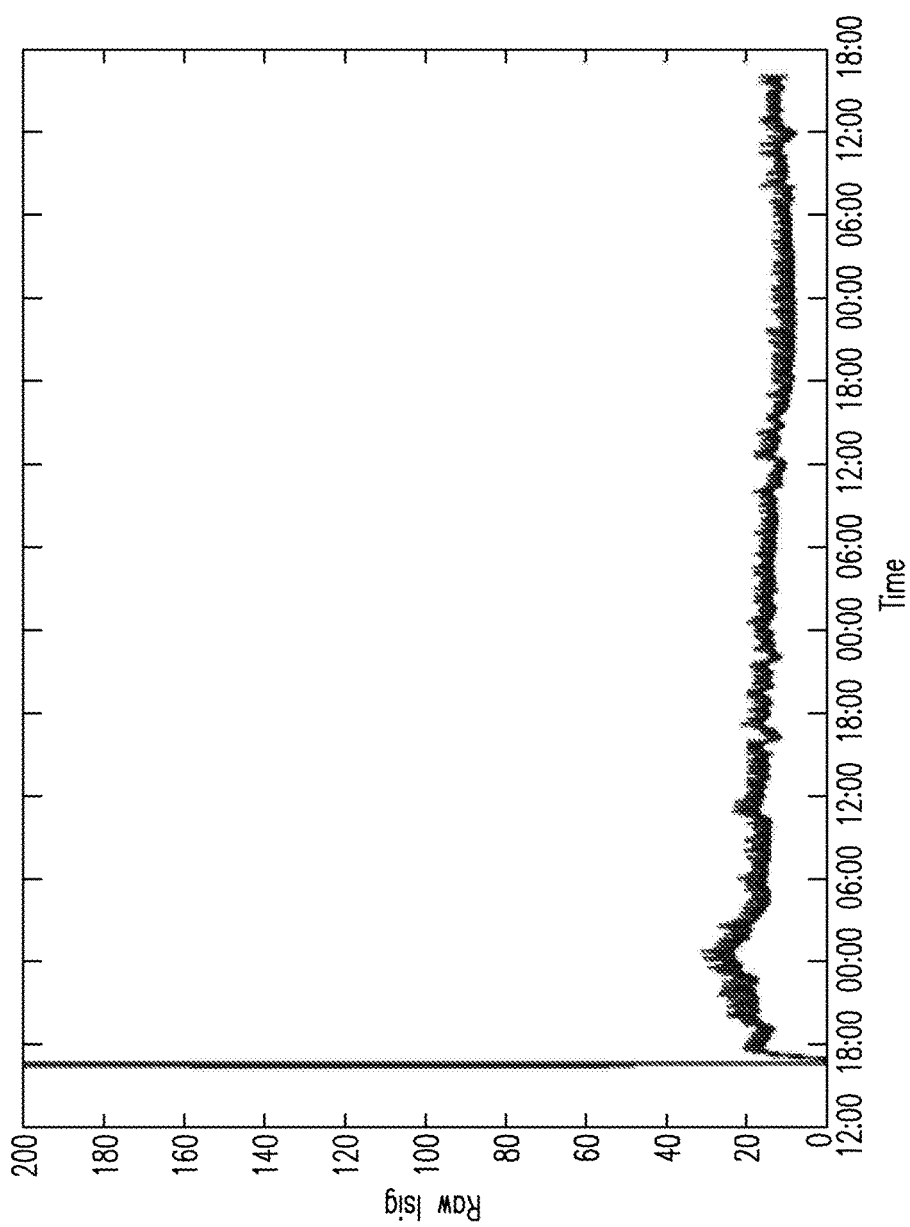
FIG. 30D shows EIS-induced spikes in the raw Isig for the example of FIGS. 30A-30C.

FIGS. 30A-30D show data for another redundant sensor, where the relative differences in 1 kHz real impedance and 1 kHz imaginary impedance, as well as 0.1 Hz real impedance, between two or more working electrodes may be used for the detection of sensitivity loss due to biofouling. In this example, WE1 exhibits more sensitivity loss than WE2, as is evident from the higher 1 kHz real impedance 3010, lower 1 kHz imaginary impedance 3020, and much higher real impedance at 0.105 kHz (3030) for WE2. In addition, however, in this example, $V_{cntr}$ 3050 does not rail. Moreover, as shown in FIG. 30D, the height of the spikes in the raw Isig data does not change much as time progresses. This indicates that, for sensitivity loss due to biofouling, $V_{cntr}$ rail and the increase in spike height are correlated. In addition, the fact that the height of the spikes in the raw Isig data does not change much with time indicates that the capacitive component of the circuit does not change significantly with time, such that sensitivity loss due to biofouling is related to the resistance component of the circuit (i.e., diffusion).

Various of the above-described impedance-related parameters may be used, either individually or in combination, as inputs into: (1) EIS-based sensor diagnostic procedures; and/or (2) fusion algorithms for generating more reliable sensor glucose values. With regard to the former, FIG. 31 illustrates how EIS-based data—i.e., impedance-related parameters, or characteristics—may be used in a diagnostic procedure to determine, in real time, whether a sensor is behaving normally, or whether it should be replaced.

Figure 31:
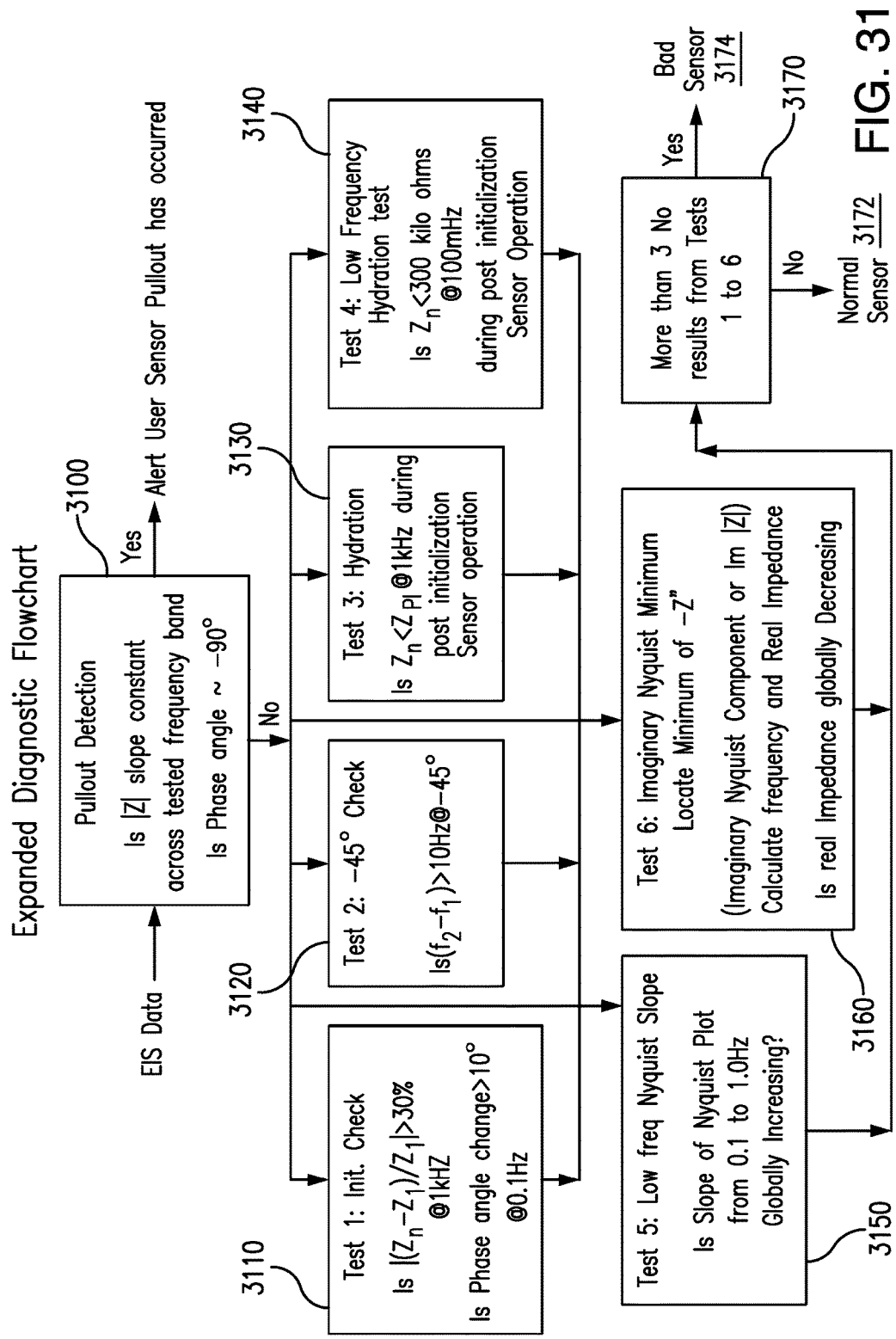
FIG. 31 shows a diagnostic procedure for sensor fault detection in accordance with embodiments of the invention.

The diagnostic procedure illustrated in the flow diagram of FIG. 31 is based on the collection of EIS data on a periodic basis, such as, e.g., hourly, every half hour, every 10 minutes, or at any other interval—including continuously—as may be appropriate for the specific sensor under analysis. At each such interval, EIS may be run for an entire frequency spectrum (i.e., a "full sweep"), or it may be run for a selected frequency range, or even at a single frequency. Thus, for example, for an hourly data collection scheme, EIS may be performed at frequencies in the μHz to MHz range, or it may be run for a narrower range of frequencies, such as, e.g., between about 0.1 Hz and about 8 kHz, as discussed hereinabove. In embodiments of the invention, EIS data acquisition may be implemented alternatingly between a full sweep and an narrower-range spectrum, or in accordance with other schemes.

The temporal frequency of EIS implementation and data collection may be dictated by various factors. For example, each implementation of EIS consumes a certain amount of power, which is typically provided by the sensor's battery, i.e., the battery running the sensor electronics, including the ASIC which is described later. As such, battery capacity, as well as the remaining sensor life, may help determine the number of times EIS is run, as well as the breadth of frequencies sampled for each such run. In addition, embodiments of the invention envision situations that may require that an EIS parameter at a specific frequency (e.g., real impedance at 1 kHz) be monitored based on a first schedule (e.g., once every few seconds, or minutes), while other parameters, and/or the same parameter at other frequencies, can be monitored based on a second schedule (e.g., less frequently). In these situations, the diagnostic procedure can be tailored to the specific sensor and requirements, such that battery power may be preserved, and unnecessary and/or redundant EIS data acquisition may be avoided.

It is noted that, in embodiments of the invention, a diagnostic procedure, such as the one shown in FIG. 31, entails a series of separate "tests" which are implemented in order to perform real-time monitoring of the sensor. The multiple tests, or markers—also referred to as "multi markers"—are implemented because each time EIS is run (i.e., each time an EIS procedure is performed), data may be gathered about a multiplicity of impedance-based parameters, or characteristics, which can be used to detect sensor condition or quality, including, e.g., whether the sensor has failed or is failing. In performing sensor diagnostics, sometimes, there can be a diagnostic test that may indicate a failure, whereas other diagnostic(s) may indicate no failure. Therefore, the availability of multiple impedance-related parameters, and the implementation of a multi-test procedure, are advantageous, as some of the multiplicity of tests may act as validity checks against some of the other tests. Thus, real-time monitoring using a multi-marker procedure may include a certain degree of built-in redundancy.

With the above in mind, the logic of the diagnostic procedure shown in FIG. 31 begins at 3100, after the sensor has been inserted/implanted, and an EIS run has been made, so as to provide the EIS data as input. At 3100, using the EIS data as input, it is first determined whether the sensor is still in place. Thus, if the |Z| slope is found to be constant across the tested frequency band (or range), and/or the phase angle is about −90°, it is determined that the sensor is no longer in place, and an alert is sent, e.g., to the patient/user, indicating that sensor pullout has occurred. The specific parameters (and their respective values) described herein for detecting sensor pullout are based on the discovery that, once the sensor is out of the body and the membrane is no longer hydrated, the impedance spectrum response appears just like a capacitor.

If it is determined that the sensor is still in place, the logic moves to step 3110 to determine whether the sensor is properly initialized. As shown, the "Init. Check" is performed by determining: (i) whether $|(Z_n - Z_1)/Z_1| > 30\%$ at 1 kHz, where $Z_1$ is the real impedance measured at a first time, and $Z_n$ is the measured impedance at the next interval, at discussed above; and (2) whether the phase angle change is greater than 10° at 0.1 Hz. If the answer to either one of the questions is "yes", then the test is satisfactory, i.e., the Test 1 is not failed. Otherwise, the Test 1 is marked as a failure.

At step 3120, Test 2 asks whether, at a phase angle of −45°, the difference in frequency between two consecutive EIS runs $(f_2 - f_1)$ is greater than 10 Hz. Again, a "No" answer is marked as a fail; otherwise, Test 2 is satisfactorily met.

Test 3 at step 3130 is a hydration test. Here, the inquiry is whether the current impedance $Z_n$ is less than the post-initialization impedance $Z_{pi}$ at 1 kHz. If it is, then this test is satisfied; otherwise, Test 3 is marked as a fail. Test 4 at step 3140 is also a hydration test, but this time at a lower frequency. Thus, this test asks whether $Z_n$ is less than 300 kOhms at 0.1 Hz during post-initialization sensor operation. Again, a "No" answer indicates that the sensor has failed Test 4.

At step 3150, Test 5 inquires whether the low-frequency Nyquist slope is globally increasing from 0.1 Hz to 1 Hz. As discussed previously, for a normally-operating sensor, the relatively lower-frequency Nyquist slope should be increasing over time. Thus, this test is satisfied if the answer to the inquiry is "yes"; otherwise, the test is marked as failed.

Step 3160 is the last test for this embodiment of the diagnostic procedure. Here, the inquiry is whether real impedance is globally decreasing. Again, as was discussed previously, in a normally-operating sensor, it is expected that, as time goes by, the real impedance should be decreasing. Therefore, a "Yes" answer here would mean that the sensor is operating normally; otherwise, the sensor fails Test 6.

Once all 6 tests have been implemented, a decision is made at 3170 as to whether the sensor is operating normally, or whether it has failed. In this embodiment, a sensor is determined to be functioning normally (3172) if it passes at least 3 out of the 6 tests. Put another way, in order to be determined to have failed (3174), the sensor must fail at least 4 out of the 6 tests. In alternative embodiments, a different rule may be used to assess normal operation versus sensor failure. In addition, in embodiments of the invention, each of the tests may be weighted, such that the assigned weight reflects, e.g., the importance of that test, or of the specific parameter(s) queried for that test, in determining overall sensor operation (normal vs. failed). For example, one test may be weighted twice as heavily as another, but only half as heavily as a third test, etc.

Figure 32A:
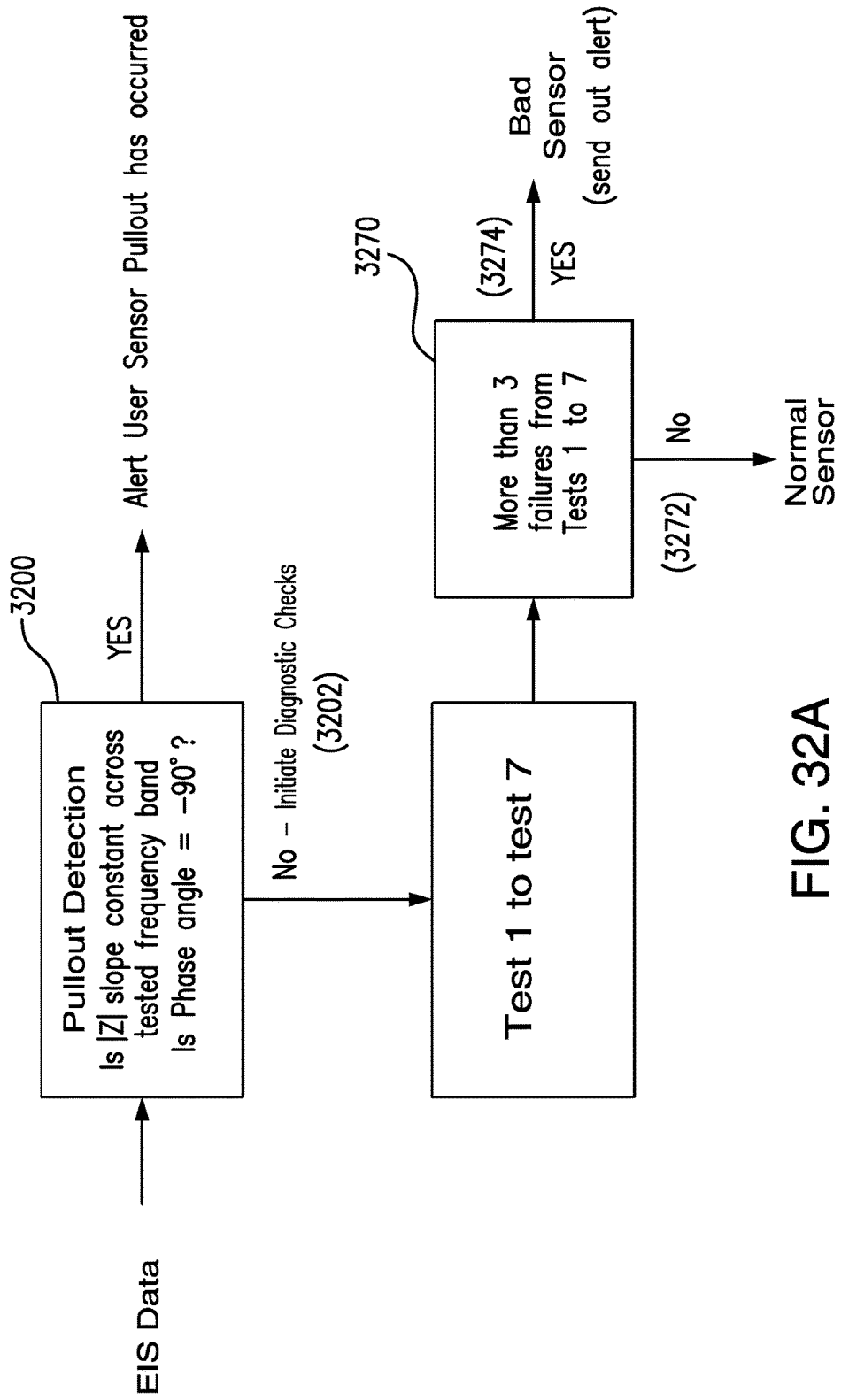
FIGS. 32A and 32B show another diagnostic procedure for sensor fault detection in accordance with embodiments of the invention.
Figure 32B:
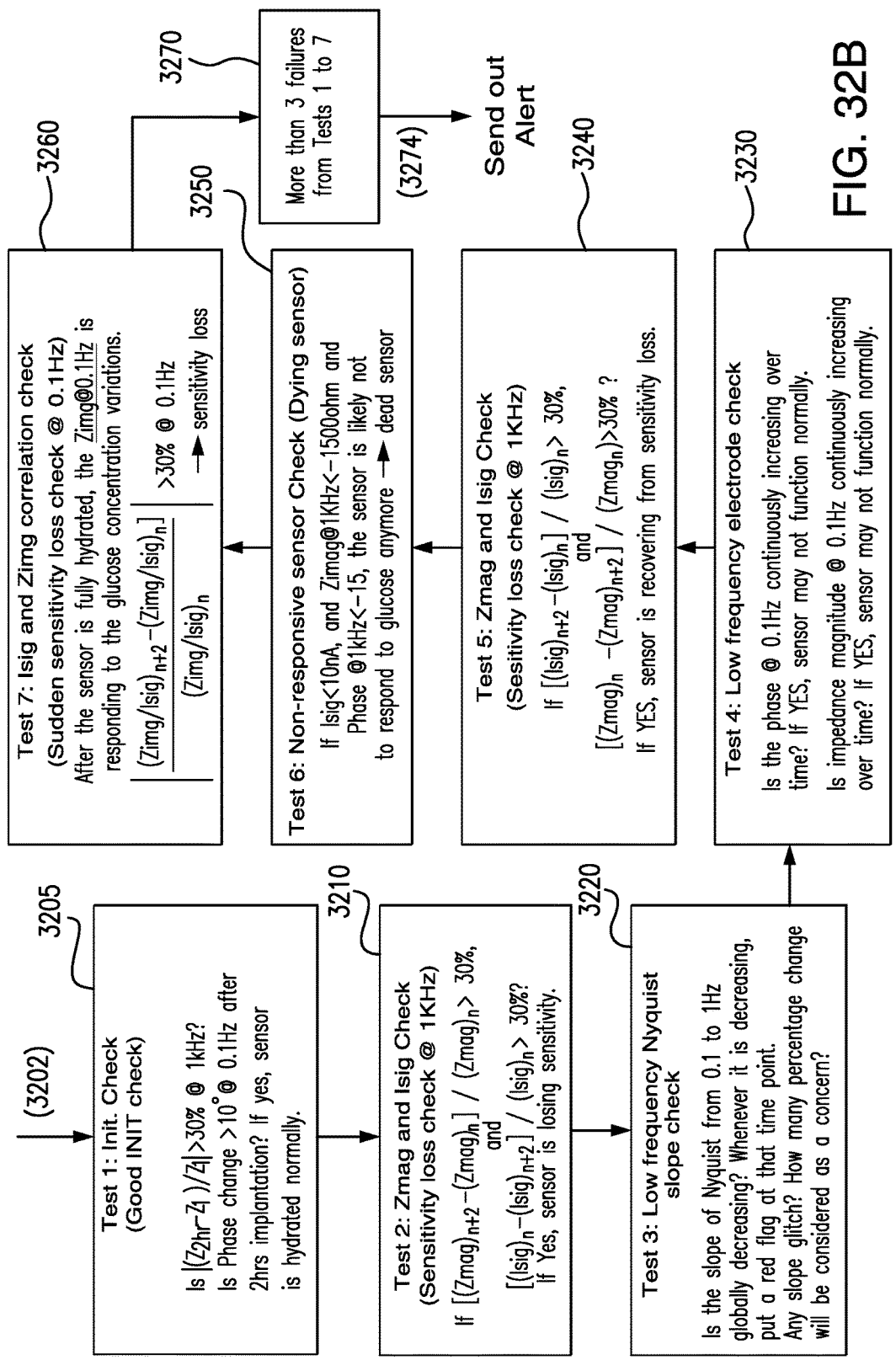

In other alternative embodiments, a different number of tests and/or a different set of EIS-based parameters for each test may be used. FIGS. 32A and 32B show an example of a diagnostic procedure for real-time monitoring that includes 7 tests. Referring to FIG. 32A, the logic begins at 3200, after the sensor has been inserted/implanted, and an EIS procedure has been performed, so as to provide the EIS data as input. At 3200, using the EIS data as input, it is first determined whether the sensor is still in place. Thus, if the |Z| slope is found to be constant across the tested frequency band (or range), and/or the phase angle is about −90°, it is determined that the sensor is no longer in place, and an alert is sent, e.g., to the patient/user, indicating that sensor pullout has occurred. If, on the other hand, the sensor is determined to be in place, the logic moves to initiation of diagnostic checks (3202).

At 3205, Test 1 is similar to Test 1 of the diagnostic procedure discussed above in connection with FIG. 31, except that the instant Test 1 specifies that the later measurement $Z_n$ is taken 2 hours after the first measurement. As such, in this example, $Z_n = Z_{2\ hr}$. More specifically, Test 1 compares the real impedance 2 hours after (sensor implantation and) initialization to the pre-initialization value. Similarly, the second part of Test 1 asks whether the difference between the phase 2 hours after initialization and the pre-initialization phase is greater than 10° at 0.1 Hz. As before, if the answer to either one of the inquiries is affirmative, then it is determined that the sensor is hydrated normally and initialized, and Test 1 is satisfied; otherwise, the sensor fails this test. It should be noted that, even though the instant test inquires about impedance and phase change 2 hours after initialization, the time interval between any two consecutive EIS runs may be shorter or longer, depending on a variety of factors, including, e.g., sensor design, the level of electrode redundancy, the degree to which the diagnostic procedure includes redundant tests, battery power, etc.

Moving to 3210, the logic next performs a sensitivity-loss check by inquiring whether, after a 2-hour interval (n+2), the percentage change in impedance magnitude at 1 kHz, as well as that in the Isig, is greater than 30%. If the answer to both inquiries is "yes", then it is determined that the sensor is losing sensitivity and, as such, Test 2 is determined to be failed. It is noted that, although Test 2 is illustrated herein based on a preferred percentage difference of 30%, in other embodiments, the percentage differences in the impedance magnitude at 1 kHz and in the Isig may fall within the range 10%-50% for purposes of conducting this test.

Test 3 (at 3220) is similar to Test 5 of the algorithm illustrated in FIG. 31. Here, as before, the question is whether the low-frequency Nyquist slope is globally increasing from 0.1 Hz to 1 Hz. If it is, then this test is passed; otherwise, the test is failed. As shown in 3220, this test is also amenable to setting a threshold, or an acceptable range, for the percent change in the low-frequency Nyquist slope, beyond which the sensor may be deemed to be failed or, at the very least, may trigger further diagnostic testing. In embodiments of the invention, such threshold value/acceptable range for the percent change in low-frequency Nyquist slope may fall within a range of about 2% to about 20%. In some preferred embodiments, the threshold value may be about 5%.

The logic next moves to 3230, which is another low-frequency test, this time involving the phase and the impedance magnitude. More specifically, the phase test inquires whether the phase at 0.1 Hz is continuously increasing over time. If it is, then the test is failed. As with other tests where the parameter's trending is monitored, the low-frequency phase test of Test 4 is also amenable to setting a threshold, or an acceptable range, for the percent change in the low-frequency phase, beyond which the sensor may be deemed to be failed or, at the very least, raise a concern. In embodiments of the invention, such threshold value/acceptable range for the percent change in low-frequency phase may fall within a range of about 5% to about 30%. In some preferred embodiments, the threshold value may be about 10%.

As noted, Test 4 also includes a low-frequency impedance magnitude test, where the inquiry is whether the impedance magnitude at 0.1 Hz is continuously increasing over time. If it is, then the test is failed. It is noted that Test 4 is considered "failed" if either the phase test or the impedance magnitude test is failed. The low-frequency impedance magnitude test of Test 4 is also amenable to setting a threshold, or an acceptable range, for the percent change in the low-frequency impedance magnitude, beyond which the sensor may be deemed to be failed or, at the very least, raise a concern. In embodiments of the invention, such threshold value/acceptable range for the percent change in low-frequency impedance magnitude may fall within a range of about 5% to about 30%. In some preferred embodiments, the threshold value may be about 10%, where the range for impedance magnitude in normal sensors is generally between about 100 KOhms and about 200 KOhms.

Test 5 (at 3240) is another sensitivity loss check that may be thought of as supplemental to Test 2. Here, if both the percentage change in the Isig and the percentage change in the impedance magnitude at 1 kHz are greater than 30%, then it is determined that the sensor is recovering from sensitivity loss. In other words, it is determined that the sensor had previously undergone some sensitivity loss, even if the sensitivity loss was not, for some reason, detected by Test 2. As with Test 2, although Test 5 is illustrated based on a preferred percentage difference of 30%, in other embodiments, the percentage differences in the Isig and the impedance magnitude at 1 kHz may fall within the range 10%-50% for purposes of conducting this test.

Moving to 3250, Test 6 provides a sensor functionality test with specific failure criteria that have been determined based on observed data and the specific sensor design. Specifically, in one embodiment, a sensor may be determined to have failed and, as such, to be unlikely to respond to glucose, if at least two out of the following three criteria are met: (1) Isig is less than 10 nA; and (2) the imaginary impedance at 1 kHz is less than −1500 Ohm; and (3) the phase at 1 kHz is less than −15°. Thus, Test 6 is determined to have been passed if any two of (1)-(3) are not met. It is noted that, in other embodiments, the Isig prong of this test may be failed if the Isig is less than about 5 nA to about 20 nA. Similarly, the second prong may be failed if the imaginary impedance at 1 kHz is less than about −1000 Ohm to about −2000 Ohms. Lastly, the phase prong may be failed if the phase at 1 kHz is less than about −10° to about −20°.

Lastly, step 3260 provides another sensitivity check, wherein the parameters are evaluated at low frequency. Thus, Test 7 inquires whether, at 0.1 Hz, the magnitude of the difference between the ratio of the imaginary impedance to the Isig (n+2), on the one hand, and the pervious value of the ratio, on the other, is larger than 30% of the magnitude of the previous value of the ratio. If it is, then the test is failed; otherwise, the test is passed. Here, although Test 7 is illustrated based on a preferred percentage difference of 30%, in other embodiments, the percentage difference may fall within the range 10%-50% for purposes of conducting this test.

Once all 7 tests have been implemented, a decision is made at 3270 as to whether the sensor is operating normally, or whether an alert should be sent out, indicating that the sensor has failed (or may be failing). As shown, in this embodiment, a sensor is determined to be functioning normally (3272) if it passes at least 4 out of the 7 tests. Put another way, in order to be determined to have failed, or to at least raise a concern (3274), the sensor must fail at least 4 out of the 7 tests. If it is determined that the sensor is "bad" (3274), an alert to that effect may be sent, e.g., to the patient/user. As noted previously, in alternative embodiments, a different rule may be used to assess normal operation versus sensor failure/concern. In addition, in embodiments of the invention, each of the tests may be weighted, such that the assigned weight reflects, e.g., the importance of that test, or of the specific parameter(s) queried for that test, in determining overall sensor operation (normal vs. failed).

As was noted previously, in embodiments of the invention, various of the above-described impedance-related parameters may be used, either individually or in combination, as inputs into one or more fusion algorithms for generating more reliable sensor glucose values. Specifically, it is known that, unlike a single-sensor (i.e., a single-working-electrode) system, multiple sensing electrodes provide higher-reliability glucose readouts, as a plurality of signals, obtained from two or more working electrodes, may be fused to provide a single sensor glucose value. Such signal fusion utilizes quantitative inputs provided by EIS to calculate the most reliable output sensor glucose value from the redundant working electrodes. It is noted that, while the ensuing discussion may describe various fusion algorithms in terms of a first working electrode (WE1) and a second working electrode (WE2) as the redundant electrodes, this is by way of illustration, and not limitation, as the algorithms and their underlying principles described herein are applicable to, and may be used in, redundant sensor systems having more than 2 working electrodes.

FIGS. 33A and 33B show top-level flowcharts for two alternative methodologies, each of which includes a fusion algorithm. Specifically, FIG. 33A is a flowchart involving a current (Isig)-based fusion algorithm, and FIG. 33B is a flowchart directed to sensor glucose (SG) fusion. As may be seen from the diagrams, the primary difference between the two methodologies is the time of calibration. Thus, FIG. 33A shows that, for Isig fusion, calibration 3590 is performed after the fusion 3540 is completed. That is, redundant Isigs from WE1 to WEn are fused into a single Isig 3589, which is then calibrated to produce a single sensor glucose value 3598. For SG fusion, on the other hand, calibration 3435 is completed for each individual Isig from WE1 to WEn to produce calibrated SG values (e.g., 3436, 3438) for each of the working electrodes. Thus, SG fusion algorithms provide for independent calibration of each of the plurality of Isigs, which may be preferred in embodiments of the invention. Once calibrated, the plurality of calibrated SG values is fused into a single SG value 3498.

It is important to note that each of flowcharts shown in FIGS. 33A and 33 B includes a spike filtering process (3520, 3420). As was described above in the discussion relating to sensitivity loss, 1 kHz or higher-frequency impedance measurements typically cause EIS-induced spikes in the Isig. Therefore, once an EIS procedure has been performed for each of the electrodes WE1 to WEn, for both SG fusion and Isig fusion, it is preferable to first filter the Isigs 3410, 3412, etc. and 3510, 3512, etc. to obtain respective filtered Isigs 3422, 3424, etc. and 3522, 3524, etc. The filtered Isigs are then either used in Isig fusion, or first calibrated and then used in SG fusion, as detailed below. As will become apparent in the ensuing discussion, both fusion algorithms entail calculation and assignment of weights based on various factors.

Figure 34:
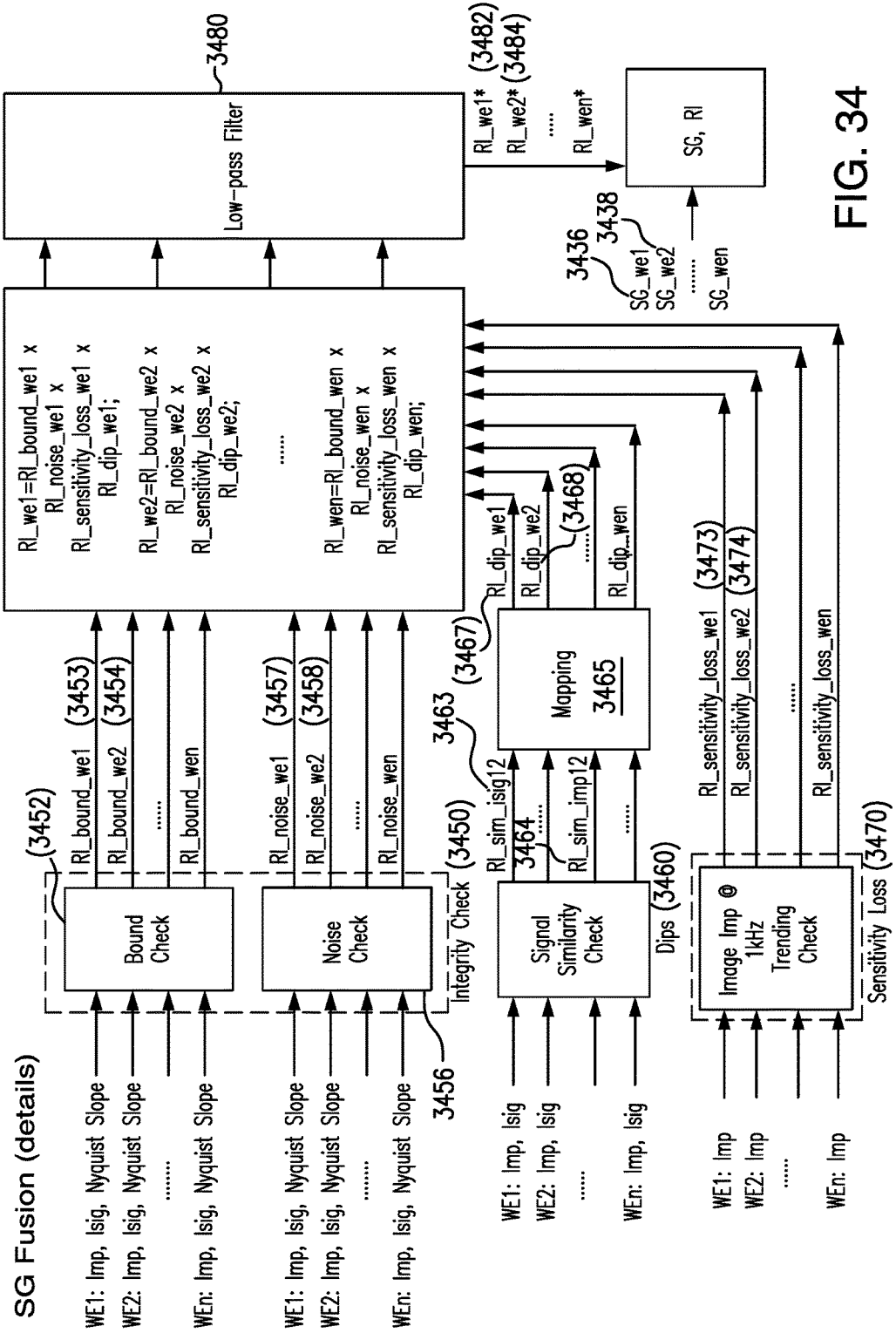
FIG. 34 shows details of the sensor glucose (SG)-based fusion algorithm of FIG. 33B in accordance with embodiments of the invention.

FIG. 34 shows the details of the fusion algorithm 3440 for SG fusion. Essentially, there are four factors that need to be checked before the fusion weights are determined. First, integrity check 3450 involves determining whether each of the following parameters is within specified ranges for normal sensor operation (e.g., predetermined lower and upper thresholds): (i) Isig; (ii) 1 kHz real and imaginary impedances; (iii) 0.105 Hz real and imaginary impedances; and (iv) Nyquist slope. As shown, integrity check 3450 includes a Bound Check 3452 and a Noise Check 3456, wherein, for each of the Checks, the above-mentioned parameters are used as input parameters. It is noted that, for brevity, real and/or imaginary impedances, at one or more frequencies, appear on FIGS. 33A-35 simply as "Imp" for impedance. In addition, both real and imaginary impedances may be calculated using impedance magnitude and phase (which is also shown as an input on FIGS. 33A and 33B).

The output from each of the Bound Check 3452 and the Noise Check 3458 is a respective reliability index (RI) for each of the redundant working electrodes. Thus, the output from the Bound Check includes, e.g., RI_bound_We$_1$ (3543) and RI_bound_We$_2$ (3454). Similarly, for the Noise Check, the output includes, e.g., RI_noise_We$_1$ (3457) and RI_noise_We$_2$ (3458). The bound and noise reliability indices for each working electrode are calculated based on compliance with the above-mentioned ranges for normal sensor operation. Thus, if any of the parameters falls outside the specified ranges for a particular electrode, the reliability index for that particular electrode decreases.

It is noted that the threshold values, or ranges, for the above-mentioned parameters may depend on various factors, including the specific sensor and/or electrode design. Nevertheless, in one preferred embodiment, typical ranges for some of the above-mentioned parameters may be, e.g., as follows: Bound threshold for 1 kHz real impedance=[0.3e+4 2e+4]; Bound threshold for 1 kHz imaginary impedance= [−2e+3, 0]; Bound threshold for 0.105 Hz real impedance= [2e+4 7e+4]; Bound threshold for 0.105 Hz imaginary impedance=[−2e+5–0.25e+5]; and Bound threshold for Nyquist slope=[2 5]. Noise may be calculated, e.g., using second order central difference method where, if noise is above a certain percentage (e.g., 30%) of median value for each variable buffer, it is considered to be out of noise bound.

Second, sensor dips may be detected using sensor current (Isig) and 1 kHz real impedance. Thus, as shown in FIG. 34, Isig and "Imp" are used as inputs for dips detection 3460. Here, the first step is to determine whether there is any divergence between Isigs, and whether any such divergence is reflected in 1 kHz real impedance data. This may be accomplished by using mapping 3465 between the Isig similarity index (RI_sim_isig12) 3463 and the 1 kHz real impedance similarity index (RI_sim_imp12) 3464. This mapping is critical, as it helps avoid false positives in instances where a dip is not real. Where the Isig divergence is real, the algorithm will select the sensor with the higher Isig.

In accordance with embodiments of the invention, the divergence/convergence of two signals (e.g., two Isigs, or two 1 kHz real impedance data points) can be calculated as follows:

diff_va1=abs(va1−(va1+va2)/2);

diff_va2=abs(va2−(va1+va2)/2);

RI_sim=1−(diff_va1+diff_va2)/(mean(abs(va1+vab 2))/4)

where va1 and va2 are two variables, and RI_sim (similarity index) is the index to measure the convergence or divergence of the signals. In this embodiment, RI_sim must be bound between 0 and 1. Therefore, if RI_sim as calculated above is less than 0, it will be set to 0, and if it is higher than 1, it will be set to 1.

The mapping 3465 is performed by using ordinary linear regression (OLR). However, when OLR does not work well, a robust median slope linear regression (RMSLR) can be used. For Isig similarity index and 1 kHz real impedance index, for example, two mapping procedures are needed: (i) Map Isig similarity index to 1 kHz real impedance similarity index; and (ii) map 1 kHz real impedance similarity index to Isig similarity index. Both mapping procedures will generate two residuals: res12 and res21. Each of the dip reliability indices 3467, 3468 can then be calculated as:

RI_dip=1−(res12+res21)/(RI_sim_*isig*+ RI_sim_1K_real_impedance).

The third factor is sensitivity loss 3470, which may be detected using 1 kHz imaginary impedance trending in, e.g., the past 8 hours. If one sensor's trending turns negative, the algorithm will rely on the other sensor. If both sensors lose sensitivity, then a simple average is taken. Trending may be calculated by using a strong low-pass filter to smooth over the 1 kHz imaginary impedance, which tends to be noisy, and by using a correlation coefficient or linear regression with respect to time during, e.g., the past 8 hours to determine whether the correlation coefficient is negative or the slope is negative. Each of the sensitivity loss reliability indices 3473, 3474 is then assigned a binary value of 1 or 0.

The total reliability index (RI) for each of we1, we2, . . . wen is calculated as follows:

$$RI\_we_1 = RI\_dip\_we_1 \times RI\_sensitivity\_loss\_we_1 \times$$
$$RI\_bound\_we_1 \times RI\_noise\_we_1$$

$$RI\_we_2 = RI\_dip\_we_2 \times RI\_sensitivity\_loss\_we_2 \times$$
$$RI\_bound\_we_2 \times RI\_noise\_we_2$$

$$RI\_we_3 = RI\_dip\_we_3 \times RI\_sensitivity\_loss\_we_3 \times$$
$$RI\_bound\_we_3 \times RI\_noise\_we_3$$

$$RI\_we_4 = RI\_dip\_we_4 \times RI\_sensitivity\_loss\_we_4 \times$$
$$RI\_bound\_we_4 \times RI\_noise\_we_4$$

$$\vdots$$

$$RI\_we_n = RI\_dip\_we_n \times RI\_sensitivity\_loss\_we_n \times$$
$$RI\_bound\_we_n \times RI\_noise\_we_n$$

Having calculated the respective reliability indices of the individual working electrodes, the weight for each of the electrodes may be calculated as follow:

$$weight\_we_1 = RI\_we_1 / (RI\_we_1 + RI\_we_2 + RI\_we_3 + RI\_we_4 + \ldots + RI\_we_n)$$

$$weight\_we_2 = RI\_we_2 / (RI\_we_1 + RI\_we_2 + RI\_we_3 + RI\_we_4 + \ldots + RI\_we_n)$$

$$weight\_we_3 = RI\_we_3 / (RI\_we_1 + RI\_we_2 + RI\_we_3 + RI\_we_4 + \ldots + RI\_we_n)$$

$$weight\_we_4 = RI\_we_4 / (RI\_we_1 + RI\_we_2 + RI\_we_3 +$$

-continued $$\text{weight\_we}_n = \text{RI\_we}_n / (\text{RI\_we}_1 + \text{RI\_we}_2 + \text{RI\_we}_3 + \text{RI\_we}_4 + \ldots + \text{RI\_we}_n)$$

Based on the above, the fused SG 3498 is then calculated as follows:

$$SG = \text{weight\_we}_1 \times SG\_we_1 + \text{weight\_we}_2 \times SG\_we_2 + \text{weight\_we}_3 \times SG\_we_3 + \text{weight\_we}_4 \times SG\_we_4 + \ldots + \text{weight\_we}_n \times SG\_we_n$$

The last factor relates to artifacts in the final sensor readout, such as may be caused by instant weight change of sensor fusion. This may be avoided by either applying a low-pass filter 3480 to smooth the RI for each electrode, or by applying a low-pass filter to the final SG. When the former is used, the filtered reliability indices—e.g., RI_We1* and RI_We2* (3482, 3484)—are used in the calculation of the weight for each electrode and, therefore, in the calculation of the fused SG 3498.

Figure 35:
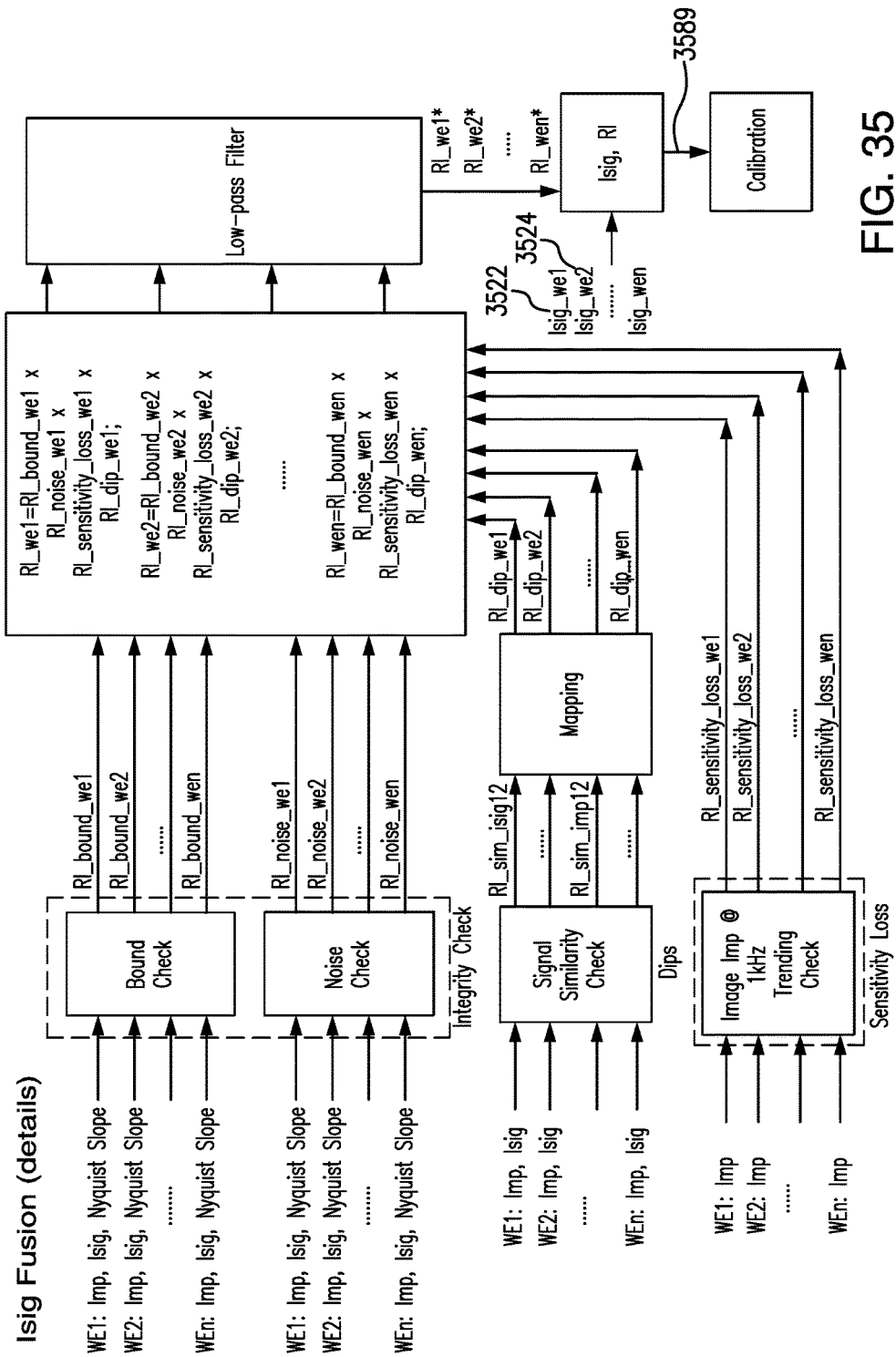
FIG. 35 shows details of the current (Isig)-based fusion algorithm of FIG. 33A in accordance with embodiments of the invention.

FIG. 35 shows the details of the fusion algorithm 3540 for Isig fusion. As can be seen, this algorithm is substantially similar to the one shown in FIG. 34 for SG fusion, with two exceptions. First, as was noted previously, for Isig fusion, calibration constitutes the final step of the process, where the single fused Isig 3589 is calibrated to generate a single sensor glucose value 3598. See also FIG. 33B. Second, whereas SG fusion uses the SG values for the plurality of electrodes to calculate the final SG value 3498, the fused Isig value 3589 is calculated using the filtered Isigs (3522, 3524, and so on) for the plurality of electrodes.

In one closed-loop study involving a non-diabetic population, it was found that the above-described fusion algorithms provided considerable improvements in the Mean Absolute Relative Difference (MARD) both on Day 1, when low start-up issues are most significant and, as such, may have a substantial impact on sensor accuracy and reliability, and overall (i.e., over a 7-day life of the sensor). The study evaluated data for an 88% distributed layout design with high current density (nominal) plating using three different methodologies: (1) calculation of one sensor glucose value (SG) via fusion using Medtronic Minimed's Ferrari Algorithm 1.0 (which is a SG fusion algorithm as discussed above); (2) calculation of one SG by identifying the better ISIG value using 1 kHz EIS data (through the Isig fusion algorithm discussed above); and (3) calculation of one SG by using the higher ISIG value (i.e., without using EIS). The details of the data for the study are presented below:

| (1) SG based on Ferrari 1.0 Alg for 88% distributed layout with high current density (nominal) plating | | | | | | | | |
|---|---|---|---|---|---|---|---|---|
| Mean-ARD Percentage | | | | | | | | |
| Day | 1 | 2 | 3 | 4 | 5 | 6 | 7 | Total |
| 040-080 | 19.39 | 17.06 |  | 22.27 | 17.50 | 37.57 | 11.43 | 19.69 |
| 080-120 | 19.69 | 09.18 | 09.34 | 08.64 | 10.01 | 08.31 | 11.33 | 11.56 |
| 120-240 | 19.01 | 17.46 | 12.44 | 07.97 | 11.75 | 08.82 | 12.15 | 12.92 |
| 240-400 |  | 10.25 | 08.36 | 14.09 | 10.86 | 12.84 | 22.70 | 12.88 |
| Total | 19.52 | 11.71 | 10.14 | 09.30 | 10.83 | 09.49 | 11.89 | 12.28 |
| Mean-Absolute Bias (sg-bg) | | | | | | | | |
| Day | 1 | 2 | 3 | 4 | 5 | 6 | 7 | Total |
| 040-080 | 14.86 | 11.78 |  | 15.81 | 11.07 | 29.00 | 07.26 | 14.05 |
| 080-120 | 19.53 | 09.37 | 09.49 | 08.78 | 09.88 | 08.44 | 11.61 | 11.62 |
| 120-240 | 30.04 | 29.73 | 19.34 | 14.45 | 18.25 | 12.66 | 18.89 | 20.60 |
| 240-400 |  | 26.75 | 22.23 | 39.82 | 29.00 | 33.00 | 61.36 | 35.19 |
| Total | 21.62 | 15.20 | 12.79 | 13.21 | 12.04 | 10.84 | 15.04 | 14.79 |
| Mean-Signed Bias (sg-bg) | | | | | | | | |
| Day | 1 | 2 | 3 | 4 | 5 | 6 | 7 | Total |
| 040-080 | 12.15 | 09.78 |  | 15.81 | 11.07 | 29.00 | 07.26 | 13.01 |
| 080-120 | −04.45 | −04.92 | −00.90 | 00.18 | 01.21 | 00.85 | 00.03 | −01.44 |
| 120-240 | −10.18 | −27.00 | −16.89 | −02.91 | −05.40 | −01.24 | −11.58 | −10.71 |
| 240-400 |  | 11.25 | 02.23 | −00.07 | −27.00 | −33.00 | −61.36 | −10.29 |
| Total | −04.81 | −09.77 | −05.09 | −00.23 | −00.22 | 00.67 | −04.98 | −03.56 |
| Eval Points | | | | | | | | |
| Day | 1 | 2 | 3 | 4 | 5 | 6 | 7 | Total |
| 040-080 | 007 | 004 | 000 | 002 | 006 | 003 | 004 | 026 |
| 080-120 | 090 | 064 | 055 | 055 | 067 | 056 | 047 | 434 |
| 120-240 | 028 | 025 | 022 | 021 | 016 | 032 | 026 | 170 |
| 240-400 | 000 | 002 | 004 | 008 | 003 | 001 | 002 | 020 |
| Total | 125 | 095 | 081 | 086 | 092 | 092 | 079 | 650 |

(2) SG based on better ISIG using 1 kHz EIS for 88% distributed layout with high current density (nominal) plating Mean-ARD Percentage

| Day | 1 | 2 | 3 | 4 | 5 | 6 | 7 | Total |
|---|---|---|---|---|---|---|---|---|
| 040-080 | 16.66 | 18.78 |  | 21.13 | 16.21 | 43.68 | 09.50 | 18.14 |
| 080-120 | 16.22 | 11.96 | 08.79 | 10.49 | 09.75 | 08.04 | 10.34 | 11.36 |
| 120-240 | 15.08 | 17.50 | 12.68 | 07.72 | 08.74 | 08.84 | 13.02 | 12.16 |
| 240-400 |  | 07.66 | 06.42 | 11.10 | 07.52 | 15.95 | 21.13 | 09.84 |
| Total | 15.96 | 13.70 | 09.92 | 09.95 | 09.96 | 09.40 | 11.31 | 11.83 |

Mean-Absolute Bias (sg-bg)

| Day | 1 | 2 | 3 | 4 | 5 | 6 | 7 | Total |
|---|---|---|---|---|---|---|---|---|
| 040-080 | 12.71 | 13.00 |  | 15.00 | 10.17 | 33.50 | 06.00 | 12.83 |
| 080-120 | 15.70 | 12.17 | 08.57 | 10.89 | 09.62 | 08.26 | 10.49 | 11.32 |
| 120-240 | 24.43 | 29.82 | 19.43 | 13.79 | 14.60 | 12.97 | 20.27 | 19.58 |
| 240-400 |  | 20.00 | 17.00 | 32.50 | 20.00 | 41.00 | 60.00 | 27.29 |
| Total | 17.72 | 17.20 | 12.56 | 13.55 | 10.95 | 11.21 | 14.12 | 14.20 |

Mean-Signed Bias (sg-bg)

| Day | 1 | 2 | 3 | 4 | 5 | 6 | 7 | Total |
|---|---|---|---|---|---|---|---|---|
| 040-080 | 08.71 | 13.00 |  | 15.00 | 10.17 | 33.50 | 06.00 | 11.67 |
| 080-120 | −04.30 | −08.62 | −01.11 | −03.64 | 02.52 | 00.40 | −01.56 | −02.52 |
| 120-240 | −11.30 | −29.64 | −17.09 | −08.74 | −10.87 | −07.23 | −15.09 | −14.05 |
| 240-400 |  | 20.00 | 00.50 | 09.50 | −17.33 | −41.00 | −60.00 | −03.18 |
| Total | −05.30 | −12.56 | −06.20 | −03.63 | −00.10 | −02.29 | −06.35 | −05.21 |

Eval Points

| Day | 1 | 2 | 3 | 4 | 5 | 6 | 7 | Total |
|---|---|---|---|---|---|---|---|---|
| 040-080 | 007 | 004 | 000 | 001 | 006 | 002 | 004 | 024 |
| 080-120 | 082 | 053 | 044 | 045 | 058 | 043 | 041 | 366 |
| 120-240 | 030 | 022 | 023 | 019 | 015 | 030 | 022 | 161 |
| 240-400 | 000 | 002 | 004 | 006 | 003 | 001 | 001 | 017 |
| Total | 119 | 081 | 071 | 071 | 082 | 076 | 068 | 568 |

40

(3) SG based on higher ISIG for 88% distributed layout with high current density (nominal) plating Mean-ARD Percentage

| Day | 1 | 2 | 3 | 4 | 5 | 6 | 7 | Total |
|---|---|---|---|---|---|---|---|---|
| 040-080 | 17.24 | 19.13 |  | 21.13 | 17.31 | 43.68 | 10.38 | 18.79 |
| 080-120 | 17.69 | 11.77 | 09.36 | 10.70 | 10.19 | 08.34 | 10.68 | 11.86 |
| 120-240 | 16.80 | 17.63 | 13.04 | 07.38 | 09.04 | 08.52 | 13.25 | 12.50 |
| 240-400 |  | 07.47 | 06.02 | 10.85 | 07.52 | 15.95 | 21.13 | 09.63 |
| Total | 17.44 | 13.60 | 10.37 | 10.00 | 10.40 | 09.36 | 11.66 | 12.26 |

Mean-Absolute Bias (sg-bg)

| Day | 1 | 2 | 3 | 4 | 5 | 6 | 7 | Total |
|---|---|---|---|---|---|---|---|---|
| 040-080 | 13.14 | 13.25 |  | 15.00 | 11.00 | 33.50 | 06.50 | 13.29 |
| 080-120 | 17.23 | 11.98 | 09.22 | 11.02 | 10.08 | 08.59 | 10.86 | 11.85 |
| 120-240 | 27.40 | 30.09 | 19.75 | 13.26 | 14.93 | 12.45 | 20.65 | 20.09 |
| 240-400 |  | 19.50 | 16.00 | 32.00 | 20.00 | 41.00 | 60.00 | 26.82 |
| Total | 19.53 | 17.09 | 13.00 | 13.35 | 11.37 | 11.18 | 14.53 | 14.67 |

Mean-Signed Bias (sg-bg)

| Day | 1 | 2 | 3 | 4 | 5 | 6 | 7 | Total |
|---|---|---|---|---|---|---|---|---|

| (3) SG based on higher ISIG for 88% distributed layout with high current density (nominal) plating | | | | | | | |
|---|---|---|---|---|---|---|---|
| 040-080 | 08.29 | 12.75 |  | 15.00 | 11.00 | 33.50 | 06.50 | 11.79 |
| 080-120 | −04.72 | −08.83 | −02.35 | −01.56 | 01.75 | −00.18 | −01.52 | −02.70 |
| 120-240 | −15.13 | −29.73 | −17.67 | −08.42 | −11.47 | −07.03 | −15.43 | −14.86 |
| 240-400 |  | 19.50 | 01.50 | 06.33 | −17.33 | −41.00 | −60.00 | −04.12 |
| Total | −06.57 | −12.70 | −07.11 | −02.46 | −00.63 | −02.56 | −06.47 | −05.57 |

| Eval Points | | | | | | | |
|---|---|---|---|---|---|---|---|
| Day | 1 | 2 | 3 | 4 | 5 | 6 | 7 | Total |
| 040-080 | 007 | 004 | 000 | 001 | 006 | 002 | 004 | 024 |
| 080-120 | 083 | 054 | 046 | 048 | 060 | 044 | 042 | 377 |
| 120-240 | 030 | 022 | 024 | 019 | 015 | 031 | 023 | 164 |
| 240-400 | 000 | 002 | 004 | 006 | 003 | 001 | 001 | 017 |
| Total | 120 | 082 | 074 | 074 | 084 | 078 | 070 | 582 |

With the above data, it was found that, with the first approach, the MARD (%) on Day 1 was 19.52%, with an overall MARD of 12.28%. For the second approach, the Day-1 MARD was 15.96% and the overall MARD was 11.83%. Lastly, for the third approach, the MARD was 17.44% on Day 1, and 12.26% overall. Thus, for this design with redundant electrodes, it appears that calculation of SG based on the better ISIG using 1 kHz EIS (i.e., the second methodology) provides the greatest advantage. Specifically, the lower Day-1 MARD may be attributable, e.g., to better low start-up detection using EIS. In addition, the overall MARD percentages are more than 1% lower than the overall average MARD of 13.5% for WE1 and WE2 in this study. It is noted that, in the above-mentioned approaches, data transitions may be handled, e.g., by a filtering method to minimize the severity of the transitions, such as by using a low-pass filter 3480 as discussed above in connection with FIGS. 33A-35.

It bears repeating that sensor diagnostics, including, e.g., assessment of low start-up, sensitivity-loss, and signal-dip events depends on various factors, including the sensor design, number of electrodes (i.e., redundancy), electrode distribution/configuration, etc. As such, the actual frequency, or range of frequencies, for which an EIS-based parameter may be substantially glucose-independent, and therefore, an independent marker, or predictor, for one or more of the above-mentioned failure modes may also depend on the specific sensor design. For example, while it has been discovered, as described hereinabove, that sensitivity loss may be predicted using imaginary impedance at the relatively higher frequencies—where imaginary impedance is substantially glucose-independent—the level of glucose dependence, and, therefore, the specific frequency range for using imaginary impedance as a marker for sensitivity loss, may shift (higher or lower) depending on the actual sensor design.

More specifically, as sensor design moves more and more towards the use of redundant working electrodes, the latter must be of increasingly smaller sizes in order to maintain the overall size of the sensor. The size of the electrodes, in turn, affects the frequencies that may be queried for specific diagnostics. In this regard, it is important to note that the fusion algorithms described herein and shown in FIGS. 33A-35 are to be regarded as illustrative, and not limiting, as each algorithm can be modified as necessary to use EIS-based parameters at frequencies that exhibit the least amount of glucose dependence, based on the type of sensor under analysis.

In addition, experimental data indicates that human tissue structure may also affect glucose dependence at different frequencies. For example, in children, real impedance at 0.105 Hz has been found to be a substantially glucose-independent indicator for low start-up detection. It is believed that this comes about as a result of a child's tissue structure changing, e.g., the Warburg impedance, which relates mostly to the resistive component. See also the subsequent discussion relating to interferent detection.

Embodiments of the invention herein are also directed to the use of EIS in optimizing sensor calibration. By way of background, in current methodologies, the slope of a BG vs. Isig plot, which may be used to calibrate subsequent Isig values, is calculated as follows:

$$\text{slope} = \frac{\Sigma \alpha \beta (isig - \text{offset}) bg}{\Sigma \alpha \beta (isig - \text{offset})^2}$$

where $\alpha$ is an exponential function of a time constant, $\beta$ is a function of blood glucose variance, and offset is a constant. For a sensor in steady condition, this method provides fairly accurate results. As shown, e.g., in FIG. 36, BG and Isig follow a fairly linear relationship, and offset can be taken as a constant.

However, there are situations in which the above-mentioned linear relationship does not hold true, such as, e.g., during periods in which the sensor experiences a transition. As shown in FIG. 37, it is clear that Isig-BG pairs 1 and 2 are significantly different from pairs 3 and 4 in terms of Isig and BG relationship. For these types of conditions, use of a constant offset tends to produce inaccurate results.

To address this issue, one embodiment of the invention is directed to the use of an EIS-based dynamic offset, where EIS measurements are used to define a sensor status vector as follows:

$$V = \{real\_imp\_1K, img\_imp\_1K, \text{Nyquist\_slope}, \text{Nyquist\_R\_square}\}$$

where all of the elements in the vector are substantially BG independent. It is noted that Nyquist_R_square is the R square of linear regression used to calculate the Nyquist slope, i.e., the square of the correlation coefficient between real and imaginary impedances at relatively-lower frequencies, and a low R square indicates abnormality in sensor performance. For each Isig-BG pair, a status vector is assigned. If a significant difference in status vector is detected—e.g., |V2–V3| for the example shown in FIG. 37—a different offset value is assigned for 3 and 4 when compared to 1 and 2. Thus, by using this dynamic offset approach, it is possible to maintain a linear relationship between Isig and BG.

In a second embodiment, an EIS-based segmentation approach may be used for calibration. Using the example of FIG. 37 and the vector V, it can be determined that sensor state during 1 and 2 is signficantly different from sensor state during 3 and 4. Therefore, the calibration buffer can be divided into two segments, as follows:

Isig_buffer1=[*Isig*1, *Isig*2]; BG_buffer1=[*BG*1, *BG*2]

Isig_buffer2=[*Isig*3, *Isig*3]; BG_buffer2=[*BG*3, *BG*3]

Thus, when the sensor operates during 1 and 2, Isig buffer1 and BG buffer1 would be used for calibration. However, when the sensor operates during 3 and 4, i.e., during a transition period, Isig_buffer2 and BG_buffer2 would be used for calibration.

Figure 38A:
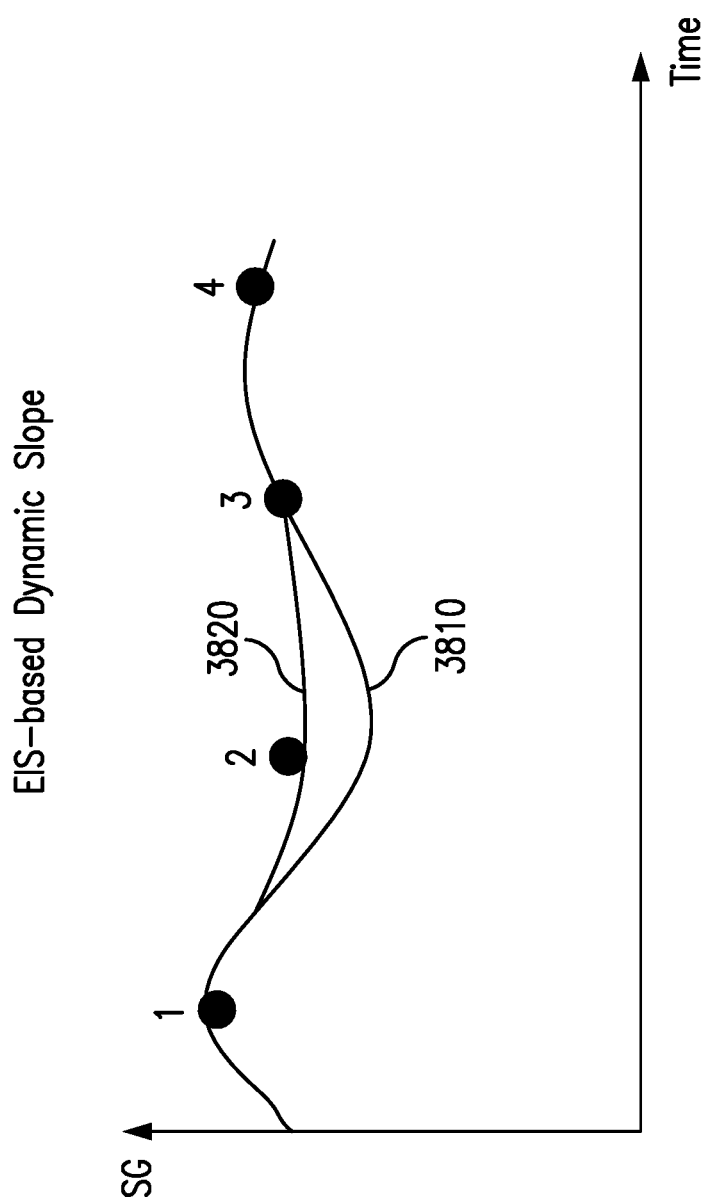
FIG. 38A is an illustration of EIS-based dynamic slope (with slope adjustment) in accordance with embodiments of the invention for sensor calibration.

In yet another embodiment, an EIS-based dynamic slope approach, where EIS is used to adjust slope, may be used for calibration purposes. FIG. 38A shows an example of how this method can be used to improve sensor accuracy. In this diagram, the data points 1-4 are discrete blood glucose values. As can be seen from FIG. 38A, there is a sensor dip 3810 between data points 1 and 3, which dip can be detected using the sensor state vector V described above. During the dip, slope can be adjusted upward to reduce the underreading, as shown by reference numeral 3820 in FIG. 38A.

In a further embodiment, EIS diagnostics may be used to determine the timing of sensor calibrations, which is quite useful for, e.g, low-startup events, sensitivity-loss events, and other similar situations. As is known, most current methodologies require regular calibrations based on a preset schedule, e.g., 4 times per day. Using EIS diagnostics, however, calibrations become event-driven, such that they may be performed only as often as necessary, and when they would be most productive. Here, again, the status vector V may be used to determine when the sensor state has changed, and to request calibration if it has, indeed, changed.

Figure 38B:
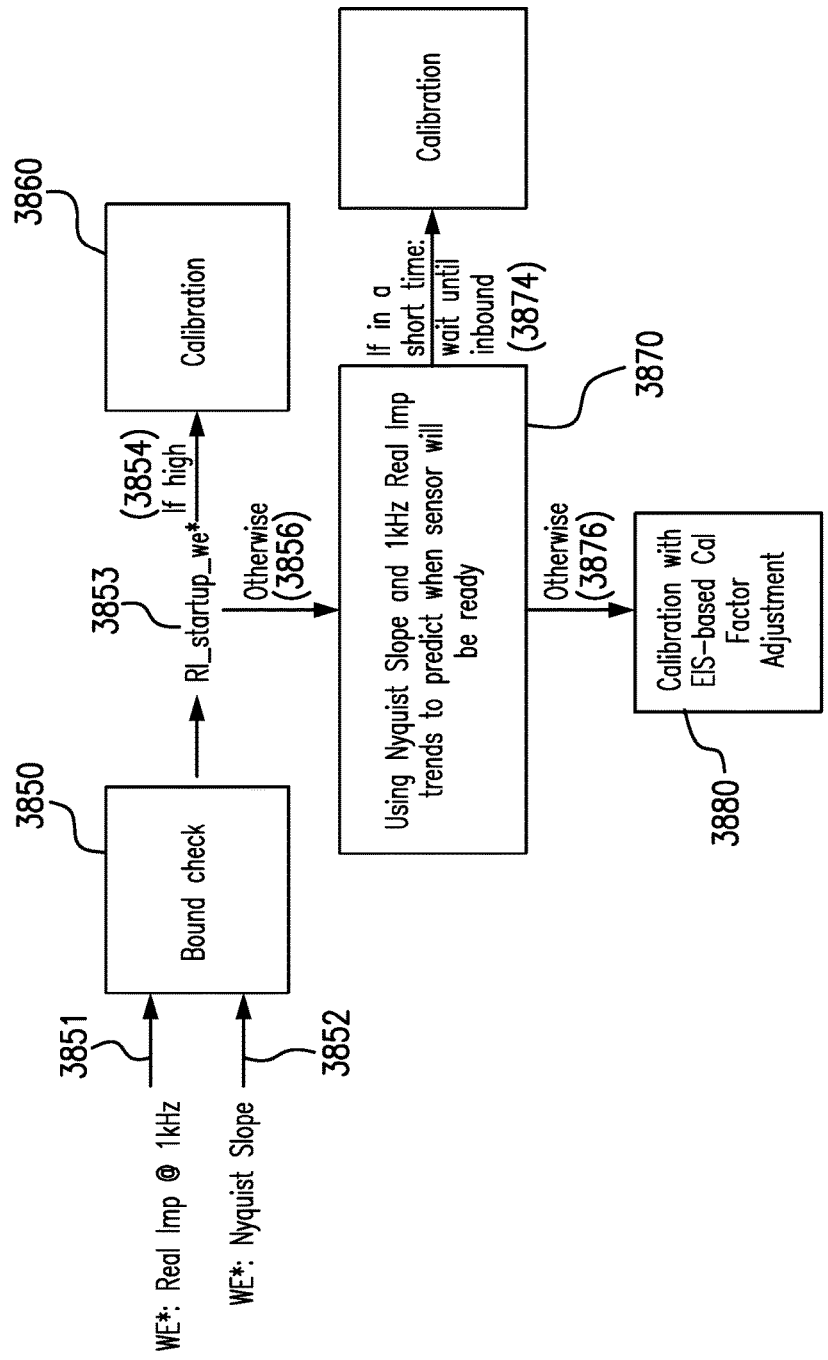
FIG. 38B shows an EIS-assisted sensor calibration flowchart involving low start-up detection in accordance with embodiments of the invention.

More specifically, in an illustrative example, FIG. 38B shows a flowchart for EIS-assisted sensor calibration involving low start-up detection. Using Nyquist slope, 1 kHz real impdance, and a bound check 3850 (see, e.g., the previously-described bound check and associated threshold values for EIS-based parameters in connection with the fusion algorithms of FIGS. 33A- 35), a reliability index 3853 can be developed for start-up, such that, when the 1 kHz real impedance 3851 and the Nyquist slope 3852 are lower than their corresponding upper bounds, RI_startup=1, and sensor is ready for calibration. In other words, the reliability index 3853 is "high" (3854), and the logic can proceed to calibration at 3860.

When, on the other hand, the 1 kHz real impedance and the Nyquist slope are higher than their corresponding upper bounds (or threshold values), RI_startup=0 (i.e., it is "low"), and the sensor is not ready for calibration (3856), i.e., a low start-up issue may exist. Here, the trend of 1 kHz real impedance and the Nyquist slope can be used to predict when both parameters will be in range (3870). If it is estimated that this will only take a very short amount of time (e.g., less than one hour), then the algorithm waits until the sensor is ready, i.e., until the above-mentioned EIS-based parameters are in-bound (3874), at which point the algorithm proceeds to calibration. If, however, the wait time would be relatively long (3876), then the sensor can be calibrated now, and then the slope or offset can be gradually adjusted according to the 1 kHz real impedance and the Nyquist slope trend (3880). It is noted that by performing the adjustment, serious over- or under-reading caused by low start-up can be avoided. As noted previously, the EIS-based parameters and related information that is used in the instant calibration algorithm is substantially glucose-independent.

It is noted that, while the above description in connection with FIG. 38B shows a single working electrode, as well as the calculation of a reliability index for start-up of that working electrode, this is by way of illustration, and not limitation. Thus, in a redundant sensor including two or more working electrodes, a bound check can be performed, and a start-up reliability index calculated, for each of the plurality of (redundant) working electrodes. Then, based on the respective reliability indices, at least one working electrode can be identified that can proceed to obtain glucose measurements. In other words, in a sensor having a single working electrode, if the latter exhibits low start-up, actual use of the sensor (for measuring glucose) may have to be delayed until the low start-up period is over. This period may typically be on the order of one hour or more, which is clearly disadvantageous. In contrast, in a redundant sensor, utilizing the methodology described herein allows an adaptive, or "smart", start-up, wherein an electrode that can proceed to data gathering can be identified in fairly short order, e.g., on the order of a few minutes. This, in turn, reduces MARD, because low start-up generally provides about a ½% increase in MARD.

In yet another embodiment, EIS can aid in the adjustment of the calibration buffer. For existing calibration algorithms, the buffer size is always 4, i.e., 4 Isig-BG pairs, and the weight is based upon α which, as noted previously, is an exponential function of a time constant, and β, which is a function of blood glucose variance. Here, EIS can help to determine when to flush the buffer, how to adjust buffer weight, and what the appropriate buffer size is.

Embodiments of the invention are also directed to the use of EIS for interferent detection. Specifically, it may be desirable to provide a medication infusion set that includes a combination sensor and medication-infusion catheter, where the sensor is placed within the infusion catheter. In such a system, the physical location of the infusion catheter relative to the sensor may be of some concern, due primarily to the potential impact on (i.e., interference with) sensor signal that may be caused by the medication being infused and/or an inactive component thereof.

For example, the diluent used with insulin contains m-cresol as a preservative. In in-vitro studies, m-cresol has been found to negatively impact a glucose sensor if insulin (and, therefore, m-cresol) is being infused in close proximity to the sensor. Therefore, a system in which a sensor and an infusion catheter are to be combined in a single needle must be able to detect, and adjust for, the effect of m-cresol on the sensor signal. Since m-cresol affects the sensor signal, it would be preferable to have a means of detecting this interferent independently of the sensor signal itself.

Experiments have shown that the effect of m-cresol on the sensor signal is temporary and, thus, reversible. Nevertheless, when insulin infusion occurs too close to the sensor, the m-cresol tends to "poison" the electrode(s), such that the latter can no longer detect glucose, until the insulin (and m-cresol) have been absorbed into the patient's tissue. In this regard, it has been found that there is typically about a 40-minute time period between initiation of insulin infusion and when the sensor has re-gained the ability to detect glucose again. However, advantageously, it has also been discovered that, during the same time period, there is a large increase in 1 kHz impedance magnitude quite independently of the glucose concentration.

Figure 39:
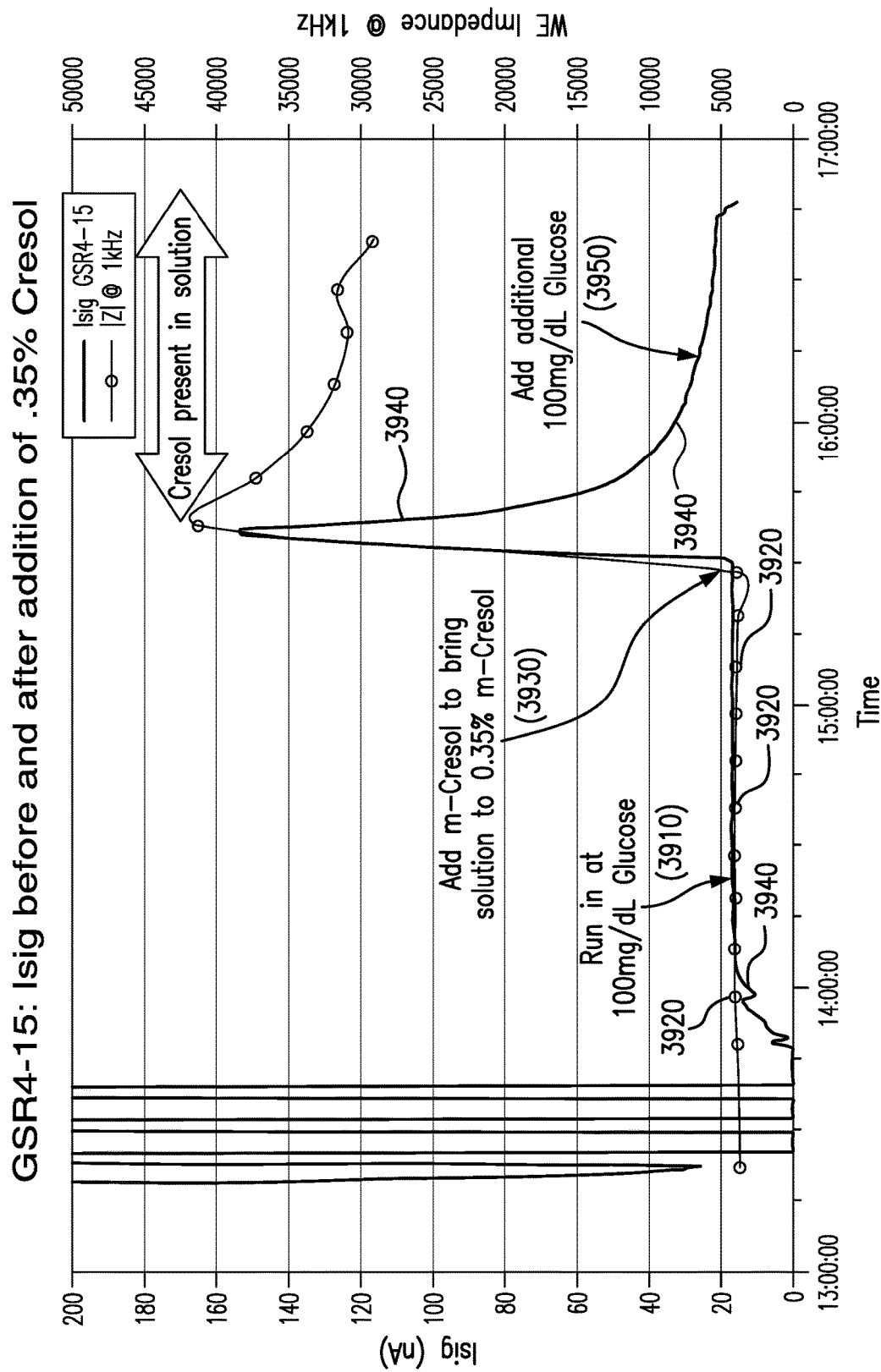
FIG. 39 shows sensor current (Isig) and 1 kHz impedance magnitude for an in-vitro simulation of an interferent being in close proximity to a sensor in accordance with embodiments of the invention.

Specifically, FIG. 39 shows Isig and impedance data for an in-vitro experiment, wherein the sensor was placed in a 100 mg/dL glucose solution, and 1 kHz impedance was measured every 10 minutes, as shown by encircled data points 3920. m-cresol was then added to bring the solution to 0.35% m-cresol (3930). As can be seen, once m-cresol has been added, the Isig 3940 initially increases dramatically, and then begins to drift down. The concentration of glucose in the solution was then doubled, by adding an addition 100 mg/dL glucose. This, however, had no effect on the Isig 3940, as the electrode was unable to detect the glucose.

Figure 40C:
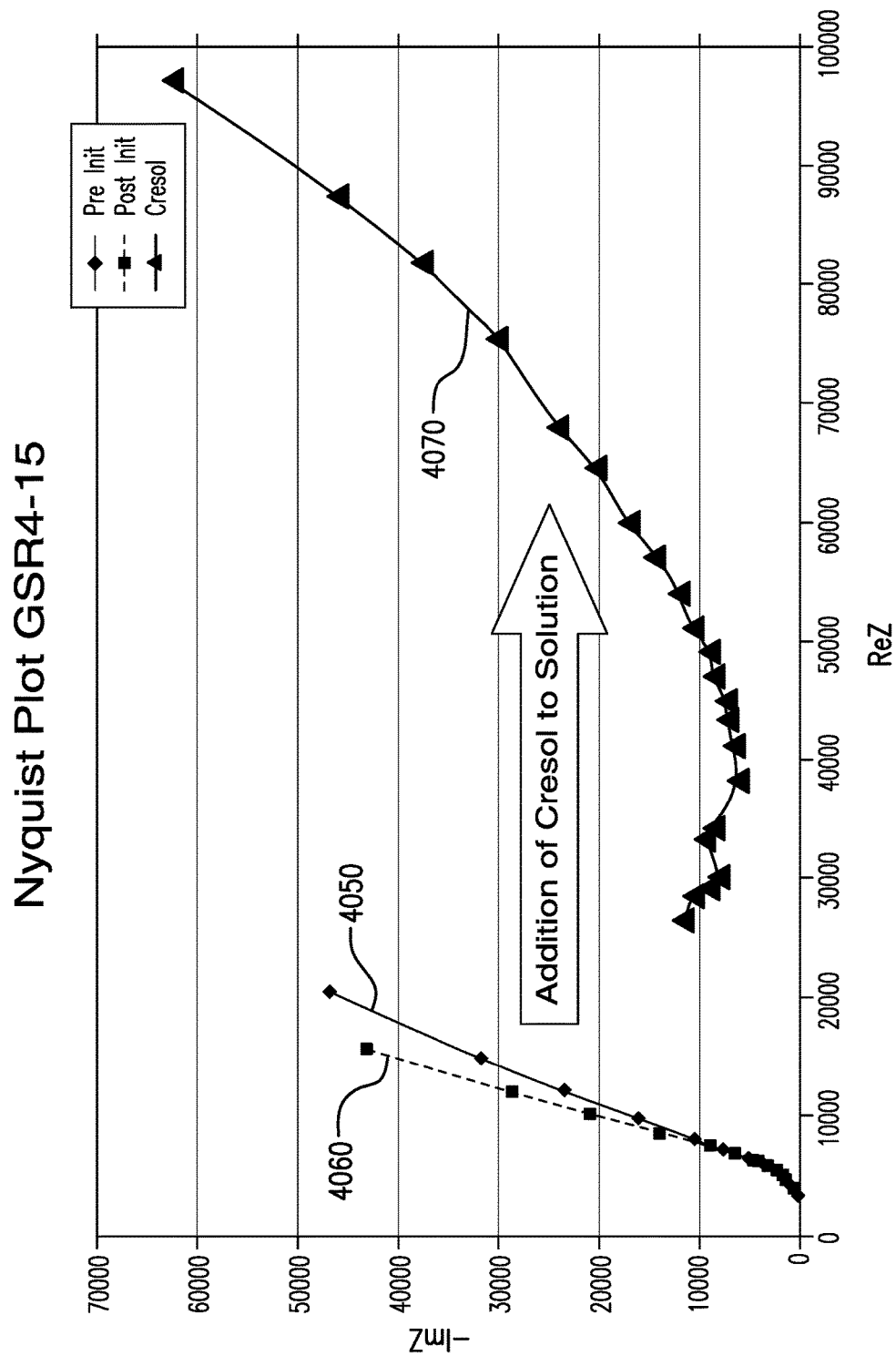
FIG. 40C shows a Nyquist plot for the simulation shown in FIG. 39.

On the other hand, the m-cresol had a dramatic effect on both impedance magnitude and phase. FIG. 40A shows a Bode plot for the phase, and FIG. 40B shows a Bode plot for impedance magnitude, for both before and after the addition of m-cresol. As can be seen, after the m-cresol was added, the impedance magnitude 4010 increased from its post-initialization value 4020 by at least an order of magnitude across the frequency spectrum. At the same time, the phase 4030 changed completely as compared to its post-initialization value 4040. On the Nyquist plot of FIG. 40C. Here, the pre-initialization curve 4050 and the post-initialization curve 4060 appear as expected for a normally-functioning sensor. However, after the addition of m-cresol, the curve 4070 becomes drastically different.

The above experiment identifies an important practical pitfall of continuing to rely on the Isig after m-cresol has been added. Referring back to FIG. 39, a patient/user monitoring the sensor signal may be put under the mistaken impression that his glucose level has just spiked, and that he should administer a bolus. The user then administers the bolus, at which the Isig has already started to drift back down. In other words, to the patient/user, everything may look normal. In reality, however, what has really happened is that the patient just administered an unneeded dose of insulin which, depending on the patient's glucose level prior to administration of the bolus, may put the patient at risk of experiencing a hypoglycemic event. This scenario reinforces the desirability of a means of detecting interferents that is as glucose-independent as possible.

Figure 41:
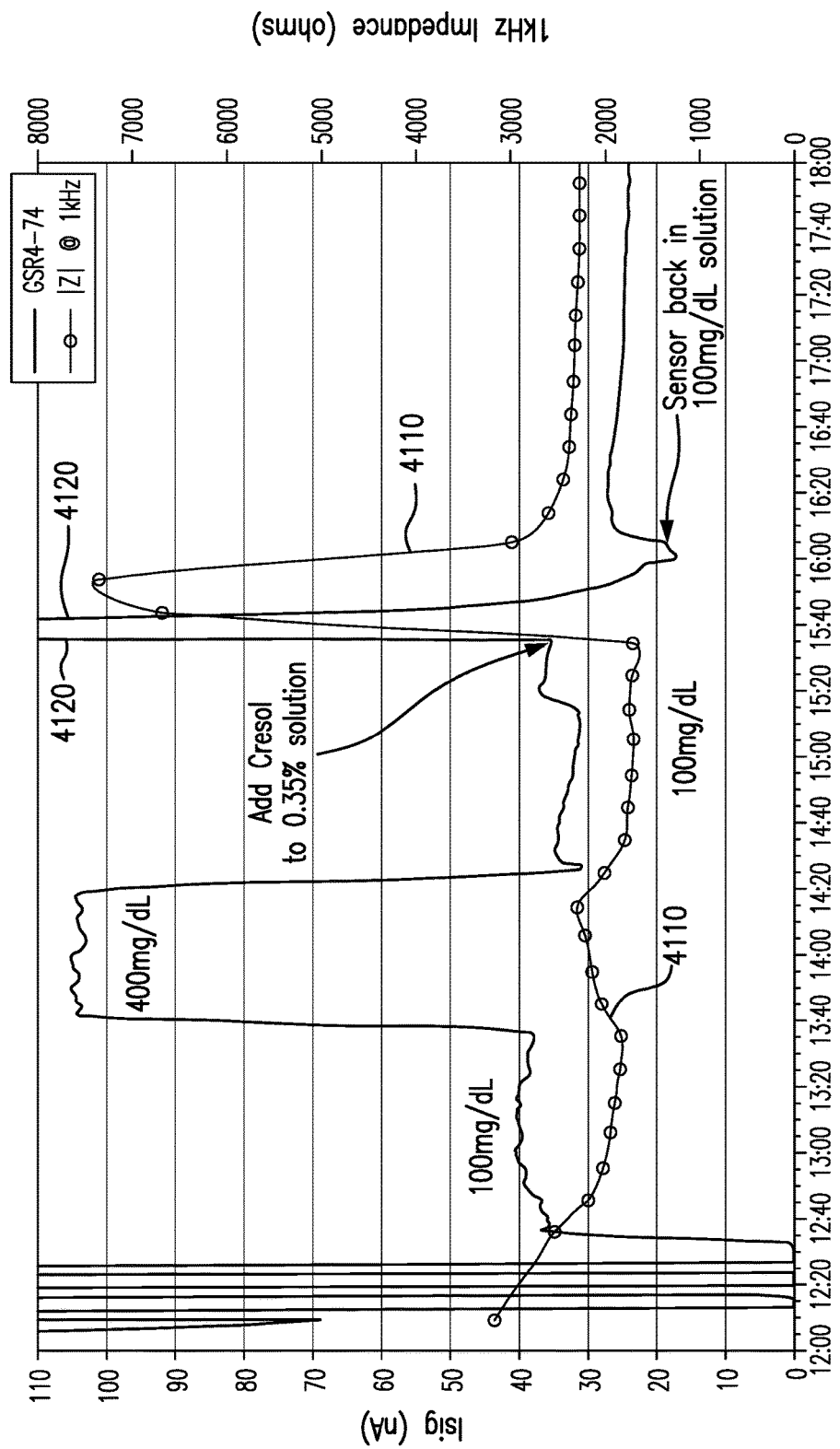
FIG. 41 shows another in-vitro simulation with an interferent in accordance to embodiments of the invention.

FIG. 41 shows another experiment, where a sensor was initialized a 100 mg/dL glucose solution, after which glucose was raised to 400 mg/dL for one hour, and then returned to 100 mg/dL. m-cresol was then added to raise the concentration to 0.35%, with the sensor remaining in this solution for 20 minutes. Finally, the sensor was placed in a 100 mg/dL glucose solution to allow Isig to recover after exposure to m-cresol. As can be seen, after initialization, the 1 kHz impedance magnitude 4110 was at about 2 kOhms. When m-cresol was added, the Isig 4120 spiked, as did impedance magnitude 4110. Moreover, when the sensor was returned to a 100 md/dL glucose solution, the impedance magnitude 4110 also returned to near normal level.

As can be seen from the above experiments, EIS can be used to detect the presence of an interfering agent—in this case, m-cresol. Specifically, since the interferent affects the sensor in such a way as to increase the impedance magnitude across the entire frequency spectrum, the impedance magnitude may be used to detect the interference. Once the interference has been detected, either the sensor operating voltage can be changed to a point where the interferent is not measured, or data reporting can be temporarily suspended, with the sensor indicating to the patient/user that, due to the administration of medication, the sensor is unable to report data (until the measured impedance returns to the pre-infusion level). It is noted that, since the impact of the interferent is due to the preservative that is contained in insulin, the impedance magnitude will exhibit the same behavior as described above regardless of whether the insulin being infused is fast-acting or slow.

Importantly, as mentioned above, the impedance magnitude, and certainly the magnitude at 1 kHz, is substantially glucose-independent. With reference to FIG. 41, it can be seen that, as the concentration of glucose is raised from 100 mg/dL to 400 mg/dL—a four-fold increase—the 1 kHz impedance magnitude increase from about 2000 Ohms to about 2200 Ohms, or about a 10% increase. In other words, the effect of glucose on the impedance magnitude measurement appears to be about an order of magnitude smaller compared to the measured impedance. This level of "signal-to-noise" ratio is typically small enough to allow the noise (i.e., the glucose effect) to be filtered out, such that the resultant impedance magnitude is substantially glucose-independent. In addition, it should be emphasized that the impedance magnitude exhibits an even higher degree of glucose-independence in actual human tissue, as compared to the buffer solution that was used for the in-vitro experiments described above.

Embodiments of the invention are also directed to an Analog Front End Integrated Circuit (AFE IC), which is a custom Application Specific Integrated Circuit (ASIC) that provides the necessary analog electronics to: (i) support multiple potentiostats and interface with multi-terminal glucose sensors based on either Oxygen or Peroxide; (ii) interface with a microcontroller so as to form a micropower sensor system; and (iii) implement EIS diagnostics, fusion algorithms, and other EIS-based processes based on measurement of EIS-based parameters. More specifically, the ASIC incorporates diagnostic capability to measure the real and imaginary impedance parameters of the sensor over a wide range of frequencies, as well as digital interface circuitry to enable bidirectional communication with a microprocessor chip. Moreover, the ASIC includes power control circuitry that enables operation at very low standby and operating power, and a real-time clock and a crystal oscillator so that an external microprocessor's power can be turned off.

Figure 42A:
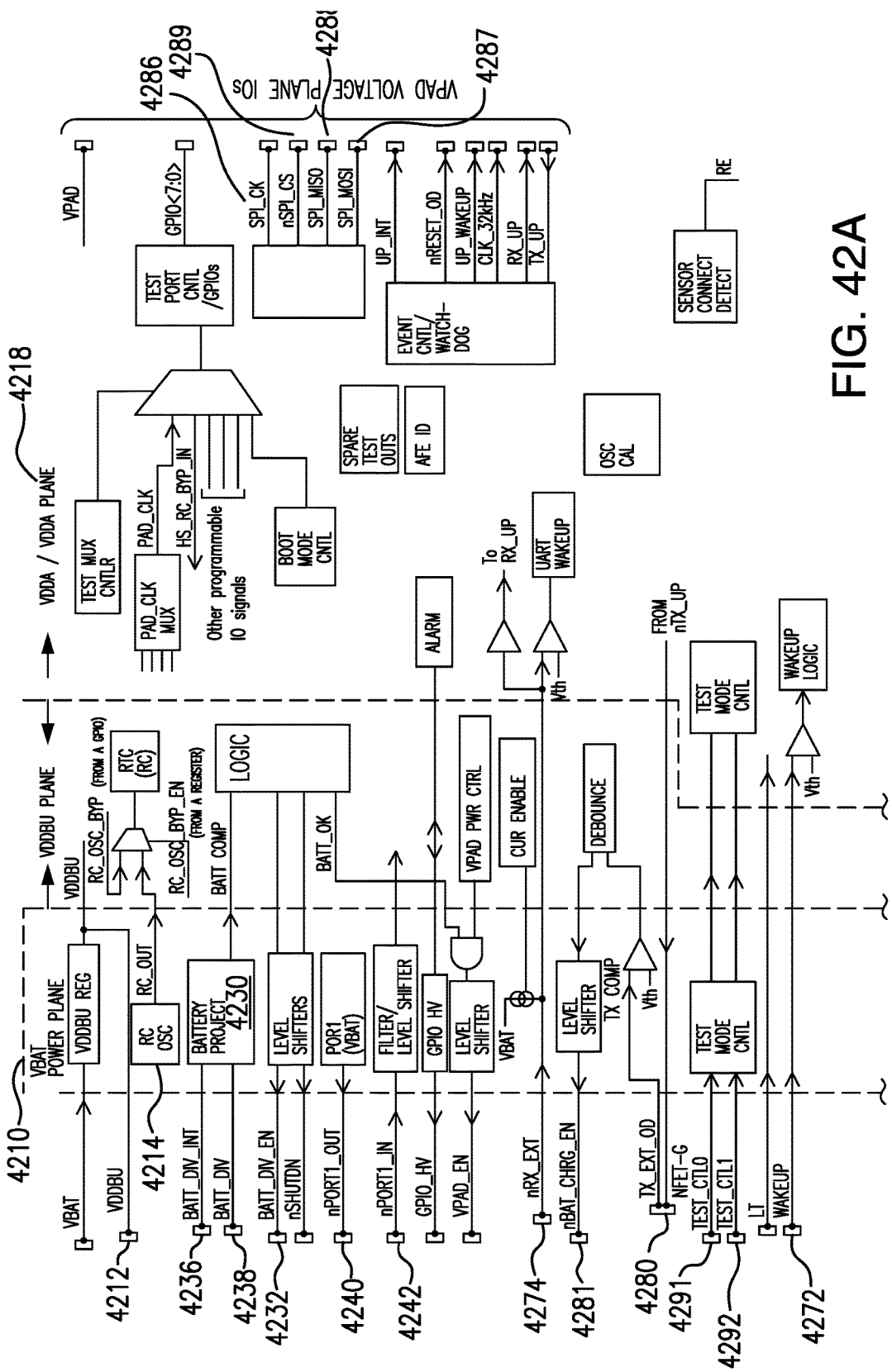
FIGS. 42A and 42B illustrate an ASIC block diagram in accordance with embodiments of the invention.
Figure 42B:
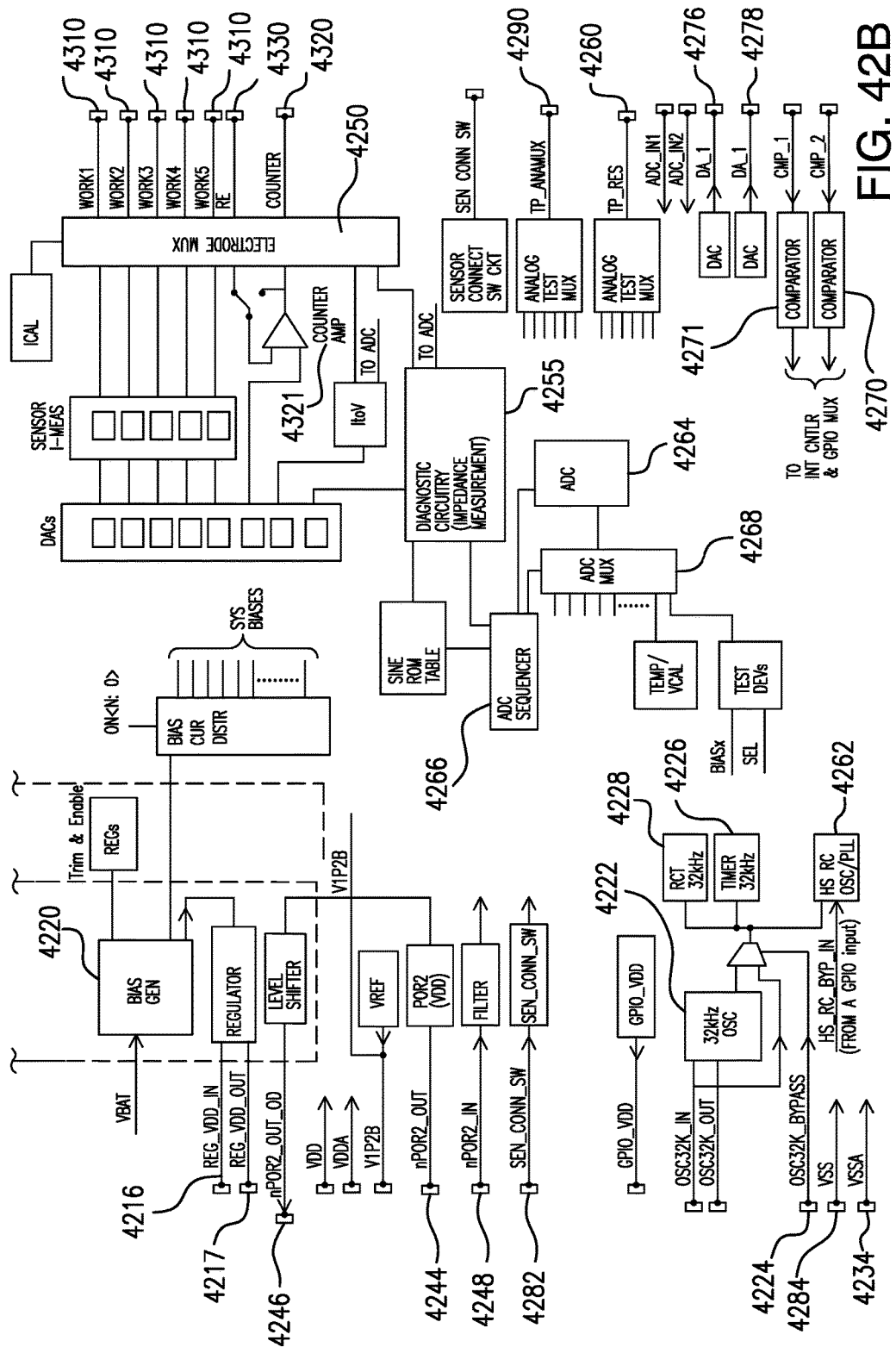

FIGS. 42A and 42B show a block diagram of the ASIC, and Table 1 below provides pad signal descriptions (shown on the left-hand side of FIGS. 42A and 42B), with some signals being multiplexed onto a single pad.

TABLE 1

Pad signal descriptions

| Pad Name | Functional Description | Power plane |
|---|---|---|
| VBAT | Battery power input 2.0 V to 4.5 V | VBAT |
| VDDBU | Backup logic power 1.4 to 2.4 V | VDDBU |
| VDD | Logic power -- 1.6-2.4 V | VDD |
| VDDA | Analog power - 1.6-2.4 V | VDDA |
| VPAD | Pad I/O power -- 1.8 V-3.3 V | VPAD |
| VSS | Logic ground return and digital pad return | |
| VSSA | Analog ground return and analog pad return | |
| ADC_IN1, 2 | ADC Inputs, VDDA max input | VDDA |
| V1P2B | 1.2 volt reference Bypass capacitor | VDDA |
| nSHUTDN | External VDD regulator control signal. Goes low when battery is low. | VBAT |
| VPAD_EN | Goes high when VPAD IOs are active. Can control external regulator. | VBAT |
| DA1, 2 | DAC outputs | VDDA |
| TP_ANA_MUX | Mux of analog test port -- output or input | VDDA |
| TP_RES | External 1 meg ohm calibration resistor & analog test port | VDDA |
| WORK1-5 | Working Electrodes of Sensor | VDDA |
| RE | Reference Electrode of Sensor | VDDA |
| COUNTER | Counter Electrode of Sensor | VDDA |
| CMP1_IN | General purpose Voltage comparator | VDDA |
| CMP2_IN | General purpose Voltage comparator | VDDA |
| WAKEUP | Debounced interrupt input | VBAT |
| XTALI, XTALO | 32.768 kHz Crystal Oscillator pads | VDDA |
| OSC_BYPASS | Test clock control | VDDA |
| SEN_CONN_SW | Sensor connection switch input. Pulled to VSSA = connection | VDDA |
| VPAD_EN | Enable the VPAD power and VPAD power plane logic | VBAT |
| nRESET_OD | Signal to reset external circuitry such as a microprocessor | |
| SPI_CK, nSPI_CS, SPI_MOIS, SPI_MISO | SPI interface signals to microprocessor | VPAD |
| UP_WAKEUP | Microprocessor wakeup signal | VPAD |
| CLK_32KHZ | Gated Clock output to external circuitry microprocessor | VPAD |
| UP_INT | Interrupt signal to microprocessor | VPAD |
| nPOR1_OUT | Backup Power on reset, output from analog | VBAT |
| nPOR1_IN | VBAT power plane reset, input to digital in battery plane (VDDBU) | VBAT |
| nPOR2_OUT | VDD POR signal, output from analog | VDD |
| nPOR2_OUT_OD | VDD POR signal open drain (nfet out only), stretched output from digital | VBAT |
| nPOR2_IN | VDD power plane logic reset. Is level shifted to VDD inside the chip, input to digital VDD logic. | VDD |

The ASIC will now be described with reference to FIGS. 42A and 42B and Table 1.

Power Planes

The ASIC has one power plane that is powered by the supply pad VBAT (4210), which has an operating input range from 2.0 volts to 4.5 volts. This power plane has a regulator to lower the voltage for some circuits in this plane. The supply is called VDDBU (4212) and has an output pad for test and bypassing. The circuits on the VBAT supply include an RC oscillator, real time clock (RC osc) 4214, battery protection circuit, regulator control, power on reset circuit (POR), and various inputs/outputs. The pads on the VBAT power plane are configured to draw less than 75 nA at 40° C. and VBAT=3.50V.

The ASIC also has a VDD supply to supply logic. The VDD supply voltage range is programmable from at least 1.6 volts to 2.4 volts. The circuits on the VDD power plane include most of the digital logic, timer (32 khz), and real time clock (32 khz). The VDD supply plane includes level shifters interfacing to the other voltage planes as necessary. The level shifters, in turn, have interfaces conditioned so that any powered power plane does not have an increase in current greater than 10 nA if another power plane is unpowered.

The ASIC includes an onboard regulator (with shutdown control) and an option for an external VDD source. The regulator input is a separate pad, REG_VDD_IN (4216), which has electrostatic discharge (ESD) protection in common with other I/Os on VBAT. The onboard regulator has an output pad, REG_VDD_OUT (4217). The ASIC also has an input pad for the VDD, which is separate from the REG_VDD_OUT pad.

The ASIC includes an analog power plane, called VDDA (4218), which is powered by either the VDD onboard regulator or an external source, and is normally supplied by a filtered VDD. The VDDA supplied circuits are configured to operate within 0.1 volt of VDD, thereby obviating the need for level shifting between the VDDA and VDD power planes. The VDDA supply powers the sensor analog circuits, the analog measurement circuits, as well as any other noise-sensitive circuitry.

The ASIC includes a pad supply, VPAD, for designated digital interface signals. The pad supply has an operating voltage range from at least 1.8 V to 3.3 V. These pads have separate supply pad(s) and are powered from an external source. The pads also incorporate level shifters to other onboard circuits to allow the flexible pad power supply range independently of the VDD logic supply voltage. The ASIC can condition the VPAD pad ring signals such that, when the VPAD supply is not enabled, other supply currents will not increase by more than 10 nA.

Bias Generator

The ASIC has a bias generator circuit, BIAS_GEN (4220), which is supplied from the VBAT power, and which generates bias currents that are stable with supply voltage for the system. The output currents have the following specifications: (i) Supply sensitivity: <±2.5% from a supply voltage of 1.6 v to 4.5V; and (ii) Current accuracy: <±3% after trimming.

The BIAS_GEN circuit generates switched and unswitched output currents to supply circuits needing a bias current for operation. The operating current drain of the BIAS_GEN circuit is less than 0.3 uA at 25° C. with VBAT from 2.5V-4.5V (excluding any bias output currents). Lastly, the temperature coefficient of the bias current is generally between 4,000 ppm/° C. and 6,000 ppm/° C.

Voltage Reference

The ASIC, as described herein is configured to have a low power voltage reference, which is powered from the VBAT power supply. The voltage reference has an enable input which can accept a signal from logic powered by VBAT or VDDBU. The ASIC is designed such that the enable signal does not cause any increase in current in excess of 10 nA from any supply from this signal interface when VBAT is powered.

The reference voltage has the following specifications: (i) Output voltage: 1.220±3 mV after trimming; (ii) Supply sensitivity: <±6 mV from 1.6 V to 4.5V input; (iii) Temperature sensitivity: <±5 mV from 0° C. to 60° C.; and (iv) Output voltage default accuracy (without trim): 1.220 V±50 mV. In addition, the supply current is to be less than 800 nA at 4.5V, 40° C. In this embodiment, the reference output will be forced to VSSA when the reference is disabled so as to keep the VDD voltage regulator from overshooting to levels beyond the breakdown voltage of the logic.

32 kHz Oscillator

The ASIC includes a low power 32.768 kHz crystal oscillator 4222 which is powered with power derived from the VDDA supply and can trim the capacitance of the crystal oscillator pads (XTALI, XTALO) with software. Specifically, the frequency trim range is at least −50 ppm to +100 ppm with a step size of 2 ppm max throughout the trim range. Here, a crystal may be assumed with a load capacitance of 7 pF, Ls=6.9512 kH, Cs=3.3952 fF, Rs=70 k, shunt capacitance=1 pF, and a PC Board parasitic capacitance of 2 pF on each crystal terminal.

The ASIC has a VPAD level output available on a pad, CLK_32 kHZ, where the output can be disabled under software and logic control. The default is driving the 32 kHz oscillator out. An input pin, OSC32K_BYPASS (4224), can disable the 32 kHz oscillator (no power drain) and allows for digital input to the XTALI pad. The circuits associated with this function are configured so as not add any ASIC current in excess of 10 nA in either state of the OSC32K_BYPASS signal other than the oscillator current when OSC32K_BYPASS is low.

The 32 kHZ oscillator is required to always be operational when the VDDA plane is powered, except for the bypass condition. If the OSC32K_BYPASS is true, the 32 KHZ oscillator analog circuitry is put into a low power state, and the XTALI pad is configured to accept a digital input whose level is from 0 to VDDA. It is noted that the 32 kHz oscillator output has a duty cycle between 40% and 60%.

Timer

The ASIC includes a Timer 4226 that is clocked from the 32 kHz oscillator divided by 2. It is pre-settable and has two programmable timeouts. It has 24 programmable bits giving a total time count to 17 minutes, 4 seconds. The Timer also has a programmable delay to disable the clock to the CLK_32 KHz pad and set the microprocessor (uP) interface signals on the VPAD plane to a predetermined state (See section below on Microprocessor Wakeup Control Signals). This will allow the microprocessor to go into suspend mode without an external clock. However, this function may be disabled by software with a programmable bit.

The Timer also includes a programmable delay to wakeup the microprocessor by enabling the CLK_32 KHZ clock output and setting UP_WAKEUP high. A transition of the POR2 (VDD POR) from supply low state to supply OK state will enable the 32 kHz oscillator, the CLK_32 KHZ clock output and set UP_WAKEUP high. The power shutdown and power up are configured to be controlled with programmable control bits.

Real Time Clock (RTC)

The ASIC also has a 48 bit readable/writeable binary counter that operates from the ungated, free running 32 kHz oscillator. The write to the real time clock 4228 requires a write to an address with a key before the clock can be written. The write access to the clock is configured to terminate between 1 msec and 20 msec after the write to the key address.

The real time clock 4228 is configured to be reset by a power on reset either by POR1_IN (the VBAT POR) or POR2_IN (the VDD_POR) to half count (MSB=1, all other bits 0). In embodiments of the invention, the real time clock has programmable interrupt capability, and is designed to be robust against single event upsets (SEUs), which may be accomplished either by layout techniques or by adding capacitance to appropriate nodes, if required.

RC Oscillator

The ASIC further includes an RC clock powered from the VBAT supply or VBAT derived supply. The RC Oscillator is always running, except that the oscillator can be bypassed by writing to a register bit in analog test mode (see section on Digital Testing) and applying a signal to the GPIO_VBAT with a 0 to VBAT level. The RC oscillator is not trimmable, and includes the following specifications: (i) a frequency between 750 Hz and 1500 Hz; (ii) a duty cycle between 50%±10%; (iii) current consumption of less than 200 nA at 25° C.; (iv) frequency change of less than ±2% from 1V to 4.5V VBAT supply and better than 1% from 1.8V to 4.5V VBAT supply; and (v) frequency change of less than +2,−2% from a temperature of 15° C. to 40° C. with VBAT=3.5V. The RC frequency can be measured with the 32 kHz crystal oscillator or with an external frequency source (See Oscillator Calibration Circuit).

Real Time RC Clock (RC Oscillator Based)

The ASIC includes a 48 bit readable/writeable binary ripple counter based on the RC oscillator. A write to the RC real time clock requires a write to an address with a key before the clock can be written. The write access to the clock terminates between 1 msec and 20 msec after the write to the key address, wherein the time for the protection window is configured to be generated with the RC clock.

The real time RC clock allows for a relative time stamp if the crystal oscillator is shutdown, and is configured to be reset on POR1_IN (the BAT POR) to half count (MSB=1, all others 0). The real time RC clock is designed to be robust against single event upsets (SEUs) either by layout techniques or by adding capacitance to appropriate nodes, where required. On the falling edge of POR2_IN, or if the ASIC goes into Battery Low state, the RT real time clock value may be captured into a register that can be read via the SPI port. This register and associated logic are on the VBAT or VDDBU power plane.

Battery Protection Circuit

The ASIC includes a battery protection circuit 4230 that uses a comparator to monitor the battery voltage and is powered with power derived from the VBAT power plane. The battery protection circuit is configured to be always running with power applied to the VBAT supply. The battery protection circuit may use the RC oscillator for clocking signals, and have an average current drain that is less than 30 nA, including a 3 MOhm total resistance external voltage divider.

The battery protection circuit uses an external switched voltage divider having a ratio of 0.421 for a 2.90V battery threshold. The ASIC also has an internal voltage divider with the ratio of 0.421±0.5%. This divider is connected between BATT_DIV_EN (4232) and VSSA (4234), and the divider output is a pin called BATT_DIV_INT (4236). To save pins in the packaged part, the BATT_DIV_INT in this embodiment is connected to BATT_DIV internally in the package. Also in this configuration, BATT_DIV_EN does not need to come out of the package, saving two package pins.

The battery protection circuit is configured to sample the voltage on an input pin, BATT_DIV (4238), at approximately 2 times per second, wherein the sample time is generated from the RC Oscillator. The ASIC is able to adjust the divider of the RC Oscillator to adjust the sampling time interval to 0.500 sec±5 msec with the RC oscillator operating within its operating tolerance. In a preferred embodiment, the ASIC has a test mode which allows more frequent sampling intervals during test.

The comparator input is configured to accept an input from 0 to VBAT volts. The input current to the comparator input, BATT_DIV, is less than 10 nA for inputs from 0 to VBAT volts. The comparator sampling circuit outputs to a pad, BATT_DIV_EN, a positive pulse which can be used by external circuitry to enable an off-chip resistor divider only during the sampling time to save power. The voltage high logic level is the VBAT voltage and the low level is VSS level.

The output resistance of the BATT_DIV_EN pad shall be less than 2 kOhms at VBAT=3.0V. This allows the voltage divider to be driven directly from this output. After a programmable number of consecutive samples indicating a low battery condition, the comparator control circuitry triggers an interrupt to the interrupt output pad, UP_INT. The default number of samples is 4, although the number of consecutive samples is programmable from 4 to 120.

After a programmable number of consecutive samples indicating a low battery after the generation of the UP_INT above, the comparator control circuitry is configured to generate signals that will put the ASIC into a low power mode: The VDD regulator will be disabled and a low signal will be asserted to the pad, VPAD_EN. This will be called the Battery Low state. Again, the number of consecutive samples is programmable from 4 to 120 samples, with the default being 4 samples.

The comparator has individual programmable thresholds for falling and rising voltages on BATT_DIV. This is implemented in the digital logic to multiplex the two values to the circuit depending on the state of the Battery Low state. Thus, if Battery Low state is low, the falling threshold applies, and if the Battery Low state is high, the rising threshold applies. Specifically, the comparator has 16 programmable thresholds from 1.22 to 1.645±3%, wherein the DNL of the programmable thresholds is set to be less than 0.2 LSB.

The comparator threshold varies less than +/−1% from 20° C. to 40° C. The default threshold for falling voltage is 1.44V (VBAT threshold of 3.41V with nominal voltage divider), and the default threshold for rising voltage is 1.53V (VBAT threshold of 3.63V with nominal voltage divider). After the ASIC has been put into the Battery Low state, if the comparator senses 4 consecutive indications of battery OK, then the ASIC will initiate the microprocessor startup sequence.

Battery Power Plane Power On Reset

A power on reset (POR) output is generated on pad nPOR1_OUT (4240) if the input VBAT slews more than 1.2 volt in a 50 usec period or if the VBAT voltage is below 1.6±0.3 volts. This POR is stretched to a minimum pulse width of 5 milliseconds. The output of the POR circuit is configured to be active low and go to a pad, nPOR1_OUT, on the VBAT power plane.

The IC has an input pad for the battery power plane POR, nPOR1_IN (4242). This input pad has RC filtering such that pulses shorter than 50 nsec will not cause a reset to the logic. In this embodiment, nPOR1_OUT is externally connected to the nPOR1_IN in normal operation, thereby separating the analog circuitry from the digital circuitry for testing. The nPOR1_IN causes a reset of all logic on any of the power planes, and initializes all registers to their default value. Thus, the reset status register POR bit is set, and all other reset status register bits are cleared. The POR reset circuitry is configured so as not to consume more than 0.1 uA from VBAT supply for time greater than 5 seconds after power up.

VDD Power On Reset (POR)

The ASIC also has a voltage comparator circuit which generates a VDD voltage plane reset signal upon power up, or if the VDD drops below a programmable threshold. The range is programmable with several voltage thresholds. The default value is 1.8V-15% (1.53V). The POR 2 has a programmable threshold for rising voltage, which implements hysteresis. The rising threshold is also programmable, with a default value of 1.60V±3%.

The POR signal is active low and has an output pad, nPOR2_OUT (4244), on the VDD power plane. The ASIC also has an active low POR open drain output, nPOR2_OUT_OD (4246), on the VBAT power plane. This could be used for applying POR to other system components.

The VDD powered logic has POR derived from the input pad, nPOR2_IN (4248). The nPOR2_IN pad is on the VDD power plane, and has RC filtering such that pulses shorter than 50 nsec will not cause a reset to the logic. The nPOR2_OUT is configured be externally connected to the nPOR2_IN input pad under normal usage, thereby separating the analog circuitry from the digital circuitry.

The reset which is generated is stretched to at least 700 msec of active time after VDD goes above the programmable threshold to assure that the crystal oscillator is stable. The POR reset circuitry is to consume no more than 0.1 uA from the VDD supply for time greater than 5 seconds after power up, and no more than 0.1 uA from VBAT supply for time greater than 5 seconds after power up. The register that stores the POR threshold value is powered from the VDD power plane.

Sensor Interface Electronics

Figure 43:
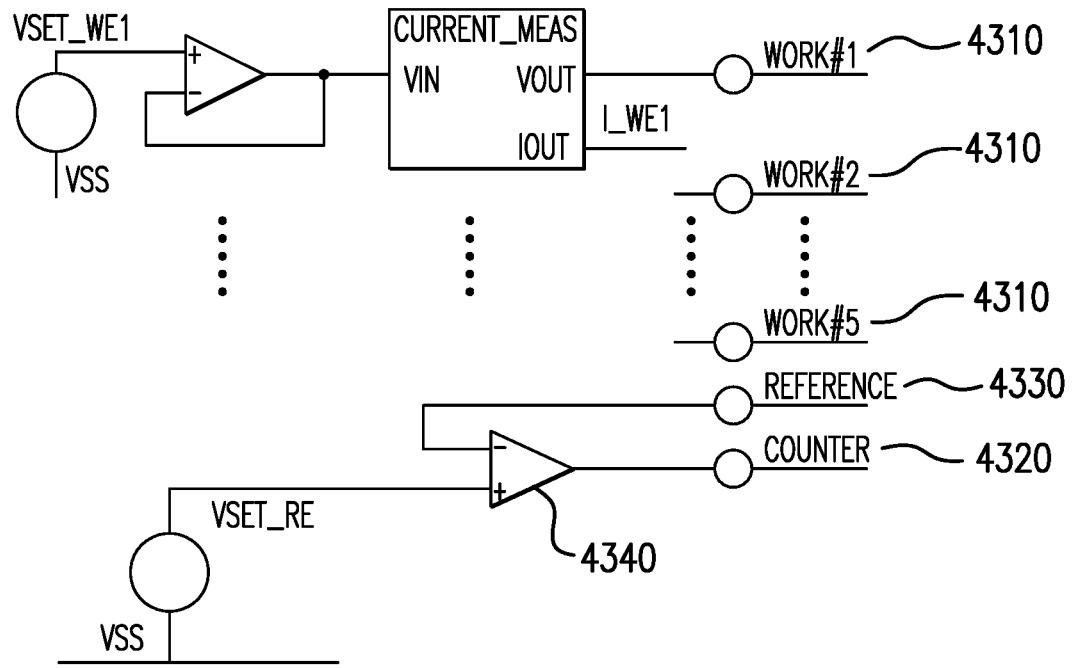
FIG. 43 shows a potentiostat configuration for a sensor with redundant working electrodes in accordance with embodiments of the invention.

In an embodiment of the invention, the sensor circuitry supports up to five sensor WORK electrodes (4310) in any combination of peroxide or oxygen sensors, although, in additional embodiments, a larger number of such electrodes may also be accommodated. While the peroxide sensor WORK electrodes source current, the oxygen sensor WORK electrodes sink current. For the instant embodiment, the sensors can be configured in the potentiostat configuration as shown in FIG. 43.

The sensor electronics have programmable power controls for each electrode interface circuit to minimize current drain by turning off current to unused sensor electronics. The sensor electronics also include electronics to drive a COUNTER electrode 4320 that uses feedback from a RE (reference) electrode 4330. The current to this circuitry may be programmed off when not in use to conserve power. The interface electronics include a multiplexer 4250 so that the COUNTER and RE electrodes may be connected to any of the (redundant) WORK electrodes.

The ASIC is configured to provide the following Sensor Interfaces: (i) RE: Reference electrode, which establishes a reference potential of the solution for the electronics for setting the WORK voltages; (ii) WORK1-WORK5: Working sensor electrodes where desired reduction/oxidation (redox) reactions take place; and (iii) COUNTER: Output from this pad maintains a known voltage on the RE electrode relative to the system VSS. In this embodiment of the invention, the ASIC is configured so as to be able to individually set the WORK voltages for up to 5 WORK electrodes with a resolution and accuracy of better than or equal to 5 mV.

The WORK voltage(s) are programmable between at least 0 and 1.22V relative to VSSA in the oxygen mode. In the peroxide mode, the WORK voltage(s) are programmable between at least 0.6 volt and 2.054 volts relative to VSSA. If the VDDA is less than 2.15V, the WORK voltage is operational to VDDA −0.1V. The ASIC includes current measuring circuits to measure the WORK electrode currents in the peroxide sensor mode. This may be implemented, e.g., with current-to-voltage or current-to-frequency converters, which may have the following specifications: (i) Current Range: 0-300 nA; (ii) Voltage output range: Same as WORK electrode in peroxide/oxygen mode; (iii) Output offset voltage: ±5 mV max; and (iv) Uncalibrated resolution: ±0.25 nA.

Current Measurement Accuracy after applying a calibration factor to the gain and assuming an acquisition time of 10 seconds or less is:

5 pA0-1 nA: ±3%±20 pA 1 nA-10 nA: ±3%±20 pA 10 nA-300 nA: ±3%±0.2 nA

For current-to-frequency converters (ItoFs) only, the frequency range may be between 0 Hz and 50 kHz. The current converters must operate in the specified voltage range relative to VSS of WORK electrodes in the peroxide mode. Here, the current drain is less than 2 uA from a 2.5V supply with WORK electrode current less than 10 nA per converter including digital-to-analog (DAC) current.

The current converters can be enabled or disabled by software control. When disabled, the WORK electrode will exhibit a very high impedance value, i.e., greater than 100 Mohm. Again, for ItoFs only, the output of the I-to-F converters will go to 32 bit counters, which can be read, written to, and cleared by the microprocessor and test logic. During a counter read, clocking of the counter is suspended to ensure an accurate read.

In embodiments of the invention, the ASIC also includes current measuring circuits to measure the WORK electrode currents in the oxygen sensor mode. The circuit may be implemented as a current-to-voltage or a current-to-frequency converter, and a programmable bit may be used to configure the current converters to operate in the oxygen mode. As before, the current converters must operate in the specified voltage range of the WORK electrodes relative to VSS in the oxygen mode. Here, again, the current range is 3.7 pA-300 nA, the voltage output range is the same as WORK electrode in oxygen mode, the output offset voltage is ±5 mV max, and the uncalibrated resolution is 3.7 pA±2 pA.

Current Measurement Accuracy after applying a calibration factor to the gain and assuming an acquisition time of 10 seconds or less is:

5 pA-1 nA: ±3%±20 pA 1 nA-10 nA: ±3%±20 pA 10 nA-300 nA: ±3%±0.2 nA

For current-to-frequency converters (ItoFs) only, the frequency range may be between 0 Hz and 50 kHz, and the current drain is less than 2 uA from a 2.5 V supply with WORK electrode current less than 10 nA per converter, including DAC current. The current converters can be enabled or disabled by software control. When disabled, the WORK electrode will exhibit a very high impedance value, i.e., greater than 100 Mohm. Also, for ItoFs only, the output of the I-to-F converters will go to 32 bit counters, which can be read, written to, and cleared by the microprocessor and test logic. During a counter read, clocking of the counter is suspended to ensure an accurate read.

In embodiments of the invention, the Reference electrode (RE) 4330 has an input bias current of less than 0.05 nA at 40° C. The COUNTER electrode adjusts its output to maintain a desired voltage on the RE electrode. This is accomplished with an amplifier 4340 whose output to the COUNTER electrode 4320 attempts to minimize the difference between the actual RE electrode voltage and the target RE voltage, the latter being set by a DAC.

The RE set voltage is programmable between at least 0 and 1.80V, and the common mode input range of the COUNTER amplifier includes at least 0.20 to (VDD-0.20)V. A register bit may be used to select the common mode input range, if necessary, and to provide for programming the mode of operation of the COUNTER. The WORK voltage is set with a resolution and accuracy of better than or equal to 5 mV. It is noted that, in the normal mode, the COUNTER voltage seeks a level that maintains the RE voltage to the programmed RE target value. In the force counter mode, however, the COUNTER electrode voltage is forced to the programmed RE target voltage.

Figure 44:
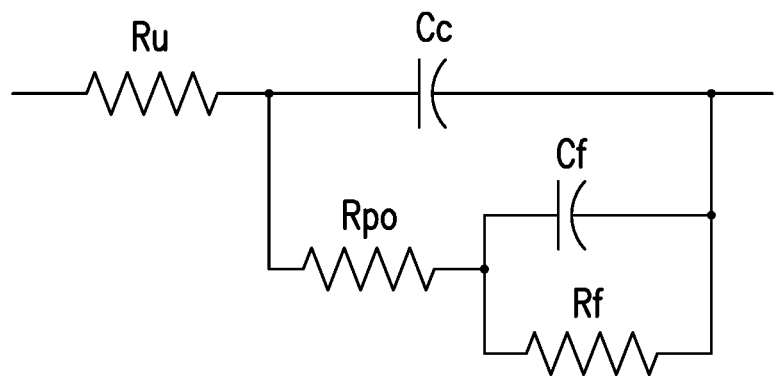
FIG. 44 shows an equivalent AC inter-electrode circuit for a sensor with the potentiostat configuration shown in FIG. 43.

All electrode driving circuits are configured to be able to drive the electrode to electrode load and be free from oscillation for any use scenario. FIG. 44 shows the equivalent ac inter-electrode circuit according to the embodiment of the invention with the potentiostat configuration as shown in FIG. 43. The equivalent circuit shown in FIG. 44 may be between any of the electrodes, i.e., WORK1-WORK5, COUNTER and RE, with value ranges as follows for the respective circuit components:

$Ru = [200\text{-}5\ k]$ Ohms $Cc = [10\text{-}2000]$ pF $Rpo = [1\text{-}20]$ kOhms $Rf = [200\text{-}2000]$ kOhms $Cf = [2\text{-}30]$ uF During initialization, the drive current for WORK electrodes and the COUNTER electrode need to supply higher currents than for the normal potentiostat operation described previously. As such, programmable register bits may be used to program the electrode drive circuits to a higher power state if necessary for extra drive. It is important to achieve low power operation in the normal potentiostat mode, where the electrode currents are typically less than 300 nA.

In preferred embodiments, during initialization, the WORK1 through WORK5 electrodes are programmable in steps equal to, or less than, 5 mV from 0 to VDD volts, and their drive or sink current output capability is a minimum of 20 uA, from 0.20V to (VDD-0.20V). Also during initialization, the ASIC is generally configured to be able to measure the current of one WORK electrode up to 20 uA with an accuracy of ±2%±40 nA of the measurement value. Moreover, during initialization, the RE set voltage is programmable as described previously, the COUNTER DRIVE CIRCUIT output must be able to source or sink 50 uA minimum with the COUNTER electrode from 0.20V to (VDD-0.20V), and the supply current (VDD and VDDA) to the initialization circuitry is required to be less than 50 uA in excess of any output current sourced.

Current Calibrator

In embodiments of the invention, the ASIC has a current reference that can be steered to any WORK electrode for the purpose of calibration. In this regard, the calibrator includes a programmable bit that causes the current output to sink current or source current. The programmable currents include at least 10 nA, 100 nA, and 300 nA, with an accuracy of better than ±1%±1 nA, assuming a 0 tolerance external precision resistor. The calibrator uses a 1 MegOhm precision resistor connected to the pad, TP_RES (4260), for a reference resistance. In addition, the current reference can be steered to the COUNTER or RE electrodes for the purpose of initialization and/or sensor status. A constant current may be applied to the COUNTER or the RE electrodes and the electrode voltage may be measured with the ADC.

High Speed RC Oscillator

With reference back to FIG. 42, the ASIC further includes a high speed RC oscillator 4262 which supplies the analog-to-digital converter (ADC) 4264, the ADC sequencer 4266, and other digital functions requiring a higher speed clock than 32 kHz. The high speed RC oscillator is phased locked to the 32 kHz clock (32.768 kHz) to give an output frequency programmable from 524.3 kHz to 1048 kHz. In addition, the high speed RC oscillator has a duty cycle of 50%±10%, a phase jitter of less than 0.5% rms, a current of less than 10 uA, and a frequency that is stable through the VDD operating range (voltage range of 1.6 to 2.5V). The default of the high speed RC oscillator is "off" (i.e., disabled), in which case the current draw is less than 10 nA. However, the ASIC has a programmable bit to enable the High Speed RC oscillator.

Analog To Digital Converter

The ASIC includes a 12-bit ADC (4264) with the following characteristics: (i) capability to effect a conversion in less than 1.5 msec with running from a 32 kHz clock; (ii) ability to perform faster conversions when clocked from the high speed RC oscillator; (iii) have at least 10 bits of accuracy (12 bit±4 counts); (iv) have a reference voltage input of 1.220V, with a temperature sensitivity of less than 0.2 mV/° C. from 20° C. to 40° C.; (v) full scale input ranges of 0 to 1.22V, 0 to 1.774V, 0 to 2.44V, and 0-VDDA, wherein the 1.774 and 2.44V ranges have programmable bits to reduce the conversion range to lower values to accommodate lower VDDA voltages; (vi) have current consumption of less than 50 uA from its power supply; (vi) have a converter capable of operating from the 32 kHz clock or the High Speed RC clock; (vii) have a DNL of less than 1 LSB; and (viii) issue an interrupt at the end of a conversion.

As shown in FIGS. 42A and 42B, the ASIC has an analog multiplexer 4268 at the input of the ADC 4264, both of which are controllable by software. In a preferred embodiment, at least the following signals are connected to the multiplexer:

(i) VDD—Core Voltage and regulator output
(ii) VBAT—Battery source
(iii) VDDA—Analog supply
(iv) RE—Reference Electrode of Sensor
(v) COUNTER—Counter Electrode of Sensor
(vi) WORK1-WORK5—Working Electrodes of Sensor
(vii) Temperature sensor
(viii) At least two external pin analog signal inputs
(ix) EIS integrator outputs
(x) ItoV current converter output.

The ASIC is configured such that the loading of the ADC will not exceed ±0.01 nA for the inputs COUNTER, RE, WORK1-WORK5, the temperature sensor, and any other input that would be adversely affected by loading. The multiplexer includes a divider for any inputs that have higher voltage than the input voltage range of the ADC, and a buffer amplifier that will decrease the input resistance of the divided inputs to less than 1 nA for load sensitive inputs. The buffer amplifier, in turn, has a common mode input range from at least 0.8V to VDDA voltage, and an offset less than 3 mV from the input range from 0.8 V to VDDA-0.1V.

In a preferred embodiment, the ASIC has a mode where the ADC measurements are taken in a programmed sequence. Thus, the ASIC includes a programmable sequencer 4266 that supervises the measurement of up to 8 input sources for ADC measurements with the following programmable parameters:

ADC MUX input
(ii) ADC range
(iii) Delay time before measurement, wherein the delays are programmable from 0 to 62 msec in 0.488 msec steps
(iv) Number of measurements for each input from 0 to 255
(v) Number of cycles of measurements: 0-255, wherein the cycle of measurements refers to repeating the sequence of up to 8 input measurements multiple times (e.g., as an outer loop in a program)
(vi) Delay between cycles of measurement, wherein the delays are programmable from 0 to 62 msec in 0.488 msec steps.

The sequencer 4266 is configured to start upon receiving an auto-measure start command, and the measurements may be stored in the ASIC for retrieval over the SPI interface. It is noted that the sequencer time base is programmable between the 32 kHz clock and the High Speed RC oscillator 4262.

Sensor Diagnostics

As was previously described in detail, embodiments of the invention are directed to use of impedance and impedance-related parameters in, e.g., sensor diagnostic procedures and Isig/SG fusion algorithms. To that end, in preferred embodiments, the ASIC described herein has the capability of measuring the impedance magnitude and phase angle of any WORK sensor electrode to the RE and COUNTER electrode when in the potentiostat configuration. This is done, e.g., by measuring the amplitude and phase of the current waveform in response to a sine-like waveform superimposed on the WORK electrode voltage. See, e.g., Diagnostic Circuitry 4255 in FIG. 42B.

The ASIC has the capability of measuring the resistive and capacitive components of any electrode to any electrode via, e.g., the Electrode Multiplexer 4250. It is noted that such measurements may interfere with the sensor equilibrium and may require settling time or sensor initialization to record stable electrode currents. As discussed previously, although the ASIC may be used for impedance measurements across a wide spectrum of frequencies, for purposes of the embodiments of the invention, a relatively narrower frequency range may be used. Specifically, the ASIC's sine wave measurement capability may include test frequencies from about 0.10 Hz to about 8192 Hz. In making such measurements, the minimum frequency resolution in accordance with an embodiment of the invention may be limited as shown in Table 2 below:

TABLE 2

| Frequency [Hz] | Min step [Hz] |
|---|---|
| .1 to 15 | <1 |
| 16 to 31 | 1 |
| 32 to 63 | 2 |
| 64 to 127 | 4 |
| 128 to 255 | 8 |
| 256 to 511 | 16 |
| 512 to 1023 | 32 |
| 1024 to 2047 | 64 |
| 2048 to 4095 | 128 |
| 4096 to 8192 | 256 |

The sinewave amplitude is programmable from at least 10 mVp-p to 50 mVp-p in 5 mV steps, and from 60 mVp-p to 100 mVp-p in 10 mV steps. In a preferred embodiment, the amplitude accuracy is better than ±5% or ±5 mV, whichever is larger. In addition, the ASIC may measure the electrode impedance with accuracies specified in Table 3 below:

TABLE 3

| Frequency Range | Impedance Range | Impedance Measurement Accuracy | Phase Measurement Accuracy |
|---|---|---|---|
| .1-10 Hz | 2k to 1 MegΩ | ±5% | ±0.5° |
| 10-100 Hz | 1k to 100 kΩ | ±5% | ±0.5° |
| 100 to 8000 Hz | .5k to 20 kΩ | ±5% | ±1.0° |

In an embodiment of the invention, the ASIC can measure the input waveform phase relative to a time base, which can be used in the impedance calculations to increase the accuracy. The ASIC may also have on-chip resistors to calibrate the above electrode impedance circuit. The on-chip resistors, in turn, may be calibrated by comparing them to the known 1 MegOhm off-chip precision resistor.

Data sampling of the waveforms may also be used to determine the impedances. The data may be transmitted to an external microprocessor with the serial peripheral interface (SPI) for calculation and processing. The converted current data is sufficiently buffered to be able to transfer 2000 ADC conversions of data to an external device through the SPI interface without losing data. This assumes a latency time of 8 msec maximum for servicing a data transfer request interrupt.

In embodiments of the invention, rather than, or in addition to, measuring electrode impedance with a sine wave, the ASIC may measure electrode current with a step input. Here, the ASIC can supply programmable amplitude steps from 10 to 200 mV with better than 5 mV resolution to an electrode and sample (measure) the resulting current waveform. The duration of the sampling may be programmable to at least 2 seconds in 0.25 second steps, and the sampling interval for measuring current may include at least five programmable binary weighted steps approximately 0.5 msec to 8 msec.

The resolution of the electrode voltage samples is smaller than 1 mV with a range up to ±0.25 volts. This measurement can be with respect to a suitable stable voltage in order to reduce the required dynamic range of the data conversion. Similarly, the resolution of the electrode current samples is smaller than 0.04 uA with a range up to 20 uA. The current measurements can be unipolar if the measurement polarity is programmable.

In embodiments of the invention, the current measurement may use an I-to-V converter. Moreover, the ASIC may have on-chip resistors to calibrate the current measurement. The on-chip resistors, in turn, may be calibrated by comparing them to the known 1 MegOhm off-chip precision resistor. The current measurement sample accuracy is better than ±3% or ±10 nA, whichever is greater. As before, the converted current data is sufficiently buffered to be able to transfer 2000 ADC conversions of data to an external device through the SPI interface without losing data. This assumes a latency time of 8 msec maximum for servicing a data transfer request interrupt.

Calibration Voltage

The ASIC includes a precision voltage reference to calibrate the ADC. The output voltage is 1.000V±3% with less than ±1.5% variation in production, and stability is better than ±3 mV over a temperature range of 20° C. to 40° C. This precision calibration voltage may be calibrated, via the on-chip ADC, by comparing it to an external precision voltage during manufacture. In manufacturing, a calibration factor may be stored in a system non-volatile memory (not on this ASIC) to achieve higher accuracy.

The current drain of the calibration voltage circuit is preferably less than 25 uA. Moreover, the calibration voltage circuit is able to power down to less than 10 nA to conserve battery power when not in use.

Temperature Sensor

The ASIC has a temperature transducer having a sensitivity between 9 and 11 mV per degree Celsius between the range −10° C. to 60° C. The output voltage of the Temperature Sensor is such that the ADC can measure the temperature-related voltage with the 0 to 1.22V ADC input range. The current drain of the Temperature Sensor is preferably less than 25 uA, and the Temperature Sensor can power down to less than 10 nA to conserve battery power when not in use.

VDD Voltage Regulator

The ASIC has a VDD voltage regulator with the following characteristics:
(i) Minimum input Voltage Range: 2.0V-4.5V.
(ii) Minimum output Voltage: 1.6-2.5V±5%, with a default of 2.0V.
(iii) Dropout voltage: Vin−Vout<0.15V at Iload=100 uA, Vin=2.0V.
(iv) The output voltage is programmable, with an accuracy within 2% of the indicated value per Table 4 below:

TABLE 4

| Hex | vout |
|---|---|
| 0 | 1.427 |
| 1 | 1.460 |
| 2 | 1.494 |
| 3 | 1.528 |
| 4 | 1.561 |
| 5 | 1.595 |
| 6 | 1.628 |
| 7 | 1.662 |
| 8 | 1.696 |
| 9 | 1.729 |
| A | 1.763 |
| B | 1.796 |
| C | 1.830 |
| D | 1.864 |
| E | 1.897 |
| F | 1.931 |
| 10 | 1.964 |
| 11 | 1.998 |
| 12 | 2.032 |
| 13 | 2.065 |
| 14 | 2.099 |
| 15 | 2.132 |
| 16 | 2.166 |
| 17 | 2.200 |
| 18 | 2.233 |
| 19 | 2.267 |
| 1A | 2.300 |
| 1B | 2.334 |
| 1C | 2.368 |
| 1D | 2.401 |
| 1E | 2.435 |
| 1F | 2.468 |

(v) The regulator can supply output of 1 mA at 2.5V with an input voltage of 2.8V.

(vi) The regulator also has input and output pads that may be open circuited if an external regulator is used. The current draw of the regulator circuit is preferably less than 100 nA in this non-operational mode.

(vii) The change of output voltage from a load of 10 uA to 1 mA is preferably less than 25 mV.

(viii) Current Drain excluding output current @ 1 mA load is less than 100 uA from source.

(ix) Current Drain excluding output current @ 0.1 mA load is less than 10 uA from source.

(x) Current Drain excluding output current @ 10 uA load is less than 1 uA from source.

General Purpose Comparators

The ASIC includes at least two comparators 4270, 4271 powered from VDDA. The comparators use 1.22V as a reference to generate the threshold. The output of the comparators can be read by the processor and will create a maskable interrupt on the rising or falling edge determined by configuration registers.

The comparators have power control to reduce power when not in use, and the current supply is less than 50 nA per comparator. The response time of the comparator is preferably less than 50 usec for a 20 mV overdrive signal, and the offset voltage is less than ±8 mV.

The comparators also have programmable hysteresis, wherein the hysteresis options include threshold=1.22V+Vhyst on a rising input, threshold=1.22−Vhyst on a falling input, or no hysteresis (Vhyst=25±10 mV). The output from either comparator is available to any GPIO on any power plane. (See GPIO section).

Sensor Connection Sensing Circuitry on RE

An analog switched capacitor circuit monitors the impedance of the RE connection to determine if the sensor is connected. Specifically, a capacitor of about 20 pF is switched at a frequency of 16 Hz driven by an inverter with an output swing from VSS to VDD. Comparators will sense the voltage swing on the RE pad and, if the swing is less than a threshold, the comparator output will indicate a connection. The above-mentioned comparisons are made on both transitions of the pulse. A swing below threshold on both transitions is required to indicate a connect, and a comparison indicating high swing on either phase will indicate a disconnect. The connect signal/disconnect signal is debounced such that a transition of its state requires a stable indication to the new state for at least ½ second.

The circuit has six thresholds defined by the following resistances in parallel with a 20 pF capacitor: 500 k, 1 Meg, 2 MEG, 4 Meg, 8 Meg, and 16 Meg ohms. This parallel equivalent circuit is between the RE pad and a virtual ground that can be at any voltage between the power rails. The threshold accuracy is better than ±30%.

The output of the Sensor Connect sensing circuitry is able to programmably generate an interrupt or processor startup if a sensor is connected or disconnected. This circuit is active whenever the nPOR2_IN is high and the VDD and VDDA are present. The current drain for this circuit is less than 100 nA average.

WAKEUP Pad

The WAKEUP circuitry is powered by the VDD supply, with an input having a range from 0V to VBAT. The WAKEUP pad 4272 has a weak pulldown of 80±40 nA. This current can be derived from an output of the BIAS_GEN 4220. The average current consumed by the circuit is less than 50 nA with 0 v input.

The WAKEUP input has a rising input voltage threshold, Vih, of 1.22±0.1 V, and the falling input threshold is −25 mV±12 mV that of the rising threshold. In preferred embodiments, the circuit associated with the WAKEUP input draws no more than 100 nA for any input whose value is from −0.2 to VBAT voltage (this current excludes the input pulldown current). The WAKEUP pad is debounced for at least ½ second.

The output of the WAKEUP circuit is able to programmably generate an interrupt or processor startup if the WAKEUP pad changes state. (See the Event Handler section). It is important to note that the WAKEUP pad circuitry is configured to assume a low current, <1 nA, if the Battery Protection Circuit indicates a low battery state.

UART WAKEUP

The ASIC is configured to monitor the nRX_EXT pad 4274. If the nRX_EXT level is continuously high (UART BREAK) for longer than ½ second, a UART WAKEUP event will be generated. The due to sampling the UART WAKEUP event could be generated with a continuous high as short as ¼ second. The UART WAKEUP event can programmably generate an interrupt, WAKEUP and/or a microprocessor reset (nRESET_OD). (See the Event Handler section).

In preferred embodiments, the circuit associated with the UART WAKEUP input draws no more than 100 nA, and the UART WAKEUP pad circuitry is configured to assume a low current, <1 nA, if the Battery Protection circuitry indicates a Battery Low state. The UART Wakeup input has a rising input voltage threshold, Vih, of 1.22±0.1 V. The falling input threshold is −25 mV±12 mV that of the rising threshold.

Microprocessor Wakeup Control Signals

The ASIC is able to generate signals to help control the power management of a microprocessor. Specifically, the ASIC may generate the following signals:

(i) nSHUTDN-nSHUTDN may control the power enable of an off chip VDD regulator. The nSHUTDN pad is on the VBAT power rail. nSHUTDN shall be low if the Battery Protection circuitry indicates a Battery Low state, otherwise nSHUTDN shall be high.

(ii) VPAD_EN-VPAD_EN may control the power enable of an external regulator that supplies VPAD power. An internal signal that corresponds to this external signal ensures that inputs from the VPAD pads will not cause extra current due to floating inputs when the VPAD power is disabled. The VPAD_EN pad is an output on the VBAT power rail. The VPAD_EN signal is low if the Battery Protection signal indicates a low battery. The VPAD_EN signal may be set low by a software command that starts a timer; the terminal count of the timer forces VPAD_EN low. The following events may cause the VPAD_EN signal to go high if the Battery Protection signal indicates a good battery (see Event Handler for more details): nPOR2_IN transitioning from low to high; SW/Timer (programmable); WAKEUP transition; low to high, and/or high to low, (programmable); Sensor Connect transition; low to high, and/or high to low, (programmable); UART Break; and RTC Time Event (programmable).

(iii) UP_WAKEUP-UP_WAKEUP may connect to a microprocessor wakeup pad. It is intended to wakeup the microprocessor from a sleep mode or similar power down mode. The UP_WAKEUP pad is an output on the VPAD power rail. The UP_WAKEUP signal can be programmed to be active low, active high or a pulse. The UP_WAKEUP signal may be set low by a software command that starts a timer; the terminal count of the timer forces UP_WAKEUP low. The following events may cause the UP_WAKEUP signal to go high if the Battery Protection signal indicates a good battery (see Event Handler for more details): nPOR2_IN transitioning from low to high; SW/Timer (programmable); WAKEUP transition; low to high, and/or high to low, (programmable); Sensor Connect transition; low to high, and/or high to low, (programmable); UART Break; and RTC Time Event (programmable). The WAKEUP signal may be delayed by a programmable amount. If WAKEUP is programmed to be a pulse, the pulse width may be programmed.

(iv) CLK_32 KHZ-CLK_32 KHZ pad may connect to a microprocessor to supply a low speed clock. The clock is on-off programmable and programmably turns on to wakeup events. The CLK_32 KHZ pad is an output on the VPAD power rail. The CLK_32 KHZ signal is low if the Battery Protection signal indicates a low battery. The CLK_32 KHZ output may be programmed off by a programmable bit. The default is ON. The CLK_32 KHZ signal may be disabled by a software command that starts a timer; The terminal count of the timer forces CLK_32 KHZ low. The following events may cause the CLK_32 KHZ signal to be enabled if the Battery Protection signal indicates a good battery (see Event Handler for more details): nPOR2_IN transitioning from low to high; SW/Timer (programmable); WAKEUP transition; low to high, and/or high to low, (programmable); Sensor Connect transition; low to high, and/or high to low, (programmable); UART Break; RTC Time Event (programmable); and Detection of low battery by Battery Protection Circuit.

(v) nRESET_OD-nRESET_OD may connect to a microprocessor to cause a microprocessor reset. The nRESET_OD is programmable to wakeup events. The nRESET_OD pad is an output on the VPAD power rail. This pad is open drain (nfet output). The nRESET_OD signal is low if the Battery Protection signal indicates a low battery. The nRESET_OD active time is programmable from 1 to 200 msec. The default is 200 ms. The following events may cause the nRESET_OD signal to be asserted low (see Event Handler for more details): nPOR2_IN; SW/Timer (programmable); WAKEUP transition; low to high, and/or high to low, (programmable); Sensor Connect transition; low to high, and/or high to low, (programmable); UART Break; and RTC Time Event (programmable).

(vi) UP_INT-UP_INT may connect to a microprocessor to communicate interrupts. The UP_INT is programmable to wakeup events. The UP_INT pad is an output on the VPAD power rail. The UP_INT signal is low if the Battery Protection signal indicates a low battery. The UP_INT signal may be set high by a software command that starts a timer; the terminal count of the timer forces UP_INT high. The following events may cause the UP_INT signal to be asserted high if the Battery Protection signal indicates a good battery (see Event Handler for more details): SW/Timer (programmable); WAKEUP transition; low to high, and/or high to low, (programmable); Sensor Connect transition; low to high and/or high to low, (programmable); UART Break; RTC Time Event (programmable); Detection of low battery by Battery Protection Circuit; and any of the ASIC interrupts when unmasked.

The ASIC has GPIO1 and GPIO0 pads able to act as boot mode control for a microprocessor. A POR2 event will reset a 2 bit counter whose bits map to GPIO1 & GPIO0 (MSB, LSB respectively). A rising edge of UART break increments the counter by one, wherein the counter counts by modulo 4, and goes to zero if it is incremented in state 11. The boot mode counter is pre-settable via SPI.

Event Handler/Watchdog

The ASIC incorporates an event handler to define the responses to events, including changes in system states and input signals. Events include all sources of interrupts (e.g. UART_BRK, WAKE_UP, Sensor Connect, etc. . . . ). The event handler responses to stimuli are programmable by the software through the SPI interface. Some responses, however, may be hardwired (non-programmable).

The event handler actions include enable/disable VPAD_EN, enable/disable CLK_32 KHZ, assert nRESET_OD, assert UP_WAKEUP, and assert UP_INT. The Event Watchdog Timer 1 through Timer 5 are individually programmable in 250 msec increments from 250 msec to 16,384 seconds. The timeouts for Event Watchdog timers 6 through 8 are hardcoded. The timeout for Timer6 and Timer7 are 1 minute; timeout for Timer8 is 5 minutes.

The ASIC also has a watchdog function to monitor the microprocessor's responses when triggered by an event. The event watchdog is activated when the microprocessor fails to acknowledge the event induced activities. The event watchdog, once activated, performs a programmable sequence of actions, Event Watchdog Timer 1-5, and followed by a hard-wired sequence of actions, Event Watchdog Timer 6-8, to re-gain the response of the microprocessor. The sequence of actions includes interrupt, reset, wake up, assert 32 KHz clock, power down and power up to the microprocessor.

During the sequences of actions, if the microprocessor regains its ability to acknowledge the activities that had been recorded, the event watchdog is reset. If the ASIC fails to obtain an acknowledgement from the microprocessor, the event watchdog powers down the microprocessor in a condition that will allow UART_BRK to reboot the microprocessor and it will activate the alarm. When activated, the alarm condition generates a square wave with a frequency of approximately 1 kHz on the pad ALARM with a programmable repeating pattern. The programmable pattern has two programmable sequences with programmable burst on and off times. The alarm has another programmable pattern that may be programmed via the SPI port. It will have two programmable sequences with programmable burst on and off times.

Digital to Analog (D/A)

In a preferred embodiment, the ASIC has two 8 bit D/A converters 4276, 4278 with the following characteristics:
(i) The D/A settles in less than 1 msec with less than 50 pF load.
(ii) The D/A has at least 8 bits of accuracy.
(iii) The output range is programmable to either 0 to 1.22V or 0 to VDDA.
(iv) Temperature sensitivity of the D/A voltage reference is less than 1 mV/° C.
(v) The DNL is less than 1 LSB.
(vi) Current consumed by the D/A is less than 2 uA from the VDDA supply.
(vii) Each D/A has an output 1 to a pad.
(viii) The D/A outputs are high impedance. Loading current must be less than 1 nA.
(ix) The D/A pads can be programmed to output a digital signal from a register. The output swing is from VSSA to VDDA.

Charger/Data Downloader Interface

The TX_EXT_OD 4280 is an open drain output whose input is the signal on the TX_UP input pad. This will allow the TX_EXT_OD pad to be open in the UART idle condition. The TX_EXT_OD pad has a comparator monitoring its voltage. If the voltage is above the comparator threshold voltage for a debounce period (¼ second), the output, nBAT_CHRG_EN (4281), will go low. This comparator and other associated circuitry with this function are on the VBAT and/or VDDBU planes.

The circuitry associated with this function must allow lows on TX_EXT_OD pad that result from normal communication with an external device without disabling the assertion of nBAT_CHRG_EN. If POR1 is active, nBAT_CHRG_EN will be high (not asserted). The comparator's threshold voltage is between 0.50V and 1.2V. The comparator will have hysteresis; The falling threshold is approximately 25 mV lower than the rising threshold.

The nRX_EXT pad inverts the signal on this pad and output it to RX_UP. In this way, the nRX_EXT signal will idle low. The nRX_EXT must accept inputs up to VBAT voltage. The nRX_EXT threshold is 1.22V±3%. The output of this comparator will be available over the SPI bus for a microprocessor to read.

The nRX_EXT pad also incorporates a means to programmably source a current, which will be 80±30 nA, with the maximum voltage being VBAT. The ASIC layout has mask programmable options to adjust this current from 30 nA to 200 nA in less than 50 nA steps with a minimal number of mask layer changes. A programmable bit will be available to block the UART break detection and force the RX_UP high. In normal operation, this bit will be set high before enabling the current sourcing to nRX_EXT and then set low after the current sourcing is disabled to ensure that no glitches are generated on RX_UP or that a UART break event is generated. Note to implement a wet connector detector, while the current source into nRX_EXT is active, an RX comparator output indicating a low input voltage would indicate leakage current. The ASIC includes a pulldown resistor approximately 100 k ohms on the nRX_EXT pad. This pulldown will be disconnected when the current source is active.

Sensor Connect Switch

The ASIC shall have a pad, SEN_CONN_SW (4282), which is able to detect a low resistance to VSS (4284). The SEN_CONN_SW sources a current from 5 to 25 uA with SEN_CONN_SW=0V and has a maximum open circuit voltage of 0.4V. The ASIC layout has mask programmable options to adjust this current from 1 uA to 20 uA in less than 5 uA steps with a minimal number of mask layer changes. The SEN_CONN_SW has associated circuitry that detects the presence of a resistance between SEN_CONN_SW and VSSA (4234) whose threshold is between 2 k and 15 k ohms. The average current drain of this circuit is 50 nA max. Sampling must be used to achieve this low current.

Oscillator Calibration Circuit

The ASIC has counters whose inputs can be steered to internal or external clock sources. One counter generates a programmable gating interval for the other counter. The gating intervals include 1 to 15 seconds from the 32 kHz oscillator. The clocks that can be steered to either counter are 32 kHz, RC oscillator, High Speed RC oscillator, and an input from any GPIO pad.

Oscillator Bypassing

The ASIC can substitute external clocks for each of the oscillators' outputs. The ASIC has a register that can be written only when a specific TEST MODE is asserted. This register has bits to enable the external input for the RC Oscillator, and may be shared with other analog test control signals. However, this register will not allow any oscillator bypass bits to be active if the TEST_MODE is not active.

The ASIC also has an input pad for an external clock to bypass the RC Oscillator. The pad, GPIO_VBAT, is on the VBAT power plane. The ASIC further includes a bypass enable pad for the 32 KHZ oscillator, OSC 32K_BYPASS. When high, the 32 KHZ oscillator output is supplied by driving the OSC32 KHZ_IN pad. It is noted that, normally, the OSC32 KHZ_IN pad is connected to a crystal.

The ASIC has inputs for an external clock to bypass the HS_RC_OSC. The bypass is enabled by a programmable register bit. The HS_RC_OSC may be supplied programmably by either the GPIO on the VDD plane or by GPIOs on the VPAD plane.

SPI Slave Port

The SPI slave port includes an interface consisting of a chip select input (SPI_nCS) 4289, a clock input (SPI_CK) 4286, a serial data input (SPI_MOSI) 4287, and a serial data output (SPI_MISO) 4288. The chip select input (SPI_nCS) is an active low input, asserted by an off-chip SPI master to initiate and qualify an SPI transaction. When SPI_nCS is asserted low, the SPI slave port configures itself as a SPI slave and performs data transactions based on the clock input (SPI_CK). When SPI_nCS is inactive, the SPI slave port resets itself and remains in reset mode. As this SPI interface supports block transfers, the master should keep SPI_nCS low until the end of a transfer.

The SPI clock input (SPI_CK) will always be asserted by the SPI master. The SPI slave port latches the incoming data on the SPI MOSI input using the rising edge of SPI_CK and driving the outgoing data on the SPI MISO output using the falling edge of SPI_CK. The serial data input (SPI_MOSI) is used to transfer data from the SPI master to the SPI slave. All data bits are asserted following the falling edge of SPI_CK. The serial data output (SPI_MISO) is used to transfer data from the SPI slave to the SPI master. All data bits are asserted following the falling edge of SPI_CK.

SPI_nCS, SPI_CK and SPI_MOSI are always driven by the SPI master, unless the SPI master is powered down. If VPAD_EN is low, these inputs are conditioned so that the current drain associated with these inputs is less than 10 nA and the SPI circuitry is held reset or inactive. SPI_MISO is only driven by the SPI slave port when SPI_nCS is active, otherwise, SPI_MISO is tri-stated.

The chip select (SPI_nCS) defines and frames the data transfer packet of an SPI data transaction. The data transfer packet consists of three parts. There is a 4-bit command section followed by a 12-bit address section, which is then followed by any number of 8 bit data bytes. The command bit 3 is used as the direction bit. A "1" indicates a write operation, and a "0" indicates a read operation. The combinations of command bit 2, 1 and 0 have the following definitions. Unused combinations are undefined.
  (i) 0000: read data and increment address.
  (ii) 0001: read data, no change to address
  (iii) 0010: read data, decrement address
  (iv) 1000: write data and increment address
  (v) 1001: write data, no change to address
  (vi) 1010: write data, decrement address
  (vii) x011: Test Port Addressing The 12-bit address section defines the starting byte address. If SPI_nCS stays active after the first data byte, to indicate a multi-byte transfer, the address is incremented by one after each byte is transferred. Bit<11> of the address (of address<11:0>) indicates the highest address bit. The address wraps around after reaching the boundary.

Data is in the byte format, and a block transfer can be performed by extending SPI_nCS to allow all bytes to be transferred in one packet.

Microprocessor Interrupt

The ASIC has an output at the VPAD logic level, UP_INT, for the purpose of sending interrupts to a host microprocessor. The microprocessor interrupt module consists of an interrupt status register, an interrupt mask register, and a function to logically OR all interrupt statuses into one microprocessor interrupt. The interrupt is implemented to support both edge sensitive and level sensitive styles. The polarity of the interrupt is programmable. The default interrupt polarity is TBD.

In a preferred embodiment, all interrupt sources on the AFE ASIC will be recorded in the interrupt status register. Writing a "1" to the corresponding interrupt status bit clears the corresponding pending interrupt. All interrupt sources on the AFE ASIC are mask-able through the interrupt mask register. Writing a "1" to the corresponding interrupt mask bit enables the masking of the corresponding pending interrupt. Writing a "0" to the corresponding interrupt mask bit disables the masking of the corresponding interrupt. The default state of the interrupt mask register is TBD.

General Purpose Input/Outputs (GPIOs)/Parallel Test Port

In embodiments of the invention, the ASIC may have eight GPIOs that operate on VPAD level signals. The ASIC has one GPIO that operates on a VBAT level signal, and one GPIO that operates on a VDD level signal. All off the GPIOs have at least the following characteristics:
  (i) Register bits control the selection and direction of each GPIO.
  (ii) The ASIC has a means to configure the GPIOs as inputs that can be read over the SPI interface.
  (iii) The ASIC has a means to configure the GPIOs as input to generate an interrupt.
  (iv) The ASIC has a means to configure each GPIO as an output to be controlled by a register bit that can be written over the SPI interface.
  (v) Programmably, the ASIC is able to output an input signal applied to GPIO_VBAT or GPIO_VDD to a GPIO (on the VPAD power plane). (Level shifting function).
  (vi) The ASIC has a means to configure each GPIO as an input to the oscillator calibration circuit.
  (vii) The ASIC has a means to configure each general purpose comparator output to at least one GPIO on each power plane. The polarity of the comparator output is programmable by a programmable bit.
  (viii) The GPIOs have microprocessor interrupt generating capability.
  (ix) The GPIOs are programmable to open drain outputs.
  (x) The GPIOs on the VPAD power plane are configurable to implement boot control of a microprocessor.

A Parallel Test Port shares the 8-bit GPIOs on the VPAD voltage plane. The test port will be used for observing register contents and various internal signals. The outputs of this port are controlled by the port configuration register in the normal mode. Writing 8'hFF to both GPIO_O1S_REG & GPIO_O2S_REG registers will steer the test port data on the GPIO outputs, while writing 8'h00 to the GPIO_ON_REG register will disable the test port data and enable the GPIO data onto the GPIO outputs.

Registers and pre-grouped internal signals can be observed over this test port by addressing the target register through the SPI slave port. The SPI packet has the command bits set to 4'b0011 followed by the 12-bit target register address. The parallel test port continues to display the content of the addressed register until the next Test Port Addressing command is received.

Analog Test Ports

The IC has a multiplexer feeding the pad, TP_ANAMUX (4290), which will give visibility to internal analog circuit nodes for testing. The IC also has a multiplexer feeding the pad, TP_RES (4260), which will give visibility to internal analog circuit nodes for testing. This pad will also accommodate a precision 1 meg resistor in usual application to perform various system calibrations.

Chip ID

The ASIC includes a 32 bit mask programmable ID. A microprocessor using the SPI interface will be able to read this ID. This ID is to be placed in the analog electronics block so that changing the ID does not require a chip reroute. The design should be such that only one metal or one contact mask change is required to change the ID.

Spare Test Outputs

The ASIC has 16 spare digital output signals that can be multiplexed to the 8 bit GPIO under commands sent over the SPI interface. These signals will be organized as two 8 bit bytes, and will be connected to VSS if not used.

Digital Testing

The ASIC has a test mode controller that uses two input pins, TEST_CTL0 (4291) and TEST_CTL1 (4292). The test controller generates signals from the combination of the test control signals that have the following functionality (TEST_CTL<1:0>):
  (i) 0 is normal operating mode;
  (ii) 1 is Analog Test Mode;
  (iii) 2 is Scan Mode;
  (iv) 3 is Analog Test mode with the VDD_EN controlled by an input to GPIO_VBAT.

The test controller logic is split between the VDD and VDDBU power planes. During scan mode, testing LT_VBAT should be asserted high to condition the analog outputs to the digital logic. The ASIC has a scan chain implemented in as much digital logic as reasonably possible for fast digital testing.

Leakage Test Pin

The ASIC has a pin called LT_VBAT that, when high, will put all the analog blocks into an inactive mode so that only leakage currents will be drawn from the supplies. LT_VBAT causes all digital outputs from analog blocks to be in a stable high or low state as to not affect interface logic current drain. The LT_VBAT pad is on the VBAT plane with a pulldown with a resistance between 10 k and 40 k ohms.

Power Requirements

In embodiments of the invention, the ASIC includes a low power mode where, at a minimum, the microprocessor clock is off, the 32 kHz real time clock runs, and circuitry is active to detect a sensor connection, a change of level of the WAKE_UP pin, or a BREAK on the nRX_EXT input. This mode has a total current drain from VBAT (VDDBU), VDD, and VDDA of 4.0 uA maximum. When the Battery Protection Circuit detects a low battery (see Battery Protection Circuit description), the ASIC goes to a mode with only the VBAT and VDDBU power planes active. This is called Low Battery state. The VBAT current in this mode is less than 0.3 uA.

With the ASIC programmed to the potentiostat configuration with any one WORK electrode active in the H2O2 (peroxide) mode with its voltage set to 1.535V, the COUNTER amplifier on with the VSET_RE set to 1.00V, a 20 MEG load resistor connected between WORK and the COUNTER, the COUNTER and RE connected together and assuming one WORK electrode current measurement per minute, the average current drain of all power supplies is less than 7 uA. The measured current after calibration should be 26.75 nA±3%. Enabling additional WORK electrodes increases the combined current drain by less than 2 uA with the WORK electrode current of 25 nA.

With the ASIC programmed to the potentiostat configuration with the diagnostic function enabled to measure the impedance of one of the WORK electrodes with respect to the COUNTER electrode, the ASIC is configured to meet the following:

(i) Test frequencies: 0.1, 0.2, 0.3, 0.5 Hz, 1.0, 2.0, 5.0, 10, 100, 1000 and 4000 Hz.
(ii) The measurement of the above frequencies is not to exceed 50 seconds.
(iii) The total charge supplied to the ASIC is less than 8 millicoulombs.

Environment

In preferred embodiments of the invention, the ASIC:
(i) Operates and meets all specifications in the commercial temperature range of 0 to 70° C.
(ii) Functionally operates between −20° C. and 80° C., but may do so with reduced accuracy.
(iii) Is expected to operate after being stored in a temperature range of −30 to 80° C.
(iv) Is expected to operate in the relative humidity range of 1% to 95%.
(v) ESD protection is greater than ±2 KV, Human Body Model on all pins when packaged in a TBD package, unless otherwise specified.
(vi) Is configured such that the WORK1-WORK5, COUNTER, RE, TX_EXT_OD, and nRX_EXT pads withstand greater than ±4 KV Human Body Model.
(vii) Is configured such that the leakage current of the WORK1-WORK5 and RE pads is less than 0.05 nA at 40° C.

In embodiments of the invention, the ASIC may be fabricated in 0.25 micron CMOS process, and backup data for the ASIC is on DVD disk, 916-TBD.

As described in detail hereinabove, the ASIC provides the necessary analog electronics to: (i) support multiple potentiostats and interface with multi-terminal glucose sensors based on either Oxygen or Peroxide; (ii) interface with a microcontroller so as to form a micropower sensor system; and (iii) implement EIS diagnostics based on measurement of EIS-based based parameters. The measurement and calculation of EIS-based parameters will now described in accordance with embodiments of the inventions herein.

As has been mentioned, previously, the impedance at frequencies in the range from 0.1 Hz to 8 kHz can provide information as to the state of the sensor electrodes. The AFE IC circuitry incorporates circuitry to generate the measurement forcing signals and circuitry to make measurements used to calculate the impedances. The design considerations for this circuitry include current drain, accuracy, speed of measurement, the amount of processing required, and the amount of on time required by a control microprocessor.

In a preferred embodiment of the invention, the technique the AFE IC uses to measure the impedance of an electrode is to superimpose a sine wave voltage on the dc voltage driving an electrode and to measure the phase and amplitude of the resultant AC current. To generate the sine wave, the AFE IC incorporates a digitally-synthesized sine wave current. This digital technique is used because the frequency and phase can be precisely controlled by a crystal derived timebase and it can easily generate frequencies from DC up to 8 kHz. The sine wave current is impressed across a resistor in series with a voltage source in order to add the AC component to the electrode voltage. This voltage is the AC forcing voltage. It is then buffered by an amplifier that drives a selected sensor electrode.

The current driving the electrode contains the resultant AC current component from the forcing sine wave and is converted to a voltage. This voltage is then processed by multiplying it by a square wave that has a fixed phase relative to the synthesized sine wave. This multiplied voltage is then integrated. After the end of a programmable number of integration intervals—an interval being an integral number of ½ periods of the driving sine wave—the voltage is measured by the ADC. By calculations involving the values of the integrated voltages, the real and imaginary parts of the impedance can be obtained.

The advantage of using integrators for the impedance measurement is that the noise bandwidth of the measurement is reduced significantly with respect to merely sampling the waveforms. Also, the sampling time requirements are significantly reduced which relaxes the speed requirement of the ADC.

Figure 45:
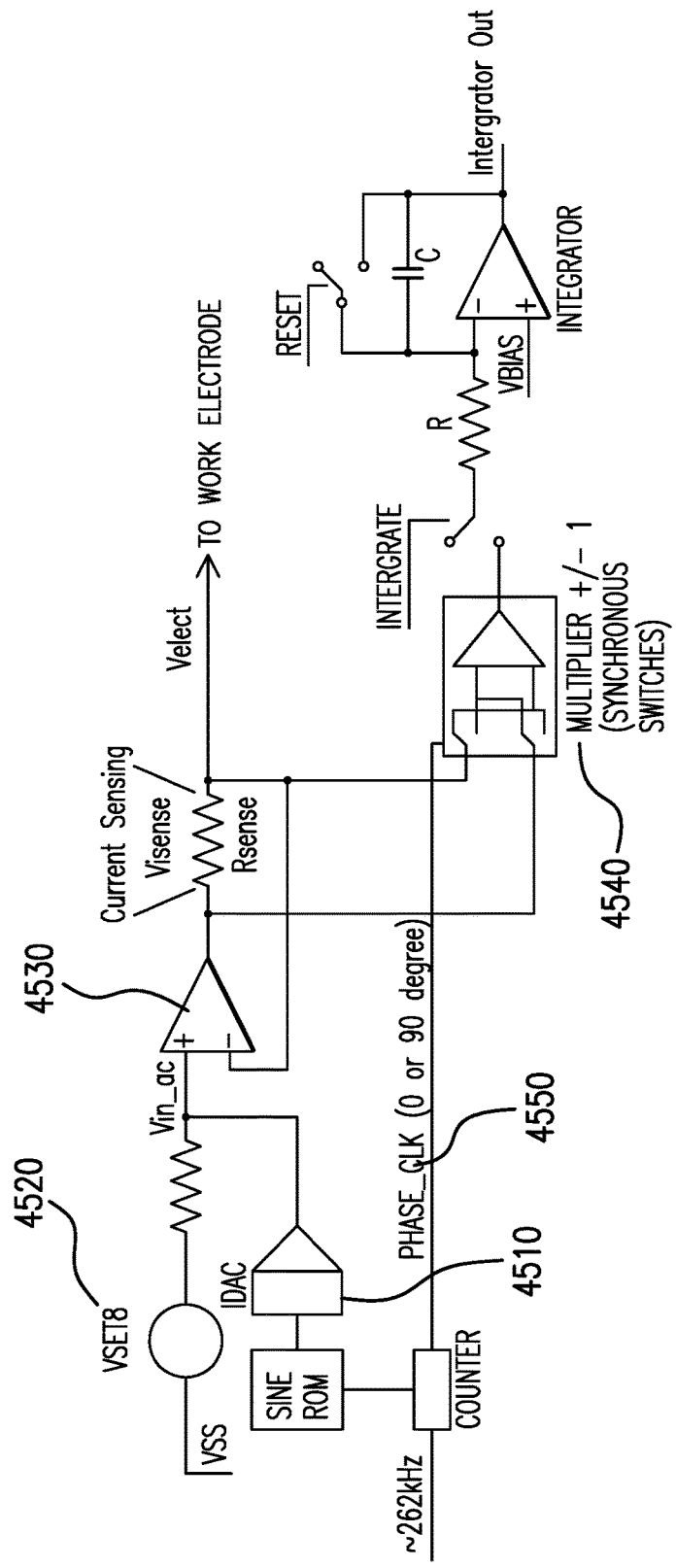
FIG. 45 shows some of the main blocks of the EIS circuitry in the analog front end IC of a glucose sensor in accordance with embodiments of the invention.
Figure 46A:
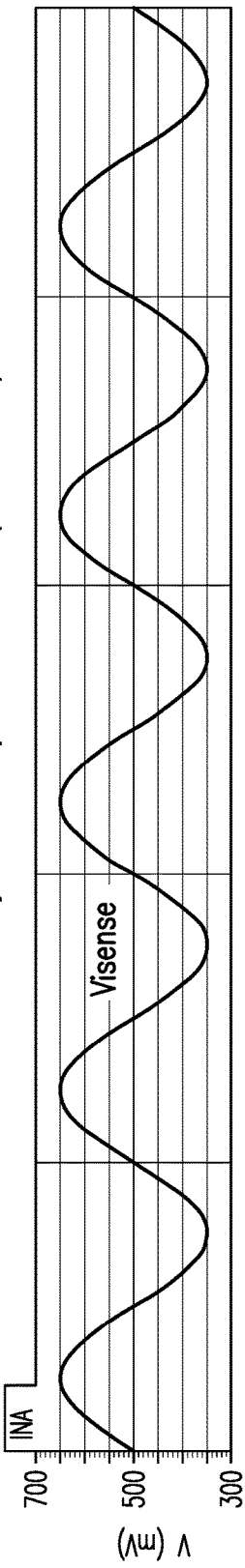
FIGS. 46A-46F show a simulation of the signals of the EIS circuitry shown in FIG. 45 for a current of 0-degree phase with a 0-degree phase multiply.
Figure 46B:
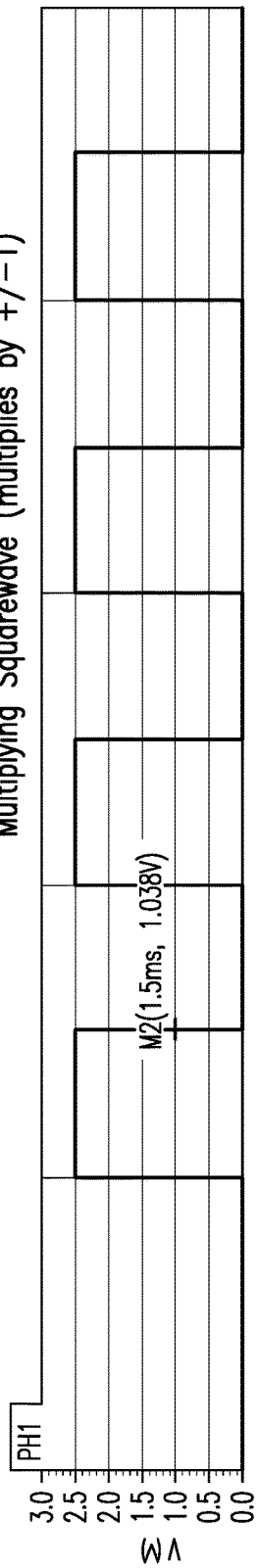
Figure 46C:
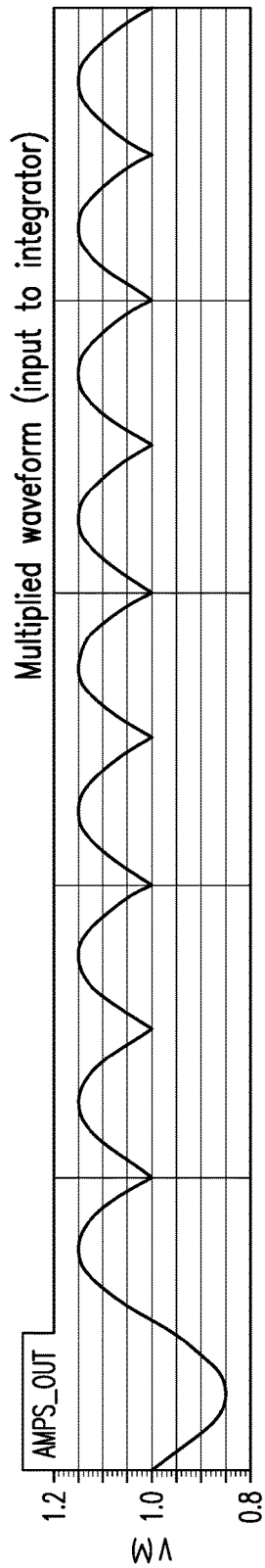
Figure 46D:
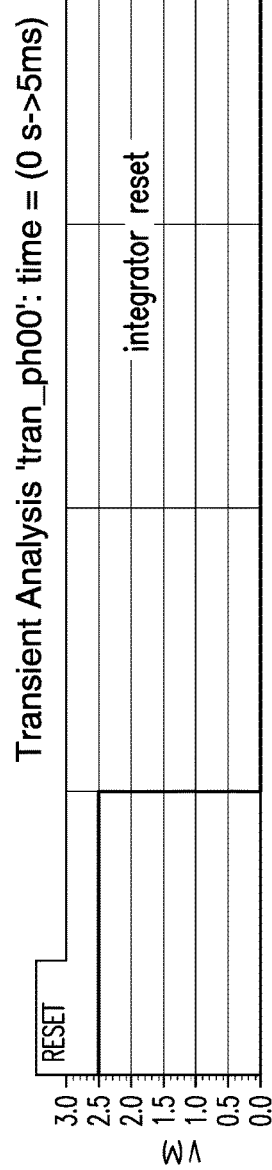
Figure 46E:
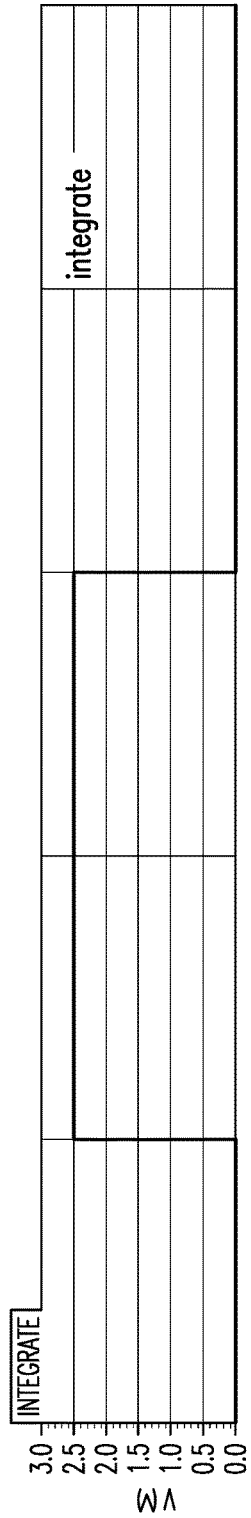
Figure 46F:
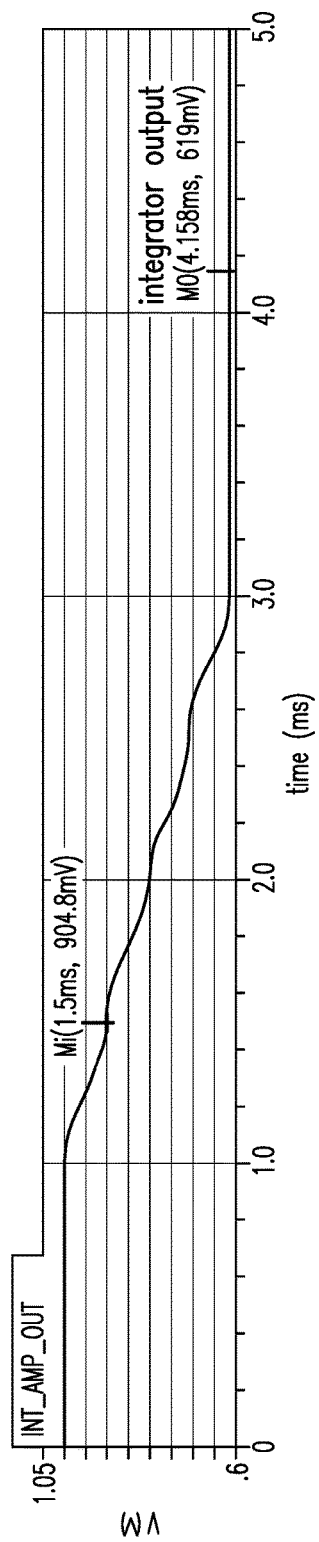
Figure 47D:
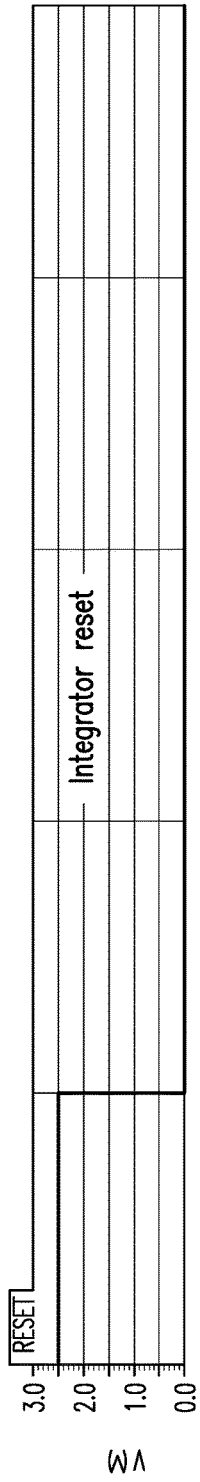
Figure 47E:
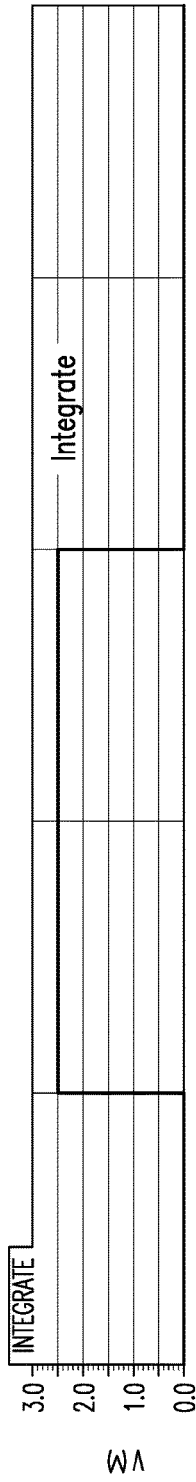
Figure 47F:
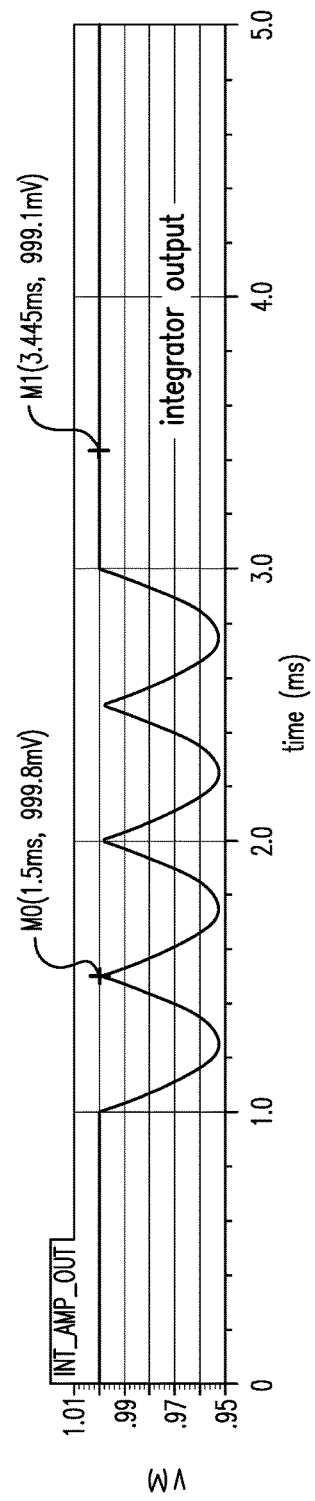

FIG. 45 shows the main blocks of the EIS circuitry in the AFE IC (designated by reference numeral 4255 in FIG. 42B). The IDAC 4510 generates a stepwise sine wave in synchrony with a system clock. A high frequency of this system clock steps the IDAC through the lookup table that contains digital code. This code drives the IDAC, which generates an output current approximating a sine wave. This sine wave current is forced across a resistor to give the AC component, Vin_ac, with the DC offset, VSET8 (4520). When the IDAC circuit is disabled, the DC output voltage reverts to VSET8, so the disturbance to the electrode equilibrium is minimized. This voltage is then buffered by an amplifier 4530 that drives the electrode through a resistor in series, Rsense. The differential voltage across Rsense is proportional to the current. This voltage is presented to a multiplier 4540 that multiplies the voltage by either +1 or −1. This is done with switches and a differential amplifier (instrumentation amplifier). The system clock is divided to generate the phase clock 4550 which controls the multiply function and can be set to 0, 90, 180 or 270 degrees relative to the sine wave.

The plots in FIGS. 46A-46F and 47A-47F show a simulation of the signals of the circuit shown in FIG. 45 to a current that has 0 degree phase shift, which represents a real resistance. For these example simulations, the simulation input values were selected to give the current sense voltage equal to 0.150V. To obtain enough information to derive the impedance and phase, two integrations are required: one with a 0 degree phase multiply (FIGS. 46A-46F) and one with a 90 degree phase multiply (FIGS. 47A-47F).

Calculation of Impedance

The equations describing the integrator output are provided below. For simplicity, only ½ of a sine wave period is considered. As can be seen from the plots of FIGS. 46A-46F and 47A-47F, total integrator output will be approximately the integrated value of a ½ sine wave cycle multiplied by the number of ½ cycles integrated. It is noted that the multiplying switches in relation with the integrate time perform a "gating" function of the signal to the integrator; this can be viewed as setting the limits of integration. The multiplying signal has a fixed phase to the generated sine wave. This can be set to 0, 90, 180, or 270 degrees with software. If the sine wave is in phase (0 degree shift) with respect to the multiply square wave, the limits of integration will be 90 (180°) and 0 (0°). If the sine wave is shifted by 90 degrees, the limits of integration can be viewed as ¾π (270°) and ¼π (90°).

The formulas with the multiplying square wave in-phase (0°) with respect to the driving sine wave are shown below. This will yield a voltage that is proportional to the real component of the current. It is noted that $\Phi$ is the phase shift of the sine wave relative to the multiplying square wave; Vout is the integrator output, and Aampl is the current sine wave amplitude. Also the period of the sine wave is 1/f, and RC is the time constant of the integrator.

$$v_{out0} =$$

$$\int_0^{\frac{1}{2f}} \frac{V_{in}}{RC} \partial t = \frac{A_{ampl}}{RC} \int_0^{\frac{1}{2f}} \sin[2\pi f \partial t + \phi] = -\frac{A_{ampl}}{2\pi fRC} \cos[2\pi ft + \phi]\Big|_0^{\frac{1}{2f}}$$

$$v_{out0} = -\frac{A_{ampl}}{2\pi fRC}[\cos[\pi + \phi] - \cos[\phi]]$$

$$\cos(\phi + \varphi) = \cos(\phi)\cos(\varphi) - \sin(\phi)\sin(\varphi);$$

$$\cos(\pi + \phi) = -\cos(\phi);$$

$$\cos(-\phi) = \cos(\phi)$$

$$v_{out0} =$$

$$\frac{-A_{ampl}}{2\pi fRC}[\cos(\pi + \phi) - \cos(\phi)] = \frac{A_{ampl}}{2\pi fRC}[\cos(\phi) + \cos(\phi)] = \frac{A_{ampl}}{\pi fRC}\cos(\phi)$$

If $\Phi$=0, $$v_{out0} = \frac{A_{ampl}}{\pi fRC}.$$

This corresponds to the real part of the current.

For the multiplying square wave quadrature phase (90°) with respect to the driving sine wave to yield an output proportional to the imaginary component of the current:

$$v_{out\,90} =$$

$$\int_{\frac{1}{4f}}^{\frac{3}{4f}} \frac{V_{in}}{RC} \partial t = \frac{A_{ampl}}{RC} \int_{\frac{1}{4f}}^{\frac{3}{4f}} \sin[2\pi f \partial t + \phi] = -\frac{A_{ampl}}{2\pi fRC} \cos[2\pi ft + \phi]\Big|_{\frac{1}{4f}}^{\frac{3}{4f}}$$

$$v_{out\,90} = -\frac{A_{ampl}}{2\pi fRC}\left[\cos\left[\frac{3}{2}\pi + \phi\right] - \cos\left[\frac{1}{2}\pi + \phi\right]\right]$$

$$\cos(\phi + \varphi) = \cos(\phi)\cos(\varphi) - \sin(\phi)\sin(\varphi);$$

$$\cos\left[\frac{3}{2}\pi + \phi\right] = \sin(\phi);$$

$$\cos\left[\frac{1}{2}\pi + \phi\right] = -\sin(\phi)$$

$$v_{out\,90} =$$

$$\frac{-A_{ampl}}{2\pi fRC}[\sin(\phi) + \sin(\phi)] = \frac{-A_{ampl}}{2\pi fRC}[\sin(\phi) + \sin(\phi)] = \frac{-A_{ampl}}{\pi fRC}\sin(\phi)$$

If $\Phi$=0, $$v_{out\,90} = \frac{A_{ampl}}{\pi fRC}\sin(\phi) = 0.$$

This corresponds to the imaginary part of the current.

In the first example plot shown in FIGS. 46A-46F, $A_{ampl}$ is 0.150 v, the frequency is 1 kHz, $\Phi$=0, the RC for the integrator is 20 M ohm and 25 pF which gives RC=0.5 msec. Plugging in those numbers into the equations, gives 0.09549 v, which favorably compares to the integrator output of the plot in FIG. 46. It is noted that the integrator output over the period of integration is the delta voltage from the start of integration to the measurement.

For the 90° square wave multiply, the result should be 0 since sin(0)=0. The simulation result is close to this value.

To calculate the phase:

since $$\frac{v_{out90}}{v_{out0}} = \frac{\sin(\phi)}{\cos(\phi)},$$

it follows:

$$\phi = \arctan\frac{\sin(\phi)}{\cos(\phi)} = \arctan\frac{v_{out90}}{v_{out0}}$$

where $V_{out90}$ is the integrator output with the 90° phase shift for the multiply, and $V_{out0}$ is the integrator output for the 0° phase shift. The $V_{out90}$ and $V_{out0}$ outputs must be integrated for the same number of ½ cycles or normalized by the number of cycles. It is important to note that, in the actual software (e.g., ASIC) implementation, only integral cycles (360°) are allowed because an integral number of cycles compensates for any offset in the circuitry before the multiplier.

The magnitude of the current can be found from $$|I| = \frac{A_{ampl}}{R_{sense}}$$

and $$A_{ampl} = \frac{V_{out\_90} \pi FRC}{\sin(\phi)}$$

or $$A_{ampl} = \frac{V_{out\_0} \pi fRC}{\cos(\phi)},$$

or $A_{ampl} = \pi fRC \sqrt{V_{out\_0}^2 + V_{out\_90}^2}$. This current has the phase angle as calculated above.

The above analysis shows that one can determine the current amplitude and its phase with respect to the multiplying signal. The forcing voltage is generated in a fixed phase (0, 90, 180 or 270 degrees) with respect to the multiplying signal—this is done digitally so that it is precisely controlled. But there is at least one amplifier in the path before the forcing sine wave is applied to the electrode; this will introduce unwanted phase shift and amplitude error. This can be compensated for by integrating the forcing sine wave signal obtained electrically near the electrode. Thus, the amplitude and any phase shift of the forcing voltage can be determined. Since the path for both the current and voltage waveform will be processed by the same circuit, any analog circuit gain and phase errors will cancel.

Since the variable of interest is the impedance, it may not be necessary to actually calculate the $A_{ampl}$. Because the current waveform and the voltage waveform are integrated through the same path, there exists a simple relationship between the ratio of the current and the voltage. Calling the integrated current sense voltage $V_{I\_out}$ and the integrated electrode voltage as $V_{V\_out}$ with the additional subscript to describe the phase of the multiplying function:

$$I = \frac{A_{I\_ampl}}{R_{sense}} \angle \phi = \frac{V_{I\_out\_0} \pi fRC}{\cos(\phi) R_{sense}} \angle \phi;$$

$$V = A_{V\_ampl} \angle \theta = \frac{V_{V\_out\_0} \pi fRC}{\cos(\theta)}$$

The impedance will be the voltage divided by the current. Thus, $$Z = \frac{|V| \angle \theta}{|I| \angle \phi} = \frac{\frac{V_{V\_out\_0} \pi fRCL\theta}{\cos(\theta)}}{\frac{V_{I\_out\_0} \pi fRCL\phi}{\cos(\theta) R_{sense}}} = R_{sense} * \frac{V_{V\_out\_0} \cos(\phi)}{V_{I\_out\_0} \cos(\theta)} \angle(\theta - \phi)$$

The magnitudes of the voltage and the current can also be obtained from the square root of the squares of the 0 and 90 degree phase integration voltages. As such, the following may also be used:

$$Z = \frac{|V| \angle \theta}{|I| \angle \phi} = \frac{\sqrt{V_{V\_out\_0}^2 + V_{V\_out\_90}^2} \angle \theta}{\sqrt{V_{I\_out\_0}^2 + V_{I\_out\_90}^2} \angle \phi} = R_{sense} * \frac{\sqrt{V_{V\_out\_0}^2 + V_{V\_out\_90}^2}}{\sqrt{V_{I\_out\_0}^2 + V_{I\_out\_90}^2}} \angle(\theta - \phi)$$

The integration of the waveforms may be done with one hardware integrator for the relatively-higher frequencies, e.g., those above about 256 Hz. The high frequencies require four measurement cycles: (i) one for the in-phase sensor current; (ii) one for the 90 degree out of phase sensor current; (iii) one for the in-phase forcing voltage; and (iv) one for the 90 degree out of phase forcing voltage.

Two integrators may be used for the relatively-lower frequencies, e.g., those lower than about 256 Hz, with the integration value consisting of combining integrator results numerically in the system microprocessor. Knowing how many integrations there are per cycle allows the microprocessor to calculate the 0 and 90 degree components appropriately.

Synchronizing the integrations with the forcing AC waveform and breaking the integration into at least four parts at the lower frequencies will eliminate the need for the hardware multiplier as the combining of the integrated parts in the microprocessor can accomplish the multiplying function. Thus, only one integration pass is necessary for obtaining the real and imaginary current information. For the lower frequencies, the amplifier phase errors will become smaller, so below a frequency, e.g., between 1 Hz and 50 Hz, and preferably below about 1 Hz, the forcing voltage phase will not need to be determined. Also, the amplitude could be assumed to be constant for the lower frequencies, such that only one measurement cycle after stabilization may be necessary to determine the impedance.

As noted above, whereas one hardware integrator is used for the relatively-higher frequencies, for the relatively-lower frequencies, two integrators may be used. In this regard, the schematic in FIG. 45 shows the EIS circuitry in the AFE IC as used for the relatively-higher EIS frequencies. At these frequencies, the integrator does not saturate while integrating over a cycle. In fact, multiple cycles are integrated for the highest frequencies as this will provide a larger output signal which results in a larger signal to noise ratio.

For the relatively-lower frequencies, such as, e.g., those below about 500 Hz, the integrator output can saturate with common parameters. Therefore, for these frequencies, two integrators are used that are alternately switched. That is, while a first integrator is integrating, the second integrator is being read by the ADC and then is reset (zeroed) to make it ready to integrate when the integration time for first integrator is over. In this way, the signal can be integrated without having gaps in the integration. This would add a second integrator and associated timing controls to the EIS circuitry shown in FIG. 45.

Stabilization Cycle Considerations

The above analysis is for steady state conditions in which the current waveform does not vary from cycle to cycle. This condition is not met immediately upon application of a sine wave to a resistor-capacitor (RC) network because of the initial state of the capacitor. The current phase starts out at 0 degrees and progresses to the steady state value. However, it would be desirable for the measurement to consume a minimum amount of time in order to reduce current drain and also to allow adequate time to make DC sensor measurements (Isigs). Thus, there is a need to determine the number of cycles necessary to obtain sufficiently accurate measurements.

The equation for a simple RC circuit—with a resistor and capacitor in series—is $$v_{ac} = R * I(t) + \frac{1}{C} \int I(t) \partial t$$

Solving the above for I(t) gives:

$$I(t) = \frac{-1}{RC}\left[V_{c0}C + \frac{\omega V_m}{R\left[\omega^2 + \frac{1}{R^2C^2}\right]}\right]e^{\frac{-t}{RC}} +$$

$$\frac{V_m}{R}\left[\frac{1}{\left[\omega^2 + \frac{1}{R^2C^2}\right]}\right]\left[\omega^2\sin(\omega t) + \frac{\omega}{RC}\cos\omega t\right]$$

where $V_{c0}$ is the initial value of the capacitor voltage, $V_m$ is the magnitude of the driving sine wave, and ω is the radian frequency (2πf).

The first term contains the terms defining the non-steady state condition. One way to speed the settling of the system would be to have the first term equal 0, which may be done, e.g., by setting $$V_{cinit}C = \frac{\omega V_m}{R\left[\omega^2 + \frac{1}{R^2C^2}\right]}$$

or $$V_{cinit} = \frac{RC\,\omega V_m}{[R^2C^2\omega^2 + 1]}$$

While this may not be necessary in practice, it is possible to set the initial phase of the forcing sine wave to jump immediately from the DC steady state point to $V_{cinit}$. This technique may be evaluated for the specific frequency and anticipated phase angle to find the possible reduction in time.

The non-steady state term is multiplied by the exponential function of time. This will determine how quickly the steady state condition is reached. The RC value can be determined as a first order approximation from the impedance calculation information. Given the following:

$$X_c = \frac{1}{\omega C} = Z\sin\phi$$

and R=Z cos φ, it follows that $$RC = \frac{Z\cos\phi}{\omega Z\sin\phi} = \frac{1}{\omega\tan\phi}$$

For a sensor at 100 Hz with a 5 degree phase angle, this would mean a time constant of 18.2 msec. For settling to less than 1%, this would mean approximately 85 msec settling time or 8.5 cycles. On the other hand, for a sensor at 0.10 Hz with a 65 degree phase angle, this would mean a time constant of 0.75 sec. For settling to less than 1%, this would mean approximately 3.4 sec settling time.

Thus, in embodiments of the invention as detailed hereinabove, the ASIC includes (at least) 7 electrode pads, 5 of which are assigned as WORK electrodes (i.e., sensing electrodes, or working electrodes, or WEs), one of which is labeled COUNTER (i.e., counter electrode, or CE), and one that is labeled REFERENCE (i.e., reference electrode, or RE). The counter amplifier 4321 (see FIG. 42B) may be programmably connected to the COUNTER, the REFERENCE, and/or any of the WORK assigned pads, and in any combination thereof. As has been mentioned, embodiments of the invention may include, e.g., more than five WEs. In this regard, embodiments of the invention may also be directed to an ASIC that interfaces with more than 5 working electrodes.

It is important to note that, with the ASIC as described herein, each of the above-mentioned five working electrodes, the counter electrode, and the reference electrode is individually and independently addressable. As such, any one of the 5 working electrodes may be turned on and measure Isig (electrode current), and any one may be turned off. Moreover, any one of the 5 working electrodes may be operably connected/coupled to the EIS circuitry for measurement of EIS-related parameters, e.g., impedance and phase. In other words, EIS may be selectively run on any one or more of the working electrodes. In addition, the respective voltage level of each of the 5 working electrodes may be independently programmed in amplitude and sign with respect to the reference electrode. This has many applications, such as, e.g., changing the voltage on one or more electrodes in order to make the electrode(s) less sensitive to interference.

In embodiments where two or more working electrodes are employed as redundant electrodes, the EIS techniques described herein may be used, e.g., to determine which of the multiplicity of redundant electrodes is functioning optimally (e.g., in terms of faster start-up, minimal or no dips, minimal or no sensitivity loss, etc.), so that only the optimal working electrode(s) can be addressed for obtaining glucose measurements. The latter, in turn, may drastically reduce, if not eliminate, the need for continual calibrations. At the same time, the other (redundant) working electrode(s) may be: (i) turned off, which would facilitate power management, as EIS may not be run for the "off" electrodes; (ii) powered down; and/or (iii) periodically monitored via EIS to determine whether they have recovered, such that they may be brought back on line. On the other hand, the non-optimal electrode(s) may trigger a request for calibration. The ASIC is also capable of making any of the electrodes—including, e.g., a failed or off-line working electrode—the counter electrode. Thus, in embodiments of the invention, the ASIC may have more than one counter electrode.

While the above generally addresses simple redundancy, wherein the redundant electrodes are of the same size, have the same chemistry, the same design, etc., the above-described diagnostic algorithms, fusion methodologies, and the associated ASIC may also be used in conjunction with spatially distributed, similarly sized or dissimilarly sized, working electrodes as a way of assessing sensor implant integrity as a function of implant time. Thus, in embodiments of the invention, sensors may be used that contain electrodes on the same flex that may have different shapes, sizes, and/or configurations, or contain the same or different chemistries, used to target specific environments.

For example, in one embodiment, one or two working electrodes may be designed to have, e.g., considerably better hydration, but may not last past 2 or 3 days. Other working electrode(s), on the other hand, may have long-lasting durability, but slow initial hydration. In such a case, an algorithm may be designed whereby the first group of working electrode(s) is used to generate glucose data during early wear, after which, during mid-wear, a switch-over may be made (e.g., via the ASIC) to the second group of electrode(s). In such a case, the fusion algorithm, e.g., may not necessarily "fuse" data for all of the WEs, and the user/patient is unaware that the sensing component was switched during mid-wear.

In yet other embodiments, the overall sensor design may include WEs of different sizes. Such smaller WEs generally output a lower Isig (smaller geometric area) and may be used specifically for hypoglycemia detection/accuracy, while larger WEs—which output a larger Isig—may be used specifically for euglycemia and hyperglycemia accuracy. Given the size differences, different EIS thresholds and/or frequencies must be used for diagnostics as among these electrodes. The ASIC, as described hereinabove, accommodates such requirements by enabling programmable, electrode-specific, EIS criteria. As with the previous example, signals may not necessarily be fused to generate an SG output (i.e., different WEs may be tapped at different times).

As was noted previously, the ASIC includes a programmable sequencer 4266 that commands the start and stop of the stimulus and coordinates the measurements of the EIS-based parameters for frequencies above about 100 Hz. At the end of the sequence, the data is in a buffer memory, and is available for a microprocessor to quickly obtain (values of) the needed parameters. This saves time, and also reduces system power requirements by requiring less microprocessor intervention.

For frequencies lower than about 100 Hz, the programmable sequencer 4266 coordinates the starting and stopping of the stimulus for EIS, and buffers data. Either upon the end of the measurement cycle, or if the buffer becomes close to full, the ASIC may interrupt the microprocessor to indicate that it needs to gather the available data. The depth of the buffer will determine how long the microprocessor can do other tasks, or sleep, as the EIS-based parameters are being gathered. For example, in one preferred embodiment, the buffer is 64 measurements deep. Again, this saves energy as the microprocessor will not need to gather the data piecemeal. It is also noted that the sequencer 4266 also has the capability of starting the stimulus at a phase different from 0, which has the potential of settling faster.

The ASIC, as described above, can control the power to a microprocessor. Thus, for example, it can turn off the power completely, and power up the microprocessor, based on detection of sensor connection/disconnection using, e.g., a mechanical switch, or capacitive or resistive sensing. Moreover, the ASIC can control the wakeup of a microprocessor. For example, the microprocessor can put itself into a low-power mode. The ASIC can then send a signal to the microprocessor if, e.g., a sensor connect/disconnect detection is made by the ASIC, which signal wakes up the processor. This includes responding to signals generated by the ASIC using techniques such as, e.g., a mechanical switch or a capacitive-based sensing scheme. This allows the microprocessor to sleep for long periods of time, thereby significantly reducing power drain.

It is important to reiterate that, with the ASIC as described hereinabove, both oxygen sensing and peroxide sensing can be performed simultaneously, because the five (or more) working electrodes are all independent, and independently addressable, and, as such, can be configured in any way desired. In addition, the ASIC allows multiple thresholds for multiple markers, such that EIS can be triggered by various factors—e.g., level of $V_{cntr}$, capacitance change, signal noise, large change in Isig, drift detection, etc.—each having its own threshold(s). In addition, for each such factor, the ASIC enables multiple levels of thresholds.

In yet another embodiment of the invention, EIS may be used as an alternative plating measurement tool, wherein the impedance of both the working and counter electrodes of the sensor substrate may be tested, post-electroplating, with respect to the reference electrode. More specifically, existing systems for performing measurements of the sensor substrate which provide an average roughness of the electrode surface sample a small area from each electrode to determine the average roughness (Ra) of that small area. For example, currently, the Zygo Non-contact Interferometer is used to quantify and evaluate electrode surface area. The Zygo interferometer measures a small area of the counter and working electrodes and provides an average roughness value. This measurement correlates the roughness of each sensor electrode to their actual electrochemical surface area. Due to the limitations of systems that are currently used, it is not possible, from a manufacturing throughput point of view, to measure the entire electrode surface, as this would be an extremely time-consuming endeavor.

In order to measure the entire electrode in a meaningful and quantitative manner, an EIS-based methodology for measuring surface area has been developed herein that is faster than current, e.g., Zygo-based, testing, and more meaningful from a sensor performance perspective. Specifically, the use of EIS in electrode surface characterization is advantageous in several respects. First, by allowing multiple plates to be tested simultaneously, EIS provides a faster method to test electrodes, thereby providing for higher efficiency and throughput, while being cost-effective and maintaining quality.

Second, EIS is a direct electrochemical measurement on the electrode under test, i.e., it allows measurement of EIS-based parameter(s) for the electrode and correlates the measured value to the true electrochemical surface area of the electrode. Thus, instead of taking an average height difference over a small section of the electrode, the EIS technique measures the double layer capacitance (which is directly related to surface area) over the whole electrode surface area and, as such, is more representative of the properties of the electrode, including the actual surface area. Third, EIS testing is non-destructive and, as such, does not affect future sensor performance. Fourth, EIS is particularly useful where the surface area to be measured is either fragile or difficult to easily manipulate.

For purposes of this embodiment of the invention, the EIS-based parameter of interest is the Imaginary impedance (Zim), which may be obtained, as discussed previously, based on measurements of the impedance magnitude (|Z|) in ohms and the phase angle ($\Phi$) in degrees of the electrode immersed in an electrolyte. It has been found that, in addition to being a high-speed process, testing using the electrochemical impedance of both the Counter Electrode (CE) and the WE is an accurate method of measuring the surface area of each electrode. This is also important because, although the role of electrode size in glucose sensor performance is dictated, at least in part, by the oxidation of the hydrogen peroxide produced by the enzymatic reaction of glucose with GOX, experiments have shown that an increased WE surface area reduces the number of low start-up events and improves sensor responsiveness—both of which are among the potential failure modes that were previously discussed at some length.

Returning to the imaginary impedance as the EIS-based parameter of interest, it has been found that the key parameters that drive the electrode surface area, and consequently, its imaginary impedance values are: (i) Electroplating conditions (time in seconds and current in micro Amperes); (ii) EIS frequency that best correlates to surface area; (iii) the number of measurements conducted on a single electrode associated to the electrolyte used in the EIS system; and (iv) DC Voltage Bias.

In connection with the above parameters, experiments have shown that using Platinum plating solution as the electrolyte presents a poor correlation between the imaginary impedance and surface area across the entire spectrum. However, using Sulfuric Acid (H2SO4) as the electrolyte presents very good correlation data, and using Phosphate Buffered saline Solution with zero mg/ml of Glucose (PBS-0) presents even better correlation data, between imaginary impedance and Surface Area Ratio (SAR), especially between the relatively-lower frequencies of 100 Hz and 5 Hz. Moreover, fitted regression analysis using a cubic regression model indicates that, in embodiments of the invention, the best correlation may occur at a frequency of 10 Hz. In addition, it has been found that reducing the Bias voltage from 535 mV to zero dramatically reduces the day-to-day variability in the imaginary impedance measurement.

Using the above parameters, the limits of acceptability of values of imaginary impedance can be defined for a given sensor design. Thus, for example, for the Comfort Sensor manufactured by Medtronic Minimed, the imaginary impedance measured between the WE and the RE (Platinum mesh) must be greater than, or equal to, −100 Ohms. In other words, sensors with an imaginary impedance value (for the WE) of less than −100 Ohms will be rejected. For the WE, an impedance value of greater than, or equal to, −100 Ohms corresponds to a surface area that is equal to, or greater than, that specified by an equivalent Ra measurement of greater than 0.55 um.

Similarly, the imaginary impedance measured between the CE and the RE (Platinum mesh) must be greater than, or equal to, −60 Ohms, such that sensors with an imaginary impedance value (for the CE) of less than −60 Ohms will be rejected. For the CE, an impedance value of greater than, or equal to, −60 Ohms corresponds to a surface area that is equal to, or greater than, that specified by an equivalent Ra measurement greater than 0.50 um.

While the description above refers to particular embodiments of the present invention, it will be understood that many modifications may be made without departing from the spirit thereof. Additional steps and changes to the order of the algorithms can be made while still performing the key teachings of the present invention. Thus, the accompanying claims are intended to cover such modifications as would fall within the true scope and spirit of the present invention. The presently disclosed embodiments are, therefore, to be considered in all respects as illustrative and not restrictive, the scope of the invention being indicated by the appended claims rather than the foregoing description. All changes that come within the meaning of, and range of, equivalency of the claims are intended to be embraced therein.

What is claimed is:

1. A method of calculating a single, fused sensor glucose value based on respective glucose measurement signals of a plurality of redundant sensing electrodes, comprising:
    performing respective electrochemical impedance spectroscopy (EIS) procedures for each of the plurality of redundant sensing electrodes to obtain values of at least one impedance-based parameter for each said sensing electrode;
    measuring the electrode current (Isig) for each of the plurality of redundant sensing electrodes;
    calculating a plurality of reliability indices for each said sensing electrode based on said values of the at least one impedance-based parameter, said plurality of reliability indices including a dip reliability index that is calculated by:
        calculating a first similarity index to determine an amount of divergence between respective Isigs of at least a first one and a second one of said plurality of redundant sensing electrodes;
        calculating a second similarity index to determine an amount of divergence between respective values of the at least one impedance-based parameter for said at least first one and second one of said plurality of redundant sensing electrodes;
        mapping said first similarity index to said second similarity index; and
        mapping said second similarity index to said first similarity index;
    calculating a single fused Isig based on said plurality of reliability indices and respective Isig of each of the plurality of redundant sensing electrodes; and
    calibrating said single fused Isig to obtain said single fused sensor glucose value.

2. The method of claim 1, wherein said impedance-based parameter is 1 kHz real impedance.

3. The method of claim 2, wherein said plurality of reliability indices include a bound check reliability index and a noise check reliability index.

4. The method of claim 3, wherein calculation of said bound check reliability index and noise check reliability index includes determining whether each said measured Isig and said values of the 1 kHz real impedance fall within respective predetermined ranges for a bound check and a noise check.

5. The method of claim 4, wherein said predetermined range for the 1 kHz real impedance bound check is between 0.3e+4 and 2e+4.

6. The method of claim 1, wherein said plurality of reliability indices include a sensitivity-loss index that is calculated based on each said electrode's imaginary impedance.

7. The method of claim 6, wherein said imaginary impedance is measured at about 1 kHz over a period of time.

8. The method of claim 7, wherein said plurality of reliability indices include a bound check reliability index and a noise check reliability index, and wherein calculation of said bound check reliability index and said noise check reliability index include determining whether said values of the 1 kHz imaginary impedance fall within respective predetermined ranges for said bound check and noise check.

9. The method of claim 8, wherein said predetermined range for the 1 kHz imaginary impedance bound check is between −2e+3 and zero.

10. The method of claim 1, wherein said plurality of reliability indices include a bound check reliability index and a noise check reliability index, and wherein said bound check reliability index and noise check reliability index are calculated based on values of 1 kHz imaginary impedance and 1 kHz real impedance.

11. The method of claim 10, wherein calculation of said bound check reliability index and noise check reliability index is further based on values of 0.105 Hz imaginary impedance and 0.105 Hz real impedance.

12. The method of claim 11, wherein calculation of said bound check reliability index and said noise check reliability index includes determining whether said values of the 0.105 Hz real impedance fall between 2e+4 and 7e+4.

13. The method of claim 11, wherein calculation of said bound check reliability index and said noise check reliability index includes determining whether said values of the 0.105 Hz imaginary impedance fall between −2e+5 and 0.25e+5.

14. The method of claim 11, wherein calculation of said bound check reliability index and noise check reliability index is further based on values of Nyquist slope.

15. The method of claim 14, wherein calculation of said bound check reliability index and said noise check reliability index includes determining whether said values of Nyquist slope fall between 2 and 5.

16. The method of claim 1, wherein said single fused Isig is calibrated by using a blood glucose (BG) value.

17. The method of claim 1, wherein, prior to calculation of said single fused Isig, said respective measured Isig of each of the plurality of redundant sensing electrodes is first filtered to remove any EIS-induced spikes therein.

18. The method of claim 1, wherein one or more of the at least one impedance-based parameter are substantially glucose-independent.

19. The method of claim 1, further including calculating, for each of the plurality of electrodes, a weight based on said plurality of reliability indices for each said electrode.

20. The method of claim 19, wherein said single fused sensor glucose value is calculated based on the respective weights and Isigs of each of the plurality of redundant sensing electrodes.

\* \* \* \* \*